(12) United States Patent
Calderwood et al.

(10) Patent No.: US 7,863,444 B2
(45) Date of Patent: *Jan. 4, 2011

(54) 4-AMINOPYRROLOPYRIMIDINES AS KINASE INHIBITORS

(75) Inventors: David Calderwood, Framingham, MA (US); Lee Arnold, Westboro, MA (US); Hormoz Mazdiyasni, Douglas, MA (US); Gavin C. Hirst, Marlboro, MA (US); Bojuan B. Deng, Shrewsbury, MA (US); David N. Johnston, Nottingham (GB); Paul Rafferty, Nottingham (GB); Gerald B. Tometzki, Hucknall (GB); Helen L. Twigger, Nottingham (GB); Rainer Munschauer, Neustadt (DE)

(73) Assignee: Abbott Laboratories, Abbott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/399,083

(22) Filed: Sep. 17, 1999

(65) Prior Publication Data
US 2003/0187001 A1  Oct. 2, 2003

Related U.S. Application Data

(63) Continuation-in-part of application No. 09/042,702, filed on Mar. 17, 1998, now Pat. No. 6,001,839.

(60) Provisional application No. 60/100,954, filed on Sep. 18, 1998, provisional application No. 60/040,836, filed on Mar. 19, 1997.

(51) Int. Cl.
*C07D 487/04* (2006.01)
*A61K 31/505* (2006.01)

(52) U.S. Cl. .................................. 544/280; 514/265.1
(58) Field of Classification Search ................ 514/258, 514/265.1; 594/280
See application file for complete search history.

(56) References Cited

U.S. PATENT DOCUMENTS

| | | | |
|---|---|---|---|
| 4,140,851 A | 2/1979 | Townsend | 536/24 |
| 4,229,453 A | 10/1980 | Roth et al. | 424/251 |
| 4,892,865 A | 1/1990 | Townsend et al. | 514/43 |
| 4,927,830 A | 5/1990 | Townsend et al. | 514/258 |
| 4,968,686 A | 11/1990 | Townsend et al. | 514/258 |
| 4,996,206 A | 2/1991 | Taylor et al. | 514/258 |
| 5,028,608 A | 7/1991 | Taylor et al. | 514/258 |
| 5,248,775 A | 9/1993 | Taylor et al. | 544/280 |
| 5,254,687 A | 10/1993 | Taylor et al. | 544/280 |
| 5,344,932 A | 9/1994 | Taylor | 544/280 |
| 5,349,064 A | 9/1994 | Akimoto et al. | 544/280 |
| 5,416,211 A | 5/1995 | Barnett et al. | 544/280 |
| 5,593,997 A | 1/1997 | Dow et al. | 514/258 |
| 5,594,121 A | 1/1997 | Froehler et al. | 536/23.5 |
| 5,612,482 A | 3/1997 | Barnett et al. | 544/280 |
| 5,639,757 A | 6/1997 | Dow et al. | 514/261 |
| 5,644,057 A | 7/1997 | Yuan et al. | 544/280 |
| 5,644,058 A | 7/1997 | Barnett et al. | 544/280 |
| 5,665,721 A | 9/1997 | Bhagwat et al. | 514/253 |
| 5,686,457 A | 11/1997 | Traxler et al. | 514/258 |
| 5,721,356 A | 2/1998 | Ugarkar et al. | 536/27.2 |
| 5,726,302 A | 3/1998 | Ugarkar et al. | 536/27.13 |
| 5,763,596 A | 6/1998 | Boyer et al. | 536/27.13 |
| 5,763,597 A | 6/1998 | Ugarkar et al. | 536/27.13 |
| 5,834,469 A | 11/1998 | Elliott et al. | 514/249 |
| 6,001,839 A * | 12/1999 | Calderwood et al. | 514/258 |
| 6,660,744 B1 * | 12/2003 | Hirst et al. | 514/262.1 |
| 6,713,474 B2 * | 3/2004 | Hirst et al. | 514/218 |

FOREIGN PATENT DOCUMENTS

| | | |
|---|---|---|
| DE | 30 36 390 A1 | 5/1982 |
| EP | 0 402 903 A1 | 12/1990 |
| EP | 0 496 617 A1 | 7/1992 |
| EP | 0 795 556 A1 | 9/1997 |
| WO | WO 94 17803 | 8/1994 |
| WO | WO 96/10028 | 4/1996 |
| WO | WO 96/40686 | 12/1996 |
| WO | WO 96/40705 | 12/1996 |
| WO | WO 96/40706 | 12/1996 |
| WO | WO 96/40707 | 12/1996 |

(Continued)

OTHER PUBLICATIONS

Hanke, J.H., et al., "Discovery of a Novel, Potent, and Src Family—selective Tyrosine Kinase Inhibitor; Study of Lck- and FynT-dependent T Cell Activation," *J Biol Chem.*, 271(2):695-701, 1996.

(Continued)

*Primary Examiner*—Deepak Rao
(74) *Attorney, Agent, or Firm*—Gayle B. O'Brien; Kenneth P. Zwicker

(57) ABSTRACT

Chemical compounds having structural formula I

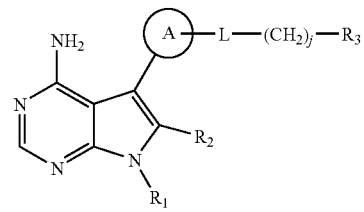

and physiologically acceptable salts thereof, are inhibitors of serine/threonine and tyrosine kinase activity. Several of the kinases whose activity is inhibited by these compounds are involved in immunologic, hyperproliferative or angiogenic processes. Thus, these compounds can ameliorate disase states where angiogenesis or endothelial cell hyperproliferaton is a factor. These compounds can be used to treat cancer, hyperproliferative disorders, rheumatoid artheritis, disorders of the immune system, transplant rejection, and inflammatory disorders.

11 Claims, No Drawings

FOREIGN PATENT DOCUMENTS

| | | |
|---|---|---|
| WO | WO 97/02266 | 1/1997 |
| WO | WO 97/03069 | 1/1997 |
| WO | WO 97/13771 | 4/1997 |
| WO | WO 97/28161 | 8/1997 |
| WO | WO 97/32879 | 9/1997 |
| WO | WO 97/34895 | 9/1997 |
| WO | WO 98 41525 | 9/1998 |

OTHER PUBLICATIONS

Traxler, P.M., et al., "4-(Phenylamino)pyrrolopyrimidines: Potent and Selective, ATP Site Directed Inhibitors of the EGF-Receptor Protein Tyrosine Kinase," *J. Med. Chem.*, 39:2285-2292 (1996).

Showalter, H.D.H., et al., "Synthesis and SAR for a series of 4-substituted 1H-pyrimido[4,5-b] and 5H-pyrimido[5,4-b]indoles as EGF receptor tyrosine kinase inhibitors," Proceedings of the American Association for Cancer Research, vol. 37, Mar. 1996 (abstract).

Missbach, M., et al., "A Novel Inhibitor of the Tyrosine Kinase Src Suppresses Phosphorylation of Its Major Cellular Substrates and Reduces Bone Resorption In Vitro and in Rodent Models In Vivo," *Bone*, 24(5):437-449 (1999).

Dave, C.G., et al., "Synthesis & Biological Activity of Pyrrolo[2,3-d]pyrimidines," *Indian J. Chem.*, 27B:778-780 (1988).

\* cited by examiner

4-AMINOPYRROLOPYRIMIDINES AS KINASE INHIBITORS

RELATED APPLICATIONS

This application claims the benefit of U.S. Provisional Application No. 60/100,954, filed Sep. 18, 1998, and is a Continuation-in-Part of U.S. application Ser. No. 09/042,702, now U.S. Pat. No. 6,001,839 filed Mar. 17, 1998, which claims the benefit of U.S. Provisional Application No. 60/040,836, filed on Mar. 19, 1997, the entire teachings of each of these referenced applications are incorporated herein by reference.

BACKGROUND OF THE INVENTION

There are at least 400 enzymes identified as protein kinases. These enzymes catalyze the phosphorylation of target protein substrates. The phosphorylation is usually a transfer reaction of a phosphate group from ATP to the protein substrate. The specific structure in the target substrate to which the phosphate is transferred is a tyrosine, serine or threonine residue. Since these amino acid residues are the target structures for the phosphoryl transfer, these protein kinase enzymes are commonly referred to as tyrosine kinases or serine/threonine kinases.

The phosphorylation reactions, and counteracting phosphatase reactions, at the tyrosine, serine and threonine residues are involved in countless cellular processes that underlie responses to diverse intracellular signals (typically mediated through cellular receptors), regulation of cellular functions, and activation or deactivation of cellular processes. A cascade of protein kinases often participate in intracellular signal transduction and are necessary for the realization of these cellular processes. Because of their ubiquity in these processes, the protein kinases can be found as an integral part of the plasma membrane or as cytoplasmic enzymes or localized in the nucleus, often as components of enzyme complexes. In many instances, these protein kinases are an essential element of enzyme and structural protein complexes that determine where and when a cellular process occurs within a cell.

Protein Tyrosine Kinases. Protein tyrosine kinases (PTKs) are enzymes which catalyse the phosphorylation of specific tyrosine residues in cellular proteins. This post-translational modification of these substrate proteins, often enzymes themselves, acts as a molecular switch regulating cell proliferation, activation or differentiation (for review, see Schlessinger and Ulrich, 1992, *Neuron* 9:383-391). Aberrant or excessive PTK activity has been observed in many disease states including benign and malignant proliferative disorders as well as diseases resulting from inappropriate activation of the immune system (e.g., autoimmune disorders), allograft rejection, and graft vs. host disease. In addition, endothelial-cell specific receptor PTKs such as KDR and Tie-2 mediate the angiogenic process, and are thus involved in supporting the progression of cancers and other diseases involving inappropriate vascularization (e.g., diabetic retinopathy, choroidal neovascularization due to age-related macular degeneration, psoriasis, arthritis, retinopathy of prematurity, infantile hemangiomas).

Tyrosine kinases can be of the receptor-type (having extracellular, transmembrane and intracellular domains) or the non-receptor type (being wholly intracellular).

Receptor Tyrosine Kinases (RTKs). The RTKs comprise a large family of transmembrane receptors with diverse biological activities. At present, at least nineteen (19) distinct RTK subfamilies have been identified. The receptor tyrosine kinase (RTK) family includes receptors that are crucial for the growth and differentiation of a variety of cell types (Yarden and Ullrich, *Ann. Rev. Biochem.* 57:433-478, 1988; Ullrich and Schlessinger, *Cell* 61:243-254, 1990). The intrinsic function of RTKs is activated upon ligand binding, which results in phosphorylation of the receptor and multiple cellular substrates, and subsequently in a variety of cellular responses (Ullrich & Schlessinger, 1990, *Cell* 61:203-212). Thus, receptor tyrosine kinase mediated signal transduction is initiated by extracellular interaction with a specific growth factor (ligand), typically followed by receptor dimerization, stimulation of the intrinsic protein tyrosine kinase activity and receptor trans-phosphorylation. Binding sites are thereby created for intracellular signal transduction molecules and lead to the formation of complexes with a spectrum of cytoplasmic signaling molecules that facilitate the appropriate cellular response. (e.g., cell division, differentiation, metabolic effects, changes in the extracellular microenvironment) see Schlessinger and Ullrich, 1992, *Neuron* 9:1-20.

Proteins with SH2 (src homology-2) or phosphotyrosine binding (PTB) domains bind activated tyrosine kinase receptors and their substrates with high affinity to propagate signals into cell. Both of the domains recognize phosphotyrosine. (Fantl et al., 1992, *Cell* 69:413-423; Songyang et al., 1994, *Mol. Cell. Biol.* 14:2777-2785; Songyang et al., 1993, *Cell* 72:767-778; and Koch et al., 1991, *Science* 252:668-678; Shoelson, *Curr. Opin. Chem. Biol.* (1997), 1(2), 227-234; Cowburn, *Curr. Opin. Struct. Biol.* (1997), 7(6), 835-838). Several intracellular substrate proteins that associate with receptor tyrosine kinases (RTKS) have been identified. They may be divided into two principal groups: (1) substrates which have a catalytic domain; and (2) substrates which lack such a domain but serve as adapters and associate with catalytically active molecules (Songyang et al., 1993, *Cell* 72:767-778). The specificity of the interactions between receptors or proteins and SH2 or PTB domains of their substrates is determined by the amino acid residues immediately surrounding the phosphorylated tyrosine residue. For example, differences in the binding affinities between SH2 domains and the amino acid sequences surrounding the phosphotyrosine residues on particular receptors correlate with the observed differences in their substrate phosphorylation profiles (Songyang et al., 1993, *Cell* 72:767-778). Observations suggest that the function of each receptor tyrosine kinase is determined not only by its pattern of expression and ligand availability but also by the array of downstream signal transduction pathways that are activated by a particular receptor as well as the timing and duration of those stimuli. Thus, phosphorylation provides an important regulatory step which determines the selectivity of signaling pathways recruited by specific growth factor receptors, as well as differentiation factor receptors.

Several receptor tyrosine kinases such as FGFR-1, PDGFR, TIE-2 and c-Met, and growth factors that bind thereto, have been suggested to play a role in angiogenesis, although some may promote angiogenesis indirectly (Mustonen and Alitalo, *J. Cell Biol.* 129:895-898, 1995). One such receptor tyrosine kinase, known as "fetal liver kinase 1" (FLK-1), is a member of the type III subclass of RTKs. An alternative designation for human FLK-1 is "kinase insert domain-containing receptor" (KDR) (Terman et al., *Oncogene* 6:1677-83, 1991). Another alternative designation for FLK-1/KDR is "vascular endothelial cell growth factor receptor 2" (VEGFR-2) since it binds VEGF with high affinity. The murine version of FLK-1/VEGFR-2 has also been called NYK (Oelrichs et al, *Oncogene* 8(1):11-15, 1993). DNAs encoding mouse, rat and human FLK-1 have been isolated, and the nucleotide and encoded amino acid sequences reported (Matthews et al., *Proc. Natl. Acad. Sci. USA*, 88:9026-30, 1991; Terman et al., 1991, supra; Terman et al., *Biochem. Biophys. Res. Comm.* 187:1579-86, 1992; Sarzani et al., supra; and Millauer et al., *Cell* 72:835-846, 1993). Numerous studies such as those reported in Millauer et al., supra, suggest that VEGF and FLK-1/KDR/VEGFR-2 are a ligand-receptor pair that play an important role in the proliferation of vascular endothelial cells, and formation and sprouting of blood vessels, termed vasculogenesis and angiogenesis, respectively.

Another type III subclass RTK designated "fms-like tyrosine kinase-1" (Flt-1) is related to FLK-1/KDR (DeVries et al. *Science* 255; 989-991, 1992; Shibuya et al., *Oncogene* 5:519-524, 1990). An alternative designation for Flt-1 is "vascular endothelial cell growth factor receptor 1" (VEGFR-1). To date, members of the FLK-1/KDR/VEGFR-2 and Flt-1/VEGFR-1 subfamilies have been found expressed primarily on endothelial cells. These subclass members are specifically stimulated by members of the vascular endothelial cell growth factor (VEGF) family of ligands (Klagsburn and D'Amore, *Cytokine & Growth Factor Reviews* 7: 259-270, 1996). Vascular endothelial cell growth factor (VEGF) binds to Flt-1 with higher affinity than to FLK-1/KDR and is mitogenic toward vascular endothelial cells (Terman et al., 1992, supra; Mustonen et al. supra; DeVries et al., supra). Flt-1 is believed to be essential for endothelial organization during vascular development. Flt-1 expression is associated with early vascular development in mouse embryos, and with neovascularization during wound healing (Mustonen and Alitalo, supra). Expression of Flt-1 in monocytes, osteoclasts, and osteoblasts, as well as in adult tissues such as kidney glomeruli suggests an additional function for this receptor that is not related to cell growth (Mustonen and Alitalo, supra).

As previously stated, recent evidence suggests that VEGF plays a role in the stimulation of both normal and pathological angiogenesis (Jakeman et al., *Endocrinology* 133: 848-859, 1993; Kolch et al., *Breast Cancer Research and Treatment* 36: 139-155, 1995; Ferrara et al., *Endocrine Reviews* 18(1); 4-25, 1997; Ferrara et al., *Regulation of Angiogenesis* (ed. L. D. Goldberg and E. M. Rosen), 209-232, 1997). In addition, VEGF has been implicated in the control and enhancement of vascular permeability (Connolly, et al., *J. Biol. Chem.* 264: 20017-20024, 1989; Brown et al., *Regulation of Angiogenesis* (ed. L. D. Goldberg and E. M. Rosen), 233-269, 1997).

Different forms of VEGF arising from alternative splicing of mRNA have been reported, including the four species described by Ferrara et al. (*J. Cell. Biochem.* 47:211-218, 1991). Both secreted and predominantly cell-associated species of VEGF have been identified by Ferrara et al. supra, and the protein is known to exist in the form of disulfide linked dimers.

Several related homologs of VEGF have recently been identified. However, their roles in normal physiological and disease processes have not yet been elucidated. In addition, the members of the VEGF family are often coexpressed with VEGF in a number of tissues and are, in general, capable of forming heterodimers with VEGF. This property likely alters the receptor specificity and biological effects of the heterodimers and further complicates the elucidation of their specific functions as illustrated below (Korpelainen and Alitalo, *Curr. Opin. Cell Biol.,* 159-164, 1998 and references cited therein).

Placenta growth factor (PlGF) has an amino acid sequence that exhibits significant homology to the VEGF sequence (Park et al., *J. Biol. Chem.* 269:25646-54, 1994; Maglione et al. *Oncogene* 8:925-31, 1993). As with VEGF, different species of PlGF arise from alternative splicing of mRNA, and the protein exists in dimeric form (Park et al., supra). PlGF-1 and PlGF-2 bind to Flt-1 with high affinity, and PlGF-2 also avidly binds to neuropilin-1 (Migdal et al, *J. Biol. Chem.* 273 (35): 22272-22278), but neither binds to FLK-1/KDR (Park et al., supra). PlGF has been reported to potentiate both the vascular permeability and mitogenic effect of VEGF on endothelial cells when VEGF is present at low concentrations (purportedly due to heterodimer formation) (Park et al., supra).

VEGF-B is produced as two isoforms (167 and 185 residues) that also appear to bind Flt-1/VEGFR-1. It may play a role in the regulation of extracellular matrix degradation, cell adhesion, and migration through modulation of the expression and activity of urokinase type plasminogen activator and plasminogen activator inhibitor 1 (Pepper et al, *Proc. Natl. Acad. Sci. U.S. A.* (1998), 95(20): 11709-11714).

VEGF-C was originally cloned as a ligand for VEGFR-3/Flt-4 which is primarily expressed by lymphatic endothelial cells. In its fully processed form, VEGF-C can also bind KDR/VEGFR-2 and stimulate proliferation and migration of endothelial cells in vitro and angiogenesis in in vivo models (Lymboussaki et al, *Am. J. Pathol.* (1998), 153(2): 395-403; Witzenbichler et al, *Am. J. Pathol.* (1998), 153(2), 381-394). The transgenic overexpression of VEGF-C causes proliferation and enlargement of only lymphatic vessels, while blood vessels are unaffected. Unlike VEGF, the expression of VEGF-C is not induced by hypoxia (Ristimaki et al, *J. Biol. Chem.* (1998), 273(14), 8413-8418).

The most recently discovered VEGF-D is structurally very similar to VEGF-C. VEGF-D is reported to bind and activate at least two VEGFRs, VEGFR-3/Flt-4 and KDR/VEGFR-2. It was originally cloned as a c-fos inducible mitogen for fibroblasts and is most prominently expressed in the mesenchymal cells of the lung and skin (Achen et al, *Proc. Natl. Acad. Sci. U.S.A.* (1998), 95(2), 548-553 and references therein).

As for VEGF, VEGF-C and VEGF-D have been claimed to induce increases in vascular permeability in vivo in a Miles assay when injected into cutaneous tissue (PCT/US97/14696; WO98/07832, Witzenbichler et al., supra). The physiological role and significance of these ligands in modulating vascular hyperpermeability and endothelial responses in tissues where they are expressed remains uncertain.

There has been recently reported a virally encoded, novel type of vascular endothelial growth factor, VEGF-E (NZ-7 VEGF), which preferentially utilizes KDR/Flk-1 receptor and carries a potent mitotic activity without heparin-binding domain (Meyer et al, *EMBO J.* (1999), 18(2), 363-374; Ogawa et al, *J. Biol. Chem.* (1998), 273(47), 31273-31282.). VEGF-E sequences possess 25% homology to mammalian VEGF and are encoded by the parapoxyirus Orf virus (OV). This parapoxyirus that affects sheep and goats and occasionally, humans, to generate lesions with angiogenesis. VEGF-E is a dimer of about 20 kDa with no basic domain nor affinity for heparin, but has the characteristic cysteine knot motif present in all mammalian VEGFs, and was surprisingly found to possess potency and bioactivities similar to the heparin-binding VEGF165 isoform of VEGF-A, i.e. both factors stimulate the release of tissue factor (TF), the proliferation, chemotaxis and sprouting of cultured vascular endothelial cells in vitro and angiogenesis in vivo. Like VEGF165, VEGF-E was found to bind with high affinity to VEGF receptor-2 (KDR) resulting in receptor autophosphorylation and a biphasic rise in free intracellular Ca2+ concentrations, while in contrast to VEGF165, VEGF-E did not bind to VEGF receptor-1 (Flt-1).

Based upon emerging discoveries of other homologs of VEGF and VEGFRs and the precedents for ligand and receptor heterodimerization, the actions of such VEGF homologs may involve formation of VEGF ligand heterodimers, and/or heterodimerization of receptors, or binding to a yet undiscovered VEGFR (Witzenbichler et al., supra). Also, recent reports suggest neuropilin-1 (Migdal et al, supra) or VEGFR-3/Flt-4 (Witzenbichler et al., supra), or receptors other than KDR/VEGFR-2 may be involved in the induction of vascular permeability (Stacker, S. A., Vitali, A., Domagala, T., Nice, E., and Wilks, A. F., "Angiogenesis and Cancer" Conference, Amer. Assoc. Cancer Res., January 1998, Orlando, Fla.; Williams, *Diabetelogia* 40: S118-120 (1997)).

Tie-2 (TEK) is a member of a recently discovered family of endothelial cell specific receptor tyrosine kinases which is involved in critical angiogenic processes, such as vessel branching, sprouting, remodeling, maturation and stability. Tie-2 is the first mammalian receptor tyrosine kinase for which both agonist ligand(s) (e.g., Angiopoietin1 ("Ang1"), which stimulates receptor autophosphorylation and signal transduction), and antagonist ligand(s) (e.g., Angiopoietin2 ("Ang2")), have been identified. Knock-out and transgenic manipulation of the expression of Tie-2 and its ligands indicates tight spatial and temporal control of Tie-2 signaling is essential for the proper development of new vasculature. The current model suggests that stimulation of Tie-2 kinase by the Ang1 ligand is directly involved in the branching, sprouting and outgrowth of new vessels, and recruitment and interaction of periendothelial support cells important in maintaining vessel integrity and inducing quiescence. The absence of Ang1 stimulation of Tie-2 or the inhibition of Tie-2 autophosphorylation by Ang2, which is produced at high levels at sites of vascular regression, may cause a loss in vascular structure and matrix contacts resulting in endothelial cell death, especially in the absence of growth/survival stimuli. The situation is however more complex, since at least two additional Tie-2 ligands (Ang3 and Ang4) have recently been reported, and the capacity for heterooligomerization of the various agonistic and antagonistic angiopoietins, thereby modifying their activity, has been demonstrated. Targeting Tie-2 ligand-receptor interactions as an antiangiogenic therapeutic approach is thus less favored and a kinase inhibitory strategy preferred.

The soluble extracellular domain of Tie-2 ("ExTek") can act to disrupt the establishment of tumor vasculature in a breast tumor xenograft and lung metastasis models and in tumor-cell mediated ocular neovasculatization. By adenoviral infection, the in vivo production of mg/ml levels ExTek in rodents may be achieved for 7-10 days with no adverse side effects. These results suggest that disruption of Tie-2 signaling pathways in normal healthy animals may be well tolerated. These Tie-2 inhibitory responses to ExTek may be a consequence sequestration of ligand(s) and/or generation of a nonproductive heterodimer with full-length Tie-2.

Recently, significant upregulation of Tie-2 expression has been found within the vascular synovial pannus of arthritic joints of humans, consistent with a role in the inappropriate neovascularization. This finding suggests that Tie-2 plays a role in the progression of rheumatoid arthritis. Point mutations producing constitutively activated forms of Tie-2 have been identified in association with human venous malformation disorders. Tie-2 inhibitors are, thereful, useful in treating such disorders, and in other situations of inappropriate neovascularization.

The Non-Receptor Tyrosine Kinases. The non-receptor tyrosine kinases represent a collection of cellular enzymes which lack extracellular and transmembrane sequences. At present, over twenty-four individual non-receptor tyrosine kinases, comprising eleven (11) subfamilies (Src, Frk, Btk, Csk, Ab1, Zap70, Fes/Fps, Fak, Jak, Ack and LIMK) have been identified. At present, the Src subfamily of non-receptor tyrosine kinases is comprised of the largest number of PTKs and include Src, Yes, Fyn, Lyn, Lck, Blk, Hck, Fgr and Yrk. The Src subfamily of enzymes has been linked to oncogenesis and immune responses. A more detailed discussion of non-receptor tyrosine kinases is provided in Bohlen, 1993, *Oncogene* 8:2025-2031, which is incorporated herein by reference.

Many of the tyrosine kinases, whether an RTK or non-receptor tyrosine kinase, have been found to be involved in cellular signaling pathways involved in numerous pathogenic conditions, including cancer, psoriasis, and other hyperproliferative disorders or hyper-immune responses.

Development of Compounds to Modulate the PTKs. In view of the surmised importance of PTKs to the control, regulation, and modulation of cell proliferation, the diseases and disorders associated with abnormal cell proliferation, many attempts have been made to identify receptor and non-receptor tyrosine kinase "inhibitors" using a variety of approaches, including the use of mutant ligands (U.S. Pat. No. 4,966,849), soluble receptors and antibodies (Application No. WO 94/10202; Kendall & Thomas, 1994, *Proc. Natl. Acad. Sci* 90:10705-09; Kim et al., 1993, *Nature* 362:841-844), RNA ligands (Jellinek, et al., *Biochemistry* 33:10450-56; Takano, et al., 1993, *Mol. Bio. Cell* 4:358A; Kinsella, et al. 1992, *Exp. Cell Res.* 199:56-62; Wright, et al., 1992, *J. Cellular Phys.* 152:448-57) and tyrosine kinase inhibitors (WO 94/03427; WO 92/21660; WO 91/15495; WO 94/14808; U.S. Pat. No. 5,330,992; Mariani, et al., 1994, *Proc. Am. Assoc. Cancer Res.* 35:2268).

More recently, attempts have been made to identify small molecules which act as tyrosine kinase inhibitors. For example, bis monocyclic, bicyclic or heterocyclic aryl compounds (PCT WO 92/20642) and vinylene-azaindole derivatives (PCT WO 94/14808) have been described generally as tyrosine kinase inhibitors. Styryl compounds (U.S. Pat. No. 5,217,999), styryl-substituted pyridyl compounds (U.S. Pat. No. 5,302,606), certain quinazoline derivatives (EP Application No. 0 566 266 A1; *Expert Opin. Ther. Pat.* (1998), 8(4): 475-478), selenoindoles and selenides (PCT WO 94/03427), tricyclic polyhydroxylic compounds (PCT WO 92/21660) and benzylphosphonic acid compounds (PCT WO 91/15495) have been described as compounds for use as tyrosine kinase inhibitors for use in the treatment of cancer. Anilinocinnolines (PCT WO97/34876) and quinazoline derivative compounds (PCT WO97/22596; PCT WO97/42187) have been described as inhibitors of angiogenesis and vascular permeability.

In addition, attempts have been made to identify small molecules which act as serine/threonine kinase inhibitors. For example, bis(indolylmaleimide) compounds have been described as inhibiting particular PKC serine/threonine kinase isoforms whose signal transducing function is associated with altered vascular permeability in VEGF-related diseases (PCT WO97/40830; PCT WO97/40831).

Plk-1 Kinase Inhibitors

Plk-1 is a serine/threonine kinase which is an important regulator of cell cycle progression. It plays critical roles in the assembly and the dynamic function of the mitotic spindle apparatus. Plk-1 and related kinases have also been shown to be closely involved in the activation and inactivation of other cell cycle regulators, such as cyclin-dependent kinases. High levels of Plk-1 expression are associated with cell proliferation activities. It is often found in malignant tumors of various origins. Inhibitors of Plk-1 are expected to block cancer cell proliferation by disrupting processes involving mitotic spindles and inappropriately activated cyclin-dependent kinases.

Cdc2/Cyclin B Kinase Inhibitors (Cdc2 is also Known as cdk1)

Cdc2/cyclin B is another serine/threonine kinase enzyme which belongs to the cyclin-dependent kinase (cdks) family. These enzymes are involved in the critical transition between various phases of cell cycle progression. It is believed that uncontrolled cell proliferation, which is the hallmark of cancer is dependent upon elevated cdk activities in these cells. The inhibition of elevated cdk activities in cancer cells by cdc2/cyclin B kinase inhibitors could suppress proliferation and may restore the normal control of cell cycle progression.

The regulation of CDK activation is complex, but requires the association of the CDK with a member of the cyclin family of regulatory subunits (Draetta, *Trends in Cell Biology*, 3:287-289 (1993)); Murray and Kirschner, *Nature*, 339:275-280 (1989); Solomon et al., *Molecular Biology of the Cell*, 3:13-27 (1992)). A further level of regulation occurs through both activating and inactivating phosphorylations of the CDK subunit (Draetta, *Trends in Cell Biology*, 3:287-289 (1993)); Murray and Kirschner, Nature, 339:275-280 (1989); Solomon et al, *Molecular Biology of the Cell*, 3:13-27 (1992); Ducommun et al., *EMBO Journal*, 10:3311-3319 (1991); Gautier et al., *Nature* 339:626-629 (1989); Gould and Nurse, *Nature*, 342:39-45 (1989); Krek and Nigg, *EMBO Journal*, 10:3331-3341 (1991); Solomon et al., *Cell*, 63:1013-1024 (1990)). The coordinate activation and inactivation of different cyclin/CDK complexes is necessary for normal progression through the cell cycle (Pines, *Trends in Biochemical Sciences*, 18:195-197 (1993); Sherr, *Cell*, 73:1059-1065 (1993)). Both the critical G1-S and G 2-M transitions are controlled by the activation of different cyclin/CDK activities. In G1, both cyclin D/CDK4 and cyclin E/CDK2 are thought to mediate the onset of S-phase (Matsushima et al., *Molecular & Cellular Biology*, 14:2066-2076 (1994); Ohtsubo and Roberts, *Science*, 259:1908-1912 (1993); Quelle et al., *Genes & Development*, 7:1559-1571 (1993); Resnitzky et al., *Molecular & Cellular Biology*, 14:1669-1679 (1994)). Progression through S-phase requires the activity of cyclin A/CDK2 (Girard et al., *Cell*, 67:1169-1179 (1991); Pagano et al., *EMBO Journal*, 11:961-971 (1992); Rosenblatt et al., *Proceedings of the National Academy of Science USA*, 89:2824-2828 (1992); Walker and Maller, *Nature*, 354:314-317 (1991); Zindy et al., *Biochemical & Biophysical Research Communications*, 182:1144-1154 (1992)) whereas the activation of cyclin A/cdc2 (CDK1) and cyclin B/cdc2 are required for the onset of metaphase (Draetta, *Trends in Cell Biology*, 3:287-289 (1993)); Murray and Kirschner, Nature, 339:275-280 (1989); Solomon et al., *Molecular Biology of the Cell*, 3:13-27 (1992); Girard et al., *Cell*, 67:1169-1179 (1991); Pagano et al., *EMBO Journal*, 11:961-971 (1992); Rosenblatt et al., *Proceedings of the National Academy of Science USA*, 89:2824-2828 (1992); Walker and Maller, *Nature*, 354:314-317 (1991); Zindy et al., *Biochemical & Biophysical Research Communications*, 182:1144-1154 (1992)). It is not surprising, therefore, that the loss of control of CDK regulation is a frequent event in hyperproliferative diseases and cancer. (Pines, *Current Opinion in Cell Biology*, 4:144-148 (1992); Lees, *Current Opinion in Cell Biology*, 7:773-780 (1995); Hunter and Pines, *Cell*, 79:573-582 (1994)).

Inhibitors of kinases involved in mediating or maintaining disease states represent novel therapies for these disorders. Examples of such kinases include, but are not limited to: (1) inhibition of c-Src (Brickell, *Critical Reviews in Oncogenesis*, 3:401-406 (1992); Courtneidge, *Seminars in Cancer Biology*, 5:236-246 (1994), raf (Powis, *Pharmacology & Therapeutics*, 62:57-95 (1994)) and the cyclin-dependent kinases (CDKs) 1, 2 and 4 in cancer (Pines, *Current Opinion in Cell Biology*, 4:144-148 (1992); Lees, *Current Opinion in Cell Biology*, 7:773-780 (1995); Hunter and Pines, *Cell*, 79:573-582 (1994)), (2) inhibition of CDK2 or PDGF-R kinase in restenosis (Buchdunger et al., *Proceedings of the National Academy of Science USA*, 92:2258-2262 (1995)), (3) inhibition of CDK5 and GSK3 kinases in Alzheimers (Hosoi et al., *Journal of Biochemistry (Tokyo)*, 117:741-749 (1995); Aplin et al., *Journal of Neurochemistry*, 67:699-707 (1996), (4) inhibition of c-Src kinase in osteoporosis (Tanaka et al., *Nature*, 383:528-531 (1996), (5) inhibition of GSK-3 kinase in type-2 diabetes (Borthwick et al., *Biochemical & Biophysical Research Communications*, 210:738-745 (1995), (6) inhibition of the p38 kinase in inflammation (Badger et al., *The Journal of Pharmacology and Experimental Therapeutics*, 279:1453-1461 (1996)), (7) inhibition of VEGF-R 1-3 and TIE-1 and -2 kinases in diseases which involve angiogenesis (Shawver et al., *Drug Discovery Today*, 2:50-63 (1997)), (8) inhibition of UL97 kinase in viral infections (He et al., *Journal of Virology*, 71:405-411 (1997)), (9) inhibition of CSF-1R kinase in bone and hematopoetic diseases (Myers et al., *Bioorganic & Medicinal Chemistry Letters*, 7:421-424 (1997), and (10) inhibition of Lck kinase in autoimmune diseases and transplant rejection (Myers et al., *Bioorganic & Medicinal Chemistry Letters*, 7:417-420 (1997)).

It is additionally possible that inhibitors of certain kinases may have utility in the treatment of diseases when the kinase is not misregulated, but it nonetheless essential for maintenance of the disease state. In this case, inhibition of the kinase activity would act either as a cure or palliative for these diseases. For example, many viruses, such as human papilloma virus, disrupt the cell cycle and drive cells into the S-phase of the cell cycle (Vousden, *FASEB Journal*, 7:8720879 (1993)). Preventing cells from entering DNA synthesis after viral infection by inhibition of essential S-phase initiating activities such as CDK2, may disrupt the virus life cycle by preventing virus replication. This same principle may be used to protect normal cells of the body from toxicity of cycle-specific chemotherapeutic agents (Stone et al., *Cancer Research*, 56:3199-3202 (1996); Kohn et al., *Journal of Cellular Biochemistry*, 54:44-452 (1994)). Inhibition of CDKs 2 or 4 will prevent progression into the cycle in normal cells and limit the toxicity of cytotoxics which act in S-phase, G2 or mitosis. Furthermore, CDK2/cyclin E activity has also been shown to regulate NF-kB. Inhibition of CDK2 activity stimulates NF-kB-dependent gene expression, an event mediated through interactions with the p300 coactivator (Perkins et al., *Science*, 275:523-527 (1997)). NF-kB regulates genes involved in inflammatory responses (such as hematopoetic growth factors, chemokines and leukocyte adhesion molecules) (Baeuerle and Henkel, *Annual Review of Immunology*, 12:141-179 (1994)) and may be involved in the suppression of apoptotic signals within the cell (Beg and Baltimore, *Science*, 274:782-784 (1996); Wang et al., *Science*, 274:784-787 (1996); Van Antwerp et al., *Science*, 274:787-789 (1996)). Thus, inhibition of CDK2 may suppress apoptosis induced by cytotoxic drugs via a mechanism which involves NF-kB. This therefore suggests that inhibition of CDK2 activity may also have utility in other cases where regulation of NF-kB plays a role in etiology of disease. A further example may be take from fungal infections: Aspergillosis is a common infection in immune-compromised patients (Armstrong, *Clinical Infectious Diseases*, 16:1-7 (1993)). Inhibition of the Aspergillus kinases Cdc2/CDC28 or Nim A (Osmani et al., *EMBO Journal*, 10:2669-2679 (1991); Osmani et al., *Cell*, 67:283-291 (1991)) may cause arrest or death in the fungi, improving the therapeutic outcome for patients with these infections.

The identification of effective small compounds which specifically inhibit signal transduction and cellular proliferation by modulating the activity of receptor and non-receptor tyrosine and serine/threonine kinases to regulate and modulate abnormal or inappropriate cell proliferation, differentiation, or metabolism is therefore desirable. In particular, the identification of methods and compounds that specifically inhibit the function of a tyrosine kinase which is essential for antiogenic processes or the formation of vascular hyperpermeability leading to edema, ascites, effusions, exudates, and macromolecular extravasation and matrix deposition as well as associated disorders would be beneficial.

SUMMARY OF THE INVENTION

The present invention provides compounds of Formula I,

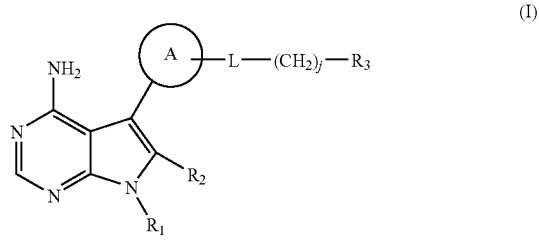

(I)

and pharmaceutically acceptable salts thereof.

In Formula I, Ring A is a six membered aromatic ring or a five or six membered heteroaromatic ring. Ring A is optionally substituted with one or more of the following substituents: a substituted or unsubstituted aliphatic group, a halogen, a substituted or unsubstituted aromatic group, substituted or unsubstituted heteroaromatic group, substituted or unsubstituted cycloalkyl, substituted or unsubstituted heterocycloalkyl, substituted or unsubstituted aralkyl, substituted or unsubstituted heteroaralkyl, cyano, nitro, —$NR_4R_5$, —$C(O)_2H$, —OH, a substituted or unsubstituted alkoxycarbonyl, —$C(O)_2$— haloalkyl, a substituted or unsubstituted alkylthio ether, a substituted or unsubstituted alkylsulfoxide, a substituted or unsubstituted alkylsulfone, a substituted or unsubstituted arylthio ether, a substituted or unsubstituted arylsulfoxide, a substituted or unsubstituted arylsulfone, a substituted or unsubstituted alkyl carbonyl, —C(O)-haloalkyl, a substituted or unsubstituted aliphatic ether, a substituted or unsubstituted aromatic ether, a substituted or unsubstituted carboxamido, tetrazolyl, trifluoromethylsulphonamido, trifluoromethylcarbonylamino, a substituted or unsubstituted alkynyl, a substituted or unsubstituted alkyl amido, a substituted or unsubstituted aryl amido, a substituted or unsubstituted styryl and a substituted or unsubstituted aralkyl amido.

L is one of the following linkers: —O—; —S—; —S(O)—; —$S(O)_2$—; —N(R)—; —N(C(O)OR)—; —N(C(O)R)—; —N($SO_2R$)—; —$CH_2O$—; —$CH_2S$—; —$CH_2N$(R)—; —CH(NR)—; —$CH_2N$(C(O)R))—; —$CH_2N$(C(O)OR)—; —$CH_2N$($SO_2R$)—; —CH(NHR)—; —CH(NHC(O)R)—; —CH($NHSO_2R$)—; —CH(NHC(O)OR)—; —CH(OC(O)R)—; —CH(OC(O)NHR)—; —CH═CH—; —C(═NOR)—; —C(O)—; —CH(OR)—; —C(O)N(R)—; —N(R)C(O)—; —N(R)S(O)—; —N(R)S(O)$_2$—; —OC(O)N(R)—; —N(R)C(O)N(R)—; —NRC(O)O—; —S(O)N(R)—; —S(O)$_2$N(R)—; N(C(O)R)S(O)—; N(C(O)R)S(O)$_2$—; —N(R)S(O)N(R)—; —N(R)S(O)$_2$N(R)—; —C(O)N(R)C(O)—; —S(O)N(R)C(O)—; —S(O)$_2$N(R)C(O)—; —OS(O)N(R)—; —OS(O)$_2$N(R)—; —N(R)S(O)O—; —N(R)S(O)$_2$O—; —N(R)S(O)C(O)—; —N(R)S(O)$_2$C(O)—; —SON(C(O)R)—; —$SO_2$N(C(O)R)—; —N(R)SON(R)—; —N(R)$SO_2$N(R)—; —C(O)O—; —N(R)P(OR')O—; —N(R)P(OR')—; —N(R)P(O)(OR')O—; —N(R)P(O)(OR')—; —N(C(O)R)P(OR')O—; —N(C(O)R)P(OR')—; —N(C(O)R)P(O)(OR')O— or —N(C(O)R)P(OR')—. R and R' are each, independently, —H, an acyl group, a substituted or unsubstituted aliphatic group, a substituted or unsubstituted aromatic group, a substituted or unsubstituted heteroaromatic group, or a substituted or unsubstituted cycloalkyl group.

Alternatively, L is —$R_bN(R)S(O)_2$—, —$R_bN(R)P(O)$—, or —$R_bN(R)P(O)O$—. $R_b$ is an alkylene group which when taken together with the sulphonamide, phosphinamide, or phosphonamide group to which it is bound forms a five or six membered ring fused to ring A.

Alternatively, L is represented by one of the following structural formulas:

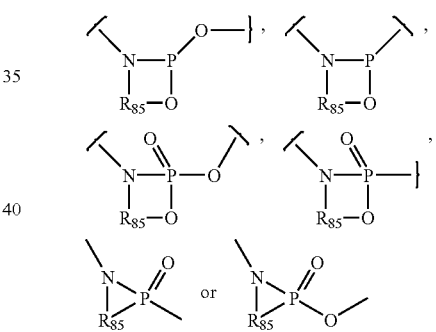

$R_{85}$ completes a 5-, 6-, or 7-membered, aromatic, heteroaromatic or heterocycloalkyl ring system.

In Formula I, $R_1$ is —H, 2-phenyl-1,3-dioxan-5-yl, a C1-C6 alkyl group, a C3-C8 cycloalkyl group, a C5-C7 cycloalkenyl group or an optionally substituted aryl(C1-C6 alkyl) group. When $R_1$ is an alkyl, cycloalkyl and cycloalkenyl group, it can be optionally substituted by one or more groups of formula —$OR^a$, provided that —$OR^a$ is not located on the carbon attached to nitrogen. $R^a$ is —H or a C1-C6 alkyl group or a C3-C6 cycloalkyl.

In Formula I, $R_2$ is —H, a substituted or unsubstituted aliphatic group, a substituted or unsubstituted cycloalkyl, a halogen, —OH, cyano, a substituted or unsubstituted aromatic group, a substituted or unsubstituted heteroaromatic group, a substituted or unsubstituted heterocycloalkyl, a substituted or unsubstituted aralkyl, a substituted or unsubstituted heteroaralkyl, —$NR_4R_5$, or —$C(O)NR_4R_5$.

In Formula I, $R_3$ is a substituted or unsubstituted cycloalkyl, a substituted or unsubstituted aromatic group, a substituted or unsubstituted heteroaromatic group, or a substituted or unsubstituted heterocycloalkyl. When L is NRSO$_2$—, NRC(O)—, —NRC(O)O—, —S(O)$_2$NR—, —C(O)NR— or —OC(O)NR—, R$_3$ can additionally be alkyl, alkenyl or aralkyl.

In Formula I, R$_4$, R$_5$ and the nitrogen atom together form a 3, 4, 5, 6 or 7-membered, substituted or unsubstituted heterocycloalkyl, substituted or unsubstituted heterobicycloalkyl or a substituted or unsubstituted heteroaromatic.

Alternatively, R$_4$ and R$_5$ are each, independently, —H, azabicycloalkyl, a substituted or unsubstituted alkyl group or Y—Z.

Y is —C(O)—, —(CH$_2$)$_p$—, —S(O)$_2$—, —C(O)O—, —SO$_2$NH—, —CONH—, (CH$_2$)$_p$O—, —(CH$_2$)$_p$NH—, —(CH$_2$)$_p$S—, —(CH$_2$)$_p$S(O)—, or —(CH$_2$)$_p$S(O)$_2$—.

p is an integer from 0 to to 6.

Z is a substituted or unsubstituted alkyl, substituted or unsubstituted amino, substituted or unsubstituted aryl, substituted or unsubstituted heteroaryl or substituted or unsubstituted heterocycloalkyl group.

j an integer from 0 to 6.

However, when L is —CH$_2$NR—, —C(O)NR— or —NRC(O)— and R$_3$ is azacycloalkyl or azaheteroaryl, j is 0. In addition, when L is —O— and R$_3$ is phenyl, j is 0.

The compounds of this invention are useful as inhibitors of serine/threonine and tyrosine kinases. In particular, compounds of this invention are useful as inhibitors of tyrosine kinases that are important in hyperproliferative diseases, especially in cancer and in the process of angiogenesis. For example, certain of these compounds are inhibitors of such receptor kinases as KDR, Flt-1, FGFR, PDGFR, c-Met, TIE-2 or IGF-1-R. Since certain of these compounds are anti-angiogenic, they are important substances for inhibiting the progression of disease states where angiogenesis is an important component. Certain compounds of the invention are effective as inhibitors of such serine/threonine kinases as PKCs, erk, MAP kinases, MAP kinase kinases, MAP kinase kinase kinases, cdks, Plk-1 or Raf-1. These compounds are useful in the treatment of cancer, and hyperproliferative disorders. In addition, certain compounds are effective inhibitors of non-receptor kinases such as those of the Src (for example, lck, blk and lyn), Tec, Csk, Jak, Map, Nik and Syk families. These compunds are useful in the treatment of cancer, hyperproliferative disorders and immunologic diseases.

Certain compounds of this invention are selective TIE-2 kinase inhibitors which may be anti-angiogenic (especially in combination with one or more VEGFR inhibitors), or pro-angiogenic, when employed in the presence of, or in conjunction with, a VEGF-related stimulus. In this manner such inhibitors can be used in the promotion of therapeutic angiogenesis to treat, for example, ischemia, infarct or occlusion, or to promote wound healing.

The present invention provides a method of inhibiting the kinase activity of tyrosine kinases and serine/threonine kinases comprising the administration of a compound represented by formula I to said kinase in sufficient concentration to inhibit the enzyme activity of said kinase.

The present invention further includes the use of these compounds in pharmaceutical compositions with a pharmaceutically effective amount of the above-described compounds and a pharmaceutically acceptable carrier or excipient. These pharmaceutical compositions can be administered to individuals to slow or halt the process of angiogenesis in angiogenesis-aided diseases, or to treat edema, effusions, exudates or ascites and other conditions associated with vascular hyperpermeability. Certain pharmaceutical compositions can be administered to individuals to treat cancer and hyperproliferative disorders by inhibiting serine/threonine kinases such as cdk, Plk-1, erk, etc.

DETAILED DESCRIPTION OF THE INVENTION

The values of substituents in a first preferred group of compounds of formula I are given below.

Preferably, L is —N(R)S(O)$_2$—, —S(O)$_2$N(R)—, —N(R)C(O)—, —C(O)N(R)—, —NH—, —NR— or —O—.

Preferably, R$_3$ is a substituted or unsubstituted phenyl, a substituted or unsubstituted naphthyl, a substituted or unsubstituted pyridyl, a substituted or unsubstituted thienyl, a substituted or unsubstituted benzotriazole, a substituted or unsubstituted tetrahydropyranyl, a substituted or unsubstituted tetrahydrofuranyl, a substituted or unsubstituted dioxane, a substituted or unsubstituted dioxolane, a substituted or unsubstituted quinoline, a substituted or unsubstituted thiazole, substituted or unsubstituted isoxazole, substituted or unsubstituted cyclopentyl, a substituted or unsubstituted benzofuran, substituted or unsubstituted benzothiophene, substituted or unsubstituted imidazole, substituted or unsubstituted pyrrole, substituted or unsubstituted pyimidinyl, substituted or unsubstituted indolynyl, substituted or unsubstituted benzisoxazle, substituted or unsubstituted benzisothiazole, substituted or unsubstituted benzothiazole, substituted or unsubstituted benzoxazole, substituted or unsubstituted benzimidazole, substituted or unsubstituted benzoxadiazole, substituted or unsubstituted benzothiadiazole, substituted or unsubstituted isoquinolinyl, substituted or unsubstituted quinoxalinyl, substituted or unsubstituted indole or substituted or unsubstituted pyrazole, substituted or un substituted phenoxy, substituted or unsubstituted pyridyloxy. In one embodiment, R$_3$ is a substituted or unsubstituted phenyl.

R$_3$ can be substituted by one or more substituents. Preferable substituents for R$_3$ are F, Cl, Br, I, CH$_3$, NO$_2$, OCF$_3$, OCH$_3$, CN, —CHO, CO$_2$CH$_3$, CF$_3$, t-butyl, pyridyl, pyridyloxy, substituted or unsubstituted oxazolyl, substituted or unsubstituted thiazolyl, substituted or unsubstituted benzyl, substituted or unsubstituted benzenesulfonyl, substituted or unsubstituted phenoxy, substituted or unsubstituted phenyl, substituted or unsubstituted amino, carboxyl, substituted or unsubstituted tetrazolyl, styryl, —S(O)$_x$— (substituted or unsubstituted aryl), —S(O)$_x$ where x=0, 1, 2-(substituted or unsubstituted heteroaryl), substituted or unsubstituted heteroaryl, substituted or unsubstituted heterocycloalkyl, alkynyl, —C(O)NR$_f$R$_g$, R$_c$ and CH$_2$OR$_c$.

R$_f$, R$_g$ and the nitrogen atom together form a 3-, 4-, 5-, 6- or 7-membered, substituted or unsubstituted heterocycloalkyl, substituted or unsubstituted heterobicycloalkyl or a substituted or unsubstituted heteroaromatic.

Alternatively, R$_f$ and R$_g$ are each, independently, —H, a substituted or unsubstituted aliphatic group or a substituted or unsubstituted aromatic group.

R$_c$ is hydrogen, or substituted or unsubstituted alkyl or substituted or unsubstituted aryl, —W—(CH$_2$)$_t$—NR$_d$R$_e$, —W—(CH$_2$)$_t$—O-alkyl, —W—(CH$_2$)$_t$—S-alkyl, —W—(CH$_2$)$_t$—OH, or —W—(CH$_2$)$_t$NH—C(O)R$_f$ t is an integer from 0 to about 6.

W is a bond or —O—, —S—, —S(O)—, —S(O)$_2$—, or —NR$_k$—.

R$_k$ is —H or alkyl.

R$_d$, R$_e$ and the nitrogen atom to which they are attached together form a 3, 4, 5, 6 or 7-membered substituted or unsubstituted heterocycloalkyl or substituted or unsubstituted heterobicyclic group.

Alternatively, R$_d$ and R$_e$ are each, independently, —H, alkyl, alkanoyl or —K-D.

K is —S(O)$_2$—, —C(O)—, —C(O)NH—, —C(O)$_2$—, or a direct bond.

D is a substituted or unsubstituted aryl, a substituted or unsubstituted heteroaryl, a substituted or unsubstituted aralkyl, a substituted or unsubstituted heteroaromatic group, a substituted or unsubstituted heteroaralkyl, a substituted or unsubstituted cycloalkyl, a substituted or unsubstituted heterocycloalkyl, a substituted or unsubstituted amino, a substituted or unsubstituted aminoalkyl, a substituted or unsubstituted aminocycloalkyl, COOR$_i$, or substituted or unsubstituted alkyl.

R$_i$ is a substituted or unsubstituted aliphatic group or a substituted or unsubstituted aromatic group.

More preferred substituents for R$_3$ are F, Cl, Br, I, cyano, nitro, OCF$_3$, CH$_3$, and CF$_3$.

Preferably, ring A is a substituted or unsubstituted phenyl, a substituted or unsubstituted thienyl, a substituted or unsubstituted naphthyl, a substituted or unsubstituted pyridyl, or a substituted or unsubstituted indole. In one embodiment, ring A is a substituted or unsubstituted phenyl.

Ring A can be substituted by one or more substituents. Preferable substituents for ring A are F, Cl, Br, I, CH$_3$, NO$_2$, OCF$_3$, OCH$_3$, CN, CO$_2$CH$_3$, CF$_3$, t-butyl, pyridyl, substituted or unsubstituted oxazolyl, substituted or unsubstituted benzyl, substituted or unsubstituted benzenesulfonyl, substituted or unsubstituted phenoxy, substituted or unsubstituted phenyl, substituted or unsubstituted amino, carboxyl, substituted or unsubstituted tetrazolyl, styryl, —S-(substituted or unsubstituted aryl), —S-(substituted or unsubstituted heteroaryl), substituted or unsubstituted heteroaryl, substituted or unsubstituted heterocycloalkyl, alkynyl, —C(O)NR$_f$R$_g$, R$_c$ and CH$_2$OR$_c$. R$_f$, R$_g$ and R$_c$ are defined as above.

Ring A is more preferably substituted with F, Cl, and nitro.

R$_2$ is preferably a hydrogen.

Preferably, R$_1$ is a cyclopentyl group or an isopropyl.

As used herein, aromatic groups include carbocyclic ring systems (e.g. benzyl and cinnamyl) and fused polycyclic aromatic ring systems (e.g. naphthyl and 1,2,3,4-tetrahydronaphthyl). An aryl group, as used herein, refer to an aromatic group.

Heteroaromatic groups, as used herein, include heteroaryl ring systems (e.g., thienyl, pyridyl, pyrazole, isoxazolyl, thiadiazolyl, oxadiazolyl, indazolyl, furans, pyrroles, imidazoles, pyrazoles, triazoles, pyrimidines, pyrazines, thiazoles, isoxazoles, isothiazoles, tetrazoles, or oxadiazoles) and heteroaryl ring systems in which a carbocyclic aromatic ring, carbocyclic non-aromatic ring or heteroaryl ring is fused to one or more other heteroaryl rings (e.g., benzo(b)thienyl, benzimidazole, benzoxazolyl, benzothiazolyl, benzothiadiozolyl, benzoxadiazolyl, indole, tetrahydroindole, azaindole, indazole, quinoline, imidazopyridine, purine, pyrrolo[2,3-d]pyrimidine, pyrazolo[3,4-d]pyrimidine) and their N-oxides.

An aralkyl group, as used herein, is an aromatic substituent that is linked to a compound by an aliphatic group having from one to about six carbon atoms.

An heteroaralkyl group, as used herein, is a heteroaromatic substituent that is linked to a compound by an aliphatic group having from one to about six carbon atoms.

A heterocycloalkyl group, as used herein, is a non-aromatic ring system that has 3 to 8 atoms and includes at least one heteroatom, such as nitrogen, oxygen, or sulfur.

An acyl group, as used herein, is an —C(O)NR$_x$Rz, —C(O)ORx, —C(O)Rx, in which R$_x$ and R$_z$ are each, independently, —H, a substituted or unsubstituted aliphatic group or a substituted or unsubstituted aromatic group.

As used herein, aliphatic groups include straight chained, branched or cyclic C$_1$-C$_8$ hydrocarbons which are completely saturated or which contain one or more units of unsaturation. A "lower alkyl group" is a saturated aliphatic group having form 1-6 carbon atoms.

Compounds of formula I may exist as salts with pharmaceutically acceptable acids. The present invention includes such salts. Examples of such salts include hydrochlorides, hydrobromides, sulfates, methanesulfonates, nitrates, maleates, acetates, citrates, fumarates, tartrates [eg (+)-tartrates, (–)-tartrates or mixtures thereof including racemic mixtures], succinates, benzoates and salts with amino acids such as glutamic acid. These salts may be prepared by methods known to those skilled in the art.

Certain compounds of formula I which have acidic substituents may exist as salts with pharmaceutically acceptable bases. The present invention includes such salts. Example of such salts include sodium salts, potassium salts, lysine salts and arginine salts. These salts may be prepared by methods known to those skilled in the art.

Certain compounds of formula I and their salts may exist in more than one crystal form and the present invention includes each crystal form and mixtures thereof.

Certain compounds of formula I and their salts may also exist in the form of solvates, for example hydrates, and the present invention includes each solvate and mixtures thereof.

Certain compounds of formula I may contain one or more chiral centres, and exist in different optically active forms. When compounds of formula I contain one chiral centre, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of formula I contains more than one chiral centre it may exist in diastereoisomeric forms. The diastereoisomeric pairs may be separated by methods known to those skilled in the art, for example chromatography or crystallization and the individual enantiomers within each pair may be separated as described above. The present invention includes each diastereoisomer of compounds of formula I and mixtures thereof.

Certain compounds of formula I may exist in different tautomeric forms or as different geometric isomers, and the present invention includes each tautomer and/or geometric isomer of compounds of formula I and mixtures thereof.

Certain compounds of formula I may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of formula I and mixtures thereof.

Certain compounds of formula I may exist in zwitterionic form and the present invention includes each zwitterionic form of compounds of formula I and mixtures thereof.

Preferred compounds of formula I include the following: N1-(4-(4-amino-7-cyclopentyl-7H-pyrrolo[2,3-d]pyrimidin-5-yl)-2-fluorophenyl)-2-(trifluoromethoxy)-1-benzenesulfonamide, N1-(4-(4-amino-7-cyclopentyl-7H-pyrrolo[2,3-d]pyrimidin-5-yl)-2-chlorophenyl)-2-chloro-1-benzenesulfonamide, N1-(4-(4-amino-7-cyclopentyl-7H-pyrrolo[2,3-d]pyrimidin-5-yl)-2-chlorophenyl)-2-fluoro-1-benzenesulfonamide, N1-(4-(4-amino-7-cyclopentyl-7H-pyrrolo[2,3-d]pyrimidin-5-yl)-2-fluorophenyl)-2-chloro-1-benzenesulfonamide, N1-(4-(4-amino-7-cyclopentyl-7H-pyrrolo[2,3-d]pyrimidin-5-yl)-2-chlorophenyl)-3-fluoro-1-benzenesulfonamide, N1-(4-(4-amino-7-cyclopentyl-7H-pyrrolo[2,3-d]pyrimidin-5-yl)-2-chlorophenyl)-1-benzenesulfonamide, N1-(4-(4-amino-7-cyclopentyl-7H-pyrrolo[2,3-d]pyrimidin-5-yl)-2-nitrophenyl)-1-benzenesulfonamide, N1-(4-(4-amino-7-cyclopentyl-7H-pyrrolo[2,3-d]pyrimidin-5-yl)-2-chlorophenyl)-3-(trifluoromethyl)-1-benzenesulfonamide, N1-(4-(4-amino-7-cyclopentyl-7H-pyrrolo[2,3-d]pyrimidin-5-yl)-2-chlorophenyl)-4-chloro-1-benzenesulfonamide, N1-(4-(4-amino-7-cyclopentyl-7H-pyrrolo[2,3-d]pyrimidin-5-yl)-2-chlorophenyl)-2-cyano-1-benzenesulfonamide, N1-(4-(4-amino-7-cyclopentyl-7H-pyrrolo[2,3-d]pyrimidin-5-yl)-2-fluorophenyl)-2-nitro-1-benzenesulfonamide, N1-(4-(4-amino-7-cyclopentyl-7H-pyrrolo[2,3-d]pyrimidin-5-yl)-2-fluorophenyl)-2,6-difluoro-1-benzenesulfonamide, N1-(4-(4-amino-7-cyclopentyl-7H-pyrrolo[2,3-d]pyrimidin-5-yl)-2-methoxyphenyl)-1-benzenesulfonamide, N1-(4-(4-amino-7-cyclopentyl-7H-pyrrolo[2,3-d]pyrimidin-5-yl)-2-fluorophenyl)-2,3,4-trifluoro-1-benzenesulfonamide, N1-(4-(4-amino-7-cyclopentyl-7H-pyrrolo[2,3-d]pyrimidin-5-yl)-2-fluorophenyl)-4-bromo-2-fluoro-1-benzenesulfonamide, N1-(4-(4-amino-7-cyclopentyl-7H-pyrrolo[2,3-d]pyrimidin-5-yl)-2-fluorophenyl)-2,5-difluoro-1-benzenesulfonamide, N1-(4-(4-amino-7-cyclopentyl-7H-pyrrolo[2,3-d]pyrimidin-5-yl)-2-fluorophenyl)-3,4-difluoro-1-benzenesulfonamide, N1-(4-(4-amino-7-cyclopentyl-7H-pyrrolo[2,3-d]pyrimidin-5-yl)-2-fluorophenyl)-2-bromo-1-benzenesulfonamide, N1-(4-(4-amino-7-cyclopentyl-7H-pyrrolo[2,3-d]pyrimidin-5-yl)-2-fluorophenyl)-2,6-dichloro-1-benzenesulfonamide, N1-(4-(4-amino-7-cyclopentyl-7H-pyrrolo[2,3-d]pyrimidin-5-yl)-2-fluorophenyl)-2,4,6-trichloro-1-benzenesulfonamide, N1-(4-(4-amino-7-cyclopentyl-7H-pyrrolo[2,3-d]pyrimidin-5-yl)-2-fluorophenyl)-2,4-dichloro-1-benzenesulfonamide, N1-(4-(4-amino-7-cyclopentyl-7H-pyrrolo[2,3-d]pyrimidin-5-yl)-2-fluorophenyl)-2-chloro-4-fluoro-1-benzenesulfonamide, N1-(4-(4-amino-7-cyclopentyl-7H-pyrrolo[2,3-d]pyrimidin-5-yl)-2-fluorophenyl)-2,4-difluoro-1-benzenesulfonamide, N1-(4-(4-amino-7-cyclopentyl-7H-pyrrolo[2,3-d]pyrimidin-5-yl)-2-fluorophenyl)-2-iodo-1-benzenesulfonamide, N1-(4-(4-amino-7-cyclopentyl-7H-pyrrolo[2,3-d]pyrimidin-5-yl)-2-fluorophenyl)-2,3-dichloro-1-benzenesulfonamide, N1-(4-(4-amino-7-cyclopentyl-7H-pyrrolo[2,3-d]pyrimidin-5-yl)-2-fluorophenyl)-4-bromo-2,5-difluoro-1-benzenesulfonamide, N1-(4-(4-amino-7-cyclopentyl-7H-pyrrolo[2,3-d]pyrimidin-5-yl)-2-fluorophenyl)-2-chloro-4-cyano-1-benzenesulfonamide, N1-(4-(4-amino-7-cyclopentyl-7H-pyrrolo[2,3-d]pyrimidin-5-yl)-2-fluorophenyl)-2-chloro-6-methyl-1-benzenesulfonamide, N1-(4-(4-amino-7-cyclopentyl-7H-pyrrolo[2,3-d]pyrimidin-5-yl)-2-fluorophenyl)-3-chloro-2-methyl-1-benzenesulfonamide, N2-(4-(4-amino-7-cyclopentyl-7H-pyrrolo[2,3-d]pyrimidin-5-yl)-2-fluorophenyl)-4,5-dibromo-2-thiophenesulfonamide, N2-(4-(4-amino-7-cyclopentyl-7H-pyrrolo[2,3-d]pyrimidin-5-yl)-2-fluorophenyl)-5-bromo-2-thiophenesulfonamide, N2-(4-(4-amino-7-cyclopentyl-7H-pyrrolo[2,3-d]pyrimidin-5-yl)-2-fluorophenyl)-3-bromo-5-chloro-2-thiophenesulfonamide, N3-(4-(4-amino-7-cyclopentyl-7H-pyrrolo[2,3-d]pyrimidin-5-yl)-2-fluorophenyl)-2,5-dichloro-3-thiophenesulfonamide, N4-(4-(4-amino-7-cyclopentyl-7H-pyrrolo[2,3-d]pyrimidin-5-yl)-2-fluorophenyl)-2,1,3-benzothiadiazole-4-sulfonamide, N4-(4-(4-amino-7-cyclopentyl-7H-pyrrolo[2,3-d]pyrimidin-5-yl)-2-fluorophenyl)-2,1,3-benzoxadiazole-4-sulfonamide, N4-(4-(4-amino-7-cyclopentyl-7H-pyrrolo[2,3-d]pyrimidin-5-yl)-2-fluorophenyl)-7-chloro-2,1,3-benzoxadiazole-4-sulfonamide, N4-(4-(4-amino-7-cyclopentyl-7H-pyrrolo[2,3-d]pyrimidin-5-yl)-2-fluorophenyl)-7-methyl-2,1,3-benzothiadiazole-4-sulfonamide, N4-(4-(4-amino-7-cyclopentyl-7H-pyrrolo[2,3-d]pyrimidin-5-yl)-2-fluorophenyl)-5-methyl-2,1,3-benzothiadiazole-4-sulfonamide, N4-(4-(4-amino-7-cyclopentyl-7H-pyrrolo[2,3-d]pyrimidin-5-yl)-2-fluorophenyl)-5-chloro-2,1,3-benzothiadiazole-4-sulfonamide, N-(4-(4-amino-7-cyclopentyl-7H-pyrrolo[2,3-d]pyrimidin-5-yl)-2-fluorophenyl)-(2-nitrophenyl)methanesulfonamide, and N1-(4-(4-amino-7-cyclopentyl-7H-pyrrolo[2,3-d]pyrimidin-5-yl)-2-fluorophenyl)-2,5-dibromo-3,6-difluoro-1-benzenesulfonamide.

The compounds of this invention have antiangiogenic properties. These antiangiogenic properties are due at least in part to the inhibition of protein tyrosine kinases essential for angiogenic processes. For this reason, these compounds can be used as active agents against such disease states as arthritis, atherosclerosis, restenosis, psoriasis, hemangiomas, myocardial angiogenesis, coronary and cerebral collaterals, ischemic limb angiogenesis, ischemia/reperfusion injury, wound healing, peptic ulcer Helicobacter related diseases, virally-induced angiogenic disorders, fractures, Crow-Fukase syndrome (POEMS), preeclampsia, menometrorrhagia, cat scratch fever, rubeosis, neovascular glaucoma and retinopathies such as those associated with diabetic retinopathy, retinopathy of prematurity, or age-related macular degeneration. In addition, some of these compounds can be used as active agents against solid tumors, malignant ascites, von Hippel Lindau disease, hematopoietic cancers and hyperproliferative disorders such as thyroid hyperplasia (especially Grave's disease), and cysts (such as hypervascularity of ovarian stroma characteristic of polycystic ovarian syndrome (Stein-Leventhal syndrome) and polycystic kidney disease.

Further, some of these compounds can be used as active agents against burns, chronic lung disease, stroke, polyps, anaphylaxis, chronic and allergic inflammation, delayed-type hypersensitivity, ovarian hyperstimulation syndrome, brain tumor-associated cerebral edema, high-altitude, trauma or hypoxia induced cerebral or pulmonary edema, ocular and macular edema, ascites, glomerulonephritis and other diseases where vascular hyperpermeability, effusions, exudates, protein extravasation, or edema is a manifestation of the disease. The compounds will also be useful in treating disorders in which protein extravasation leads to the deposition of fibrin and extracellular matrix, promoting stromal proliferation (e.g. keloid, fibrosis, cirrhosis and carpal tunnel syndrome). Increased VEGF production potentiates inflammatory processes such as monocyte recruitment and activation. The compounds of this invention will also be useful in treating inflammatory disorders such as inflammatory bowel disease (IBD) and Crohn's disease.

VEGF's are unique in that they are the only angiogenic growth factors known to contribute to vascular hyperpermeability and the formation of edema. Indeed, vascular hyperpermeability and edema that is associated with the expression or administration of many other growth factors appears to be mediated via VEGF production. Inflammatory cytokines stimulate VEGF production. Hypoxia results in a marked upregulation of VEGF in numerous tissues, hence situations involving infarct, occlusion, ischemia, anemia, or circulatory impairment typically invoke VEGF/VPF mediated responses. Vascular hyperpermeability, associated edema, altered transendothelial exchange and macromolecular extravasation, which is often accompanied by diapedesis, can result in excessive matrix deposition, aberrant stromal proliferation, fibrosis, etc. Hence, VEGF-mediated hyperpermeability can significantly contribute to disorders with these etiologic features.

Because blastocyst implantation, placental development and embryogenesis are angiogenesis dependent, certain compounds of the invention are useful as contraceptive agents and antifertility agents.

It is envisaged that the disorders listed above are mediated to a significant extent by protein tyrosine kinase activity involving the KDR/VEGFR-2 and/or the Flt-1/VEGFR-1 and/or TIE-2 tyrosine kinases. By inhibiting the activity of these tyrosine kinases, the progression of the listed disorders is inhibited because the angiogenic or vascular hyperpermeability component of the disease state is severely curtailed. The action of certain compounds of this invention, by their selectivity for specific tyrosine kinases, result in a minimization of side effects that would occur if less selective tyrosine kinase inhibitors were used. Certain compounds of the invention are also effective inhibitors of FGFR, PDGFR, c-Met and IGF-1-R. These receptor kinases can directly or indirectly potentiate angiogenic and hyperproliferative responses in various disorders, hence their inhibition can impede disease progression.

The compounds of this invention have inhibitory activity against protein kinases. That is, these compounds modulate signal transduction by protein kinases. Compounds of this invention inhibit protein kinases from serine/threonine and tyrosine kinase classes. In particular, these compounds selectively inhibit the activity of the KDR/FLK-1/VEGFR-2 tyrosine kinases. Certain compounds of this invention also inhibit the activity of additional tyrosine kinases such as Flt-1/VEGFR-1, Tie-2, FGFR, PDGFR, IGF-1R, c-Met, Src-subfamily kinases such as Lck, Src, fyn, yes, etc. Additionally, some compounds of this invention significantly inhibit serine/threonine kinases such as PKC, MAP kinases, erk, CDKs, Plk-1, or Raf-1 which play an essential role in cell proliferation and cell-cycle progression. The potency and specificity of the generic compounds of this invention towards a particular protein kinase can often be altered and optimized by variations in the nature, number and arrangement of the substituents (i.e., $R_1$, $R_2$, $R_3$, A and ring 1) and conformational restrictions. In addition the metabolites of certain compounds may also possess significant protein kinase inhibitory activity.

The compounds of this invention, when administered to individuals in need of such compounds, inhibit vascular hyperpermeability and the formation of edema in these individuals. These compounds act, it is believed, by inhibiting the activity of KDR tyrosine kinase which is involved in the process of vascular hyperpermeability and edema formation. The KDR tyrosine kinase may also be referred to as FLK-1 tyrosine kinase, NYK tyrosine kinase or VEGFR-2 tyrosine kinase. KDR tyrosine kinase is activated when vascular endothelial cell growth factor (VEGF) or another activating ligand (such as VEGF-C, VEGF-D, VEGF-E or HIV Tat protein) binds to a KDR tyrosine kinase receptor which lies on the surface of vascular endothelial cells. Following such KDR tyrosine kinase activation, hyperpermeability of the blood vessels occurs and fluid moves from the blood stream past the blood vessel walls into the interstitial spaces, thereby forming an area of edema. Diapedesis also often accompanies this response. Similarly, excessive vascular hyperperneability can disrupt normal molecular exchange across the endothelium in critical tissues and organs (e.g., lung and kidney), thereby causing macromolecular extravasation and deposition. Following this acute response to KDR stimulation which is believed to facilitate the subsequent angiogenic process, prolonged KDR tyrosine kinase stimulation results in the proliferation and chemotaxis of vascular endothelial cells and formation of new vessels. By inhibiting KDR tyrosine kinase activity, either by blocking the production of the activating ligand, by blocking the activating ligand binding to the KDR tyrosine kinase receptor, by preventing receptor dimerization and transphosphorylation, by inhibiting the enzyme activity of the KDR tyrosine kinase (inhibiting the phosphorylation function of the enzyme) or by some other mechanism that interrupts its downstream signaling (D. Mukhopedhyay et al., Cancer Res. 58:1278-1284 (1998) and references therein), hyperpermeability, as well as associated extravasation, subsequent edema formation and matrix deposition, and angiogenic responses, may be inhibited and minimized.

One group of preferred compounds of this invention have the property of inhibiting KDR tyrosine kinase activity without significantly inhibiting Flt-1 tyrosine kinase activity (Flt-1 tyrosine kinase is also referred to as VEGFR-1 tyrosine kinase). Both KDR tyrosine kinase and Flt-1 tyrosine kinase are activated by VEGF binding to KDR tyrosine kinase receptors and to Flt-1 tyrosine kinase receptors, respectively. Certain preferred compounds of this invention are unique because they inhibit the activity of one VEGF-receptor tyrosine kinase (KDR) that is activated by activating ligands but do not inhibit other receptor tyrosine kinases, such as Flt-1, that are also activated by certain activating ligands. In this manner, certain preferred compounds of this invention are, therefore, selective in their tyrosine kinase inhibitory activity.

In one embodiment, the present invention provides a method of treating a protein kinase-mediated condition in a patient, comprising adiminstering to the patient a therapeutically or prophylactically effective amount of one or more compounds of Formula I.

A "protein kinase-mediated condition" is a medical condition, such as a disease or other undesirable physical condition, the genesis or progression of which depends, at least in part, on the activity of at least one protein kinase. The protein kinase can be, for example, a protein tyrosine kinase or a protein serine/threonine kinase.

The patient to be treated can be any animal, and is preferably a mammal, such as a domesticated animal or a livestock animal. More preferably, the patient is a human.

A therapeutically effective amount" is an amount of a compound of Formula I or a combination of two or more such compounds, which inhibits, totally or partially, the progression of the condition or alleviates, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount can be determined by methods known to those of skill in the art.

The method of the present invention is useful in the treatment of protein kinase-mediated conditions, such as any of the conditions described above. In one embodiment, the protein kinase-mediated condition is characterized by undesired angiogenesis, edema, or stromal deposition. For example, the condition can be one or more ulcers, such as ulcers caused by bacterial or fungal infections, Mooren ulcers and ulcerative colitis. The condition can also be due to a microbial infection, such as Lyme disease, sepsis, septic shock or infections by Herpes simplex, Herpes Zoster, human immunodeficiency virus, protozoa, toxoplasmosis or parapoxyirus; an angiogenic disorders, such as von Hippel Lindau disease, polycystic kidney disease, pemphigoid, Paget's disease and psoriasis; a reproductive condition, such as endometriosis, ovarian hyperstimulation syndrome, preeclampsia or menometrorrhagia; a fibrotic and edemic condition, such as sarcoidosis, fibrosis, cirrhosis, thyroiditis, hyperviscosity syndrome systemic, Osler-Weber-Rendu disease, chronic occlusive pulmonary disease, asthma, and edema following burns, trauma, radiation, stroke, hypoxia or ischemia; or an inflammatory/immunologic condition, such as systemic lupus, chronic inflammation, glomerulonephritis, synovitis, inflammatory bowel disease, Crohn's disease, rheumatoid arthritis, osteoarthritis, multiple sclerosis and graft rejection. Suitable protein kinase-mediated conditions also include sickle cell anaemia, osteoporosis, osteopetrosis, tumor-induced hypercalcemia and bone metastases. Additional protein kinase-mediated conditions which can be treated by the method of the present invention include ocular conditions such as ocular and macular edema, ocular neovascular disease, scleritis, radial keratotomy, uveitis, vitritis, myopia, optic pits, chronic retinal detachment, post-laser complications, conjunctivitis, Stargardt's disease and Eales disease, in addition to retinopathy and macular degeneration.

The compounds of the present invention are also useful in the treatment of cardiovascular conditions such as atherosclerosis, restenosis, vascular occlusion and carotid obstructive disease.

The compounds of the present invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukaemia and lymphoma, tumor-induced pleural or pericardial effusions, and malignant ascites.

The compounds of the present invention are also useful in the treatment of Crow-Fukase (POEMS) syndrome and diabetic conditions such as glaucoma, diabetic retinopathy and microangiopathy.

The Src, Tec, Jak, Map, Csk, NFκB and Syk families of kinases play pivotal roles in the regulation of immune function. The Src family currently includes Fyn, Lck, Fgr, Fes, Lyn, Src, Yrk, Fyk, Yes, Hck, and Blk. The Syk family is currently understood to include only Zap and Syk. The TEC family includes Tec, Btk, Rlk and Itk. The Janus family of kinases is involved in the transduction of growth factor and proinflammatory cytokine signals through a number of receptors. Although BTK and ITK, members of the Tec family of kinases, play a less well understood role in immunobiology, their modulation by an inhibitor may prove therapeutically beneficial. The Csk family is currently understood to include Csk and Chk. The kinases RIP, IRAK-1, IRAK-2, NIK, p38 MAP kinases, Jnk, IKK-1 and IKK-2 are involved in the signal transduction pathways for key pro-inflammatory cytokines, such as TNF and IL-1. By virtue of their ability to inhibit one or more of these kinases, compounds of formula I may function as immunomodulatory agents useful for the maintenance of allografts, the treatment of autoimmune disorders and treatment of sepsis and septic shock. Through their ability to regulate the migration or activation of T cells, B-cells, mast cells, monocytes and neutrophils, these compounds could be used to treat such autoimmune diseases and sepsis. Prevention of transplant rejection, either host versus graft for solid organs or graft versus host for bone marrow, are limited by the toxicity of currently available immunosuppressive agents and would benefit from an efficacious drug with improved therapeutic index. Gene targeting experiments have demonstrated the essential role of Src in the biology of osteoclasts, the cells responsible for bone resorption. Compounds of formula I, through their ability to regulate Src, may also be useful in the treatment of osteoporosis, osteopetrosis, Paget's disease, tumor-induced hypercalcemia and in the treatment of bone metastases.

A number of protein kinases have been demonstrated to be protooncogenes. Chromosome breakage (at the 1tk kinase break point on chromosome 5), translocation as in the case of the Ab1 gene with BCR (Philadelphia chromosome), truncation in instances such as c-Kit or EGFR, or mutation (e.g., Met) result in the creation of dysregulated proteins converting them from protooncogene to oncogene products. In other tumors, oncogenesis is driven by an autocrine or paracrine ligand/growth factor receptor interactions. Members of the src-family kinases are typically involved in downstream signal transduction thereby potentiating the oncogenesis and themselves may become oncogenic by over-expression or mutation. By inhibiting the protein kinase activity of these proteins the disease process may be disrupted. Vascular restenosis may involve FGF and/or PDGF—promoted smooth muscle and endothelial cell proliferation. The ligand stimulation of FGFR, PDGFR, IGF1-R and c-Met in vivo is proangiogenic, and potentiates angiogenesis dependent disorders. Inhibition of FGFr, PDGFr, c-Met, or IGF1-R kinase activities individually or in combination may be an efficacious strategy for inhibiting these phenomena. Thus compounds of formula I which inhibit the kinase activity of normal or aberrant c-kit, c-met, c-fms, src-family members, EGFr, erbB2, erbB4, BCR-Ab1, PDGFr, FGFr, IGF1-R and other receptor or cytosolic tyrosine kinases may be of value in the treatment of benign and neoplastic proliferative diseases.

In many pathological conditions (for example, solid primary tumors and metastases, Kaposi's sarcoma, rheumatoid arthritis, blindness due to inappropriate ocular neovascularization, psoriasis and atherosclerosis) disease progression is contingent upon persistent angiogenesis. Polypeptide growth factors often produced by the disease tissue or associated inflammatory cells, and their corresponding endothelial cell specific receptor tyrosine kinases (e.g., KDR/VEGFR-2, Flt-1/VEGFR-1, Tie-2/Tek and Tie) are essential for the stimulation of endothelial cell growth, migration, organization, differentiation and the establishment of the requisite new functional vasculature. As a result of the vascular permeability factor activity of VEGF in mediating vascular hyperpermeability, VEGF-stimulation of a VEGFR kinase is also believed to play an important role in the formation of tumor ascites, cerebral and pulmonary edema, pleural and pericardial effusions, delayed-type hypersensitivity reactions, tissue edema and organ dysfunction following trauma, burns, ischemia, diabetic complications, endometriosis, adult respiratory distress syndrome (ARDS), post-cardiopulmonary bypass-related hypotension and hyperpermeability, and ocular edema leading to glaucoma or blindness due to inappropriate neovascularization. In addition to VEGF, recently identified VEGF-C and VEGF-D, and virally-encoded VEGF-E or HIV-Tat protein can also cause a vascular hyperpermeability response through the stimulation of a VEGFR kinase. KDR/VEGFR-2 and/or Tie-2 are expressed also in a select population of hematopoietic stem cells. Certain members of this population are pluripotent in nature and can be stimulated with growth factors to differentiate into endothelial cells and participate in vasculogenetic angiogenic processes. For this reason these have been called Endothelial Progenitor Cells (EPCs) (*J. Clin. Investig.* 103: 1231-1236 (1999)). In some progenitors, Tie-2 may play a role in their recruitment, adhesion, regulation and differentiation (*Blood,* 4317-4326 (1997)). Certain agents according to formula I capable of blocking the kinase activity of endothelial cell specific kinases could therefore inhibit disease progression involving these situations.

Vascular destabilization of the antagonist ligand of Tie-2 (Ang2) is believed to induce an unstable "plastic" state in the endothelium. In the presence of high VEGF levels a robust angiogenic response may result; however, in the absence of VEGF or a VEGF-related stimulus, frank vessel regression and endothelial apoptosis can occur (Genes and Devel. 13: 1055-1066 (1999)). In an analogous manner a Tie-2 kinase inhibitor can be proangiogenic or antiangiogenic in the presence or absence of a VEGF-related stimulus, respectively. Hence Tie-2 inhibitors can be employed with appropriate proangiogenic stimuli, such as VEGF, to promote therapeutic angiogenesis in situations such as wound healing, infarct and ischemia.

The compounds of formula I or a salt thereof or pharmaceutical compositions containing a therapeutically effective amount thereof may be used in the treatment of protein kinase-mediated conditions, such as benign and neoplastic proliferative diseases and disorders of the immune system, as described above. For example, such diseases include autoimmune diseases, such as rheumatoid arthritis, thyroiditis, type 1 diabetes, multiple sclerosis, sarcoidosis, inflammatory bowel disease, Crohn's disease, myasthenia gravis and systemic lupus erythematosus; psoriasis, organ transplant rejection (eg. kidney rejection, graft versus host disease), benign and neoplastic proliferative diseases, human cancers such as lung, breast, stomach, bladder, colon, pancreas, ovarian, prostate and rectal cancer and hematopoietic malignancies (leukemia and lymphoma), and diseases involving inappropriate vascularization for example diabetic retinopathy, retinopathy of prematurity, choroidal neovascularization due to age-related macular degeneration, and infantile hemangiomas in human beings. In addition, such inhibitors may be useful in the treatment of disorders involving VEGF mediated edema, ascites, effusions, and exudates, including for example macular edema, cerebral edema, acute lung injury and adult respiratory distress syndrome (ARDS).

The compounds of the present invention may also be useful in the prophylaxis of the above diseases.

It is envisaged that the disorders listed above are mediated to a significant extent by protein tyrosine kinase activity involving the VEGF receptors (e.g. KDR, Flt-1 and/or Tie-2). By inhibiting the activity of these receptor tyrosine kinases, the progression of the listed disorders is inhibited because the angiogenic component of the disease state is severely curtailed. The action of the compounds of this invention, by their selectivity for specific tyrosine kinases, result in a minimization of side effects that would occur if less selective tyrosine kinase inhibitors were used.

In another aspect the present invention provides compounds of formula I as defined initially above for use as medicaments, particularly as inhibitors of protein kinase activity for example tyrosine kinase activity, serine kinase activity and threonine kinase activity. In yet another aspect the present invention provides the use of compounds of formula I as defined initially above in the manufacture of a medicament for use in the inhibition of protein kinase activity.

In this invention, the following definitions are applicable:

"Physiologically acceptable salts" refers to those salts which retain the biological effectiveness and properties of the free bases and which are obtained by reaction with inorganic acids such as hydrochloric acid, hydrobromic acid, sulfuric acid, nitric acid, phosphoric acid or organic acids such as aryl-sulfonic acid, carboxylic acid, organic phosphoric acid, methanesulfonic acid, ethanesulfonic acid, p-toluenesulfonic acid, salicylic acid, lactic acid, tartaric acid maleic acid, and the like.

"Alkyl" refers to a saturated aliphatic hydrocarbon, including straight-chain and branched-chain groups having 1 to 6 carbons or cyclic hydrocarbons having 3 to 6 carbons.

"Alkoxy" refers to an "O-alkyl" group, where "alkyl" is defined as described above.

Pharmaceutical Formulations

The compounds of this invention can be administered to a human patient by themselves or in pharmaceutical compositions where they are mixed with suitable carriers or excipient(s) at doses to treat or ameliorate vascular hyperpermeability, edema and associated disorders. Mixtures of these compounds can also be administered to the patient as a simple mixture or in suitable formulated pharmaceutical compositions. A therapeutically effective dose further refers to that amount of the compound or compounds sufficient to result in the prevention or attenuation of inappropriate neovascularization, progression of hyperproliferative disorders, edema, VEGF-associated hyperpermeability and/or VEGF-related hypotension. Techniques for formulation and administration of the compounds of the instant application may be found in "Remington's Pharmaceutical Sciences," Mack Publishing Co., Easton, Pa., latest edition.

Routes of Administration

Suitable routes of administration may, for example, include oral, eyedrop, rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer the compound in a local rather than a systemic manner, for example, via injection of the compound directly into an edematous site, often in a depot or sustained release formulation.

Furthermore, one may administer the drug in a targeted drug delivery system, for example, in a liposome coated with endothelial cell-specific antibody.

Composition/Formulation

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds can be formulated for parenteral administration by injection, e.g. bolus injection or continuous infusion. Formulations for injection may be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly or by intramuscular injection). Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

An example of a pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethysulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Effective Dosage

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art.

For any compound used in the method of the invention, the therapeutically effective dose can be estimated initially from cellular assays. For example, a dose can be formulated in cellular and animal models to achieve a circulating concentration range that includes the $IC_{50}$ as determined in cellular assays (i.e., the concentration of the test compound which achieves a half-maximal inhibition of a given protein kinase activity). In some cases it is appropriate to determine the $IC_{50}$ in the presence of 3 to 5% serum albumin since such a determination approximates the binding effects of plasma protein on the compound. Such information can be used to more accurately determine useful doses in humans. Further, the most preferred compounds for systemic administration effectively inhibit protein kinase signaling in intact cells at levels that are safely achievable in plasma.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. Compounds which exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1 p1). In the treatment of crises, the administration of an acute bolus or an infusion approaching the MTD may be required to obtain a rapid response.

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g. the concentration necessary to achieve 50-90% inhibition of protein kinase using the assays described herein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen which maintains plasma levels above the MEC for 10-90% of the time, preferably between 30-90% and most preferably between 50-90% until the desired amelioration of symptoms is achieved. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

Packaging

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

In some formulations it may be beneficial to use the compounds of the present invention in the form of particles of very small size, for example as obtained by fluid energy milling.

The use of compounds of the present invention in the manufacture of pharmaceutical compositions is illustrated by the following description. In this description the term "active compound" denotes any compound of the invention but particularly any compound which is the final product of one of the preceding Examples.

a) Capsules

In the preparation of capsules, 10 parts by weight of active compound and 240 parts by weight of lactose can be de-aggregated and blended. The mixture can be filled into hard gelatin capsules, each capsule containing a unit dose or part of a unit dose of active compound.

b) Tablets

Tablets can be prepared from the following ingredients.

| Parts by weight | |
|---|---|
| Active compound | 10 |
| Lactose | 190 |
| Maize starch | 22 |
| Polyvinylpyrrolidone | 10 |
| Magnesium stearate | 3 |

The active compound, the lactose and some of the starch can be de-aggregated, blended and the resulting mixture can be granulated with a solution of the polyvinyl-pyrrolidone in ethanol. The dry granulate can be blended with the magnesium stearate and the rest of the starch. The mixture is then compressed in a tabletting machine to give tablets each containing a unit dose or a part of a unit dose of active compound.

c) Enteric Coated Tablets

Tablets can be prepared by the method described in (b) above. The tablets can be enteric coated in a conventional manner using a solution of 20% cellulose acetate phthalate and 3% diethyl phthalate in ethanol:dichloromethane (1:1).

d) Suppositories

In the preparation of suppositories, 100 parts by weight of active compound can be incorporated in 1300 parts by weight of triglyceride suppository base and the mixture formed into suppositories each containing a therapeutically effective amount of active ingredient.

In the compositions of the present invention the active compound may, if desired, be associated with other compatible pharmacologically active ingredients. For example, the compounds of this invention can be administered in combination with one or more additional pharmaceutical agents that inhibit or prevent the production of VEGF or angiopoietins, attenuate intracellular responses to VEGF or angiopoietins, block intracellular signal transduction, inhibit vascular hyperpermeability, reduce inflammation, or inhibit or prevent the formation of edema or neovascularization. The compounds of the invention can be administered prior to, subsequent to or simultaneously with the additional pharmaceutical agent, whichever course of administration is appropriate. The additional pharmaceutical agents include but are not limited to anti-inflammatory or anti-edemic steroids, NSAIDS, ras inhibitors, anti-TNF agents, anti-IL1 agents, antihistamines, PAF-antagonists, COX-1 inhibitors, COX-2 inhibitors, NO synthase inhibitors, Akt/PTB inhibitors, IGF-1R inhibitors, PKC inhibitors and PI3 kinase inhibitors. The compounds of the invention and the additional pharmaceutical agents act either additively or synergistically. Thus, the administration of such a combination of substances that inhibit angiogenesis, vascular hyperpermeability and/or inhibit the formation of edema can provide greater relief from the deleterious effects of a hyperproliferative disorder, angiogenesis, vascular hyperpermeability or edema than the administration of either substance alone. In the treatment of malignant disorders combinations with antiproliferative or cytotoxic chemotherapies, hyperthermia, hyperoxia or radiation are anticipated.

The present invention also comprises the use of a compound of formula I as a medicament.

A further aspect of the present invention provides the use of a compound of formula I or a salt thereof in the manufacture of a medicament for treating vascular hyperpermeability, angiogenesis-dependent disorders, proliferative diseases and/or disorders of the immune system in mammals, particularly human beings.

The present invention also provides a method of treating vascular hyperpermeability, inappropriate neovascularization, proliferative diseases and/or disorders of the immune system which comprises the administration of a therapeutically effective amount of a compound of formula I to a mammal, particularly a human being, in need thereof.

The in vitro potency of compounds in inhibiting these protein kinases may be determined by the procedures detailed below.

The potency of compounds can be determined by the amount of inhibition of the phosphorylation of an exogenous substrate (e.g., synthetic peptide (Z. Songyang et al., *Nature*. 373:536-539) by a test compound relative to control.

KDR Tyrosine Kinase Production Using Baculovirus System:

The coding sequence for the human KDR intra-cellular domain (aa789-1354) was generated through PCR using cDNAs isolated from HUVEC cells. A poly-His6 sequence was introduced at the N-terminus of this protein as well. This fragment was cloned into transfection vector pVL1393 at the Xba 1 and Not 1 site. Recombinant baculovirus (BV) was generated through co-transfection using the BaculoGold Transfection reagent (PharMingen). Recombinant BV was plaque purified and verified through Western analysis. For protein production, SF-9 cells were grown in SF-900-II medium at 2×106/ml, and were infected at 0.5 plaque forming units per cell (MOI). Cells were harvested at 48 hours post infection.

Purification of KDR

SF-9 cells expressing $(His)_6$KDR(aa789-1354) were lysed by adding 50 ml of Triton X-100 lysis buffer (20 mM Tris, pH 8.0, 137 mM NaCl, 10% glycerol, 1% Triton X-100, 1 mM PMSF, 10 μg/ml aprotinin, 1 μg/ml leupeptin) to the cell pellet from 1L of cell culture. The lysate was centrifuged at 19,000 rpm in a Sorval SS-34 rotor for 30 min at 4° C. The cell lysate was applied to a 5 ml $NiCl_2$ chelating sepharose column, equilibrated with 50 mM HEPES, pH 7.5, 0.3 M NaCl. KDR was eluted using the same buffer containing 0.25 M imidazole. Column fractions were analyzed using SDS-PAGE and an ELISA assay (below) which measures kinase activity. The purified KDR was exchanged into 25 mM HEPES, pH 7.5, 25 mM NaCl, 5 mM DTT buffer and stored at −80° C.

Human Tie-2 Kinase Production and Purification

The coding sequence for the human Tie-2 intra-cellular domain (aa775-1124) was generated through PCR using cDNAs isolated from human placenta as a template. A poly-$His_6$ sequence was introduced at the N-terminus and this construct was cloned into transfection vector pVL1939 at the Xba 1 and Not 1 site. Recombinant BV was generated through co-transfection using the BaculoGold Transfection reagent (PharMingen). Recombinant BV was plaque purified and verified through Western analysis. For protein production, SF-9 insect cells were grown in SF-900-II medium at 2×106/ml, and were infected at MOI of 0.5. Purification of the His-tagged kinase used in screening was analogous to that described for KDR.

Human Flt-1 Tyrosine Kinase Production and Purification

The baculoviral expression vector pVL1393 (Phar Mingen, Los Angeles, Calif.) was used. A nucleotide sequence encoding poly-His6 was placed 5' to the nucleotide region encoding the entire intracellular kinase domain of human Flt-1 (amino acids 786-1338). The nucleotide sequence encoding the kinase domain was generated through PCR using cDNA libraries isolated from HUVEC cells. The histidine residues enabled affinity purification of the protein as a manner analogous to that for KDR and ZAP70. SF-9 insect cells were infected at a 0.5 multiplicity and harvested 48 hours post infection.

EGFR Tyrosine Kinase Source

EGFR was purchased from Sigma (Cat # E-3641; 500 units/50 μl) and the EGF ligand was acquired from Oncogene Research Products/Calbiochem (Cat # PF011-100).

Expression of ZAP70

The baculoviral expression vector used was pVL1393. (Pharmingen, Los Angeles, Calif.) The nucleotide sequence encoding amino acids $M(H)_6$ $LVPR_9S$ was placed 5' to the region encoding the entirety of ZAP70 (amino acids 1-619). The nucleotide sequence encoding the ZAP70 coding region was generated through PCR using cDNA libraries isolated from Jurkat immortalized T-cells. The histidine residues enabled affinity purification of the protein (vide infra). The LVPR₉S bridge constitutes a recognition sequence for proteolytic cleavage by thrombin, enabling removal of the affinity tag from the enzyme. SF-9 insect cells were infected at a multiplicity of infection of 0.5 and harvested 48 hours post infection.

Extraction and Purification of ZAP70

SF-9 cells were lysed in a buffer consisting of 20 mM Tris, pH 8.0, 137 mM NaCl, 10% glycerol, 1% Triton X-100, 1 mM PMSF, 1 µg/ml leupeptin, 10 µg/ml aprotinin and 1 mM sodium orthovanadate. The soluble lysate was applied to a chelating sepharose HiTrap column (Pharmacia) equilibrated in 50 mM HEPES, pH 7.5, 0.3 M NaCl. Fusion protein was eluted with 250 mM imidazole. The enzyme was stored in buffer containing 50 mM HEPES, pH 7.5, 50 mM NaCl and 5 mM DTT.

Protein Kinase Source

Lck, Fyn, Src, Blk, Csk, and Lyn, and truncated forms thereof may be commercially obtained (e.g. from Upstate Biotechnology Inc. (Saranac Lake, N.Y.) and Santa Cruz Biotechnology Inc. (Santa Cruz, Ca.)) or purified from known natural or recombinant sources using conventional methods.

Enzyme Linked Immunosorbent Assay (ELISA) for PTKs

Enzyme linked immunosorbent assays (ELISA) were used to detect and measure the presence of tyrosine kinase activity. The ELISA were conducted according to known protocols which are described in, for example, Voller, et al., 1980, "Enzyme-Linked Immunosorbent Assay," In: *Manual of Clinical Immunology*, 2d ed., edited by Rose and Friedman, pp 359-371 Am. Soc. of Microbiology, Washington, D.C.

The disclosed protocol was adapted for determining activity with respect to a specific PTK. For example, preferred protocols for conducting the ELISA experiments is provided below. Adaptation of these protocols for determining a compound's activity for other members of the receptor PTK family, as well as non-receptor tyrosine kinases, are well within the abilities of those in the art. For purposes of determining inhibitor selectivity, a universal PTK substrate (e.g., random copolymer of poly(Glu₄ Tyr), 20,000-50,000 MW) was employed together with ATP (typically 5 µM) at concentrations approximately twice the apparent Km in the assay.

The following procedure was used to assay the inhibitory effect of compounds of this invention on KDR, Flt-1, Tie-2, EGFR, FGFR, PDGFR, IGF-1-R, c-Met, Lck, Blk, Csk, Src, Lyn, Fyn and ZAP70 tyrosine kinase activity:

Buffers and Solutions:

PGTPoly (Glu,Tyr) 4:1

Store powder at −20° C. Dissolve powder in phosphate buffered saline (PBS) for 50 mg/ml solution. Store 1 ml aliquots at −20° C. When making plates dilute to 250 µg/ml in Gibco PBS.

Reaction Buffer: 100 mM Hepes, 20 mM MgCl₂, 4 mM MnCl₂, 5 mM DTT, 0.02%BSA, 200 µM NaVO₄, pH 7.10

ATP: Store aliquots of 100 mM at −20° C. Dilute to 20 µM in water

Washing Buffer: PBS with 0.1% Tween 20

Antibody Diluting Buffer: 0.1% bovine serum albumin (BSA) in PBS

TMB Substrate: mix TMB substrate and Peroxide solutions 9:1 just before use or use K-Blue Substrate from Neogen Stop Solution: 1M Phosphoric Acid Procedure 1. Plate Preparation:

Dilute PGT stock (50 mg/ml, frozen) in PBS to a 250 µg/ml. Add 125 µl per well of Corning modified flat bottom high affinity ELISA plates (Corning #25805-96). Add 125 µl PBS to blank wells. Cover with sealing tape and incubate overnight 37° C. Wash 1× with 250 µl washing buffer and dry for about 2 hrs in 37° C. dry incubator. Store coated plates in sealed bag at 4° C. until used.

2. Tyrosine Kinase Reaction:

Prepare inhibitor solutions at a 4× concentration in 20% DMSO in water.

Prepare reaction buffer

Prepare enzyme solution so that desired units are in 50 µl, e.g. for KDR make to 1 ng/µl for a total of 50 ng per well in the reactions. Store on ice.

Make 4×ATP solution to 20 µM from 100 mM stock in water. Store on ice

Add 50 µl of the enzyme solution per well (typically 5-50 ng enzyme/well depending on the specific activity of the kinase)

Add 25 µl 4× inhibitor

Add 25 µl 4×ATP for inhibitor assay

Incubate for 10 minutes at room temperature

Stop reaction by adding 50 µl 0.05N HCl per well

Wash plate

**Final Concentrations for Reaction: 5 µM ATP, 5% DMSO

3. Antibody Binding

Dilute 1 mg/ml aliquot of PY20-HRP (Pierce) antibody (a phosphotyrosine antibody) to 50 ng/ml in 0.1% BSA in PBS by a 2 step dilution (100×, then 200×)

Add 100 µl Ab per well. Incubate 1 hr at room temp. Incubate 1 hr at 4 C.

Wash 4× plate

4. Color Reaction

Prepare TMB substrate and add 100 µl per well

Monitor OD at 650 nm until 0.6 is reached

Stop with 1M Phosphoric acid. Shake on plate reader.

Read OD immediately at 450 nm

Optimal incubation times and enzyme reaction conditions vary slightly with enzyme preparations and are determined empirically for each lot.

For Lck, the Reaction Buffer utilized was 100 mM MOPSO, pH 6.5, 4 mM MnCl₂, 20 mM MgCl₂, 5 mM DTT, 0.2% BSA, 200 mM NaVO₄ under the analogous assay conditions.

Compounds of formula I may have therapeutic utility in the treatment of diseases involving both identified, including those not mentioned herein, and as yet unidentified protein tyrosine kinases which are inhibited by compounds of formula I. All compounds exemplified herein significantly inhibit either FGFR, PDGFR, KDR, Tie-2, Lck, Fyn, Blk, Lyn or Src at concentrations of 50 micromolar or below. Some compounds of this invention also significantly inhibit other tyrosine or serine/threonine kinases such as cdc2 (cdk1) at concentrations of 50 micromolar or below.

Cdc2 Source

The human recombinant enzyme and assay buffer may be obtained commercially (New England Biolabs, Beverly, Mass. USA) or purified from known natural or recombinant sources using conventional methods.

Cdc2 Assay

The protocol used was that provided with the purchased reagents with minor modifications. In brief, the reaction was carried out in a buffer consisting of 50 mM Tris pH 7.5, 100 mM NaCl, 1 mM EGTA, 2 mM DTT, 0.01% Brij, 5% DMSO and 10 nM $MgCl_2$ (commercial buffer) supplemented with fresh 300 μM ATP (31 μCi/ml) and 30 μg/ml histone type IIIss final concentrations. A reaction volume of 80 μL, containing units of enzyme, was run for 20 minutes at 25 degrees C. in the presence or absence of inhibitor. The reaction was terminated by the addition of 120 μL of 10% acetic acid. The substrate was separated from unincorporated label by spotting the mixture on phosphocellulose paper, followed by 3 washes of 5 minutes each with 75 mM phosphoric acid. Counts were measured by a betacounter in the presence of liquid scintillant.

Certain compounds of this invention significantly inhibit cdc2 at concentrations below 50 uM.

PKC Kinase Source

The catalytic subunit of PKC may be obtained commercially (Calbiochem).

PKC Kinase Assay

A radioactive kinase assay was employed following a published procedure (Yasuda, I., Kirshimoto, A., Tanaka, S., Tominaga, M., Sakurai, A., Nishizuka, Y. *Biochemical and Biophysical Research Communication* 3:166, 1220-1227 (1990)). Briefly, all reactions were performed in a kinase buffer consisting of 50 mM Tris-HCl pH 7.5, 10 mM $MgCl_2$, 2 mM DTT, 1 mM EGTA, 100 μM ATP, 8 μM peptide, 5% DMSO and $^{33}P$ ATP (8 Ci/mM). Compound and enzyme were mixed in the reaction vessel and the reaction initiated by addition of the ATP and substrate mixture. Following termination of the reaction by the addition of 10 μL stop buffer (5 mM ATP in 75 mM phosphoric acid), a portion of the mixture was spotted on phosphocellulose filters. The spotted samples were washed 3 times in 75 mM phosphoric acid at room temperature for 5 to 15 minutes. Incorporation of radiolabel was quantified by liquid scintillation counting.

Erk2 Enzyme Source

The recombinant murine enzyme and assay buffer may be obtained commercially (New England Biolabs, Beverly Mass. USA) or purified from known natural or recombinant sources using conventional methods.

Erk2 Enzyme Assay

In brief, the reaction was carried out in a buffer consisting of 50 mM Tris pH 7.5, 1 mM EGTA, 2 mM DTT, 0.01% Brij, 5% DMSO and 10 mM $MgCl_2$ (commercial buffer) supplemented with fresh 100 μM ATP (31 μCi/ml) and 30 μM myelin basic protein under conditions recommended by the supplier. Reaction volumes and method of assaying incorporated radioactivity were as described for the PKC assay (vide supra).

In Vitro Models for T-Cell Activation

Upon activation by mitogen or antigen, T-cells are induced to secrete IL-2, a growth factor that supports their subsequent proliferative phase. Therefore, one may measure either production of IL-2 from or cell proliferation of, primary T-cells or appropriate T-cell lines as a surrogate for T-cell activation. Both of these assays are well described in the literature and their parameters well documented (in Current Protocols in Immunology, Vol 2, 7.10.1-7.11.2).

In brief, T-cells may be activated by co-culture with allogenic stimulator cells, a process termed the one-way mixed lymphophocyte reaction. Responder and stimulator peripheral blood mononuclear cells are purified by Ficoll-Hypaque gradient (Pharmacia) per directions of the manufacturer. Stimulator cells are mitotically inactivated by treatment with mitomycin C (Sigma) or gamma irradiation. Responder and stimulator cells are co-cultured at a ratio of two to one in the presence or absence of the test compound. Typically $10^5$ responders are mixed with $5 \times 10^4$ stimulators and plated (200 μl volume) in a U bottom microtiter plate (Costar Scientific). The cells are cultured in RPMI 1640 supplemented with either heat inactivated fetal bovine serum (Hyclone Laboratories) or pooled human AB serum from male donors, $5 \times 10^{-5}$ M 2-mercaptoethanol and 0.5% DMSO, The cultures are pulsed with 0.5 μCi of $^3H$ thymidine (Amersham) one day prior to harvest (typically day three). The cultures are harvested (Betaplate harvester, Wallac) and isotope uptake assessed by liquid scintillation (Betaplate, Wallac).

The same culture system may be used for assessing T-cell activation by measurement of IL-2 production. Eighteen to twenty-four hours after culture initiation, the supernatants are removed and the IL-2 concentration is measured by ELISA (R and D Systems) following the directions of the manufacturer.

In-Vivo Models of T-Cell Activation

The in vivo efficacy of compounds can be tested in animal models known to directly measure T-cell activation or for which T-cells have been proven the effectors. T-cells can be activated in vivo by ligation of the constant portion of the T-cell receptor with a monoclonal anti-CD3 antibody (Ab). In this model, BALB/c mice are given 10 μg of anti-CD3 Ab intraperitoneally two hours prior to exsanguination. Animals to receive a test drug are pre-treated with a single dose of the compound one hour prior to anti-CD3 Ab administration. Serum levels of the proinflammatory cytokines interferon-γ (IFN-γ) and tumor necrosis factor-α (TNF-α), indicators of T-cell activation, are measured by ELISA. A similar model employs in vivo T-cell priming with a specific antigen such as keyhole limpet hemocyanin (KLH) followed by a secondary in vitro challenge of draining lymph node cells with the same antigen. As previously, measurement of cytokine production is used to assess the activation state of the cultured cells. Briefly, C57BL/6 mice are immunized subcutaneously with 100 μg KLH emulsified in complete Freund's adjuvant (CFA) on day zero. Animals are pre-treated with the compound one day prior to immunization and subsequently on days one, two and three post immunization. Draining lymph nodes are harvested on day 4 and their cells cultured at $6 \times 10^6$ per ml in tissue culture medium (RPMI 1640 supplemented with heat inactivated fetal bovine serum (Hyclone Laboratories) $5 \times 10^{-5}$ M 2-mercaptoethanol and 0.5% DMSO) for both twenty-four and forty-eight hours. Culture supernatants are then assessed for the autocrine T-cell growth factor Interleukin-2 (IL-2) and/or IFN-γ levels by ELISA.

Lead compounds can also be tested in animal models of human disease. These are exemplified by experimental autoimmune encephalomyelitis (EAE) and collagen-induced arthritis (CIA). EAE models which mimic aspects of human multiple sclerosis have been described in both rats and mice (reviewed FASEB J. 5:2560-2566, 1991; murine model: Lab. Invest. 4(3):278, 1981; rodent model: J. Immunol 146(4): 1163-8, 1991). Briefly, mice or rats are immunized with an emulsion of myelin basic protein (MBP), or neurogenic peptide derivatives thereof, and CFA. Acute disease can be induced with the addition of bacterial toxins such as *bordetella pertussis*. Relapsing/remitting disease is induced by adoptive transfer of T-cells from MBP/peptide immunized animals.

CIA may be induced in DBA/1 mice by immunization with type II collagen (J. Immunol:142(7):2237-2243). Mice will develop signs of arthritis as early as ten days following antigen challenge and may be scored for as long as ninety days after immunization. In both the EAE and CIA models, a compound may be administered either prophylactically or at the time of disease onset. Efficacious drugs should reduce severity and/or incidence.

Certain compounds of this invention which inhibit one or more angiogenic receptor PTK, and/or a protein kinase such as lck involved in mediating inflammatory responses can reduce the severity and incidence of arthritis in these models.

Compounds can also be tested in mouse allograft models, either skin (reviewed in Ann. Rev. Immunol., 10:333-58, 1992; Transplantation: 57(12): 1701-17D6, 1994) or heart (Am. J. Anat.: 113:273, 1963). Briefly, full thickness skin grafts are transplanted from C57BL/6 mice to BALB/c mice. The grafts can be examined daily, beginning at day six, for evidence of rejection. In the mouse neonatal heart transplant model, neonatal hearts are ectopically transplanted from C57BL/6 mice into the ear pinnae of adult CBA/J mice. Hearts start to beat four to seven days post transplantation and rejection may be assessed visually using a dissecting microscope to look for cessation of beating.

Cellular Receptor PTK Assays

The following cellular assay was used to determine the level of activity and effect of the different compounds of the present invention on KDR/VEGFR$_2$. Similar receptor PTK assays employing a specific ligand stimulus can be designed along the same lines for other tyrosine kinases using techniques well known in the art.

VEGF-Induced KDR Phosphorylation in Human Umbilical Vein Endothelial Cells (HUVEC) as Measured by Western Blots:

1. HUVEC cells (from pooled donors) were purchased from Clonetics (San Diego, Calif.) and cultured according to the manufacturer directions. Only early passages (3-8) were used for this assay. Cells were cultured in 100 mm dishes (Falcon for tissue culture; Becton Dickinson; Plymouth, England) using complete EBM media (Clonetics).

2. For evaluating a compound's inhibitory activity, cells were trypsinized and seeded at $0.5-1.0 \times 10^5$ cells/well in each well of 6-well cluster plates (Costar; Cambridge, Mass.).

3. 3-4 days after seeding, plates were 90-100% confluent. Medium was removed from all the wells, cells were rinsed with 5-10 ml of PBS and incubated 18-24 h with 5 ml of EBM base media with no supplements added (i.e., serum starvation).

4. Serial dilutions of inhibitors were added in 1 ml of EBM media (25 µM, 5 µM, or 1 µM final concentration to cells and incubated for one hour at 37 C. Human recombinant VEGF$_{165}$ (R & D Systems) was then added to all the wells in 2 ml of EBM medium at a final concentration of 50 ng/ml and incubated at 37 C for 10 minutes. Control cells untreated or treated with VEGF only were used to assess background phosphorylation and phosphorylation induction by VEGF.

All wells were then rinsed with 5-10 ml of cold PBS containing 1 mM Sodium Orthovanadate (Sigma) and cells were lysed and scraped in 200 µl of RIPA buffer (50 mM Tris-HCl) pH 7, 150 mM NaCl, 1% NP-40, 0.25% sodium deoxycholate, 1M EDTA) containing protease inhibitors (PMSF 1 mM, aprotinin 1 µg/ml, pepstatin 1 µg/ml, leupeptin 1 g/ml, Na vanadate 1 mM, Na fluoride 1 mM) and 1 µg/ml of Dnase (all chemicals from Sigma Chemical Company, St Louis, Mo.). The lysate was spun at 14,000 rpm for 30 min, to eliminate nuclei.

Equal amounts of proteins were then precipitated by addition of cold (−20 C) Ethanol (2 volumes) for a minimum of 1 hour or a maximum of overnight. Pellets were reconstituted in Laemli sample buffer containing 5%-mercaptoethanol (Bio-Rad; Hercules, Calif.) and boiled for 5 min. The proteins were resolved by polyacrylamide gel electrophoresis (6%, 1.5 mm Novex, San Deigo, Calif.) and transferred onto a nitrocellulose membrane using the Novex system. After blocking with bovine serum albumin (3%), the proteins were probed overnight with anti-KDR polyclonal antibody (C20, Santa Cruz Biotechnology; Santa Cruz, Calif.) or with anti-phosphotyrosine monoclonal antibody (4G10, Upstate Biotechnology, Lake Placid, N.Y.) at 4 C. After washing and incubating for 1 hour with HRP-conjugated F(ab)$_2$ of goat anti-rabbit or goat-anti-mouse IgG the bands were visualized using the emission chemiluminescience (ECL) system (Amersham Life Sciences, Arlington Height, Ill.). Certain examples of the present invention significantly inhibit cellular VEGF-induced KDR tyrosine kinase phosphorylation at concentrations of less than 50%M.

In Vivo Uterine Edema Model

This assay measures the capacity of compounds to inhibit the acute increase in uterine weight in mice which occurs in the first few hours following estrogen stimulation. This early onset of uterine weight increase is known to be due to edema caused by increased permeability of uterine vasculature. Cullinan-Bove and Koss (*Endocrinology* (1993), 133:829-837) demonstrated a close temporal relationship of estrogen-stimulated uterine edema with increased expression of VEGF mRNA in the uterus. These results have been confirmed by the use of neutralizing monoclonal antibody to VEGF which significantly reduced the acute increase in uterine weight following estrogen stimulation (WO 97/42187). Hence, this system can serve as a model for in vivo inhibition of VEGF signalling and the associated hyperpermeability and edema.

Materials: All hormones were purchased from Sigma (St. Louis, Mo.) or Cal Biochem (La Jolla, Calif.) as lyophilized powders and prepared according to supplier instructions.

Vehicle components (DMSO, Cremaphor EL) were purchased from Sigma (St. Louis, Mo.).

Mice (Balb/c, 8-12 weeks old) were purchased from Taconic (Germantown, N.Y.) and housed in a pathogen-free animal facility in accordance with institutional Animal Care and Use Committee Guidelines.

Method:

Day 1: Balb/c mice were given an intraperitoneal (i.p.) injection of 12.5 units of pregnant mare's serum gonadotropin (PMSG).

Day 3: Mice received 15 units of human chorionic gonadotropin (hCG) i.p.

Day 4: Mice were randomized and divided into groups of 5-10. Test compounds were administered by i.p., i.v. or p.o. routes depending on solubility and vehicle at doses ranging from 1-100 mg/kg. Vehicle control group received vehicle only and two groups were left untreated.

Thirty minutes later, experimental, vehicle and 1 of the untreated groups were given an i.p. injection of 17-estradiol (500 μg/kg). After 2-3 hours, the animals were sacrificed by $CO_2$ inhalation. Following a midline incision, each uterus was isolated and removed by cutting just below the cervix and at the junctions of the uterus and oviducts. Fat and connective tissue were removed with care not to disturb the integrity of the uterus prior to weighing (wet weight). Uteri were blotted to remove fluid by pressing between two sheets of filter paper with a one liter glass bottle filled with water. Uteri were weighed following blotting (blotted weight). The difference between wet and blotted weights was taken as the fluid content of the uterus. Mean fluid content of treated groups was compared to untreated or vehicle treated groups. Significance was determined by Student's test. Non-stimulated control group was used to monitor estradiol response.

Results demonstrate that certain compounds of the present invention inhibit the formation of edema when administered systemically by various routes.

Certain compounds of this invention which are inhibitors of angiogenic receptor tyrosine kinases can also be shown active in a Matrigel implant model of neovascularization. The Matrigel neovascularization model involves the formation of new blood vessels within a clear "marble" of extracellular matrix implanted subcutaneously which is induced by the presence of proangiogenic factor producing tumor cells (for examples see: Passaniti, A., et al, Lab. Investig. (1992), 67(4), 519-528; Anat. Rec. (1997), 249(1), 63-73; Int. J. Cancer (1995), 63(5), 694-701; Vasc. Biol. (1995), 15(11), 1857-6). The model preferably runs over 3-4 days and endpoints include macroscopic visual/image scoring of neovascularization, microscopic microvessel density determinations, and hemoglobin quantitation (Drabkin method) following removal of the implant versus controls from animals untreated with inhibitors. The model may alternatively employ bFGF or HGF as the stimulus.

Certain compounds of this invention which inhibit one or more oncogenic, protooncogenic, or proliferation-dependent protein kinases, or angiogenic receptor PTK also inhibit the growth of primary murine, rat or human xenograft tumors in mice, or inhibit metastasis in murine models.

EXEMPLIFICATION

Processes for the preparation of compounds of formula I will now be described. These processes form a further aspect of the present invention. The processes are preferably carried out at atmospheric pressure.

Compounds of formula I may be prepared by condensing a compound of formula (II)

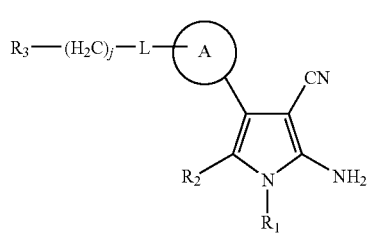

in which $R_1$, $R_2$, $R_3$, L and ring A are as previously defined, with formamide at a temperature in the range of 50 to 250° C. optionally in the presence of a catalyst for example 4-dimethylaminopyridine.

Compounds of formula I may be prepared by reacting a compound of formula (III)

(III)

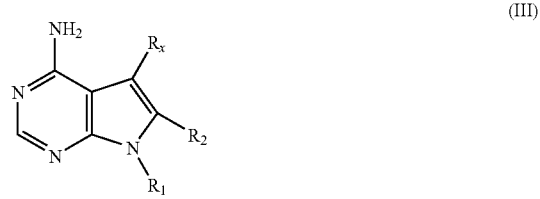

wherein $R_x$ is bromo or iodo bromo or iodo with one of the following compounds: $R_3B(OH)_2$, $R_3SnCH_3$ or a compound represented by formula III

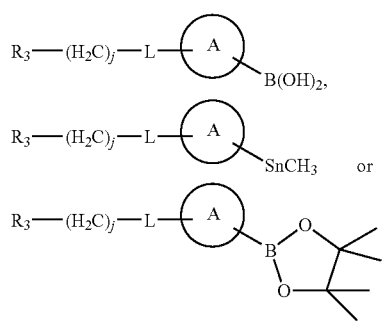

in which $R_3$ is as defined above, in the presence of a catalyst for example palladium (0) compounds eg. $Pd(PPh_3)_4$.

Compounds of formula I in which $R_1$ represents an alkyl group or an aralkyl group may be prepared by alkylating a compound of formula (IV)

(IV)

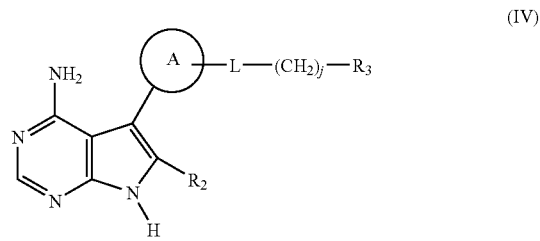

in which $R_2$ and $R_3$ are as previously defined with a compound of formula $R_1X'$ in which $R_1$ represents an alkyl group or an aralkyl group and X' represents a leaving group, for example halo, mesyloxy or tosyloxy.

Compounds of formula I in which $R_1$ represents an optionally substituted cyclic ether, such as tetrahydrofuryl or tetrahydropyranyl, may be prepared by alkylating a compound of formula IV

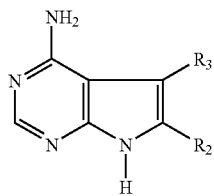

IV in which $R_2$ and $R_3$ are as previously defined with a compound of formula $R_1X'$ in which $X'$ is as previously defined and $R_1$ is an optionally substituted cyclic ether.

Compounds of formula I in which $R_1$ represents cyclic ether, such as tetrahydrofuryl or tetrahydropyranyl, optionally substituted by formyl may be prepared by alkylating a compound of formula IV with a compound $R_1X$ in which $R_1$ represents a cyclic ether substituted by a formyl group which has been protected, by a method known to those skilled in the art, for example by means of an acetal, (See for example Tet. Letts. 30 (46) 1989, 6259-6262) followed by deprotection. Compounds in which $R_1$ represents a cyclic ether, such as tetrahydrofuryl or tetrahydropyranyl, substituted by an (optionally substituted amino)methyl group may be prepared by reductive amination of a compound in which $R_1$ represents a cyclic ether substituted by formyl.

Compounds of formula I in which $R_1$ represents optionally substituted furyl, thienyl or pyrrolyl may be prepared by reacting 4-chloro-5-iodo-7H-pyrrolo[2,3-d]ppyrimidine with the appropriate heteroarylboronic acid in the presence of a copper salt catalyst, for example copper (II) acetate in the presence of a solvent for the reactants, e.g. a halogenated solvent for example, dichloromethane, in the presence of a drying agent, for example 4 Å molecular sieves, in the presence of an organic base, e.g. triethylamine or pyridine, at a temperature in the range of 0-50° C., preferably at ambient temperature. (For conditions see *Tet. Letts*. (1998), volume 39:2942-2944 and references cited therein. This paper is incorporated herein by reference.) These compounds may be formulated by methods known to those skilled in the art to give compounds in which $R_1$ represents furyl, thienyl or pyrrolyl substituted by formyl. The formyl group in these compounds may be productively aminated by methods known to those skilled in the art to give compounds in which $R_1$ represents furyl, thienyl or pyrrolyl substituted by aminomethyl groups. Alternatively intermediates in which $R_1$ represents furyl, thienyl or pyrrolyl may be subjected to a Mannich reaction to give intermediates in which $R_1$ represents furyl, thienyl or pyrrolyl substituted by an aminomethyl group.

Compounds of formula I may be prepared by reacting a compound of formula V

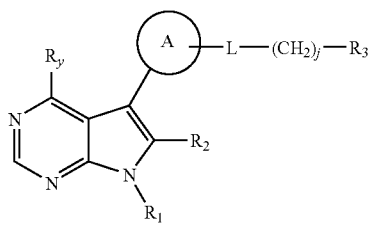

V in which $R_1$, $R_2$, $R_3$, L and ring A are as previously defined, and $R_y$ represents a leaving group, for example halo or phenoxy, with ammonia or an ammonium salt, for example ammonium acetate, at a temperature in the range of 15-250° C., preferably in a pressure vessel.

Compounds of formula I in which $R_2$ represents chloro, bromo or iodo may be prepared by reacting a compound of formula VI

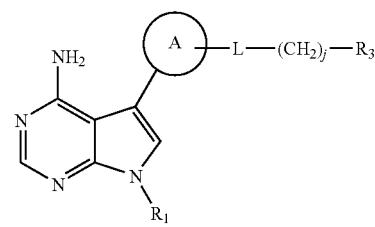

(VI)

in which $R_1$, $R_3$, L and ring A are as previously defined with a halogenating agent for example an iodinating agent, e.g. N-iodosuccinimide, or a brominating agent, e.g. N-bromosuccinimide, or a chlorinating agent, e.g. N-chlorosuccinimide.

Compounds of formula I in which $-L-R_3$ represents $-NHC(O)R_3$ may be prepared by reacting a compound of formula VII

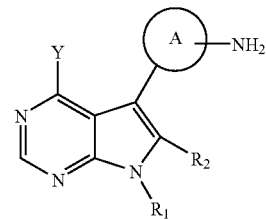

VII in which $R_1$, $R_2$ and ring A are as previously defined and Y represents a protected amine, with a compound of formula $R_3COR_x$ in which $R_x$ represents a leaving group, for example chloro. Alternatively compounds of formula VII in which Y represents halo, for example chloro, may be reacted with a compound of formula $R_3COR_x$ and the product reacted with ammonia to give a compound of formula I. Analogous methods may be used to prepare compounds of formula I in which $-L-R_3$ is $-NRSO_2R_3$. Analogous methods may be used to prepare compound of formula I in which $-L-R_3$ is $-NRCO_2-R_3$ or $-NRCONR'$. R and R' are as previously defined.

Compounds of formula I in which -L-R$_3$ is —OSO$_2$— may be prepared by reacting a compound of formula VIII

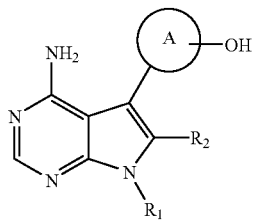

VIII in which R$_1$, R$_2$ and ring A are as previously defined with a compound of formula R$_4$SO$_2$R$_x$.

Compounds of formula I may then be prepared from such intermediates following Scheme 2 or the alternative for Scheme 2, which is described later.

Compounds of formula II may be prepared as shown in Scheme 1 in which IPA represents propan-2-ol.

Scheme 1

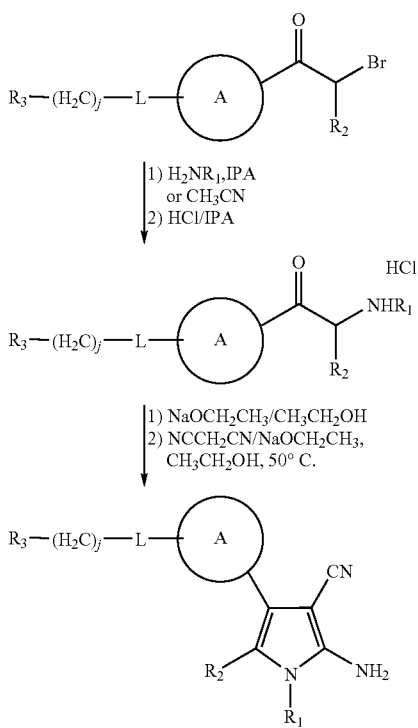

It will be appreciated by those skilled in the art that compounds of formula I may be converted into other compounds of formula I by known chemical reactions. For example, an alkoxy group may be cleaved to give hydroxy, nitro groups may be reduced to amines, amines may be acylated sulfonylated or phosphorylated and N-acyl compounds may be hydrolyzed to amines. Compounds of formula I in which -L- is S may be oxidized to give compounds of formula I in which -L- represents SO and SO$_2$, respectively, by methods known to those skilled in the art.

Compounds of formula III are commercially available or may be prepared by methods known to those skilled in the art.

Compounds of formula IV in which R$_2$ represents hydrogen may be prepared as shown in Scheme 2. The amino group may be protected prior to the final step and then deprotected after the final step of scheme 2 by methods known to those skilled in the art. Compounds of formula IV in which R$_2$ is other than hydrogen may be prepared by analogous methods. (see *J. Med. Chem.* (1990), 33, 1984.)

Scheme 2

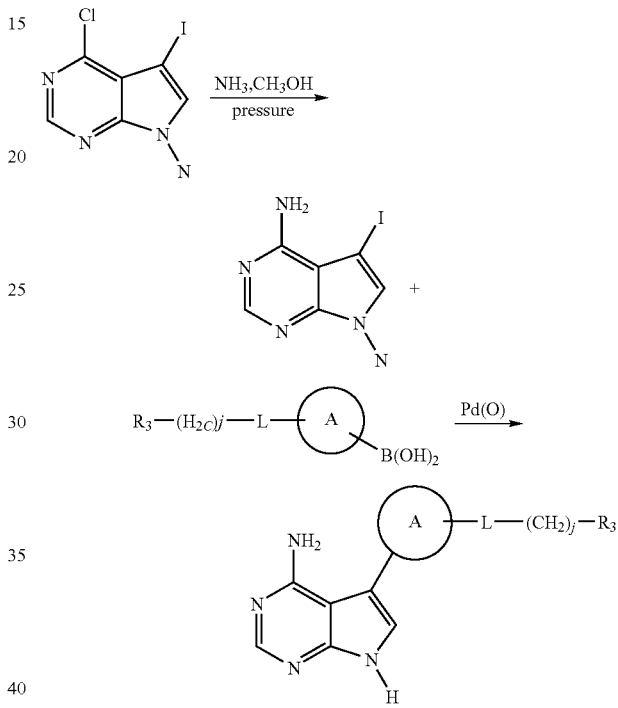

Alternatively in Scheme 2, (ring A)-L-R$_3$ may be coupled first, prior to amination. Alternatively a substituent R$_1$ as defined previously may be present prior to carrying out either process.

Compounds of formula V may be prepared as shown in Scheme 3.

Scheme 3

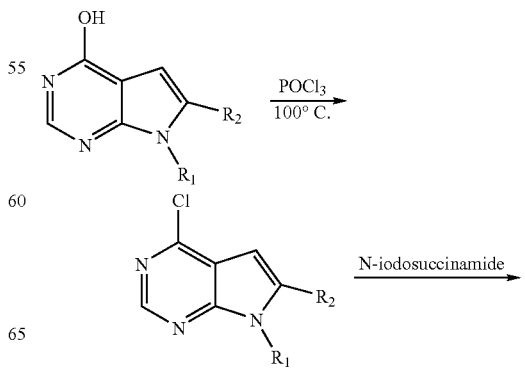

-continued

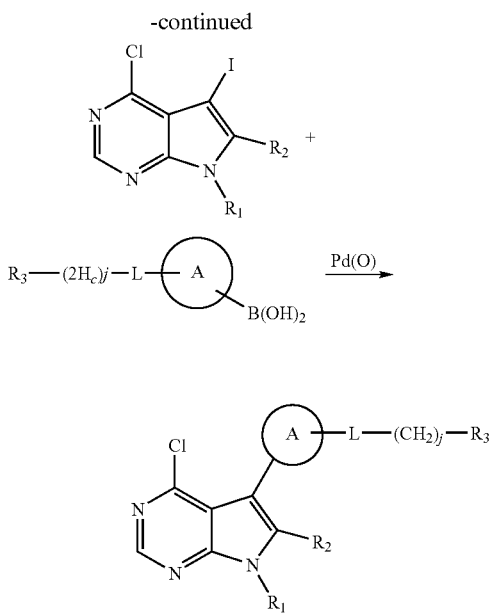

Compounds in which (ring A)-L-$R_3$ is absent may be prepared as in Scheme 4 and as described in *J. Med. Chem.*, (1988), 31:390 and references cited therein. Compounds in which (ring A)-L-$R_3$ is other than hydrogen may be prepared by analogous methods.

Scheme 4

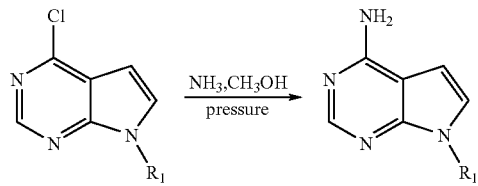

Compounds of formula VII may be prepared by coupling a 5-iodo compound in an analogous manner to that described for the preparation of compounds of formula IV.

It will be appreciated by those skilled in the art that in cases where a substituent is identical with, or similar to, a functional group which has been modified in one of the above processes that these substituents will require protection before the process is undertaken, followed by deprotection after the process. Otherwise competing side-reactions will occur. Alternatively, another of the processes described above, in which the substituent does not interfere, may be used. Examples of suitable protecting groups and methods for their addition and removal may be found in the textbook "Protective Groups in Organic Synthesis" by T. W. Green, John Wiley and Sons, 1981. For example suitable protecting groups for amines are formyl or acetyl.

The following examples were prepared using the general preparation methods outlined above:

Example 1

N1-[4-(4-Amino-7-cyclopentyl-7H-pyrrolo[2,3-d]pyrimidin-5-yl)-2-methoxyphenyl]-4-cyano-1-benzenesulfonamide a) tert-Butyl N-(4-bromo-2-methoxyphenyl)carbamate A mixture of 4-bromo-2-methoxyaniline (34.0 g, 0.17 mol) and di-tert-butyl dicarbonate (44.5 g, 0.20 mol) in tetrahydrofuran (350 ml) was heated at reflux for 22 h. The mixture was allowed to cool to ambient temperature and the solvent was removed under reduced pressure. The residue was dissolved in ethyl acetate (350 ml) and washed with 1 N citric acid (200 ml), dried over magnesium sulfate, filtered and evaporated to give tert-butyl N-(4-bromo-2-methoxyphenyl)carbamate as a yellow oil (80% pure, 57.10 g, 0.15 mol): $^1$H NMR (DMSO-$d_6$, 400 MHz) δ 8.01 (s, 1H), 7.63 (d, 1H), 7.17 (d, 1H), 7.07 (dd, 1H), 3.82 (s, 3H), 1.45 (s, 9H); TLC (n-heptane/ethyl acetate=2:1) $R_f$ 0.67.

b) tert-Butyl N-[2-methoxy-4-(4,4,5,5-tetramethyl-1,3,2-dioxaborolan-2-yl)phenyl]-carbamate A mixture of tert-butyl N-(4-bromo-2-methoxyphenyl)carbamate (80% pure) (6.25 g, 16.56 mmol), diboron pinacol ester (5.05 g, 19.88 mmol), [1,1'-bis(diphenylphosphino)ferrocene]dichloropalladium(II) complex with dichloromethane (1:1) (0.41 g, 0.50 mmol) and potassium acetate (4.88 g, 49.80 mmol) in N,N-dimethylformamide (100 ml) was heated at 80° C. under an atmosphere of nitrogen overnight. The mixture was allowed to cool to ambient temperature and then most of the solvent was removed under reduced pressure. Dichloromethane (100 ml) was added to the residue and the resulting solids were removed by filtration through a pad of celite. The filtrate was concentrated to leave a dark oil which was purified by flash column chromatography on silica using dichloromethane/n-heptane (1:2) with 2.5% triethylamine as mobile phase to give tert-butyl N-[2-methoxy-4-(4,4,5,5-tetramethyl-1,3,2-dioxaborolan-2-yl)phenyl]carbamate as white solids (65% pure, 4.25 g, 7.92 mmol): $^1$H NMR (DMSO-$d_6$, 400 MHz) δ 7.93 (s, 1H), 7.83 (d, 1H), 7.25 (d, 1H), 7.16 (s, 1H), 3.83 (s, 3H), 1.46 (s, 9H), 1.30 (s, 12H); RP-HPLC (Hypersil C18, 5 μm, 200 A, 25 cm; 50%-100% acetonitrile-0.1M ammonium acetate over 25 min, 1 ml/min) $R_t$ 18.28 min.

c) tert-Butyl N-[4-(4-chloro-7-cyclopentyl-7H-pyrrolo[2,3-d]pyrimidin-5-yl)-2-methoxy-phenyl]carbamate A mixture of water (25 ml) and tert-butyl N-[2-methoxy-4-(4,4,5,5-tetramethyl-1,3,2-dioxaborolan-2-yl)phenyl]carbamate (65% pure) (4.25 g, 7.92 mmol) was frozen and subjected to vacuum followed by filling with nitrogen while defreezing. 4-Chloro-7-cyclopentyl-5-iodo-7H-pyrrolo[2,3-d]pyrimidine (1.83 g, 5.28 mmol), tetrakis(triphenylphosphine)palladium(0) (0.37 g, 0.32 mmol), sodium carbonate (1.40 g, 13.20 mmol) and ethylene glycol dimethyl ether (50 ml) were added and the resulting mixture was heated at 80° C. under an atmosphere of nitrogen overnight. The mixture was allowed to cool to ambient temperature and the solvent was removed under reduced pressure to give a residue which was partitioned between water and ethyl acetate. The organic layer was separated and the aqueous layer was further extracted with ethyl acetate twice. The combined ethyl acetate extracts were dried over magnesium sulfate and evaporated to give a dark oil which was purified by flash column chromatography on silica using n-heptane/ethyl acetate (3:1) with 2% triethylamine as the mobile phase. Appropriate fractions were collected, combined and concentrated to give tert-butyl N-[4-(4-chloro-7-cyclopentyl-7H-pyrrolo[2,3-d]pyrimidin-5-yl)-2-methoxyphenyl]carbamate as white solids (1.90 g, 4.29 mmol): $^1$H NMR (DMSO-$d_6$, 400 MHz) δ 8.65 (s, 1H), 7.94 (s, 2H), 7.74 (d, 1H), 7.19 (d, 1H), 7.07 (dd, 1H), 5.22 (m, 1H), 3.87 (s, 3H), 2.19 (m, 2H), 1.99 (m, 2H), 1.91 (m, 2H), 1.73 (m, 2H), 1.48 (s, 9H); TLC (n-heptane/ethyl acetate=1:1) $R_f$ 0.58.

d) 4-(4-Chloro-7-cyclopentyl-7H-pyrrolo[2,3-d]pyrimidin-5-yl)-2-methoxyaniline Trifluoroacetic acid (2 ml) was added dropwise to a solution of tert-butyl N-[4-(4-chloro-7-cyclopentyl-7H-pyrrolo[2,3-d]pyrimidin-5-yl)-2-methoxyphenyl]carbamate (0.58 g, 1.31 mmol) in dichloromethane (20 ml) at 0° C. The ice bath was removed and the reaction mixture was stirred at room temperature for 3 h. Most of trifluoroacetic acid and dichloromethane were removed under reduced pressure. The residue was redissolved in dichloromethane and washed with saturated aqueous sodium bicarbonate solution, dried over magnesium sulfate, filtered and evaporated to give 4-(4-chloro-7-cyclopentyl-7H-pyrrolo[2,3-d]pyrimidin-5-yl)-2-methoxyaniline as white solids (0.45 g, 1.31 mmol): $^1$H NMR (DMSO-$d_6$, 400 MHz) δ 8.61 (s, 1H), 7.78 (s, 1H), 6.97 (d, 1H), 6.85 (dd, 1H), 6.67 (d, 1H), 5.20 (m, 1H), 4.78 (broad, 2H), 3.81 (s, 3H), 2.18 (m, 2H), 1.88-2.00 (m, 4H), 1.72 (m, 2H); MH$^+$343.

e) 5-(4-Amino-3-methoxyphenyl)-7-cyclopentyl-7H-pyrrolo[2,3-d]pyrimidin-4-amine A mixture of 4-(4-chloro-7-cyclopentyl-7H-pyrrolo[2,3-d]pyrimidin-5-yl)-2-methoxyaniline (0.45 g, 1.31 mmol), ammonia (115 ml, SG 0.88) and 1,4-dioxane (115 ml) was heated and stirred at 120° C. in a pressure vessel overnight. The mixture was allowed to cool to ambient temperature and the solvent was removed under reduced pressure to give a residue which was partitioned between water and ethyl acetate. The organic layer was separated and the aqueous layer was further extracted with ethyl acetate twice. The combined ethyl acetate extracts were washed with saturated aqueous sodium chloride solution, dried over magnesium sulfate, filtered and evaporated to give 5-(4-amino-3-methoxyphenyl)-7-cyclopentyl-7H-pyrrolo[2,3-d]pyrimidin-4-amine as brown solids (0.32 g, 0.99 mmol): $^1$H NMR (DMSO-$d_6$, 400 MHz) δ 8.09 (s, 1H), 7.24 (s, 1H), 6.88 (d, 1H), 6.79 (dd, 1H), 6.71 (d, 1H), 6.01 (broad, 2H), 5.06 (m, 1H), 4.79 (broad, 2H), 3.81 (s, 3H), 2.10 (m, 2H), 1.87-1.92 (m, 4H), 1.68 (m, 2H); MH$^+$324.

f) N1-[4-(4-Amino-7-cyclopentyl-7H-pyrrolo[2,3-d]pyrimidin-5-yl)-2-methoxyphenyl]-4-cyano-1-benzenesulfonamide A mixture of 5-(4-amino-3-methoxyphenyl)-7-cyclopentyl-7H-pyrrolo[2,3-d]pyrimidin-4-amine (0.026 g, 0.08 mmol), 4-cyanobenzenesulfonyl chloride (0.019 g, 0.10 mmol) and pyridine (0.40 ml) was stirred at room temperature overnight. Most of pyridine was removed under reduced pressure and the residue was purified by preparative RP-HPLC (Rainin C18, 8 μm, 300 A, 25 cm; 25%-100% acetonitrile-0.1M ammonium acetate over 25 min, 21 ml/min) to give N1-[4-(4-amino-7-cyclopentyl-7H-pyrrolo[2,3-d]pyrimidin-5-yl)-2-methoxy-phenyl]-4-cyano-1-benzenesulfonamide as yellow solids (0.018 g, 0.04 mmol): $^1$H NMR (DMSO-$d_6$, 400 MHz) δ 9.91 (s, 1H), 8.13 (s, 1H), 8.05 (d, 2H), 7.89 (d, 2H), 7.44 (s, 1H), 7.27 (d, 1H), 7.00 (dd, 1H), 6.98 (d, 1H), 6.07 (broad, 2H), 5.07 (m, 1H), 3.49 (s, 3H), 2.11 (m, 2H), 1.88 (m, 4H), 1.69 (m, 2H); MH$^+$489; TLC (ethyl acetate/methanol=9:1) $R_f$ 0.49; RP-HPLC (Hypersil C18, 5 μm, 200 A, 25 cm; 25%-100% acetonitrile-0.1M ammonium acetate over 25 min, 1 ml/min) $R_t$ 14.65 min.

Example 2

N1-[4-(4-Amino-7-cyclopentyl-7H-pyrrolo[2,3-d]pyrimidin-5-yl)-2-methoxyphenyl]-4-(trifluoromethyl)-1-benzenesulfonamide Example 2 was synthesized using the same method as for N1-[4-(4-Amino-7-cyclopentyl-7H-pyrrolo[2,3-d]pyrimidin-5-yl)-2-methoxyphenyl]-4-cyano-1-benzenesulfonamide.

$^1$H NMR (DMSO-$d_6$, 400 MHz) δ 9.90 (s, 1H), 8.22 (s, 1H), 7.96 (s, 4H), 7.55 (m, 1H), 7.29 (d, 2H), 7.01 (m, 2H), 5.09 (m, 1H), 3.49 (s, 3H), 2.10 (m, 2H), 1.90 (m, 4H), 1.69 (m, 2H); MH$^-$530; TLC (ethyl acetate/methanol=9:1) $R_f$ 0.64; RP-HPLC (Hypersil C18, 5 μm, 200 A, 25 cm; 25%-98% acetonitrile-0.1M ammonium acetate over 25 min, 1 ml/min) $R_t$ 17.78 min.

Example 3

N1-[4-(4-Amino-7-cyclopentyl-7H-pyrrolo[2,3-d]pyrimidin-5-yl)-2-methoxyphenyl]-4-(trifluoromethoxyl)-1-benzenesulfonamide Example 3 was synthesized using the same method as for N1-[4-(4-Amino-7-cyclopentyl-7H-pyrrolo[2,3-d]pyrimidin-5-yl)-2-methoxyphenyl]-4-cyano-1-benzenesulfonamide.

$^1$H NMR (CDCl$_3$, 400 MHz) δ 8.30 (s, 1H), 7.86 (d, 2H), 7.59 (d, 1H), 7.27 (d, 2H), 7.13 (broad, 1H), 7.05 (dd, 1H), 7.00 (s, 1H), 6.86 (d, 1H), 5.26 (s, 2H), 5.19 (m, 1H), 3.68 (s, 3H), 2.26 (m, 2H), 1.89 (m, 4H), 1.79 (m, 2H); MH$^+$548; TLC (ethyl acetate) $R_f$ 0.34; RP-HPLC (Hypersil C18, 5 μm, 200 A, 25 cm; 25%-98% acetonitrile-0.1M ammonium acetate over 25 min, 1 ml/min) $R_t$ 18.18 min.

Example 4

N2-[4-(4-Amino-7-cyclopentyl-7H-pyrrolo[2,3-d]pyrimidin-5-yl)-2-methoxyphenyl]-2-pyridinesulfonamide a) 2-Pyridinesulfonyl chloride was prepared as described in Heterocycles, 1989, 28, 1115. chlorine gas was bubbled into the solution of 2-pyridinethiol (2.00 g, 17.99 mmol) in concentrated hydrochloric acid (30 ml) at 0° C. for 3 h. The reaction mixture was poured into ice-cold water (40 ml) and the resulting precipitate was collected by filtration. The precipitate was further washed with ice-cold water and then dried over phosphorus pentaoxide in vacuo at 0° C. for 2 h to afford 2-pyridinesulfonyl chloride as white solids (2.00 g, 11.26 mmol).

b) N2-[4-(4-amino-7-cyclopentyl-7H-pyrrolo[2,3-d]pyrimidin-5-yl)-2-methoxyphenyl]-2-pyridinesulfonamide. A mixture of 5-(4-amino-3-methoxyphenyl)-7-cyclopentyl-7H-pyrrolo[2,3-d]pyrimidin-4-amine (0.040 g, 0.12 mmol), 2-pyridinesulfonyl chloride (0.026 g, 0.15 mmol) and pyridine (0.40 ml) was stirred at 0° C. for 3 h. The reaction mixture was diluted with ether and the resulting solution was washed successively with 2 N hydrochloric acid, water and saturated aqueous sodium chloride solution. The organic layer was concentrated to leave a residue which was purified by preparative RP-HPLC (Rainin C18, 8 μm, 300 A, 25 cm; 25%-100% acetonitrile-0.1M ammonium acetate over 25 min, 21 ml/min) to give N2-[4-(4-amino-7-cyclopentyl-7H-pyrrolo[2,3-d]pyrimidin-5-yl)-2-methoxyphenyl]-2-pyridinesulfonamide as white solid (0.022 g, 0.05 mmol): $^1$H NMR (CDCl$_3$, 400 MHz) δ 8.71 (d, 1H), 8.31 (s, 1H), 8.01 (d, 1H), 7.87 (m, 1H), 7.64 (d, 1H), 7.47 (m, 1H), 7.41 (m, 1H), 6.99 (m, 2H), 6.87 (s, 1H), 5.19 (m, 1H), 5.07 (s, 2H), 3.79 (s, 3H), 2.23 (m, 2H), 1.76-1.88 (m, 4H), 1.63 (m, 2H); MH$^+$465; RP-HPLC (Hypersil C18, 5 μm, 200 A, 25 cm; 25%-98% acetonitrile-0.1M ammonium acetate over 25 min, 1 ml/min) R$_t$ 12.65 min.

Example 5

N3-[4-(4-Amino-7-cyclopentyl-7H-pyrrolo[2,3-d]pyrimidin-5-yl)-2-methoxyphenyl]-3-pyridinesulfonamide a) 3-Pyridinesulfonyl chloride was prepared as described in J. Heterocyclo. Chem. 1992, 29, 61. A mixture of 3-pyridinesulfonic acid (1.45 g, 9.01 mmol) and phosphorus pentachloride (2.00 g, 9.62 mmol) was heated at 110° C. for 3 h. The mixture was allowed to cool to room temperature and distilled (b.p. 60-65° C.) under reduced pressure (0.1 mmHg) to afford 3-pyridinesulfonyl chloride as white solids (1.12 g, 6.31 mmol) which was used directly without further purification.

b) N3-[4-(4-amino-7-cyclopentyl-7H-pyrrolo[2,3-d]pyrimidin-5-yl)-2-methoxyphenyl]-3-pyridinesulfonamide. A mixture of 5-(4-amino-3-methoxyphenyl)-7-cyclopentyl-7H-pyrrolo[2,3-d]pyrimidin-4-amine (0.040 g, 0.12 mmol), 3-pyridinesulfonyl chloride (0.030 g, 0.17 mmol) and pyridine (0.40 ml) was stirred at 0° C. for 0.5 h. Water was added into the reaction mixture followed by removal of most of pyridine and water under reduced pressure. The residue was purified by preparative RP-HPLC (Rainin C18, 8 μm, 300 A, 25 cm; 25%-100% acetonitrile-0.1M ammonium acetate over 25 min, 21 ml/min) to give N3-[4-(4-amino-7-cyclopentyl-7H-pyrrolo[2,3-d]pyrimidin-5-yl)-2-methoxyphenyl]-3-pyridinesulfonamide as white solids (0.020 g, 0.04 mmol): $^1$H NMR (CDCl$_3$, 400 MHz) δ 8.97 (d, 1H), 8.76 (d, 1H), 8.29 (s, 1H), 8.10 (dd, 1H), 7.62 (d, 1H), 7.40 (m, 1H), 7.05 (d, 1H), 7.00 (s, 1H), 6.85 (s, 1H), 5.31 (broad, 2H), 5.20 (m, 1H), 3.68 (s, 3H), 2.26 (m, 2H), 1.80-2.00 (m, 6H); MH$^+$465; RP-HPLC (Hypersil C18, 5 μm, 200 A, 25 cm; 25%-98% acetonitrile-0.1M ammonium acetate over 25 min, 1 ml/min) R$_t$ 12.23 min.

Example 6

N1-[5-(4-amino-7-cyclopentyl-7H-pyrrolo[2,3-d]pyrimidin-5-yl)-2-(trifluoromethyl)phenyl]-1-benzenesulfonamide a) N1-[4-bromo-2-(trifluoromethyl)phenyl]-1-benzenesulfonamide. Benzenesulfonyl chloride (1.06 g, 6.00 mmol) was added dropwise to a stirring solution of 4-bromo-2-(trifluoromethyl)-aniline (1.20 g, 5.00 mmol) and pyridine (1.98 g, 25.0 mmol) in dichloromethane (10 ml) at 0° C. under an atmosphere of nitrogen. The mixture was warmed to ambient temperature and stirred for 16 hours. The mixture was diluted with ethyl acetate (35 ml) then washed with water (3×10 ml), 2N citric acid (3×10 ml) and brine (10 ml) then evaporated in vacuo. The residue was purified by silica gel flash column chromatography using 3:2 heptane:methylene chloride as an eluent to give N1-[4-bromo-2-(trifluoromethyl)phenyl]-1-benzenesulfonamide (1.3 g) as a white solid. $^1$H NMR (DMSO-d$_6$, 400 MHz) δ 10.10 (1H, s), 7.60-8.16 (7H, m), 6.9 (1H, dd); t$_R$=24.27 min (RP-HPLC, 5-100% acetonitrile-0.1%TFA, 30 min)

b) N1-[5-(4-amino-7-cyclopentyl-7H-pyrrolo[2,3-d]pyrimidin-5-yl)-2-(trifluoromethyl)phenyl]-1-benzenesulfonamide. A mixture of N1-[4-bromo-2-(trifluoromethyl)phenyl]-1-benzenesulfonamide (0.5 g, 1.31 mmol), bis(pinacolato) diboron (0.402 g, 1.58 mmol), potassium acetate (0.387 g, 3.95 mmol) and [1,1'-bis(diphenylphosphino)ferrocene]dichloropalladium(II) (32 mg, 0.040 mmol) in DMF (10 ml) was heated under an atmosphere of nitrogen at 100° C. for 17 hours. The mixture was cooled and [1,1'-bis(diphenylphosphino)ferrocene]dichloropalladium(II) (32 mg, 0.040 mmol) was added then heating at 100° C. was continued for another 24 hours. The solvent was then removed in vacuo and the residue triturated with 25 ml 4:1 heptane:methylene chloride and the solids removed by filtration through a pad of celite. Removal of the solvent in vacuo resulted in a gummy residue (0.42 g) of which (123 mg, 0.28 mmol) was added to a mixture of 1,2-dimethoxyethane (2.5 ml) and water (1.25 ml). Sodium carbonate (39 mg, 0.36 mmol), 4-chloro-7-cyclopentyl-5-iodo-7H-pyrrolo[2,3-d]pyrimidine (50 mg, 0.144 mmol) and tetrakis (triphenylphosphine)palladium(0) (9.0 mg, 0.008 mol) were added to the mixture which was then heated to reflux under an atmosphere of nitrogen for 16 hours, cooled and the solvent removed in vacuo. The residue was partitioned between ethyl acetate (10 ml) and water (6 ml). The aqueous layer was separated and washed with ethyl acetate (10 ml). The combined organics were evaporated and the residue dissolved in 1,4-dioxane (5 ml) and concentrated aqueous ammonium hydroxide (5 ml) then heated at 120° C. in a sealed tube for 16 hours. The solvents were removed in vacuo and purification by reverse phase MPLC using a C18 column and 25-75% acetonitrile-0.1% TFA, 25 min as an eluent followed by lyophilization afforded N1-[5-(4-amino-7-cyclopentyl-7H-pyrrolo[2,3-d]pyrimidin-5-yl)-2-(trifluoromethyl) phenyl]-1-benzenesulfonamide (9 mg) as a tan amorphous solid. $^1$H NMR (DMSO-d$_6$, 400 MHz) δ 10.05 (1H, brs), 8.38 (1H, s), 7.57-7.87 (10H, m), 7.09 (1H, d), 5.11 (1H, m), 2.14 (2H, m), 1.95 (4H, m), 1.7 (2H, m); low resolution MS, m/e (MH$^+$), 502; t$_R$ 16.78 min (RP-HPLC, 25-100% acetonitrile-0.1% TFA, 25 min)

Example 7

N1-[4-(4-amino-7-cyclopentyl-7H-pyrrolo[2,3-d]pyrimidin-5-yl)-2-phenyl-phenyl]-1-benzenesulfonamide a) 2-Amino-5-bromobiphenyl. 2,4,4,6-tetrabromo-2,5-cyclohexadien-1-one (12.1 g, 29.55 mmol) was added in portions to a solution of 2-aminobiphenyl (5.0 g, 29.55 mmol) in methylene chloride (65 ml) while maintaining the temperature between −5° C. and −10° C. The mixture was allowed to warm to ambient temperature and stirred for 20 hours. The solution was extracted twice with 1N sodium hydroxide (1×50 ml, 1×20 ml), then dried over MgSO$_4$, treated with activated charcoal, filtered through celite and evaporated to give 2-Amino-5-bromobiphenyl (7.2 g) as a black oil which solidified on standing. $^1$H NMR (DMSO-d$_6$, 400 MHz) δ 7.36-7.48 (5H, m), 7.2 (1H, dd), 7.08 (1H, d), 6.7 (1H, d), 4.95 (2H, bs); low-resolution MS m/e 249 (MH$^+$); t$_R$ 16.03 min (RP-HPLC, 25-100% acetonitrile-0.1% TFA, 25 min); $^{13}$C NMR (DMSO-d$_6$, 100 MHz) δ 144.5, 138.2, 131.9, 130.6, 128.8, 128.5, 127.7, 127.3, 117.1, 107.1 b) 1-(4-bromo-2-phenyl-phenyl)-1-benzenesulfonamide. Benzene sulfonylchloride (1.71 g, 9.67 mmol) was added dropwise under an atmosphere of nitrogen to a stirring solution of 2-amino-5-bromo-biphenyl (2.0 g, 8.06 mmol) and pyridine (3.19 g, 40.3 mmol) in methylene chloride (20 ml) at <0° C. The mixture was warmed to ambient temperature and stirred for 16 hours. The mixture was then diluted with ethyl acetate (75 ml) and washed with water (3×15 ml), 2N aqueous citric acid (3×15 ml), brine (15 ml), dried over MgSO$_4$, treated with charcoal and filtered through celite. Evaporation of the solvent in vacuo provided N1-(4-bromo-2-phenylbenzene)-1-benzenesulfonamide (2.9 g) as a brown solid. $^1$H NMR (DMSO-d$_6$, 400 MHz) δ 9.62 (1H, s), 7.34-8.07 (10H, m), 7.19 (2H, m), 7.01 (1H, d); low-resolution MS m/e 388 (MH$^+$); t$_R$=21.2 min (RP-HPLC, 25-100% acetonitrile-0.1% TFA, 25 min)

c) N1-[2-phenyl-4-(4,4,5,5-tetramethyl-1,3,2-dioxaborolan-2-yl)-phenyl]-1-benzenesulfonamide. A mixture of the N1-(4-bromo-2-phenylbenzene)-1-benzenesulfonamide (0.388 g, 1.00 mmol), bis(pinacolato)diboron (0.305 g, 1.20 mmol), potassium acetate (0.294 g, 3.00 mmol) and [1,1'-bis(diphenylphosphino) ferrocene]dichloropalladium(II) (25 mg, 0.030 mmol) in DMF (10 ml) was heated under an atmosphere of nitrogen at 100° C. for 16.5 hours. The DMF was evaporated in vacuo and the residue purified by silica gel flash chromatography using methylene chloride/heptane 7:3 plus 2% triethyl amine to provide N1-[4-(4,4,5,5-tetramethyl-1,3,2-dioxaborolan-2-yl)-2-phenyl-benzene]-1-benzenesulfonamide (0.135 g) as an oil. t$_R$=23.13 min (RP-HPLC, 25-100% acetonitrile-0.1% TFA, 25 min); low resolution MS m/e 434 (M–H$^+$)

d) N1-[4-(4-chloro-7-cyclopentyl-7H-pyrrolo[2,3-d]pyrimidin-5-yl)-2-phenyl-phenyl]-1-benzenesulfonamide. A mixture of sodium carbonate (57 mg, 0.54 mmol), 4-chloro-7-cyclopentyl-5-iodo-7H-pyrrolo[2,3-d]pyrimidine (75 mg, 0.216 mmol), N1-[4-(4,4,5,5-tetramethyl-1,3,2-dioxaborolan-2-yl)-2-phenylbenzene]-1-benzenesulfonamide (135 mg, 0.269 mmol), tetrakis(triphenylphosphine)palladium(0) (12.5 mg, 0.0108 mmol), water (1.25 ml) and DME (2.5 ml) was heated at reflux under an atmosphere of nitrogen for 16 hours, cooled and the solvent removed in vacuo. The residue was partitioned between ethyl acetate (10 ml) and water (5 ml). The organic layer was evaporated and the residue purified by silica gel flash chromatography to give N1-[4-(2-benzene-4-chloro-7-cyclopentyl-7H-pyrrolo[2,3-d]pyrimidin-5-yl)-phenyl]-1-benzenesulfonamide (55 mg) as a tan solid. $^1$H NMR (DMSO-d$_6$, 400 MHz) δ 9.56 (1H, s), 8.65 (1H, s), 8.03 (1H, s), 7.3-7.65 (12H, m), 7.08 (1H, d), 5.21 (1H, m), 2.17 (2H, m), 1.92 (4H, m), 1.71 (2H, m); t$_R$=23.77 min (RP-HPLC, 25-100% acetonitrile-0.1% TFA, 25 min)

e) N1-[4-(4-amino-7-cyclopentyl-7H-pyrrolo[2,3-d]pyrimidin-5-yl)-2-phenyl-phenyl]-1-benzenesulfonamide. A mixture of the N1-[4-(2-benzene-4-chloro-7-cyclopentyl-7H-pyrrolo[2,3-d]pyrimidin-5-yl)-phenyl]-1-benzenesulfonamide (55 mg, 0.104 mmol), concentrated aqueous ammonium hydroxide (5 ml), and 1,4-dioxane (5 ml) was heated at 120° C. in a sealed tube for 16 hours. The solution was cooled to room temperature and the solvent remove in vacuo. Purification by MPLC using a C18 column and 25-100% acetonitrile-0.1N ammonium acetate, 25 min as an eluent followed by lyophilization afforded N1-[4-(4-amino-2-benzene-7-cyclopentyl-7H-pyrrolo[2,3-d]pyrimidin-5-yl)-phenyl]-1-benzenesulfonamide (14 mg) as a tan solid. $^1$H NMR (DMSO-d$_6$, 400 MHz) δ 9.56 (1H, s), 8.13 (1H, s), 7.31-7.65 (13H, m), 7.1 (1H, d), 6.08 (2H, s), 5.07 (1H, m), 2.08 (2H, m), 1.9 (4H, m), 1.67 (2H, m); low-resolution MS m/e 510 (MH$^+$); t$_R$ 19.22 min (RP-HPLC, 25-100% acetonitrile-0.1N ammonium acetate, 25 min)

Example 8

7-cyclopentyl-5-[1-(phenylsulfonyl)-2,3-dihydro-1H-5-indolyl]-7H-pyrrolo[2,3-d]pyrimidin-4-amine a) 5-bromo-1-(phenylsulfonyl)indoline. Benzene sulfonylchloride (1.85 g, 10.53 mmol) was added dropwise under an atmosphere of nitrogen to a stirred solution of 5-bromoindoline (2.0 g, 8.77 mmol) and pyridine (3.47 g, 43.9 mmol) in methylene chloride (30 ml) at <0° C. The mixture was warmed to ambient temperature and stirred for 16 hours. The mixture was then diluted with methylene chloride (30 ml) and washed with 2N aqueous citric acid (3×20 ml), brine (20 ml), dried over MgSO$_4$, treated with charcoal and filtered through celite. Evaporation of the solvent in vacuo provided 5-bromo-1-(phenylsulfonyl)indoline (3.2 g). $^1$H NMR (DMSO-d$_6$, 400 MHz) δ 7.83 (2H, d), 7.68 (1H, t), 7.61 (2H, t), 7.31-7.43 (3H, m), 3.93 (2H, t), 2.92 (2H, t); t$_R$=19.30 min (RP-HPLC, 25-100% acetonitrile-0.1N ammonium acetate, 25 min)

b) 1-(phenylsulfonyl)-5-(4,4,5,5-tetramethyl-1,3,2-dioxaborolan-2-yl)indoline. A mixture of the 5-bromo-1-(phenylsulfonyl)indoline (1.0 g, 3.07 mmol), bis(pinacolato)diboron (0.935 g, 3.68 mmol), potassium acetate (0.902 g, 9.202 mmol) and [1,1'-bis(diphenylphosphino)ferrocene]dichloropalladium(II) (88 mg, 0.092 mmol) in DMF (20 ml) was heated under an atmosphere of nitrogen at 100° C. for 16 hours. The DMF was evaporated in vacuo and the residue triturated with toluene (20 ml) then the solids were removed by filtration through celite. The filtrate was washed with water (3×15 ml) then dried over MgSO$_4$, filtered and evaporated to a residue which was used crude in the next step. $^1$H NMR (DMSO-d$_6$, 400 MHz) δ 7.83 (2H, d), 7.43-7.68 (6H, m), 3.94 (2H, t), 2.94 (2H, t), 1.26 (12H, s); t$_R$=21.23 min (RP-HPLC, 25-100% acetonitrile-0.1N ammonium acetate, 25 min;

c) 7-cyclopentyl-5-[1-(phenylsulfonyl)-2,3-dihydro-1H-5-indolyl]-7H-pyrrolo[2,3-d]pyrimidin-4-amine. A mixture of sodium carbonate (92 mg, 0.087 mmol), 4-chloro-7-cyclopentyl-5-iodo-7H-pyrrolo[2,3-d]pyrimidine (100 mg, 0.288 mmol), 1-(phenylsulfonyl)-5-(4,4,5,5-tetramethyl-1,3,2-dioxaborolan-2-yl)indoline (200 mg, 0.431 mmol), tetrakis(triphenylphosphine)palladium(0) (17 mg, 0.0144 mmol), water (3 ml) and DME (6 ml) was heated at reflux under an atmosphere of nitrogen for 16 hours, cooled and the solvent removed in vacuo. The residue was partitioned between ethyl acetate (10 ml) and water (5 ml). The organic layer was evaporated and the residue was dissolved in 1,4-dioxane (6 ml) and concentrated aqueous ammonium hydroxide (6 ml) then heated at 120° C. in a sealed tube for 16 hours. The solution was cooled and the solvent removed in vacuo. Purification by reverse phase MPLC using a C18 column and 25-75% acetonitrile-0.1 N ammonium acetate, 25 min as an eluent followed by lyophilization gave 7-cyclopentyl-5-[1-(phenylsulfonyl)-2,3-dihydro-1H-5-indolyl]-7H-pyrrolo[2,3-d]pyrimidin-4-amine (23 mg) as a tan solid. $^1$H NMR (DMSO-d$_6$, 400 MHz) δ 8.11 (1H, d), 7.85 (2H, d), 7.70 (1H, t), 7.54-7.61 (3H, m), 7.25-7.33 (3H, m), 6.0 (2H, s), 5.06 (1H, m), 3.96 (2H, t), 2.95 (2H, t), 2.11 (2H, m), 1.90 (4H, m), 1.67 (2H, m); t$_R$=16.37 min (RP-HPLC, 25-100% acetonitrile-0.1N ammonium acetate, 25 min)

Example 9

N1-[4-(4-amino-7-cyclopentyl-7H-pyrrolo[2,3-d]pyrimidin-5-yl)-2-chlorophenyl]-N1-methyl-1-benzenesulfonamide a) N1-(4-bromo-2-chlorophenyl)-1-benzenesulfonamide. Benzene sulfonylchloride (2.11 g, 12.0 mmol) was added dropwise under an atmosphere of nitrogen to a stirring solution of 4-bromo-2-chloroaniline (2.06 g, 10.0 mmol), pyridine (3.95 g, 50 mmol) and methylene chloride (15 ml). The mixture was stirred for 3 hours then diluted with ethyl acetate (75 ml) and washed with water (3×20 ml), brine (20 ml) and then dried over MgSO$_4$, filtered and evaporated to give 3.2 g (92%) of N1-(4-bromo-2-chlorophenyl)-1-benzenesulfonamide as an orange solid. $^1$H NMR (DMSO-d$_6$, 400 MHz) δ 10.10 (1H, s), 7.7 (2H, d), 7.53-7.65 (4H, m), 7.46 (1H, d), 7.18 (1H, d); $^{13}$C NMR (DMSO-d$_6$, 100 MHz) δ 140.0, 131.1, 133.0, 132.0, 130.8, 130.3, 129.2, 128.8, 126.6, 119.0; low-resolution MS m/e 346 (M–H$^+$)

b) N1-(4-bromo-2-chlorophenyl)-N1-methyl-1-benzenesulfonamide. The N1-(4-bromo-2-chlorophenyl)-1-benzenesulfonamide (1.0 g, 2.89 mmol) in DMF (8 ml) was added under an atmosphere of nitrogen to a mixture of sodium hydride (0.14 g of a 60% dispersion in mineral oil, 3.47 mmol) in DMF (7 ml) at 0° C. The mixture was then treated with iodomethane (0.452 g, 3.18 mmol) while maintaining the temperature at <0° C. The mixture was warmed to ambient temperature, stirred for 16 hours then water (100 ml) was added. The mixture was extracted with ethyl acetate (3×20 ml) and the combined organic layers washed with water (3×20 ml), dried over MgSO$_4$, filtered and evaporated to give N1-(4-bromo-2-chlorophenyl)-N1-methyl-1-benzenesulfonamide (0.55 g). $^1$H NMR (DMSO-d$_6$, 400 MHz) δ 7.87 (1H, s), 7.55-7.80 (6H, m), 7.00 (1H, d), 3.11 (3H, s); t$_R$=19.58 min (RP-HPLC, 25-100% acetonitrile-0.1N ammonium acetate, 25 min)

c) N1-[2-chloro-4-(4,4,5,5-tetramethyl-1,3,2-dioxaborolan-2-yl)phenyl]-N1-methyl-1-benzenesulfonamide. A mixture of the N1-(4-bromo-2-chlorophenyl)-N1-methyl-1-benzenesulfonamide (0.5 g, 1.389 mmol), bis(pinacolato)diboron (0.423 g, 1.66 mmol), potassium acetate (0.408 g, 4.167 mmol) and [1,1'-bis(diphenylphosphino) ferrocene]dichloropalladium(II) (34 mg, 0.042 mmol) in DMF (20 ml) was heated under an atmosphere of nitrogen at 100° C. for 16 hours. The DMF was evaporated in vacuo and the residue triturated with toluene (15 ml) then filtered through celite to give N1-[2-chloro-4-(4,4,5,5-tetramethyl-1,3,2-dioxaborolan-2-yl)phenyl]-N1-methyl-1-benzenesulfonamide (0.25 g) as a dark oil which was used crude in the next step. $^1$H NMR (DMSO-d$_6$, 400 MHz) δ 7.93 (2H, d), 7.57-7.75 (5H, m), 7.07 (1H, d), 3.12 (3H, s), 1.29 (12H, s)

d) N1-[4-(4-amino-7-cyclopentyl-7H-pyrrolo[2,3-d]pyrimidin-5-yl)-2-chlorophenyl]-N1-methyl-1-benzenesulfonamide. A mixture of sodium carbonate (92 mg, 0.087 mmol), 4-chloro-7-cyclopentyl-5-iodo-7H-pyrrolo[2,3-d]pyrimidine (100 mg, 0.288 mmol), N1-[2-chloro-4-(4,4,5,5-tetramethyl-1,3,2-dioxaborolan-2-yl)phenyl]-N1-methyl-1-benzenesulfonamide (244 mg (72% pure by weight), 0.432 mmol), tetrakis(triphenylphosphine)palladium(0) (17 mg, 0.0144 mmol), water (3 ml) and DME (6 ml) was heated at reflux under an atmosphere of nitrogen for 16 hours, cooled and the solvent removed in vacuo. The residue was partitioned between ethyl acetate (20 ml) and water (10 ml). The organic layer was evaporated and the residue was dissolved in 1,4-dioxane (7 ml) and aqueous concentrated ammonium hydroxide (7 ml) then heated at 120° C. in a sealed tube for 16 hours. The solution was cooled and the solvent removed in vacuo. Purification by reverse phase MPLC using a C18 column and 25-75% acetonitrile-0.1 N ammonium acetate, 25 min as an eluent followed by lyophilization N1-[4-(4-amino-7-cyclopentyl-7H-pyrrolo[2,3-d]pyrimidin-5-yl)-2-chlorophenyl]-N1-methyl-1-benzenesulfonamide (20 mg) as a tan solid. $^1$H NMR (DMSO-d$_6$, 400 MHz) δ 8.15 (1H, s), 7.74-7.80 (3H, m), 7.64-7.66 (2H, m), 7.60 (1H, s), 7.39 (1H, d), 7.08 (1H, d), 6.20 (2H, s), 3.16 (3H, s), 2.14 (2H, m), 1.91 (4H, m), 1.69 (2H, m); low-resolution MS m/e 481 (M–H$^+$); t$_R$=22.45 min (RP-HPLC, 25-75% acetonitrile-0.1N ammonium acetate, 25 min)

Example 10

N1-[5-(4-amino-7-cyclopentyl-7H-pyrrolo[2,3-d]pyrimidin-5-yl)-2-pyridyl]-1-benzenesulfonamide a) tert-butyl N-(5-bromo-2-pyridyl)carbamate. A mixture of 5-bromo-2-pyridinamine (4.0 g, 23.1 mmol) and di-tert-butyl dicarbonate (6.31 g, 28.9 mmol) in tetrahydrofuran (50 ml) was heated at reflux for 20 hours. The mixture was allowed to cool to ambient temperature and the solvent was removed under reduced pressure. Methylene chloride (30 ml) and ethyl acetate (30 ml) were added and the mixture was extracted with saturated aqueous sodium bicarbonate (25 ml). The organic layer was evaporated in vacuo and approximately one quarter of the residue was purified by silica gel flash column chromatography using 95:5 n-heptane/ethyl acetate as an eluent to give tert-butyl N-(5-bromo-2-pyridyl)carbamate (0.61 g) as an oil. $^1$H NMR (DMSO-d$_6$, 400 MHz) δ 9.96 (1H, s), 8.34 (1H, d), 7.93 (1H, dd), 7.77 (1H, d), 1.47 (9H, s)

b) tert-butyl N-[5-(1,1,1-trimethylstannyl)-2-pyridyl]carbamate. A mixture of tert-butyl N-(5-bromo-2-pyridyl)carbamate (0.5 g, 1.83 mmol), hexamethylditin (0.6 g, 1.832 mmol) and tetrakis(triphenylphosphine)palladium(0) (130 mg, 0.107 mmol) and dimethoxyethane (10 ml) was heated at 80° C. under an atmosphere of nitrogen for 15 hours. The mixture was allowed to cool to ambient temperature and then the solvent was removed under reduced pressure. The residue was purified by flash column chromatography on silica using heptane/ethyl acetate (95:5 as an eluent to give tert-butyl N-[5-(1,1,1-trimethylstannyl)-2-pyridyl]carbamate (242 mg) as an oil: $^1$H NMR (DMSO-d$_6$, 400 MHz) δ 9.31 (1H, s), 8.15 (1H, s), 7.65-7.72 (2H, m), 1.44 (9H, s), 0.24 (9H, s); low-resolution MS m/e 481 c) tert-butyl N-[5-(4-amino-7-cyclopentyl-7H-pyrrolo[2,3-d]pyrimidin-5-yl)-2-pyridyl]carbamate. A mixture of tert-butyl N-[5-(1,1,1-trimethylstannyl)-2-pyridyl]carbamate (230 mg, 0.644 mmol), 4-Chloro-7-cyclopentyl-5-iodo-7H-pyrrolo[2,3-d]pyrimidine (225 mg, 0.644 mmol), tris (dibenzylideneacetone) dipalladium(0) (30 mg, 0.0322 mmol), triphenylarsine (50 mg, 0.161 mmol) and DMF (8 ml) was heated at 80° C. under an atmosphere of nitrogen for 18 hours. The mixture was allowed to cool to ambient temperature and the solvent was removed under reduced pressure to give a residue which was partitioned between water (5 ml) and ethyl acetate (20 ml). The organic layer was separated and the organic layer was further extracted with water (5 ml) brine (5 ml), dried over MgSO$_4$, filtered and evaporated to give a residue which was purified by silica gel flash chromatography using heptane/ethyl acetate (8:2) as an eluent to give tert-butyl N-[5-(4-amino-7-cyclopentyl-7H-pyrrolo[2,3-d]pyrimidin-5-yl)-2-pyridyl]carbamate (170 mg) as a tan solid.; $^1$H NMR (DMSO-d$_6$, 400 MHz) δ 9.66 (1H, s), 8.58 (1H, s), 8.35 (1H, s), 7.89 (1H, s), 7.82 (2H, m), 5.2 (1H, m), 2.16 (2H, m), 1.92 (4H, m), 1.71 (2H, m), 1.47 (9H, s);

d) 5-(4-chloro-7-cyclopentyl-7H-pyrrolo[2,3-d]pyrimidin-5-yl)-2-pyridinamine. Trifluoroacetic acid (2 ml) was added dropwise to a solution of tert-butyl N-[5-(4-amino-7-cyclopentyl-7H-pyrrolo[2,3-d]pyrimidin-5-yl)-2-pyridyl]carbamate (165 mg, 0.4 mmol) in dichloromethane (7 ml) at 0° C. The ice bath was removed and the reaction mixture was stirred at room temperature for 6 h. The solvents were removed in vacuo then the residue was redissolved in ethyl acetate (55 ml) and washed with saturated aqueous sodium bicarbonate solution (10 ml), dried over magnesium sulfate, filtered and evaporated to give 5-(4-chloro-7-cyclopentyl-7H-pyrrolo[2,3-d]pyrimidin-5-yl)-2-pyridinamine (133 mg): $^1$H NMR (DMSO-d$_6$, 400 MHz) δ 8.63 (1H, s), 8.05 (1H, dd), 7.86 (1H, d), 7.55 (1H, d), 6.52 (1H, d), 6.06 (2H, bs), 5.20 (2H, m), 2.16 (2H, m), 1.97 (4H, m), 1.72 (2H, m); low resolution MS, m/e (MH$^+$) 314.

e) N1-[5-(4-chloro-7-cyclopentyl-7H-pyrrolo[2,3-d]pyrimidin-5-yl)-2-pyridyl]-1-benzenesulfonamide. Benzenesulfonyl chloride (366 mg, 2.07 mmol) was added under an atmosphere of nitrogen to a stirred solution of the 5-(4-chloro-7-cyclopentyl-7H-pyrrolo[2,3-d]pyrimidin-5-yl)-2-pyridinamine (125 mg, 0.4 mmol) and pyridine (294 mg, 3.7 mmol) in methylene chloride (10 ml). The mixture was heated at 80° C. for 20 hours in a sealed tube. The mixture was cooled and the solvents evaporated in vacuo. The residue was redissolved in methylene chloride (50 ml) and washed with saturated sodium bicarbonate (15 ml), dried over MgSO$_4$, filtered and evaporated to a residue which was purified by silica gel flash column chromatography using heptane/ethyl acetate as an eluent to give N1-[5-(4-chloro-7-cyclopentyl-7H-pyrrolo[2,3-d]pyrimidin-5-yl)-2-pyridyl]-1-benzenesulfonamide (90 mg) as a tan solid. $^1$H NMR (DMSO-d$_6$, 400 MHz) δ 11.3 (1H, bs), 8.66 (1H, s), 8.2 (1H, bs), 7.89-7.99 (4H, m), 7.54-7.62 (3H, m), 7.2 (1H, bs), 5.2 (1H, m), 2.16 (2H, m), 1.92 (4H, m), 1.71 (2H, m); low resolution MS, m/e (MH$^+$) 454.

f) N1-[5-(4-amino-7-cyclopentyl-7H-pyrrolo[2,3-d]pyrimidin-5-yl)-2-pyridyl]-1-benzenesulfonamide. A mixture of the N1-[5-(4-chloro-7-cyclopentyl-7H-pyrrolo[2,3-d]pyrimidin-5-yl)-2-pyridyl]-1-benzenesulfonamide (90 mg), concentrated aqueous ammonium hydroxide (5 ml), and 1,4-dioxane (5 ml) was heated at 120° C. in a sealed tube for 16 hours. The solution was cooled to room temperature and the solvent remove in vacuo. Purification by MPLC using a C18 column and 25-100% acetonitrile-0.1N ammonium acetate, 25 min as an eluent followed by lyophilization afforded N1-[5-(4-amino-7-cyclopentyl-7H-pyrrolo[2,3-d]pyrimidin-5-yl)-2-pyridyl]-1-benzenesulfonamide (20 mg) as a tan solid. $^1$H NMR (DMSO-d$_6$, 400 MHz) δ 8.12 (1H, s), 8.08 (1H, bs), 7.92 (2H, d), 7.79 (2H, d), 7.60 (3H, m), 7.44 (1H, s), 7.23 (1H, d), 6.19 (2H, bs), 5.05 (1H, m), 2.10 (2H, m), 1.91 (4H, m), 1.67 (2H, m); low-resolution MS m/e 435 (MH$^+$).

Example 11

N1-[4-(4-Amino-7-cyclopentyl-7H-pyrrolo[2,3-d]pyrimidin-5-yl)-2-chlorophenyl]-2-cyano-1-benzenesulfonamide a) 5-(4-Amino-3-chlorophenyl)-7-cyclopentyl-7H-pyrrolo[2,3-d]pyrimidin-4-amine. Example 11 was prepared using the same method as for 5-(4-amino-3-methoxyphenyl)-7-cyclopentyl-7H-pyrrolo[2,3-d]pyrimidin-4-amine $^1$H NMR (DMSO-d$_6$, 400 MHz) δ 8.10 (s, 1H), 7.29 (s, 2H), 7.12 (dd, 1H), 6.88 (d, 1H), 6.00 (broad, 2H), 5.41 (s, 2H), 5.06 (m, 1H), 2.09 (m, 2H), 1.87 (m, 4H), 1.68 (m, 2H); MH$^+$329; TLC (ethyl acetate) R$_f$ 0.27; RP-HPLC (Hypersil C18, 5 μm, 200 A, 25 cm; 25%-100% acetonitrile-0.1M ammonium acetate over 25 min, 1 ml/min) R$_t$ 14.02 min.

b) N1-[4-(4-Amino-7-cyclopentyl-7H-pyrrolo[2,3-d]pyrimidin-5-yl)-2-chlorophenyl]-2-cyano-1-benzenesulfonamide. A mixture of 5-(4-amino-3-chlorophenyl)-7-cyclopentyl-7H-pyrrolo[2,3-d]pyrimidin-4-amine (0.098 g, 0.30 mmol), 2-cyanobenzenesulfonyl chloride (0.072 g, 0.36 mmol) and pyridine (0.98 ml) was stirred at room temperature for 16 h. Most of pyridine was removed under reduced pressure and the residue was purified by preparative RP-HPLC (Rainin C18, 8 μm, 300 A, 25 cm; 25%-100% acetonitrile–0.1M ammonium acetate over 25 min, 21 ml/min) to give N1-[4-(4-amino-7-cyclopentyl-7H-pyrrolo[2,3-d]pyrimidin-5-yl)-2-chlorophenyl]-2-cyano-1-benzenesulfonamide as a white solid (0.025 g, 0.05 mmol): $^1$H NMR (CDCl$_3$, 400 MHz) δ 8.31 (s, 1H), 8.17 (d, 1H), 7.70-7.82 (m, 5H), 7.44 (s, 1H), 7.40 (dd, 1H), 7.00 (s, 1H), 5.27 (broad, 2H), 5.00 (m, 1H), 2.23 (m, 2H), 1.79-1.90 (m, 6H); MH$^+$493; TLC (ethyl acetate) R$_f$ 0.30; RP-HPLC (Hypersil C18, 5 μm, 200 A, 25 cm; 25%-100% acetonitrile-0.1M ammonium acetate over 25 min, 1 ml/min) R$_t$ 15.27 min.

Example 12

N1-[4-(4-Amino-7-cyclopentyl-7H-pyrrolo[2,3-d]pyrimidin-5-yl)-2-chlorophenyl]-3-cyano-1-benzenesulfonamide Example 12 was prepared using the same method as for N1-[4-(4-Amino-7-cyclopentyl-7H-pyrrolo[2,3-d]pyrimidin-5-yl)-2-chlorophenyl]-2-cyano-1-benzenesulfonamide (Example 11).
$^1$H NMR (CDCl$_3$, 400 MHz) δ 8.30 (s, 1H), 8.07 (m, 2H), 7.86 (d, 1H), 7.73 (d, 1H), 7.65 (dd, 1H), 7.43 (s, 2H), 7.05 (s, 1H), 5.30 (broad, 2H), 5.20 (m, 1H), 2.44 (m, 2H), 1.77-1.89 (m, 6H); MH$^+$493; RP-HPLC (Hypersil C18, 5 μm, 200 A, 25 cm; 25%-98% acetonitrile-0.1M ammonium acetate over 25 min, 1 ml/min) R$_t$ 15.52 min.

Example 13

N3-[4-(4-Amino-7-cyclopentyl-7H-pyrrolo[2,3-d]pyrimidin-5-yl)-2-chlorophenyl]-3-pyridinesulfonamide Example 13 was prepared using the same method as for N1-[4-(4-Amino-7-cyclopentyl-7H-pyrrolo[2,3-d]pyrimidin-5-yl)-2-chlorophenyl]-2-cyano-1-benzenesulfonamide I (Example 11).
$^1$H NMR (CDCl$_3$, 400 MHz) δ 8.97 (s, 1H), 8.81 (dd, 1H), 8.33 (s, 1H), 8.13 (dd, 1H), 7.77 (d, 1H), 7.44 (m, 3H), 7.02 (s, 1H), 5.21 (m, 1H), 5.06 (broad, 2H), 2.24 (m, 2H), 1.78-1.89 (m, 6H); MH$^+$469; RP-HPLC (Hypersil C18, 5 µm, 200 A, 25 cm; 25%-98% acetonitrile-0.1M ammonium acetate over 25 min, 1 ml/min) R$_t$ 13.03 min.

Example 14

N1-[4-(4-Amino-7-cyclopentyl-7H-pyrrolo[2,3-d] pyrimidin-5-yl)-2-chlorophenyl]-2-trifluoromethyl-1-benzenesulfonamide Example 14 was prepared using the same method as for N1-[4-(4-Amino-7-cyclopentyl-7H-pyrrolo[2,3-d]pyrimidin-5-yl)-2-chlorophenyl]-2-cyano 1-benzenesulfonamide (Example 11).

$^1$H NMR (CDCl$_3$, 400 MHz) δ 8.33 (s, 1H), 8.09 (d, 1H), 7.92 (d, 1H), 7.72 (m, 2H), 7.64 (m, 1H), 7.41 (s, 1H), 7.36 (d, 1H), 7.00 (s, 1H), 5.21 (multiple, 1H), 5.01 (broad, 2H), 2.25 (m, 2H), 1.77-1.91 (m, 6H); MH$^+$536; RP-HPLC (Hypersil C18, 5 µm, 200 A, 25 cm; 25%-98% acetonitrile-0.1M ammonium acetate over 25 min, 1 ml/min) R$_t$ 18.15 min.

Example 15

N1-[4-(4-Amino-7-cyclopentyl-7H-pyrrolo[2,3-d] pyrimidin-5-yl)-2-chlorophenyl]-3-trifluoromethyl-1-benzenesulfonamide Example 15 was prepared using the same method as for. N1-[4-(4-Amino-7-cyclopentyl-7H-pyrrolo[2,3-d]pyrimidin-5-yl)-2-chlorophenyl]-2-cyano-1-benzenesulfonamide (Example 11).

$^1$H NMR (CDCl$_3$, 400 MHz) δ 8.29 (s, 1H), 8.04 (d, 2H), 7.85 (d, 1H), 7.77 (d, 1H), 7.65 (m, 1H), 7.38 (m, 2H), 7.07 (s, 1H), 6.01 (broad, 2H), 5.20 (m, 1H), 2.27 (m, 2H), 1.79-1.90 (m, 6H); MH$^+$536; RP-HPLC (Hypersil C18, 5 µm, 200 A, 25 cm; 25%-98% acetonitrile-0.1M ammonium acetate over 25 min, 1 ml/min) R$_t$ 18.43 min.

Example 16

N1-4-[4-amino-7-(3-hydroxycyclopentyl)-7H-pyrrolo[2,3-d]pyrimidin-5-yl]-2-chlorophenyl-1-benzenesulfonamide a) 4-(4-chloro-5-iodo-7H-pyrrolo[2,3-d]pyrimidin-7-yl)-2-cyclopenten-1-ol. Dimethyl sulfoxide (3.5 ml) was degassed and then stirred under an atmosphere of nitrogen. The reaction vessel was protected from light and then 4-chloro-5-iodo-7H-pyrrolo[2,3-d]pyrimidine (570 mg, 2.03 mmol) and tetrakis (triphenylphosphine) palladium (0) (0.05 g, 0.041 mmol) were added. The mixture was stirred for 2 minutes then cooled to 0° C. The mixture was then treated with the 2,4a-dihydro-1aH-cyclopenta[b]oxirene (200 mg, 2.44 mmol) which was dissolved in tetrahydrofuran (3.5 ml) and added in a dropwise fashion over approximately 15 minutes. The reaction mixture was stirred at 0° C. for three hours then warmed to ambient temperature and stirred for 15 hours. The mixture was then treated with an additional portion of epoxide (85 mg, 1.04 mmol) and tetrakis(triphenylphosphine)palladium(0) (0.025 g, 0.020 mmol) and stirring continued for another 24 hours. The mixture was then partitioned between ethyl acetate (20 ml) and water (20 ml). The layers were separated and the aqueous layer washed with methylene chloride (3×20 ml). The organic layers were combined, washed with water (20 ml), dried over magnesium sulfate, filtered and evaporated. Purification of the residue by reverse phase MPLC using a C18 column and 25-50% acetonitrile-0.1 N ammonium acetate, 15 min as an eluent followed by evaporation of the acetonitrile and collection of the resulting solids by filtration afforded 4-(4-chloro-5-iodo-7H-pyrrolo[2,3-d]pyrimidin-7-yl)-2-cyclopenten-1-ol (365 mg) as a tan solid. $^1$H NMR (DMSO-d$_6$, 400 MHz) δ 8.66 (1H, s), 7.87 (1H, s), 6.20 (1H, m), 5.93 (1H, m), 5.77 (1H, m), 5.27 (1H, d), 4.72 (1H, m), 2.89 (1H, m), 1.62 (1H, m); $^{13}$C NMR (DMSO-d$_6$, 100 MHz) δ 150.9, 150.4, 149.9, 139.7, 133.8, 130.9, 116.2, 73.5, 57.8, 52.2, 41.1; low-resolution MS m/e 362 (MH$^+$).

b) N1-2-chloro-4-[4-chloro-7-(4-hydroxy-2-cyclopentenyl)-7H-pyrrolo[2,3-d]pyrimidin-5-yl]phenyl-1-benzenesulfonamide. A mixture of sodium carbonate (130 mg, 1.213 mmol), 4-(4-chloro-5-iodo-7H-pyrrolo[2,3-d]pyrimidin-7-yl)-2-cyclopenten-1-ol (175 mg, 0.485 mmol), N1-[2-chloro-4-(4,4,5,5-tetramethyl-1,3,2-dioxaborolan-2-yl)phenyl]-1-benzenesulfonamide (475 mg, 0.727 mmol), tetrakis(triphenylphosphine) palladium(0) (30 mg, 0.024 mmol), water (4 ml) and DME (8 ml) was heated at reflux under an atmosphere of nitrogen for 16 hours, cooled and the solvent removed in vacuo. The residue was partitioned between ethyl acetate (20 ml) and water (5 ml). The aqueous layer was washed further with ethyl acetate (20 ml) and methylene chloride (2×20 ml). The combined organic layers were dried over MgSO$_4$, filtered and evaporated to give an oil which solidified upon standing. Purification silica gel flash chromatography using heptane/ethyl acetate (7:3) as an eluent provided the N1-2-chloro-4-[4-chloro-7-(4-hydroxy-2-cyclopentenyl)-7H-pyrrolo[2,3-d]pyrimidin-5-yl]phenyl-1-benzenesulfonamide (45 mg) as a tan solid. $^1$H NMR (DMSO-d$_6$, 400 MHz) δ 10.06 (1H, s), 8.69 (1H, s), 7.29-7.80 (9H, m), 6.19 (1H, m), 5.96 (1H, m), 5.85 (1H, m), 5.22 (1H, d), 2.92 (1H, m), 1.68 (1H, m); low-resolution MS m/e 501 (MH$^+$); t$_R$=14.82 min (RP-HPLC, 25-100% acetonitrile-0.1N ammonium acetate, 25 min).

c) N1-4-[4-amino-7-(4-hydroxy-2-cyclopentenyl)-7H-pyrrolo[2,3-d]pyrimidin-5-yl]-2-chlorophenyl-1-benzenesulfonamide. The N1-2-chloro-4-[4-chloro-7-(4-hydroxy-2-cyclopentenyl)-7H-pyrrolo[2,3-d]pyrimidin-5-yl] phenyl-1-benzenesulfonamide (45 mg) was dissolved in 1,4-dioxane (7 ml) and aqueous concentrated ammonium hydroxide (7 ml) then heated at 120° C. in a sealed tube for 16 hours. The solution was cooled and the solvent removed in vacuo to give the N1-4-[4-amino-7-(4-hydroxy-2-cyclopentenyl)-7H-pyrrolo[2,3-d]pyrimidin-5-yl]-2-chlorophenyl-1-benzenesulfonamide which was used without further purification in the next step. low-resolution MS m/e 482 (MH$^+$); t$_R$=10.75 min (RP-HPLC, 25-100% acetonitrile-0.1N ammonium acetate, 25 min).

d) N1-4-[4-amino-7-(3-hydroxycyclopentyl)-7H-pyrrolo[2,3-d]pyrimidin-5-yl]-2-chlorophenyl-1-benzenesulfonamide. A mixture of alkene (45 mg) and 10% palladium on carbon (25 mg) was stirred under an atmosphere of hydrogen at room temperature and atmospheric pressure for 19 hours then filtered through a 0.2 um cartridge filter and the solvent removed in vacuo. Purification by reverse phase MPLC using a C18 column and 25-100% acetonitrile-0.1 N ammonium acetate, 25 min as an eluent followed by lyophilization provided N1-4-[4-amino-7-(3-hydroxycyclopentyl)-7H-pyrrolo[2,3-d]pyrimidin-5-yl]-2-chlorophenyl-1-benzenesulfonamide (20 mg) as a tan solid. $^1$H NMR (DMSO-d$_6$, 400 MHz) δ 10.03 (1H, bs), 8.15 (1H, s), 7.77 (2H, d), 7.29-7.67 (7H, m), 6.12 (1H, bs), 5.14 (1H, m), 4.98 (1H, d), 4.23 (1H, d), 2.37 (1H, m), 2.02-2.12 (2H, m)<1.77 (3H, m); low-resolution MS m/e 484 (MH$^+$); $t_R$=11.00 min (RP-HPLC, 25-100% acetonitrile-0.1N ammonium acetate, 25 min)

Example 17

Neopentyl N-(4-(4-amino-7-cyclopentyl-7H-pyrrolo [2,3-d]pyrimidin-5-yl)-2-methoxyphenyl)carbamate Neopentylchloroformate (28 uL, 0.186 mmol) was added dropwise to a stirring solution of 5-(4-amino-3-methoxyphenyl)-7-cyclopentyl-7H-pyrrolo[2,3-d]pyrimidin-4-amine (50 mg, 0.155 mmol) in pyridine (1 mL) and dichloromethane (1 mL) under nitrogen at 0° C. After 10 minutes, the ice water bath was removed and the resulting mixture was stirred for 4 hours. The solvent was evaporated and the residue was taken into ethyl acetate. The organic layer was washed, dried and evaporated. The solid was purified by preparative TLC using dichloromethane/methanol (95:5) as the mobile phase to give neopentyl N-[4-(4-amino-7-cyclopentyl-7H-pyrrolo[2,3-d] pyrimidin-5-yl)-2-methoxyphenyl]carbamate. $^1$H NMR (CDCl$_3$) δ 1.00 (s 9H), 1.78 (m, 2H), 1.90 (m, 4H), 2.26 (m, 2H), 3.91 (s, 2H), 3.94 (s, 3H), 5.22 (m, 3H), 6.22 (s, 1H), 7.01 (s, 1H), 7.08 (d, J=8 Hz, 1H), 7.25 (s, 1H), 8.17 (br. d, 1H), 8.32 (s, 1H); LC/MS (MH$^+$=438).

Example 18

3-Pyridylmethyl N-(4-(4-amino-7-cyclopentyl-7H-pyrrolo[2,3-d]pyrimidin-5-yl)-2-methoxyphenyl) carbamate a) 4-Nitrophenyl (3-pyridylmethyl) carbonate. N-Methylmorpholine (2.0 mL, 18.5 mmol) was added dropwise to solution of p-nitrophenyl chloroformate (2.49 g, 12.3 mmol) in dichloromethane (20 mL) with stirring under nitrogen at 0° C. After 20 minutes, the ice-water bath was removed and the mixture was allowed to warm up to ambient temperature. 3-pyridylcarbinol (1.0 mL, 10.3 mmol) was added to the mixture and the resulting solution was stirred for 30 minutes. The reaction mixture was diluted with ethyl acetate and washed with water, saturated sodium bicarbonate, brine. The organic layer was dried (MgSO$_4$), filtered and evaporated to give a dark brown solid. The solid was recrystallized from ethyl acetate and heptane to give 4-nitrophenyl (3-pyridylmethyl) carbonate. $^1$H NMR (CDCl$_3$) δ 5.32 (s, 2H), 7.38 (m, 3H), 7.79 (m 1H), 7.28 (m, 2H), 8.66 (d, J=4 Hz, 1H), 8.72 (s, 1H).

b) 3-Pyridylmethyl N-[4-(4-amino-7-cyclopentyl-7H-pyrrolo[2,3-d]pyrimidin-5-yl)-2-methoxyphenyl]carbamate. 4-Nitrophenyl (3-pyridylmethyl) carbonate (111 mg, 0.405 mmol) was added to a solution of 5-(4-amino-3-methoxyphenyl)-7-cyclopentyl-7H-pyrrolo[2,3-d]pyrimidin-4-amine (79 mg, 0.244 mmol) in pyridine (1 mL) followed by catalytic amount of N,N-dimethylpyridine. The resulting mixture was stirred under nitrogen at ambient temperature for 2 days. The solvent was evaporated and the residue was taken into ethyl acetate. The organic layer was washed, dried and evaporated. The solid was purified by preparative TLC using dichloromethane/methanol (95:5) as the mobile phase to give 3-pyridylmethyl N-[4-(4-amino-7-cyclopentyl-7H-pyrrolo[2,3-d]pyrimidin-5-yl)-2-methoxyphenyl]carbamate. $^1$H NMR (CDCl$_3$) δ 1.78 (m, 2H), 1.90 (m, 4H), 2.26 (m, 2H), 3.91 (s, 3H), 5.25 (m, 5H), 6.98 (s, 1H), 7.01 (s, 1H), 7.09 (d, J=8 Hz, 1H) 7.32 (m, 1H), 7.77 (d, J=8 Hz, 1H), 8.20 (br. d, 1H), 8.32 (s, 1H), 8.64 (m, 1H), 8.70 (s, 1H); LC/MS (MH$^+$=459).

c) 3-Pyridylmethyl N-[4-(4-amino-7-cyclopentyl-7H-pyrrolo[2,3-d]pyrimidin-5-yl)-2-methoxyphenyl]carbamate hydrochloride. 3-Pyridylmethyl N-[4-(4-amino-7-cyclopentyl-7H-pyrrolo[2,3-d]pyrimidin-5-yl)-2-methoxyphenyl]carbamate (50 mg, 0.109 mmol) was dissolved in ethyl acetate (3.0 mL). The mixture was cooled to 0° C. and hydrogen chloride gas was passed through for half a minute. Precipitate formed immediately. The flask was capped and the solution stirred for additional 10 minutes at 0° C. The solid was collected by filtration to give 3-pyridylmethyl N-[4-(4-amino-7-cyclopentyl-7H-pyrrolo[2,3-d] pyrimidin-5-yl)-2-methoxyphenyl]carbamate hydrochloride. $^1$H NMR (DMSO-d$_6$) δ 1.72 (m, 2H), 1.93 (m, 4H), 2.16 (m, 2H), 3.87 (s, 3H), 5.15 (m, 1H), 5.26 (s, 1H), 7.06 (d, J=2 Hz, 1H), 7.14 (s, 1H), 7.64 (d, J=5 Hz, 1H) 7.81 (m, 2H), 8.10 (d, J=8 Hz, 1H), 8.47 (s, 1H), 8.66 (d, J=5 Hz, 1H), 8.78 (s, 1H), 8.87 (s, 1H); LC/MS (MH$^+$=459)

Example 19

3-Chlorocyclohexyl N-(4-(4-amino-7-cyclopentyl-7H-pyrrolo[2,3-d]pyrimidin-5-yl)-2-methoxyphenyl) carbamate 3-Chlorocyclohexylchloroformate (34 mg, 0.186 mmol) was added dropwise to a stirring solution of 5-(4-amino-3-methoxyphenyl)-7-cyclopentyl-7H-pyrrolo[2,3-d]pyrimidin-4-amine (50 mg, 0.155 mmol) in pyridine (1 mL) and dichloromethane (1 mL) under nitrogen at 0° C. After 10 minutes, the ice water bath was removed and the resulting mixture was stirred for 4 hours. The solvent was evaporated and the residue was taken into ethyl acetate. The organic layer was washed, dried and evaporated. The solid was purified by preparative TLC using dichloromethane/methanol (95:5) as the mobile phase to give 3-chlorocyclohexyl N-[4-(4-amino-7-cyclopentyl-7H-pyrrolo[2,3-d]pyrimidin-5-yl)-2-methoxyphenyl]carbamate. $^1$H NMR (CDCl$_3$) δ 1.46 (m, 2H), 1.78 (m, 4H), 1.88 (m, 4H), 2.00 (m, 2H), 2.28 (m, 4H), 3.93 (m, 4H), 4.84 (m, 1H), 5.22 (m, 1H), 5.27 (s, 2H), 6.97 (s, 1H), 7.03 (s, 1H), 7.08 (d, J=8 Hz, 1H), 7.31 (s, 1H), 8.18 (br. d, 1H), 8.32 (s, 1H); LC/MS (MH$^+$=484).

Example 20

N-(4-(4-Amino-7-cyclopentyl-7H-pyrrolo[2,3-d] pyrimidin-5-yl)-2-methoxyphenyl)-N'-benzylurea Benzylisocyanate (24 uL, 0.194 mmol) in dichloromethane (1 mL) was added dropwise to a stirring solution of 5-(4-amino-3-methoxyphenyl)-7-cyclopentyl-7H-pyrrolo [2,3-d]pyrimidin-4-amine (50 mg, 0.155 mmol) in N,N-diisopropylethylamine (153 uL, 0.881 mmol) and methylene chloride (2 mL) under nitrogen. The resulting mixture was stirred for 24 hours. The solvent was evaporated and the solid was purified by preparative TLC using dichloromethane/ methanol (95:5) as the mobile phase to give N-(4-(4-amino-7-cyclopentyl-7H-pyrrolo[2,3-d]pyrimidin-5-yl)-2-methoxyphenyl)-N'-benzylurea. $^1$H NMR (CDCl$_3$) δ 1.78 (m, 2H), 1.90 (m, 4H), 2.26 (m, 2H), 3.86 (s, 3H), 4.48 (d, J=6 Hz, 3H), 5.24 (m, 4H), 6.93 (s, 1H), 6.98 (s, 1H), 7.00 (s, 1H), 7.04 (d, J=8 Hz, 1H), 7.29 (m, 5H), 8.17 (d, J=8 Hz, 1H), 8.31 (s, 1H); LC/MS (MH$^+$=457).

Example 21

Benzyl N-[4-(4-amino-7-cyclopentyl-7H-pyrrolo[2,3-d]pyrimidin-5-yl)-2-methoxyphenyl]carbamate A mixture of 5-(4-amino-3-methoxyphenyl)-7-cyclopentyl-7H-pyrrolo[2,3-d]pyrimidin-4-amine (0.025 g, 0.08 mmol), benzyl chloroformate (0.016 g, 0.09 mmol), pyridine (0.50 ml) and dichloromethane (0.50 ml) was stirred at room temperature over the weekend and poured into water. The resulting precipitate was collected by filteration and purified by flash column chromatography on silica using ethyl acetate/n-heptane (9:1) as the mobile phase to give benzyl N-[4-(4-amino-7-cyclopentyl-7H-pyrrolo[2,3-d]pyrimidin-5-yl)-2-methoxyphenyl]carbamate as a white solid (0.002 g, 0.004 mmol): $^1$H NMR (DMSO-d$_6$, 400 MHz) δ 8.64 (s, 1H), 8.13 (s, 1H), 7.74 (d, 1H), 7.34-7.45 (m, 6H), 7.10 (d, 1H), 7.02 (dd, 1H), 6.08 (broad, 2H), 5.16 (s, 2H), 5.08 (m, 1H), 3.86 (s, 3H), 2.11 (m, 2H), 1.91 (m, 4H), 1.69 (m, 2H); MH$^+$458; TLC (ethyl acetate) R$_f$ 0.32; RP-HPLC (Hypersil C18, 5 µm, 200 A, 25 cm; 25%-100% acetonitrile-0.1M ammonium acetate over 25 min 1 ml/min) R$_t$ 19.00 min.

Example 22

Benzyl N-[5-(4-amino-7-cyclopentyl-7H-pyrrolo[2,3-d]pyrimidin-5-yl)-2-methoxyphenyl]carbamate a) 5-bromo-2-methoxyaniline. A mixture of 4-bromo-1-methoxy-2-nitrobenzene (3.0 g, 12.9 mmol) and glacial acetic acid (25 ml) was heated at 100° C. under an atmosphere of nitrogen. Iron powder (2.2 g, 38.8 mmol) was added and the mixture was stirred for one hour at a temperature of 100° C. The mixture was cooled to ambient temperature then water (100 ml) was added and the mixture was extracted with ethyl acetate (3×25 ml). The combined organic extracts were washed with saturated aqueous sodium bicarbonate (3×25 ml) and then brine. The organic solution was dried over magnesium sulfate filtered and the filtrate evaporated under reduced pressure to give a residue. Purification of the material by flash chromatography on silica gel using heptane/ethyl acetate (6:4) as an eluent yielded 5-bromo-2-methoxyaniline (2.0 g): $^1$H NMR (DMSO-d$_6$, 400 MHz) δ 6.76 (s, 1H), 6.71 (d, 1H), 6.61 (d, 1H), 4.99 (bs, 2H), 3.74 (s, 3H); (TLC (heptane/ethyl acetate 1:1) R$_f$ 0.5; RP-HPLC (Hypersil HyPurity Elite C18, 5 µm, 200 A, 250×4.6 mm; 25-100% acetonitrile-0.1 M ammonium acetate over 25 min, 1 ml/min) t$_r$=13.33 min.; MS: MH$^+$443.

b) tert-butyl N-(5-bromo-2-methoxyphenyl)carbamate. A mixture of 5-bromo-2-methoxyaniline (1.50 g, 7.43 mmol), and di-tert-butyl dicarbonate (1.95 g, 8.91 mmol) in THF (20 ml) was heated at reflux for 20 hours. The mixture was cooled to ambient temperature and then the solvent was removed under reduced pressure. The resulting oil was purified by flash chromatography on silica gel using ethyl acetate/heptane (1:9) as an eluent to yield tert-butyl N-(5-bromo-2-methoxyphenyl)carbamate (2.19 g) as a colorless oil: $^1$H NMR (DMSO-d$_6$, 400 MHz) δ 8.05 (s, 1H), 7.93 (d, 1H), 7.16 (d, 1H), 6.95 (d, 1H), 3.8 (s, 1H), 1.47 (s, 9H); TLC (ethyl acetate/heptane 2:8) R$_f$ 0.4; RP-HPLC (Hypersil HyPurity Elite C18, 5 µm, 200 Å, 250×4.6 mm; 25-100% acetonitrile-0.1 M ammonium acetate over 25 min, 1 ml/min) t$_r$=21.8 min.

c) tert-butyl N-[2-methoxy-5-(4,4,5,5-tertamethyl-1,3,2-dioxaborolan-2-yl)phenyl]carbamate. A mixture of tert-butyl N-(5-bromo-2-methoxyphenyl)carbamate (1.10 g, 3.64 mmol), diboron pinacol ester (1.11 g, 4.37 mmol), [1,1'-bis(diphenylphosphino) ferrocene]dichloropalladium (II) complex with dichloromethane (1:1) (0.09 g, 0.11 mol) and potassium acetate (1.07 g, 10.9 mol) in N,N-dimethylformamide (20 mL) was heated at 80° C. under an atmosphere of nitrogen for 16 hours. The mixture was allowed to cool to ambient temperature and the solvent removed under reduced pressure. Dichloromethane (20 mL) was added to the residue and the resulting solid was removed by filtration through a pad of celite. The filtrate was concentrated to leave a yellow oil which was purified by flash chromatography on silica using ethyl acetate/heptane (2:8) as mobile phase to yield tert-butyl N-[2-methoxy-5-(4,4,5,5-tetramethyl-1,3,2-dioxaborolan-2-yl)phenyl]carbamate (0.96 g): $^1$H NMR (DMSO-d$_6$, 400 MHz) δ 8.03 (s, 1H), 7.86 (s, 1H), 7.35 (d, 1H), 7.0 (d, 1H), 3.82 (s, 3H), 1.46 (s, 9H), 1.28 (s, 12H); TLC (ethyl acetate/heptane 2:8) R$_f$=0.35; RP-HPLC (Hypersil HyPurity Elite C18, 5 µm, 200 A, 250×4.6 mm; 25-100% acetonitrile-0.1 M ammonium acetate over 25 min, ml/min) t$_r$=22.8 min d) tert-butyl N-(5-(chloro-7-cyclopentyl-7H-pyrrolo[2,3-d]pyrimidin-5-yl)-2-methoxyphenyl)carbamate. A mixture of 4-chloro-7-cyclopentyl-5-iodo-7H-pyrrolo[2,3-d]pyrimidine (0.35 g, 1.0 mmol), tert-butyl N-[2-methoxy-5-(4,4,5,5-tetramethyl-1,3,2-dioxaborolan-2-yl)phenyl]carbamate (0.524 g, 1.5 mmol), tetrakis(triphenylphosphine) palladium (0.07 g, 0.06 mmol) and sodium carbonate (0.265 g, 2.5 mmol) was heated in a mixture of ethylene glycol dimethyl ether (10 mL) and water (5 mL) at 80° C. for 18 hours under an atmosphere of nitrogen. The mixture was allowed to cool to ambient temperature and solvents were removed under reduced pressure. The residue was partitioned between water (15 mL) and ethyl acetate (25 ml), the organic layer separated and the aqueous layer further extracted with ethyl acetate (2×25 ml). The combined organic extracts were washed with water (3×20 ml) then dried over magnesium sulfate, filtered and the filtrate concentrated to an oily residue under reduced pressure. The material was purified by flash column chromatography on silica using heptane/ethyl acetate (5:1) as an eluent to give tert-butyl N-(5-(chloro-7-cyclopentyl-7H-pyrrolo[2,3-d]pyrimidin-5-yl)-2-methoxyphenyl)carbamate (0.325 g): $^1$H NMR (DMSO-d$_6$, 400 MHz) δ 8.64 (s, 1H), 7.93 (s, 1H), 7.87 (m, 2H), 7.17 (d, 1H), 7.06 (d, 1H), 5.21 (m, 1H), 3.86 (s, 3H), 1.65-2.25 (m, 8H), 1.45 (s, 9H); RP-HPLC (Hypersil HyPurity Elite C18, 5 µm, 200 A, 250×4.6 mm; 25-100% acetonitrile-0.1 M ammonium acetate over 25 min, 1 ml/min) t$_r$=24.25 min. MS: MH$^+$443.

e) 5-(3-amino-4-methoxyphenyl)-7-cyclopentyl-7H-pyrrolo[2,3-d]pyrimidin-4-amine. A solution of tert-butyl N-(5-(chloro-7-cyclopentyl-7H-pyrrolo[2,3-d]pyrimidin-5-yl)-2-methoxyphenyl)carbamate (0.325 g, 0.735 mmol) in dichloromethane (14 ml) was cooled to 0° C. then treated with trifluoroacetic acid (1.4 ml). The solution was stirred at 0° C. for 5 min then warmed to ambient temperature and stirred for a further 16 hours. The solvents were evaporated under reduced pressure then the residue was partitioned between dichloromethane (30 ml) and saturated aqueous sodium bicarbonate (10 ml). The organic solution was dried over magnesium sulfate, filtered and the filtrate evaporated under reduced pressure to a foam. The material was then dissolved in dioxane (4 ml) and concentrated (28-30%) ammonium hydroxide (4 ml) and the resulting solution was heated at 120° C. in a sealed pressure tube for 20 hours. The solvents were evaporated and the residue was purified by preparative C18 RP-HPLC to give, after lyophilization 5-(3-amino-4-methoxyphenyl)-7-cyclopentyl-7H-pyrrolo[2,3-d]pyrimidin-4-amine (85 mg): $^1$H NMR (DMSO-$d_6$, 400 MHz) δ 8.10 (s, 1H), 7.21 (s, 1H), 6.87 (d, 1H), 6.74 (s, 1H), 6.58 (d, 1H), 5.06 (1H, m), 4.87 (bs, 2H), 3.8 (s, 3H), 1.6-2.2 (m, 8H); RP-HPLC (Hypersil HyPurity Elite C18, 5 μm, 200 A, 250×4.6 mm; 25-100% acetonitrile-0.1 M ammonium acetate over 25 min, 1 ml/min) $t_r$=11.87 min.; MS: MH$^+$324.

f) benzyl N-[5-(4-amino-7-cyclopentyl-7H-pyrrolo[2,3-d]pyrimidin-5-yl)-2-methoxyphenyl]carbamate. A solution of 5-(3-amino-4-methoxyphenyl)-7-cyclopentyl-7H-pyrrolo[2,3-d]pyrimidin-4-amine (40 mg, 0.124 mmol) in dichloromethane (1 ml) and pyridine (1 ml) was cooled to 0° C. and then treated with benzyl chloroformate (32 mg, 0.186 mmol) while maintaining a temperature of less than 5° C. The solution was stirred for another 1 hour at 0° C. then the solvents were removed under reduced pressure. Purification by preparative C-18 RP-HPLC then lyophilization provided benzyl N-[5-(4-amino-7-cyclopentyl-7H-pyrrolo[2,3-d]pyrimidin-5-yl)-2-methoxyphenyl]carbamate (25 mg) as a white powder: $^1$H NMR (DMSO-$d_6$, 400 MHz) δ 8.75 (s, 1H), 8.11 (s, 1H), 7.75 (s, 1H), 7.1-7.4 (m, 8H), 6.2 (bs, 2H), 5.15 (s, 2H), 5.07 (m, 1H), 3.8 (s 3H), 1.6-2.2 (m, 8H), RP-HPLC (Hypersil HyPurity Elite C18, 5 μm, 200 A, 250×4.6 mm; 25-100% acetonitrile-0.1 M ammonium acetate over 25 min, 1 ml/min) $t_r$=18.63 min.; MS: MH$^+$458.

Example 23

Benzyl N-[5-(4-amino-7-cyclopentyl-7H-pyrrolo[2,3-d]pyrimidin-5-yl)-2-pyridyl]carbamate a) tert-butyl N-(5-bromo-2-pyridyl)carbamate. The compound was prepared from 5-bromo-2-pyridinamine in the manner described for compound (2): $^1$H NMR (DMSO-$d_6$, 400 MHz) δ 9.96 (s, 1H), 8.49 (d, 1H), 7.93 (dd, 1H), 7.78 (d, 1H), 1.47 (s, 9H); TLC (ethyl acetate/heptane 5:95) $R_f$ 0.28; RP-HPLC (Hypersil HyPurity Elite C18, 5 μm, 200 A, 250×4.6 mm; 25-100% acetonitrile-0.1 M ammonium acetate over 25 min, 1 ml/min) $t_r$=18.50 min.

b) tert-butyl N-[5-(1,1,1-trimethylstannyl)-2-pyridyl]carbamate. A mixture of tert-butyl N-(5-bromo-2-pyridyl)carbamate (1.67 g, 6.12 mmol), hexamethylditin (2.0 g, 6.12 mmol) and tetrakis(triphenylphosphine)palladium (0.424 g, 0.367 mmol) in ethylene glycol dimethyl ether (30 ml) was heated at 80° C. under an atmosphere of nitrogen for 15 hours. The mixture was cooled to ambient temperature and then the solvent was removed under reduced pressure. The resulting material was purified by flash chromatography on silica gel using heptane/ethyl acetate (95:5) as an eluent to yield tert-butyl N-[5-(1,1,1-trimethylstannyl)-2-pyridyl]carbamate (1.11 g): $^1$H NMR (DMSO-$d_6$, 400 MHz) δ 9.98 (s, 1H), 8.2 (t, 1H), 7.74 (m, 2H), 1.47 (s, 9H), 0.30 (t, 9H); TLC (heptane/ethyl acetate 95:5) $R_f$ 0.2; MS: MH$^+$359.

c) tert-butyl N-[5-(4-chloro-7-cyclopentyl-7H-pyrrolo[2,3-d]pyrimidin-5-yl)-2-pyridyl]carbamate. A mixture of 4-chloro-7-cyclopentyl-5-iodo-7H-pyrrolo[2,3-d]pyrimidine (0.25 g, 0.72 mmol), tert-butyl N-[5-(1,1,1-trimethylstannyl)-2-pyridyl]carbamate (0.386 g, 1.08 mmol), trwas(dibenzylideneacetone) dipalladium(0) (0.033 g, 0.076 mmol) and triphenylarsine (0.055 g, 0.18 mmol) in N,N-dimethylformamide (8 ml) was heated at 65° C. under an atmosphere of nitrogen for 18 hours. The mixture was cooled to ambient temperature and then the solvent was removed under reduced pressure. The resulting material was purified by flash chromatography on silica gel using heptane/ethyl acetate (75:25) as an eluent to yield tert-butyl N-[5-(4-chloro-7-cyclopentyl-7H-pyrrolo[2,3-d]pyrimidin-5-yl)-2-pyridyl]carbamate (0.13 g): $^1$H NMR (DMSO-$d_6$, 400 MHz) δ 9.83 (s, 1H), 8.68 (s, 1H), 8.40 (d, 1H), 8.02 (s, 1H), 7.85-7.93 (m, 2H), 5.21 (m, 1H), 1.65-2.25 (m, 8H), 1.49 (s, 9H); TLC (heptane/ethyl acetate 8:2) $R_f$ 0.18; RP-HPLC (Hypersil HyPurity Elite C18, 5 μm, 200 A, 250×4.6 mm; 25-100% acetonitrile-0.1 M ammonium acetate over 25 min, 1 ml/min) $t_r$=21.68 min.

d) 5-(4-chloro-7-cyclopentyl-7H-pyrrolo[2,3-d]pyrimidin-5-yl)-2-pyridin-4-amine. A solution of tert-butyl N-[5-(4-chloro-7-cyclopentyl-7H-pyrrolo[2,3-d]pyrimidin-5-yl)-2-pyridyl]carbamate (0.13 g, 0.315 mmol) in dichloromethane (5.5 ml) was cooled to 0° C. then treated with trifluoroacetic acid (0.6 ml). The solution was stirred at 0° C. for 5 minutes then warmed to ambient temperature and stirred for a further 18 hours. The solvents were evaporated under reduced pressure then the residue was partitioned between dichloromethane (30 ml) and saturated aqueous sodium bicarbonate (10 ml). The organic solution was dried over magnesium sulfate filtered and the filtrate evaporated under reduced pressure to give 5-(4-chloro-7-cyclopentyl-7H-pyrrolo[2,3-d]pyrimidin-5-yl)-2-pyridin-4-amine (92 mg): RP-HPLC (Hypersil HyPurity Elite C18, 5 μm, 200 A, 250×4.6 mm; 25-100% acetonitrile-0.1 M ammonium acetate over 25 min, 1 ml/min) $t_r$=10.73 min; MS: MH$^+$314.

e) 5-(6-amino-3-pyridyl)-7-cyclopentyl-7H-pyrrolo[2,3-d]pyrimidin-4-amine. The 5-(4-chloro-7-cyclopentyl-7H-pyrrolo[2,3-d]pyrimidin-5-yl)-2-pyridin-4-amine (92 mg, 0.291 mmol) was dissolved in dioxane (2 ml) and concentrated (28-30%) ammonium hydroxide (2 ml) and the resulting solution was heated at 120° C. in a sealed pressure tube for 24 hours. The solvents were evaporated to give 5-(6-amino-3-pyridyl)-7-cyclopentyl-7H-pyrrolo[2,3-d]pyrimidin-4-amine (105 mg): RP-HPLC (Hypersil HyPurity Elite C18, 5 μm, 200 A, 250×4.6 mm; 25-100% acetonitrile-0.1 M ammonium acetate over 25 min, 1 ml/min) $t_r$=6.33 min.; MS: MH$^+$295.

f) N-[5-(4-amino-7-cyclopentyl-7H-pyrrolo[2,3-d]pyrimidin-5-yl)-2-pyridyl]carbamate. A solution of 5-(6-amino-3-pyridyl)-7-cyclopentyl-7H-pyrrolo[2,3-d]pyrimidin-4-amine (105 mg, 0.29 mmol) in dichloromethane (1.5 ml) and pyridine (1.5 ml) was cooled to 0° C. and then treated with benzyl chloroformate (75 mg, 0.44 mmol) while maintaining a temperature of less than 5° C. The solution was warmed to ambient temperature then stirred for 3 hours. Benzyl chloroformate (75 mg, 0.44 mmol) was added and the mixture stirred for 18 hours, additional benzyl chloroformate (75 mg, 0.44 mmol) was added and the mixture stirred for another 24 hours. Benzyl chloroformate (150 mg, 0.88 mmol) and pyridine (1 ml) were added and the mixture stirred for another 24 hours. The solvents were evaporated under reduced pressure then the residue was partitioned between ethyl acetate (25 ml) and water (10 ml). The organic solution was dried over magnesium sulfate, filtered and the filtrate evaporated under reduced pressure to give a residue. Purification by preparative C-18 RP-HPLC then trituration with diethyl ether provided N-[5-(4-amino-7-cyclopentyl-7H-pyrrolo[2,3-d]pyrimidin-5-yl)-2-pyridyl]carbamate (21 mg) as a white powder: $^1$H NMR (DMSO-$d_6$, 400 MHz) δ 10.33 (s, 1H), 8.36 (d, 1H), 8.14 (s, 1H), 7.91 (d, 1H), 7.84 (d, 1H), 7.33-7.47 (m, 6H), 6.11 (bs, 2H), 5.2 (s, 2H), 5.06 (m, 1H), 1.6-2.2 (m, 8H); RP-HPLC (Hypersil HyPurity Elite C18, 5 μm, 200 A, 250×4.6 mm; 25-100% acetonitrile-0.1 M ammonium acetate over 25 min, 1 ml/min) $t_r$=16.22 min; MS: MH$^+$429.

Example 24

Benzyl N-[4-(4-amino-7-cyclopentyl-7H-pyrrolo[2,3-d]pyrimidin-5-yl)-3-methoxyphenyl]carbamate a) 4-bromo-3-methoxyaniline. A mixture of 1-bromo-2-methoxy-4-nitrobenzene (3.0 g, 12.9 mmol) and glacial acetic acid (25 ml) was heated at 100° C. under an atmosphere of nitrogen. Iron powder (2.2 g, 38.8 mmol) was added and the mixture was stirred for one hour at a temperature of 100° C. The mixture was cooled to ambient temperature, water (100 ml) was added and the mixture was then extracted with ethyl acetate (3×25 ml). The combined organic extracts were washed with saturated aqueous sodium bicarbonate (3×25 ml) and then brine. The organic solution was dried over magnesium sulfate filtered and the filtrate evaporated under reduced pressure to give a residue. Purification of the material by flash chromatography on silica gel using heptane/ethyl acetate (6:4) as an eluent yielded 4-bromo-3-methoxyaniline (1.22 g): $^1$H NMR (DMSO-d$_6$, 400 MHz) δ 7.1 (d, 1H), 6.31 (s, 1H), 6.1 (d, 1H), 5.27 (bs, 2H), 3.72 (s, 3H); TLC (heptane/ethyl acetate 1:1) R$_f$ 0.33; RP-HPLC (Hypersil HyPurity Elite C18, 5 μm, 200 A, 250×4.6 mm; 25-100% acetonitrile-0.1 M ammonium acetate over 25 min, 1 ml/min) $t_r$=11.05 ml.

b) tert-butyl N-(4-bromo-3-methoxyphenyl)carbamate. The compound was prepared from 4-bromo-3-methoxyaniline in the manner described for compound (2): $^1$H NMR (DMSO-d$_6$, 400 MHz) δ 9.46 (s, 1H), 7.4 (d, 1H), 7.35 (s, 1H), 6.95 (d, 1H), 3.78 (s, 3H), 1.48 (s, 9H); TLC (heptane/ethyl acetate 8:2) R$_f$ 0.37; RP-HPLC (Hypersil HyPurity Elite C18, 5 μm, 200 A, 250×4.6 mm; 25-100% acetonitrile-0.1 M ammonium acetate over 25 min, 1 ml/min) $t_r$=18.60 min.

c) tert-butyl N-[3-methoxy-4-(4,4,5,5-tetramethyl-1,3,2-dioxaborolan-2-yl)phenyl]carbamate. The compound was prepared from tert-butyl N-(4-bromo-3-methoxyphenyl)carbamate in the manner described for compound (3): $^1$H NMR (DMSO-d$_6$, 400 MHz) δ 9.44 (s, 1H), 7.41 (d, 1H), 7.17 (s, 1H), 7.01 (d, 1H), 3.68 (s, 3H), 1.48 (s, 9H), 1.24 (s, 12H); TLC (heptane/ethyl acetate 8:2) R$_f$ 0.28; RP-HPLC (Hypersil HyPurity Elite C18, 5 μm, 200 A, 250×4.6 mm; 25-100% acetonitrile-0.1 M ammonium acetate over 25 min, 1 ml/min) $t_r$=18.83 min.

d) tert-butyl N-[4-(4-(chloro-7-cyclopentyl-7H-pyrrolo[2,3-d]pyrimidin-5-yl)-3-methoxyphenyl)carbamate. The compound was prepared from tert-butyl N-[3-methoxy-4-(4,4,5,5-tetramethyl-1,3,2-dioxaborolan-2-yl)phenyl]carbamate and 4-chloro-7-cyclopentyl-5-iodo-7H-pyrrolo[2,3-d]pyrimidine in the manner described for compound (4): $^1$H NMR (DMSO-d$_6$, 400 MHz) δ 9.41 (s, 1H)<8.59 (s, 1H), 7.72 (s, 1H), 7.33 (s, 1H), 7.15 (d, 1H), 7.04 (d, 1H), 5.17 (m, 1H), 3.66 (s, 3H), 1.6-2.2 (m, 3H), 1.49 (s, 9H); RP-HPLC (Hypersil HyPurity Elite C18, 5 μm, 200 A, 250×4.6 mm; 25-100% acetonitrile-0.1 M ammonium acetate over 25 min, 1 ml/min) $t_r$=21.22 min; MS: MH$^+$443.

e) benzyl N-[4-(4-amino-7-cyclopentyl-7H-pyrrolo[2,3-d]pyrimidin-5-yl)-3-methoxyphenyl]carbamate. The compound was prepared from tert-butyl N-[4-(4-(chloro-7-cyclopentyl-7H-pyrrolo[2,3-d]pyrimidin-5-yl)-3-methoxyphenyl) carbamate in the manner described for conversion of compound (4) into compound (6): $^1$H NMR (DMSO-d$_6$, 400 MHz) δ 9.87 (s, 1H), 8.08 (s, 1H), 7.34-7.45 (m, 6H), 7.09-7.18 (m, 3H), 5.79 (bs, 2H), 5.18 (s, 2H), 5.04 (m, 1H), 3.7 (s, 3H), 1.6-2.2 (m, 8H); RP-HPLC (Hypersil HyPurity Elite C18, 5 μm, 200 A, 250×4.6 mm; 25-100% acetonitrile-0.1 M ammonium acetate over 25 min, 1 ml/min) $t_r$=16.87 min; MS: MH$^+$458.

Example 25

Benzyl N-[4-(4-amino-7-cyclopentyl-7H-pyrrolo[2,3-d]pyrimidin-5-yl)-2-fluorophenyl]carbamate a) 4-[{[7-cyclopentyl-5-(4,4,5,5-tetramethyl-1,3,2-dioxaborolan-2-yl)-7H-pyrrolo[2,3-d]pyrimidin-4-yl]amino}(2,4-dimethoxyphenyl)methyl]phenoxy resin. Rink amide resin [4-(2',4'-dimethoxyphenyl-Fmoc-aminomethyl)-phenoxy resin with a loading of 0.66 mmol/g] (6.55 g, 4.32 mmol) was deprotected by washing with N,N-dimethylformamide (2×2 min), 20% piperidine in N,N-dimethylformamide (1×5 min, 1×15 min), N,N-dimethylformamide (5×2 min), dichloromethane (3×2 min), and then methanol (3×2 min). The resin was dried at a temperature of 40° C. under reduced pressure. The deprotected resin, 4-chloro-7-cyclopentyl-5-iodo-7H-pyrrolo[2,3-d]pyrimidine (1.80 g, 5.19 mmol), dimethylsulfoxide (100 ml), and N,N-diisopropylethylamine (4.5 ml) were heated at 100° C. for 3 days, cooled to ambient temperature and then the resin was collected by filtration and washed with N,N-dimethylformamide. The resin was then stirred for 30 min with acetic acid (0.13 g, 2.16 mmol), O-benzothiazol-1-yl-N,N,N',N'-tetramethyluronium tetrafluoroborate (0.69 g, 2.16 mmol), N,N-diisopropylethylamine (0.56 g, 4.32 mmol) and N,N-dimethylformamide (30 ml). The resin was collected by filtration and washed with N,N-dimethylformamide, dichloromethane and methanol. The resin was dried to a constant weight (6.25 g) under reduced pressure. The resin, diboron pinacol ester (1.11 g, 4.37 mmol), potassium acetate (0.822 g, 8.39 mmol) and tetrakis (triphenylphosphine)palladium (0.24 g, 0.21 mmol) in dimethylsulfoxide (125 ml) was heated at 85° C. under an atmosphere of nitrogen for 17 hours. The resin was collected by filtration then washed with N,N-dimethylformamide, dichloromethane, ethyl acetate then ether. The resin was dried under reduced pressure to a weight of 5.49 grams.

b) Benzyl N-[4-(4-amino-7-cyclopentyl-7H-pyrrolo[2,3-d]pyrimidin-5-yl)-2-fluorophenyl]carbamate. A mixture of 4-[{[7-cyclopentyl-5-(4,4,5,5-tetramethyl-1,3,2-dioxaborolan-2-yl)-7H-pyrrolo[2,3-d]pyrimidin-4-yl]amino}(2,4-dimethoxyphenyl)methyl]phenoxy resin (0.5 g, 0.254 mmol), 4-bromo-2-fluoroaniline (0.484 g, 2.54 mmol), tetrakis(triphenylphosphine) palladium (0.044 g, 0.038 mmol), 2 M aqueous potassium phosphate (1.27 ml, 2.54 mmol) and dimethylsulfoxide (10 ml) was heated at 85° C. for 18 hours. The mixture was cooled and the resin collected by filtration then washed with N,N-dimethylformamide and dichloromethane. The resin was then subjected to the coupling conditions described above a second time. The resin was suspended in dichloromethane (2 ml) and pyridine (2 ml) then the mixture was cooled to 0° C. and treated with benzyl chloroformate (0.44 g, 2.6 mmol). After stirring at 0° C. for one hour the mixture was allowed to warm to ambient temperature for 18 hours. The resin was collected by filtration then treated with 5% trifluoroacetic acid in dichloromethane (10 ml) for 30 minutes. Removal of the resin by filtration yielded a filtrate which was evaporated under reduced pressure to yield a residue which was purified by preparative C-18 RP-HPLC to give benzyl N-[4-(4-amino-7-cyclopentyl-7H-pyrrolo[2,3-d]pyrimidin-5-yl)-2-fluorophenyl]carbamate (~10 mg): RP-HPLC (Hypersil HS C18, 5 µm, 100 A, 250×4.6 mm; 25-100% acetonitrile-0.1 M ammonium acetate over 10 min, 1 ml/min) $t_r$=11.47 min; MS: MH$^+$446.

Example 27

Benzyl N-[4-(4-amino-7-cyclopentyl-7H-pyrrolo[2,3-d]pyrimidin-5-yl)-2-(trifluoromethyl)phenyl]carbamate This compound was prepared in the same manner as described for Example 25: RP-HPLC (Hypersil HS C18, 5 µm, 100 A, 250×4.6 mm; 25-100% acetonitrile-0.1 M ammonium acetate over 10 min, 1 ml/min) $t_r$=12.07 min; MS: MH$^+$496.

Example 28

Benzyl N-[4-(4-amino-7-cyclopentyl-7H-pyrrolo[2,3-d]pyrimidin-5-yl)-2-cyanophenyl]carbamate This compound was prepared in the same manner as described for Example 25: RP-HPLC (Hypersil HS C18, 5 µm, 100 A, 250×4.6 mm; 25-100% acetonitrile-0.1 M ammonium acetate over 10 min, 1 ml/min) $t_r$=10.93 min; MS: MH$^+$453.

Example 29

Methyl 5-(4-amino-7-cyclopentyl-7H-pyrrolo[2,3-d]pyrimidin-5-yl)-2-{[(benzyloxy)carbonyl]amino}benzoate This compound was prepared in the same manner as described for Example 25: RP-HPLC (Hypersil HS C18, 5 µm, 100 A, 250×4.6 mm; 25-100% acetonitrile-0.1 M ammonium acetate over 10 min, 1 ml/min) $t_r$=13.28 min; MS: MH$^+$486.

Example 30

Benzyl N-[4-(4-amino-7-cyclopentyl-7H-pyrrolo[2,3-d]pyrimidin-5-yl)-2-methylphenyl]carbamate This compound was prepared in the same manner as described for Example 25: RP-HPLC (Hypersil HS C18, 5 µm, 100 A, 250×4.6 mm; 25-100% acetonitrile-0.1 M ammonium acetate over 10 min, 1 ml/min) $t_r$=11.25 min; MS: MH$^+$442.

Example 31

Benzyl N-[4-(4-amino-7-cyclopentyl-7H-pyrrolo[2,3-d]pyrimidin-5-yl)phenyl]carbamate This compound was prepared in the same manner as described for Example 25: RP-HPLC (Hypersil HS C18, 5 µm, 100 A, 250×4.6 mm; 25-100% acetonitrile-0.1 M ammonium acetate over 10 min, 1 ml/min) $t_r$=11.27 min; MS: MH$^+$428.

Example 32

N-[4-(4-Amino-7-cyclopentyl-7H-pyrrolo[2,3-d]pyrimidin-5-yl)-2-methoxyphenyl]phenylmethanesulfonamide 5-(4-Amino-3-methoxyphenyl)-7-cyclopentyl-7H-pyrrolo[2,3-d]pyrimidin-4-amine (27 mg, 0.083 mmol) was dissolved in dichloromethane (0.8 mL). Pyridine (0.8 mL) was added followed by phenylmethanesulfonyl chloride (19 mg, 0.105 mmol). After stirring overnight, another 19 mg of phenylmethanesulfonyl chloride was added and the reaction mixture was stirred overnight. The solvent was removed and the residue was purified by preparative thin layer chromatogram eluted with dichlormethane/Methanol (95:5) to give N-[4-(4-amino-7-cyclopentyl-7H-pyrrolo[2,3-d]pyrimidin-5-yl)-2-methoxyphenyl]phenylmethanesulfonamide (9 mg, 0.0188 mmol). 1H NMR (DMSO-d$_6$) δ 1.89 (m, 6H), 2.28 (m, 2H), 3.85 (s, 3H), 4.38 (s, 2H), 5.23 (m, 3H), 6.08 (bs, 1H), 6.99 (m, 2H), 7.27, (m, 2H), 7.33 (m, 3H), 7.58 (d, J=8.17 Hz, 1H), 8.34 (s, 1H). LC/MS MH$^+$=478

Example 33

N1-[4-(4-Amino-7-cyclopentyl-7H-pyrrolo[2,3-d]pyrimidin-5-yl)-2-methoxyphenyl]-2-phenylacetamide 5-(4-Amino-3-methoxyphenyl)-7-cyclopentyl-7H-pyrrolo[2,3-d]pyrimidin-4-amine (28 mg, 0.086 mmol) was dissolved in dichloromethane (1 mL). Pyridine (1 mL) was added followed by 2-phenylethanoyl chloride (14 uL, 0.105 mmol). After stirring overnight, another 14 uL of phenylmethanesulfonyl chloride was added and the reaction mixture was stirred overnight. The solvent was removed and the residue was purified by preparative thin layer chromatogram eluted with dichlormethane/methanol (95:5) to give N1-[4-(4-amino-7-cyclopentyl-7H-pyrrolo[2,3-d]pyrimidin-5-yl)-2-methoxyphenyl]-2-phenylacetamide (7 mg, 0.0158 mmol). 1H NMR (DMSO-d$_6$) δ 1.89 (m, 6H), 2.25 (m, 2H), 3.77 (s, 3H), 3.79 (s, 2H), 5.21 (m, 1H), 5.56 (bs, 2H), 6.89 (s, 1H), 6.99 (s, 1H), 7.05 (d, J=8.22, 1H), 7.36 (m, 5H), 7.81 (s, 1H), 8.27 (s, 1H), 8.43 (d, J=8.23 Hz, 1H). LC/MS MH$^+$=442.

Example 34

N1-[4-(4-Amino-7-cyclopentyl-7H-pyrrolo[2,3-d]pyrimidin-5-yl)-2-methoxyphenyl]-2-(2-thienyl)acetamide 5-(4-Amino-3-methoxyphenyl)-7-cyclopentyl-7H-pyrrolo[2,3-d]pyrimidin-4-amine (31 mg, 0.096 mmol) was dissolved in dichloromethane (1 mL). Pyridine (1 mL) was added followed by 2-(2-thienyl)ethanoyl chloride (14 uL, 0.113 mmol). After stirring overnight, another 14 uL of 2-(2-thienyl)ethanoyl chloride was added and the reaction mixture was stirred overnight. The solvent was removed and the residue was purified by preparative thin layer chromatography eluting with dichlormethane/methanol (95:5) to give N1-[4-(4-amino-7-cyclopentyl-7H-pyrrolo[2,3-d]pyrimidin-5-yl)-2-methoxyphenyl]-2-(2-thienyl)acetamide (14 mg, 0.031 mmol). 1H NMR (DMSO-d$_6$) δ 1.89 (m, 6H), 2.25 (m, 2H), 3.82 (s, 3H), 3.99 (s, 2H), 5.19 (bs, 2H), 5.21 (m, 1H), 6.93 (s, 1H), 6.94 (s, 1H), 7.06 (m, 3H), 7.31 (m, 1H), 8.02 (s, 1H), 8.32 (s, 1H), 8.42 (d, J=8.22 Hz, 1H). LC/MS MH+=448.

Examples 35-108

General Method

The Examples listed in Table J were prepared by reacting a phenol with a fluorobenzene listed in Table I as shown in the scheme below.

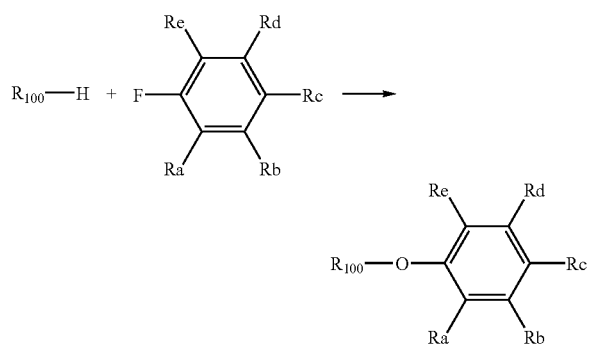

$R_1$ is isopropyl. $R_{100}$ is as shown above.

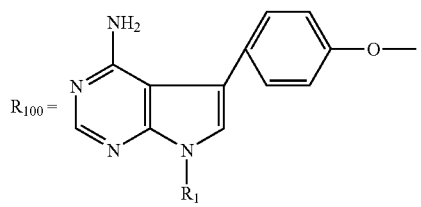

5-(4-Hydroxyphenyl)-7-isopropylpyrrolo[2,3-d]pyrimidin-4-ylamine (1 molar equivalent) as a stock solution in N,N-dimethylformamide (6 g in 240 ml) was added to a mixture of the fluorobenzene (1.25 molar equivalents) and potassium carbonate (2 molar equivalents) in a septum sealed tube via a Gilson 215 liquid auto sampler. The reactions were heated, with shaking, at 120° C. for 4 hours and 140° C. for a further 1 hour and then evaporated to dryness in a centrifugal evaporator.

The reaction residues were dissolved in ethyl acetate/triethylamine (1 ml) (9:1) and eluted through a silica pad (3 g SiO2: 12 mm diameter×20 mm height) with 9:1 ethyl acetate/triethylamine (4×2 ml). The combined column eluents were evaporated to yield the products as waxy solids, smears or expanded foams.

TABLE I

| Ex No. | Fluorobenzene Employed |
|---|---|
| 35 | 4-fluoro-3-(trifluoromethyl)benzaldehyde |
| 36 | 3-chloro-4-fluoroacetophenone |
| 37 | 3-chloro-4-fluorobenzaldehyde |
| 38 | 4-fluoroacetophenone |
| 39 | 4-fluorobenzaldehyde |
| 40 | 2-fluoro-5-(trifluoromethyl)propiophenone |
| 41 | 2-fluoro-3-(trifluoromethyl)acetophenone |
| 42 | 3-cyano-4-dimethylamino-2-fluorobenzaldehyde |
| 43 | 2-fluoro-3-(trifluoromethyl)benzaldehyde |
| 44 | 2-fluoro-4-methoxyacetophenone |

TABLE I-continued

| Ex No. | Fluorobenzene Employed |
|---|---|
| 45 | 4-chloro-2-fluorobenzaldehyde |
| 46 | 2,5-difluoroacetophenone |
| 47 | 2-fluoro-5-methoxybenzaldehyde |
| 48 | 2-fluoro-4-methoxybenzaldehyde |
| 49 | 2-fluoropropiophenone |
| 50 | 2,3-difluorobenzaldehyde |
| 51 | 2-fluoroacetophenone |
| 52 | 2-fluorobenzaldehyde |
| 53 | 4-fluoro-3-(trifluoromethyl)propiophenone |
| 54 | (4-fluorophenyl)-(2-thienyl)ketone |
| 55 | 4-fluoro-2-(trifluoromethyl)acetophenone |
| 56 | 4-fluoro-2-(trifluoromethyl)benzaldehyde |
| 57 | 4'-fluoro-1'-acetonaphthone |
| 58 | 4-fluoro-2-methoxybenzaldehyde |
| 59 | 2-fluoro-4-(trifluoromethyl)propiophenone |
| 60 | 2-fluoro-4-(trifluoromethyl)acetophenone |
| 61 | 2-fluoro-5-(trifluoromethyl)acetophenone |
| 62 | 4-chloro-2-fluoro-5-methylacetophenone |
| 63 | 2-fluoro-5-nitrobenzaldehyde |
| 64 | 4-(4-fluorobenzoyl)-1-methylpyrrole-2-aldehyde |
| 65 | 4'-fluoro-2-(methylsulphonyl)acetophenone |
| 66 | 5-fluoro-1-indanone |
| 67 | 2-amino-5-chloro-2'-fluorobenzophenone |
| 68 | 2'-fluoro-5'-nitrooacetophenone |
| 69 | 4-fluoro-3-(trifluoromethyl)benzonitrile |
| 70 | 3-chloro-4-fluorobenzonitrile |
| 71 | 2-chloro-4-fluorobenzonitrile |
| 72 | 3,4-difluorobenzonitrile |
| 73 | 4-fluorobenzonitrile |
| 74 | 2-fluoro-6-(4-methylphenylthio)benzonitrile |
| 75 | 2-fluoro-6-(2-pyridylthio)benzoflitrile |
| 76 | 2-fluoro-6-(methoxycarbonylmethylthio)benzonitrile |
| 77 | 2-fluoro-3-(trifluoromethyl)benzonitrile |
| 78 | 2-fluoro-5-(trifluoromethyl)benzonitrile |
| 79 | 2-fluoro-6-(1-pyrrolo)benzonitrile |
| 80 | 2-fluoro-5-nitrobenzonitrile |
| 81 | 2-fluorobenzonitrile |
| 82 | 5-fluoro-2-nitrobenzaldehyde |
| 83 | 4-fluoro-3-nitrophenylmethylsulfone |
| 84 | 4-fluoro-3-nitrobenzotrifluoride |
| 85 | 2'-chloro-4'-fluoroacetophenone |
| 86 | 4'-fluoro-2'-methylacetophenone |
| 87 | 3-phenyl-7-fluoroindan-1-one |
| 88 | 2-fluoro-6-(trifluoromethyl)acetophenone |
| 89 | 1-fluoro-9-fluorenone |
| 90 | 6-fluoroveratraldehyde |
| 91 | 2-fluoro-5-methylacetophenone |
| 92 | 2-fluoro-6-(2-oxo-azepin-3-ylamino)benzonitrile |
| 93 | 2-fluoro-6-(4-carbamoylpiperidin-1-yl)benzonitrile |
| 94 | 2-fluoro-6-[3-(imidazol-1-yl)propylamino]benzonitrile |
| 95 | 2-fluoro-6-[2-(4-pyridyl)ethylamino]benzonitrile |
| 96 | 2-fluoro-6-(2-thienylmethylamino)benzonitrile |
| 97 | 2-fluoro-6-(4-cyanopiperidin-1-yl)benzonitrile |
| 98 | 2-fluoro-6-(3-pyridylmethylamino)benzonitrile |
| 99 | 2-fluoro-6-(4-methylphenoxy)benzonitrile |
| 100 | 2-fluoro-6-thiamorpholinobenzonitrile |
| 101 | 2-fluoro-6-[(3-dimethylamino)propylamino]benzonitrile |
| 102 | 2-fluoro-6-(2,2,2-trifluoroethoxy)benzonitrile |
| 103 | 2-fluoro-6-(3-methoxypropylamino)benzonitrile |
| 104 | 2-dimethylamino-6-fluorobenzonitrile |
| 105 | 2-fluoro-5-methoxybenzonitrile |
| 106 | 2,5-difluorobenzonitrile |
| 107 | 2-fluoro-5-nitrobenzotrifluoride |
| 108 | 3-chloro-4-fluoro-5-nitrobenzotrifluoride |

The products obtained are shown in Table J. $R_{100}$ is as previously stated.

The conditions used in LCMS are given later. HPLC RT (mins) is the HPLC retention time in minutes.

TABLE J

PRODUCT

| EX | Ra | Rb | Rc | Rd | Re | HPLC RT (mins) |
|---|---|---|---|---|---|---|
| 35 | CF$_3$ | H | CHO | H | H | 4.45 |
| 36 | Cl | H | COCH$_3$ | H | H | 4.44 |
| 37 | Cl | H | CHO | H | H | 4.4 |
| 38 | H | H | COCH$_3$ | H | H | 4.13 |
| 39 | H | H | CHO | H | H | 4.1 |
| 40 | COC$_2$H$_5$ | H | CF$_3$ | H | H | 4.91 |
| 41 | COCH$_3$ | H | H | H | CF$_3$ | 4.35 |
| 42 | CHO | H | H | N(CH$_3$)$_2$ | CN | 3.88 |
| 43 | CHO | H | H | H | CF$_3$ | 4.39 |
| 44 | COCH$_3$ | H | H | OCH$_3$ | H | 4.16 |
| 45 | CHO | H | H | C$_1$ | H | 4.57 |
| 46 | COCH$_3$ | H | F | H | H | 4.29 |
| 47 | CHO | H | OCH$_3$ | H | H | 4.27 |
| 48 | CHO | H | H | OCH$_3$ | H | 4.12 |
| 49 | COC$_2$H$_5$ | H | H | H | H | 4.46 |
| 50 | CHO | H | H | H | F | 4.12 |
| 51 | COCH$_3$ | H | H | H | H | 4.14 |
| 52 | CHO | H | H | H | H | 4.15 |
| 53 | CF$_3$ | H | COC$_2$H$_5$ | H | H | 5.61 |
| 54 | H | H | 2-ThCO 1 | H | H | 5.37 |
| 55 | H | CF$_3$ | COCH$_3$ | H | H | 5.17 |
| 56 | H | CF$_3$ | CHO | H | H | 5.40 |
| 57 | H | H | COCH$_3$ | —CH=CH—CH=CH-2 | | 5.42 |
| 58 | H | OCH$_3$ | CHO | H | H | 4.64 |
| 59 | COC$_2$H$_5$ | H | H | CF$_3$ | H | 5.63 |
| 60 | COCH$_3$ | H | H | CF$_3$ | H | 5.28 |
| 61 | COCH$_3$ | H | CF$_3$ | H | H | 5.38 |
| 62 | COCH$_3$ | H | CH$_3$ | Cl | H | 5.57 |
| 63 | CHO | H | NO$_2$ | H | H | 4.74 |
| 64 | H | H | P$_3$ | H | H | 4.17 |
| 65 | H | H | COCH$_2$SO$_2$CH$_3$ | H | H | 3.73 |
| 66 | H | —CH$_2$—CH$_2$—CO— | | H | H | 4.00 |
| 67 | COA4 | H | H | H | H | 4.80 |
| 68 | COCH$_3$ | H | NO$_2$ | H | H | 4.25 |
| 69 | CF$_3$ | H | CN | H | H | 4.51 |
| 70 | Cl | H | CN | H | H | 4.74 |
| 71 | H | Cl | CN | H | H | 4.52 |
| 72 | F | H | CN | H | H | 4.22 |
| 73 | H | H | CN | H | H | 4.21 |
| 74 | CN | 4-methyl phenylthio | H | H | H | 5.25 |
| 75 | CN | 2-pyridylthio | H | H | H | 4.29 |
| 76 | CN | Methoxy-carbonyl-methylthio | H | H | H | 4.85 |
| 77 | CN | H | H | H | CF$_3$ | 4.31 |
| 78 | CN | H | CF$_3$ | H | H | 4.51 |
| 79 | CN | Pyrrol-1-yl | H | H | H | 4.47 |
| 80 | CN | H | NO$_2$ | H | H | 4.14 |
| 81 | CN | H | H | H | H | 4.09 |
| 82 | H | CHO | NO$_2$ | H | H | 4.22 |
| 83 | NO$_2$ | H | SO$_2$CH$_3$ | H | H | 3.78 |
| 84 | NO$_2$ | H | CF$_3$ | H | H | 4.60 |
| 85 | H | Cl | COCH$_3$ | H | H | 4.39 |
| 86 | H | CH$_3$ | COCH$_3$ | H | H | 4.96 |
| 87 | 3-phenylindan-1-one-7-yl | | H | H | H | 5.57 |
| 88 | COCH$_3$ | CF$_3$ | H | H | H | 5.23 |
| 89 | Fluoren-9-one-1-yl | | H | H | H | 5.23 |
| 90 | CHO | H | OCH$_3$ | OCH$_3$ | H | 4.20 |
| 91 | COCH$_3$ | H | CH$_3$ | H | H | 5.02 |
| 92 | CN | 2-oxoazepin-3-ylamino | H | H | H | 4.47 |
| 93 | CN | 4-carbamoyl piperidin-1-yl | H | H | H | 3.81 |

TABLE J-continued

PRODUCT

| EX | Ra | Rb | Rc | Rd | Re | HPLC RT (mins) |
|---|---|---|---|---|---|---|
| 94 | CN | 3-(imidazol-1-yl)propylamino | H | H | H | 3.56 |
| 95 | CN | 2-(4-pyridyl)ethylamino | H | H | H | 4.36 |
| 96 | CN | 2-thienyl methylamino | H | H | H | 5.32 |
| 97 | CN | 4-cyano piperidin-1-yl | H | H | H | 4.89 |
| 98 | CN | 3-pyridyl methylamino | H | H | H | 4.22 |
| 99 | CN | 4-methylphenoxy | H | H | H | 4.89 |
| 100 | CN | Thiamorpholino | H | H | H | 5.32 |
| 101 | CN | 3-(dimethyl amino)propyl amino | H | H | H | 3.35 |
| 102 | CN | OCH$_2$CF$_3$ | H | H | H | 5.01 |
| 103 | CN | 3-methoxy propylamino | H | H | H | 4.92 |
| 104 | CN | N(CH$_3$)$_2$ | H | H | H | 4.91 |
| 105 | CN | H | OCH$_3$ | H | H | 4.75 |
| 106 | CN | H | F | H | H | 4.74 |
| 107 | CF$_3$ | H | NO$_2$ | H | H | 5.51 |
| 108 | NO$_2$ | H | CF$_3$ | H | Cl | 5.56 |

RT = Retention time in minutes.
1 = 2-Thenoyl
2. = Fused ring to give naphthyl group
3. P = 2-formyl-1-methylpyrrol-4-ylcarbonyl
4. A = 2-amino-5-chlorophenyl The compounds prepared in Examples 35-108 are as follows.

Example 35

4-[4-(4-Amino-7-isopropyl-7H-pyrrolo[2,3-d]pyrimidin-5-yl)phenoxy]-3-trifluoromethyl-benzaldehyde.

Example 36

4-[4-(4-Amino-7-isopropyl-7H-pyrrolo[2,3-d]pyrimidin-5-yl)phenoxy]-3-chloroacetophenone.

Example 37

4-[4-(4-amino-7-isopropyl-7H-pyrrolo[2,3-d]pyrimidin-5-yl)phenoxy]-3-chloro-benzaldehyde.

Example 38

4-[4-(4-amino-7-isopropyl-7H-pyrrolo[2,3-d]pyrimidin-5-yl)phenoxy]acetophenone.

Example 39

4-[4-(4-amino-7-isopropyl-7H-pyrrolo[2,3-d]pyrimidin-5-yl)phenoxy]benzaldehyde.

Example 40

2'-[4-(4-amino-7-isopropyl-7H-pyrrolo[2,3-d]pyrimidin-5-yl)phenoxy]-5'-trifluoromethyl-propiophenone.

Example 41

2'-[4-(4-amino-7-isopropyl-7H-pyrrolo[2,3-d]pyrimidin-5-yl)phenoxy]-3'-trifluoromethyl-acetophenone.

Example 42

2-[4-(4-amino-7-isopropyl-7H-pyrrolo[2,3-d]pyrimidin-5-yl)phenoxy]-3-formyl-6-dimethyl-aminobenzonitrile.

Example 43

2-[4-(4-amino-7-isopropyl-7H-pyrrolo[2,3-d]pyrimidin-5-yl)phenoxy]-3-trifluoromethyl-benzaldehyde.

Example 44

2'-[4-(4-amino-7-isopropyl-7H-pyrrolo[2,3-d]pyrimidin-5-yl)phenoxy]-4'-methoxy-acetophenone.

Example 45

2-[4-(4-amino-7-isopropyl-7H-pyrrolo[2,3-d]pyrimidin-5-yl)phenoxy]-4-chloro-benzaldehyde.

Example 46

2'-[4-(4-amino-7-isopropyl-7H-pyrrolo[2,3-d]pyrimidin-5-yl)phenoxy]-5'-fluoro-acetophenone.

Example 47

2'-[4-(4-amino-7-isopropyl-7H-pyrrolo[2,3-d]pyrimidin-5-yl)phenoxy]-5-methoxy-acetophenone.

Example 48

2-[4-(4-amino-7-isopropyl-7H-pyrrolo[2,3-d]pyrimidin-5-yl)phenoxy]-4-methoxy-benzaldehyde.

Example 49

2'-[4-(4-amino-7-isopropyl-7H-pyrrolo[2,3-d]pyrimidin-5-yl)phenoxy]propiophenone.

Example 50

2-[4-(4-amino-7-isopropyl-7H-pyrrolo[2,3-d]pyrimidin-5-yl)phenoxy]-3-fluoro-benzaldehyde.

Example 51

2'-[4-(4-amino-7-isopropyl-7H-pyrrolo[2,3-d]pyrimidin-5-yl)phenoxy]acetophenone.

Example 52

2-[4-(4-amino-7-isopropyl-7H-pyrrolo[2,3-d]pyrimidin-5-yl)phenoxy]benzaldehyde.

Example 53

4'-[4-(4-amino-7-isopropyl-7H-pyrrolo[2,3-d]pyrimidin-5-yl)phenoxy]-2-trifluoromethyl-propiophenone.

Example 54

4-[4-(4-amino-7-isopropyl-7H-pyrrolo[2,3-d]pyrimidin-5-yl)phenoxy]phenyl 2-thienyl-ketone.

Example 55

4'-[4-(4-amino-7-isopropyl-7H-pyrrolo[2,3-d]pyrimidin-5-yl)phenoxy]-2'-trifluoromethyl-acetophenone.

Example 56

4-[4-(4-amino-7-isopropyl-7H-pyrrolo[2,3-d]pyrimidin-5-yl)phenoxy]-2-trifluoromethyl-benzaldehyde.

Example 57

4'-[4-(4-amino-7-isopropyl-7H-pyrrolo[2,3-d]pyrimidin-5-yl)phenoxy]-1'-acetonaphthone.

Example 58

4-[4-(4-amino-7-isopropyl-7H-pyrrolo[2,3-d]pyrimidin-5-yl)phenoxy]-2-methoxybenzaldehyde.

Example 59

2-[4-(4-amino-7-isopropyl-7H-pyrrolo[2,3-d]pyrimidin-5-yl)phenoxy]-4-trifluoromethyl-propiophenone.

Example 60

2-[4-(4-amino-7-isopropyl-7H-pyrrolo[2,3-d]pyrimidin-5-yl)phenoxy]-4-trifluoromethyl-acetophenone.

Example 61

2-[4-(4-amino-7-isopropyl-7H-pyrrolo[2,3-d]pyrimidin-5-yl)phenoxy]-5-trifluoromethyl-acetophenone.

Example 62

2-[4-(4-amino-7-isopropyl-7H-pyrrolo[2,3-d]pyrimidin-5-yl)phenoxy]-4-chloro-5-methylacetophenone.

Example 63

2-[4-(4-amino-7-isopropyl-7H-pyrrolo[2,3-d]pyrimidin-5-yl)phenoxy]-5-nitrobenzaldehyde.

Example 64

4-[4-(4-amino-7-isopropyl-7H-pyrrolo[2,3-d]pyrimidin-5-yl)phenoxy]benzoyl-1-methylpyrrole-2-aldehyde.

Example 65

4'-[4-(4-amino-7-isopropyl-7H-pyrrolo[2,3-d]pyrimidin-5-yl)phenoxy]2-(methylsulphonyl)acetophenone.

Example 66

5-[4-(4-amino-7-isopropyl-7H-pyrrolo[2,3-d]pyrimidin-5-yl)phenoxy]-1-indanone.

Example 67

2-amino-2'-[4-(4-amino-7-isopropyl-7H-pyrrolo[2,3-d]pyrimidin-5-yl)phenoxy]-5-chlorobenzophenone.

Example 68

2'-[4-(4-amino-7-isopropyl-7H-pyrrolo[2,3-d]pyrimidin-5-yl)phenoxy]-5-nitro-acetophenone.

Example 69

4-[4-(4-amino-7-isopropyl-7H-pyrrolo[2,3-d]pyrimidin-5-yl)phenoxy]-3-trifluoromethyl-benzonitrile.

Example 70

4-[4-(4-amino-7-isopropyl-7H-pyrrolo[2,3-d]pyrimidin-5-yl)phenoxy]-3-chloro-benzonitrile

Example 71

4-[4-(4-amino-7-isopropyl-7H-pyrrolo[2,3-d]pyrimidin-5-yl)phenoxy]-2-chloro-benzonitrile.

Example 72

4-[4-(4-amino-7-isopropyl-7H-pyrrolo[2,3-d]pyrimidin-5-yl)phenoxy]-3-fluoro-benzonitrile

Example 73

4-[4-(4-amino-7-isopropyl-7H-pyrrolo[2,3-d]pyrimidin-5-yl)phenoxy]benzonitrile.

Example 74

2-[4-(4-amino-7-isopropyl-7H-pyrrolo[2,3-d]pyrimidin-5-yl)phenoxy]-6-(4-methylphenylthio)benzonitrile.

Example 75

2-[4-(4-amino-7-isopropyl-7H-pyrrolo[2,3-d]pyrimidin-5-yl)phenoxy]-6-(2-pyridylthio) benzonitrile.

Example 76

Methyl {3-[4-(4-amino-7-isopropyl-7H-pyrrolo[2,3-d]pyrimidin-5-yl)phenoxy]2-cyanophenylthio}acetate.

Example 77

2-[4-(4-amino-7-isopropyl-7H-pyrrolo[2,3-d]pyrimidin-5-yl)phenoxy]-3-trifluoromethyl-benzonitrile

Example 78

2-[4-(4-amino-7-isopropyl-7H-pyrrolo[2,3-d]pyrimidin-5-yl)phenoxy]-5-trifluoromethyl-benzonitrile.

Example 79

2-[4-(4-amino-7-isopropyl-7H-pyrrolo[2,3-d]pyrimidin-5-yl)phenoxy]6-(pyrrol-1-yl) benzonitrile.

Example 80

2-[4-(4-amino-7-isopropyl-7H-pyrrolo[2,3-d]pyrimidin-5-yl)phenoxy]-5-nitrobenzonitrile.

Example 81

2-[4-(4-amino-7-isopropyl-7H-pyrrolo[2,3-d]pyrimidin-5-yl)phenoxy]benzonitrile.

Example 82

5-[4-(4-amino-7-isopropyl-7H-pyrrolo[2,3-d]pyrimidin-5-yl)phenoxy]-2-nitrobenzaldehyde.

Example 83

4-[4-(4-amino-7-isopropyl-7H-pyrrolo[2,3-d]pyrimidin-5-yl)phenoxy]-3-nitrophenyl Methyl Sulphone.

Example 84

1-[4-(4-amino-7-isopropyl-7H-pyrrolo[2,3-d]pyrimidin-5-yl)phenoxy]-2-nitro-4-trifluoromethylbenzene.

Example 85

4'-[4-(4-amino-7-isopropyl-7H-pyrrolo[2,3-d]pyrimidin-5-yl)phenoxy]-2'-chloroacetophenone.

Example 86

4'-[4-(4-amino-7-isopropyl-7H-pyrrolo[2,3-d]pyrimidin-5-yl)phenoxy]-2'-methylacetophenone.

Example 87

7-[4-(4-amino-7-isopropyl-7H-pyrrolo[2,3-d]pyrimidin-5-yl)phenoxy]-3-phenylindan-1-one.

Example 88

2-[4-(4-amino-7-isopropyl-7H-pyrrolo[2,3-d]pyrimidin-5-yl)phenoxy]-6-trifluoromethyl-acetophenone.

Example 89

1-[4-(4-amino-7-isopropyl-7H-pyrrolo[2,3-d]pyrimidin-5-yl)phenoxy]-9-fluorenone.

Example 90

6-[4-(4-amino-7-isopropyl-7H-pyrrolo[2,3-d]pyrimidin-5-yl)phenoxy]-3,4-dimethoxy-benzaldehyde.

Example 91

2-[4-(4-amino-7-isopropyl-7H-pyrrolo[2,3-d]pyrimidin-5-yl)phenoxy]-5-methyl acetophenone.

Example 92

2-[4-(4-amino-7-isopropyl-7H-pyrrolo[2,3-d]pyrimidin-5-yl)phenoxy]-6-(2-oxoazepin-3-ylamino)benzonitrile.

Example 93

2-[4-(4-amino-7-isopropyl-7H-pyrrolo[2,3-d]pyrimidin-5-yl)phenoxy]-6-(4-carbamoylpiperidin-1-yl)benzonitrile.

Example 94

2-[4-(4-amino-7-isopropyl-7H-pyrrolo[2,3-d]pyrimidin-5-yl)phenoxy]-6-(3-imidazol-1-yl)propylamino]benzonitrile.

Example 95

2-[4-(4-amino-7-isopropyl-7H-pyrrolo[2,3-d]pyrimidin-5-yl)phenoxy]-6-[2-(4-pyridyl)ethylamino]benzonitrile.

Example 96

2-[4-(4-amino-7-isopropyl-7H-pyrrolo[2,3-d]pyrimidin-5-yl)phenoxy]-6-(2-thienyl-methylamino)benzonitrile.

Example 97

2-[4-(4-amino-7-isopropyl-7H-pyrrolo[2,3-d]pyrimidin-5-yl)phenoxy]-6-(4-cyanopiperidin-1-yl)benzonitrile.

Example 98

2-[4-(4-amino-7-isopropyl-7H-pyrrolo[2,3-d]pyrimidin-5-yl)phenoxy]-6-(3-pyridyl-methylamino)benzonitrile

Example 99

2-[4-(4-amino-7-isopropyl-7H-pyrrolo[2,3-d]pyrimidin-5-yl)phenoxy]-6-(4-methyl-phenoxy)benzonitrile.

Example 100

2-[4-(4-amino-7-isopropyl-7H-pyrrolo[2,3-d]pyrimidin-5-yl)phenoxy]-6-thiamorpholino-benzonitrile

Example 101

2-[4-(4-amino-7-isopropyl-7H-pyrrolo[2,3-d]pyrimidin-5-yl)phenoxy]-6-[(3-dimethylamino)propylamino]benzonitrile.

Example 102

2-[4-(4-amino-7-isopropyl-7H-pyrrolo[2,3-d]pyrimidin-5-yl)phenoxy]-6-(2,2,2,-trifluoroethoxy)benzonitrile.

Example 103

2-[4-(4-amino-7-isopropyl-7H-pyrrolo[2,3-d]pyrimidin-5-yl)phenoxy]-6-(3-methoxypropylamino)benzonitrile.

Example 104

2-[4-(4-amino-7-isopropyl-7H-pyrrolo[2,3-d]pyrimidin-5-yl)phenoxy]-6-dimethylamino-benzonitrile.

Example 105

2-[4-(4-amino-7-isopropyl-7H-pyrrolo[2,3-d]pyrimidin-5-yl)phenoxy]-5-methoxy-benzonitrile.

Example 106

2-[4-(4-amino-7-isopropyl-7H-pyrrolo[2,3-d]pyrimidin-5-yl)phenoxy]-5-fluoro benzonitrile.

Example 107

1-[4-(4-amino-7-isopropyl-7H-pyrrolo[2,3-d]pyrimidin-5-yl)phenoxy]-4-nitro-2-trifluoromethyl-benzene.

Example 108

1-[4-(4-amino-7-isopropyl-7H-pyrrolo[2,3-d]pyrimidin-5-yl)phenoxy]-6-chloro-2-nitro-4-trifluoromethyl-benzene.

Examples 109-137 were prepared by the general method described below.

General Method

A carbonyl compound (approx. 50 mg) listed in Table J was dissolved in methanol (2 ml) and then polymer-supported sodium borohydride [on Amberlite; IRA-400; 2.5 mmol of borohydride per g of resin; 2 equivalents (50 mg of the starting materials ranged from 0.106 mmol to 0.1345 mmol) were added.

The mixtures were shaken (orbital shaker) at ambient temperature for 24 h then filtered and the resins washed with methanol (2×1 ml) and the filtrates evaporated and the residues analysed. The products obtained are listed in Table K. HPLC RT is the retention time in minutes.

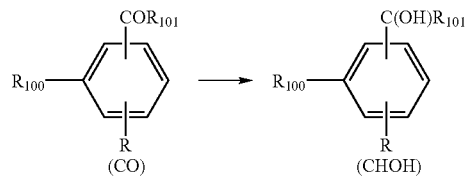

TABLE K

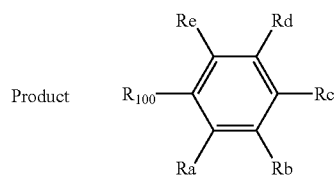

| SM EX | PD EX | Ra | Rb | Rc | Rd | Re | HPLC RT |
|---|---|---|---|---|---|---|---|
| 35 | 109 | $CF_3$ | H | $CH_2OH$ | H | H | 3.96 |
| 36 | 110 | Cl | H | $CH(OH)CH_3$ | H | H | 3.99 |
| 37 | 111 | Cl | H | $CH_2OH$ | H | H | 3.81 |
| 38 | 112 | H | H | $CH(OH)CH_3$ | H | H | 3.75 |
| 39 | 113 | H | H | $CH_2OH$ | H | H | 3.57 |
| 40 | 114 | $CH(OH)C_2H_5$ | H | $CF_3$ | H | H | 4.57 |
| 41 | 115 | $CH(OH)CH_3$ | H | H | H | $CF_3$ | 4.14 |
| 42 | 116 | $CH_2OH$ | H | H | $N(CH_3)_2$ | CN | 3.57 |
| 43 | 117 | $CH_2OH$ | H | H | H | $CF_3$ | 3.99 |
| 44 | 118 | $CH(OH)CH_3$ | H | H | $OCH_3$ | H | 3.79 |
| 45 | 119 | $CH_2OH$ | H | H | Cl | H | 4.01 |
| 46 | 120 | $CH(OH)CH_3$ | H | F | H | H | 3.97 |
| 47 | 121 | $CH_2OH$ | H | $OCH_3$ | H | H | 3.68 |
| 48 | 122 | $CH_2OH$ | H | H | $OCH_3$ | H | 3.61 |

TABLE K-continued

Product: benzene ring with R100, Ra, Rb, Rc, Rd, Re substituents

| SM EX | PD EX | Ra | Rb | Rc | Rd | Re | HPLC RT |
|---|---|---|---|---|---|---|---|
| 49 | 123 | CH(OH)C$_2$H$_5$ | H | H | H | H | 4.08 |
| 50 | 124 | CH$_2$OH | H | H | H | F | 3.63 |
| 51 | 125 | CH(OH)CH$_3$ | H | H | H | H | 3.83 |
| 52 | 126 | CH$_2$OH | H | H | H | H | 3.64 |
| 53 | 127 | CF$_3$ | H | CH(OH)C$_2$H$_5$ | H | H | 4.85 |
| 54 | 128 | H | H | 2-ThCHOH 1 | H | H | 4.66 |
| 55 | 129 | H | CF$_3$ | CH(OH)CH$_3$ | H | H | 4.74 |
| 56 | 130 | H | CF$_3$ | CH$_2$OH | H | H | 4.48 |
| 57 | 131 | H | H | CH(OH)CH$_3$ | —CH=CH—CH=CH— 2 | | 4.65 |
| 58 | 132 | H | OCH$_3$ | CH$_2$OH | H | H | 3.82 |
| 59 | 133 | CH(OH)C$_2$H$_5$ | H | H | CF$_3$ | H | 5.03 |
| 60 | 134 | CH(OH)CH$_3$ | H | H | CF$_3$ | H | 4.72 |
| 61 | 135 | CH(OH)CH$_3$ | H | CF$_3$ | H | H | 4.81 |
| 62 | 136 | CH(OH)CH$_3$ | H | CH$_3$ | Cl | H | 4.87 |
| 63 | 137 | CH$_2$OH | H | NO$_2$ | H | H | 3.96 |

1 - Th = Thienyl
2 = fused ring to give naplithyl.

Example 109

4-[4-(4-Amino-7-isopropyl-7H-pyrrolo[2,3-d]pyrimidin-5-yl)phenoxy]-3-trifluoromethyl-benzyl Alcohol.

Example 110

4-[4-(4-Amino-7-isopropyl-7H-pyrrolo[2,3-d]pyrimidin-5-yl)phenoxy]-3-chloro-α-methylbenzyl Alcohol.

Example 111

4-[4-(4-amino-7-isopropyl-7H-pyrrolo[2,3-d]pyrimidin-5-yl)phenoxy]-3-chloro-benzyl Alcohol.

Example 112

4-[4-(4-amino-7-isopropyl-7H-pyrrolo[2,3-d]pyrimidin-5-yl)phenoxy]acetophenone.

Example 113

4-[4-(4-amino-7-isopropyl-7H-pyrrolo[2,3-d]pyrimidin-5-yl)phenoxy]benzyl Alcohol.

Example 114

2'-[4-(4-amino-7-isopropyl-7H-pyrrolo[2,3-d]pyrimidin-5-yl)phenoxy]-5'-trifluoromethyl-α-ethylbenzyl Alcohol.

Example 115

2'-[4-(4-amino-7-isopropyl-7H-pyrrolo[2,3-d]pyrimidin-5-yl)phenoxy]-3'-trifluoromethyl-α-methylbenzyl Alcohol.

Example 116

2-[4-(4-amino-7-isopropyl-7H-pyrrolo[2,3-d]pyrimidin-5-yl)phenoxy]-3-hydroxymethyl-6-(dimethylamino)benzonitrile.

Example 117

2-[4-(4-amino-7-isopropyl-7H-pyrrolo[2,3-d]pyrimidin-5-yl)phenoxy]-3-trifluoromethyl-benzyl Alcohol.

Example 118

2'-[4-(4-amino-7-isopropyl-7H-pyrrolo[2,3-d]pyrimidin-5-yl)phenoxy]-4'-methoxy-α-methylbenzyl Alcohol.

Example 119

2-[4-(4-amino-7-isopropyl-7H-pyrrolo[2,3-d]pyrimidin-5-yl)phenoxy]-4-chlorobenzyl Alcohol.

Example 120

2'-[4-(4-amino-7-isopropyl-7H-pyrrolo[2,3-d]pyrimidin-5-yl)phenoxy]-5'-fluoro-α-methylbenzyl Alcohol.

Example 121

2'-[4-(4-amino-7-isopropyl-7H-pyrrolo[2,3-d]pyrimidin-5-yl)phenoxy]-5-methoxy-α-methylbenzyl Alcohol.

Example 122

2-[4-(4-amino-7-isopropyl-7H-pyrrolo[2,3-d]pyrimidin-5-yl)phenoxy]-4-methoxybenzyl Alcohol.

Example 123

2'-[4-(4-amino-7-isopropyl-7H-pyrrolo[2,3-d]pyrimidin-5-yl)phenoxy]-α-ethylbenzyl Alcohol.

Example 124

2-[4-(4-amino-7-isopropyl-7H-pyrrolo[2,3-d]pyrimidin-5-yl)phenoxy]-3-fluorobenzyl Alcohol.

Example 125

2'-[4-(4-amino-7-isopropyl-7H-pyrrolo[2,3-d]pyrimidin-5-yl)phenoxy]-α-methylbenzyl Alcohol.

Example 126

2-[4-(4-amino-7-isopropyl-7H-pyrrolo[2,3-d]pyrimidin-5-yl)phenoxy]benzyl Alcohol.

Example 127

4'-[4-(4-amino-7-isopropyl-7H-pyrrolo[2,3-d]pyrimidin-5-yl)phenoxy]-2-trifluoromethyl-α-ethylbenzyl Alcohol.

Example 128

4-[4-(4-amino-7-isopropyl-7H-pyrrolo[2,3-d]pyrimidin-5-yl)phenoxy]-α-(2-thienyl)benzyl Alcohol.

Example 129

4'-[4-(4-amino-7-isopropyl-7H-pyrrolo[2,3-d]pyrimidin-5-yl)phenoxy]-2'-trifluoromethyl-α-methylbenzyl Alcohol.

Example 130

4-[4-(4-amino-7-isopropyl-7H-pyrrolo[2,3-d]pyrimidin-5-yl)phenoxy]-2-trifluoromethyl-benzyl Alcohol.

Example 131

1-{1-4-[4-(4-amino-7-isopropyl-7H-pyrrolo[2,3-d]pyrimidin-5-yl)phenoxy]naphthyl}-ethanol.

Example 132

4-[4-(4-amino-7-isopropyl-7H-pyrrolo[2,3-d]pyrimidin-5-yl)phenoxy]-2-methoxybenzyl Alcohol.

Example 133

2-[4-(4-amino-7-isopropyl-7H-pyrrolo[2,3-d]pyrimidin-5-yl)phenoxy]-4-trifluoromethyl-α-ethylbenzyl Alcohol.

Example 134

2-[4-(4-amino-7-isopropyl-7H-pyrrolo[2,3-d]pyrimidin-5-yl)phenoxy]-4-trifluoromethyl-α-methylbenzyl Alcohol.

Example 135

2-[4-(4-amino-7-isopropyl-7H-pyrrolo[2,3-d]pyrimidin-5-yl)phenoxy]-5-trifluoromethyl-α-methylbenzyl Alcohol

Example 136

2-[4-(4-amino-7-isopropyl-7H-pyrrolo[2,3-d]pyrimidin-5-yl)phenoxy]-4-chloro-5-methyl-α-methylbenzyl Alcohol.

Example 137

2-[4-(4-amino-7-isopropyl-7H-pyrrolo[2,3-d]pyrimidin-5-yl)phenoxy]-nitrobenzyl Alcohol.

The Examples listed in Table L were prepared by reacting aldehydes of formula (AL) with diethylamine in the presence of Na(OAc)$_3$BH to give compounds of formula (AM). The starting aldehyde was prepared in an earlier Example which is given in the Table.

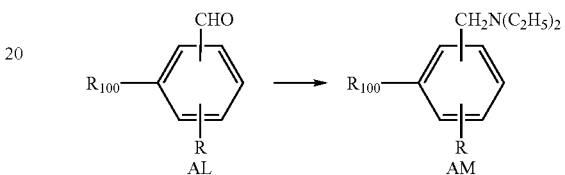

General Method

The aldehyde was treated with 1 ml of a stock solution of THF (50 ml) and diethylamine (2 ml) [equivalent to 40 μl diethylamine] and left at room temperature for 1 hour in a septum sealed tube. Na (OAc)$_3$BH. (20 mg±2 mg) was added to each reaction which was then flushed with N$_2$, re-capped and left at ambient temperature for 24 hours. A solution of acetic acid (3 ml) in 100 ml THF was added to each of the ketone reactions and left at room temperature over the weekend. Reactions were quenched by addition of saturated Na$_2$CO$_3$ aq (1 ml) and extracted into dichloromethane (2 mls) by shaking capped tube, collected and allowed to evaporate. LCMS was carried out on all products and the target mass found in each case.

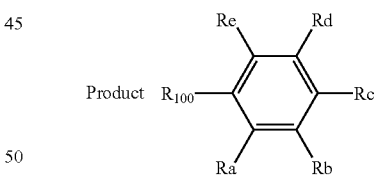

TABLE L

| SM EX | PD EX | PRODUCT | | | | | HPLC RT |
|---|---|---|---|---|---|---|---|
| | | Ra | Rb | Rc | Rd | Re | |
| 65 | 138 | H | H | CO(P) 1 | H | H | 3.62 |
| 35 | 139 | CF$_3$ | H | CH$_2$N(C$_2$H$_5$)$_2$ | H | H | 3.83 |
| 40 | 140 | H | H | CH$_2$N(C$_2$H$_5$)$_2$ | H | H | 3.36 |
| 43 | 141 | CH$_2$N(C$_2$H$_5$)$_2$ | H | H | N(CH$_3$)$_2$ | CN | 3.34 |
| 44 | 142 | CH$_2$N(C$_2$H$_5$)$_2$ | H | H | H | CF$_3$ | 3.80 |
| 49 | 143 | CH$_2$N(C$_2$H$_5$)$_2$ | H | H | OCH$_3$ | H | 3.42 |
| 51 | 144 | CH$_2$N(C$_2$H$_5$)$_2$ | H | H | H | F | 3.27 |
| 53 | 145 | CH$_2$N(C$_2$H$_5$)$_2$ | H | H | H | H | 3.31 |

TABLE L-continued

| | | PRODUCT | | | | | |
|---|---|---|---|---|---|---|---|
| SM EX | PD EX | Ra | Rb | Rc | Rd | Re | HPLC RT |
| 57 | 146 | H | $CF_3$ | $CH_2N(C_2H_5)_2$ | H | H | 4.12 |
| 59 | 147 | H | $OCH_3$ | $CH_2N(C_2H_5)_2$ | H | H | 3.52 |
| 91 | 148 | $CH_2N(C_2H_5)_2$ | H | $OCH_3$ | $OCH_3$ | H | 3.25 |

1 P = 1-methyl-2-(diethylaminomethyl)pyrrol-3-carbonyl

Example 138

4-[4-(4-amino-7-isopropyl-7H-pyrrolo[2,3-d]pyrimidin-5-yl)phenoxy]benzoyl-1-methyl-2-(diethylaminomethyl)pyrrole.

Example 139

5-[4-(4-diethylaminomethyl-2-trifluoromethylphenoxy)phenyl]-7-isopropyl-7H-pyrrolo[2,3-d]pyrimidin-4-ylamine.

Example 140

5-[4-(4-diethylaminomethylphenoxy)phenyl]-7-isopropyl-7H-pyrrolo[2,3-d]pyrimidin-4-ylamine.

Example 141

2-[4-(4-amino-7-isopropyl-7H-pyrrolo[2,3-d]pyrimidin-5-yl)phenoxy]-3-diethylaminomethyl-6-(dimethylamino)benzonitrile.

Example 142

5-[4-(2-diethylaminomethyl-6-trifluoromethylphenoxy)phenyl]-7-isopropyl-7H-pyrrolo[2,3-d]pyrimidin-4-ylamine.

Example 143

5-[4-(2-diethylaminomethyl-5-methoxyphenoxy)phenyl]-7-isopropyl-7H-pyrrolo[2,3-d]pyrimidin-4-ylamine.

Example 144

5-[4-(2-diethylaminomethyl-6-fluorophenoxy)phenyl]-7-isopropyl-7H-pyrrolo[2,3-d]pyrimidin-4-ylamine.

Example 145

5-[4-(2-diethylaminomethylphenoxy)phenyl]-7-isopropyl-7H-pyrrolo[2,3-d]pyrimidin-4-ylamine.

Example 146

5-[4-(4-diethylaminomethyl-3-trifluoromethylphenoxy)phenyl]-7-isopropyl-7H-pyrrolo[2,3-d]pyrimidin-4-ylamine.

Example 147

5-[4-(2-diethylaminomethyl-5-methoxyphenoxy)phenyl]-7-isopropyl-7H-pyrrolo[2,3-d]-pyrimidin-4-ylamine.

Example 148

5-[4-(2-diethylaminomethyl-4,5-dimethoxyphenoxy)phenyl]-7-isopropyl-7H-pyrrolo[2,3-d]pyrimidin-4-ylamine.

General Formula Q

Examples 149 to 158 were prepared by reacting compounds of formula (AL2) with an amine of formula (AM2) as shown in the scheme below in which $R_{100}$ is as previously stated using the procedure outlined in the general method. The products obtained are shown in Table Q

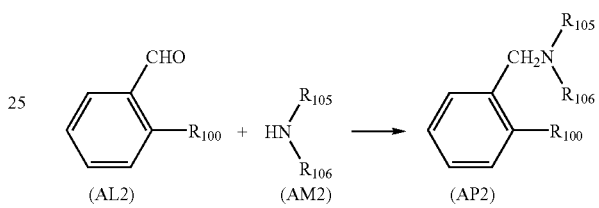

General Method Q

The stock solution of the aldehyde (440 mg) in THF (11 ml) was dispensed equally into 11 septum sealed vials. Each reaction (containing 40 mg of CHO 0.1075 mmol) was treated with an excess of the amine (3-10 molar equivalents) listed in Table Q and Na $(OAc)_3BH$ (113 mg; 0.5375 mmol) and left at room temperature for 48 hours. The mixture was quenched with saturated $Na_2CO_3$ aq. solution (1 ml) and shaken for 1 hour and extracted with dichloromethane (3 ml) and separated by the use of Empore cartridge. The organics were allowed to evaporate at room temperature overnight and the residues dissolved in EtOAc (2 ml) and extracted with 2N HCl (1 ml) and vortex mixing. The acid layer was pipetted off, washed with EtOAc (2×1 ml) pipette manipulations and then basified with 4N NaOH. The mixture was extracted into EtOAc (2 ml) vortex mixing/pipette separations and washed with water (2×1 ml). The final EtOAc layer was dried by passing through a small EMPORE cartridge and evaporated to dryness.

TABLE Q

| Ex. No. | $NR_{105}R_{106}$ | HPLC RT |
|---|---|---|
| 149 | —N⟩N—$CO_2C_2H_5$ | 4.36 |
| 150 | —N⟩ with $CO_2C_2H_5$ | 5.37 |
| 151 | —HN—$CO_2C_2H_5$ | 3.64 |

TABLE Q-continued

| Ex. No. | NR$_{105}$R$_{106}$ | HPLC RT |
|---|---|---|
| 152 | —HN—CH$_2$CH$_2$—OH | 2.95 |
| 153 | —HN—CH(CH$_3$)$_2$ | 3.24 |
| 154 | —HN-(2-thiazolyl) | 4.55 |
| 155 | —N(piperazinyl)-N—Me | 3.35 |
| 156 | —N(morpholinyl) | 3.47 |
| 157 | —N(piperidinyl) | 3.39 |
| 158 | —N(pyrrolidinyl) | 3.25 |

The compounds prepared in Table Q are as follows:

Example 149

Ethyl 4-{4-[4-(4-amino-7-isopropyl-7H-pyrrolo[2,3-d]pyrimidin-5-yl)phenoxy]phenyl}-piperazine-1-carboxylate.

Example 150

Ethyl-1-{[4-(4-amino-7-isopropyl-7H-pyrrolo[2,3-d]pyrimidin-5-yl)phenoxy]phenyl]-piperidine-2-carboxylate.

Example 151

Ethyl N-{4-[4-(4-amino-7-isopropyl-7H-pyrrolo[2,3-d]pyrimidin-5-yl)phenoxy]phenyl-aminoacetate.

Example 152

N-{2-[4-(4-amino-7-isopropyl-7H-pyrrolo[2,3-d]pyrimidin-5-yl)phenoxy]phenylmethyl}-2-aminoethanol.

Example 153

7-Isopropyl-5-[4-(2-dimethylaminomethylphenoxy)phenyl]-7H-pyrrolo[2,3-d]pyrimidin-4-ylamine.

Example 154

7-Isopropyl-5-[4-(2-(2-thiazolylaminomethylphenoxy)phenyl]-7H-pyrrolo[2,3-d]-pyrimidin-4-ylamine.

Example 155

7-Isopropyl-5-[4-(2-(4-methylpiperazin-1-ylmethyl)phenoxy)phenyl]-7H-pyrrolo[2,3-d]-pyrimidin-4-ylamine.

Example 156

7-Isopropyl-5-[4-(2-morpholinomethylphenoxy)phenyl]-7H-pyrrolo[2,3-d]pyrimidin-4-ylamine.

Example 157

7-Isopropyl-5-[4-(2-piperidinomethylphenoxy)phenyl]-7H-pyrrolo[2,3-d]pyrimidin-4-ylamine.

Example 158

7-Isopropyl-5-[4-(2-pyrrolodinomethylphenoxy)phenyl]-7H-pyrrolo[2,3-d]pyrimidin-4-ylamine.

The conditions used in LCMS for Examples 35-158 are given below.

Examples 35-52, 64-84 and 109-126

| | |
|---|---|
| Column: | Peco R Activity 3 mm × 3 xm C18-PK/5 (Perkin Elmer) |
| Mobile Phase: | 0.1 M Ammonium Acetate Buffer [pH 4.55]: Acetonitrile (gradient - see below). |
| Conditions: | 10-100% MeCN in 5 minutes. 100% MeCN for 1 minute. 100-10% MeCN in 2 minutes. (Total analysis run time 8 minutes). |
| Wavelength Range: | 250-320 nm. |
| Flow Rate: | 1 ml/minute. |
| Injection Volume: | 20 μl. |
| MS Method: | APCI11H. |
| Ionisation: | APcI +ve/−ve. |
| Mass Range: | 100-700 m/z. |

Examples 53-63, 85-108 and 126-137

| | |
|---|---|
| Column: | 5 μl Hypersil 100 × 2.1 mm BDS C18 |
| Mobile Phase: | 0.1 M Ammonium Acetate Buffer [pH 4.55]: Acetonitrile (gradient - see below). |
| Conditions: | 10-100% MeCN in 8 minutes. 100-10% MeCN for 3 minute. (Total analysis run time 11 minutes). |
| Wavelength Range: | 250-320 nm. |
| Flow Rate: | 1 ml/minute. |
| Injection Volume: | 20° μl. |
| MS Method: | APCI11H. |
| Ionisation: | APcI +ve/−ve. |
| Mass Range: | 100-700 m/z. |

Examples 138-158

| | |
|---|---|
| Column: | 5 μl Hypersil 100 × 2.1 mm BDS C18 |
| Mobile Phase: | 0.1 M Ammonium Acetate Buffer [pH 4.55]: Acetonitrile (gradient - see below). |
| Conditions: | 10-100% MeCN in 8 minutes. 100% MeCN for 1 minute. 100-10% MeCN for 2 minutes. (Total analysis run time 11 minutes). |
| Wavelength Range: | 250-320 nm. |
| Flow Rate: | 1 ml/minute. |

| Injection Volume: | 20° μl. |
| MS Method: | APCI11H. |
| Ionisation | APcI +ve/–ve. |
| Mass Range: | 100-700 m/z. |

Example 159

7-isopropyl-5-(4-(pyrimidin-2-yloxy)phenyl-7H-pyrrolo[2,3-d]pyrimidin-4-ylamine a) Iodine (52.9 g) was added to a stirred solution of 4-chloro-7H-pyrrolo[2,3-d]-pyrimidine (29.1 g, J. Chem. Soc. 1960, 131) in N,N-dimethylformamide (400 ml). Potassium hydroxide pellets (31.9 g) were added in portions to the cooled mixture so that the temperature of the reaction mixture was maintained around 20° C. and this mixture was stirred at ambient temperature for 2 hours. A solution of sodium thiosulphate (900 ml of a 10% aqueous solution) was added in a steady stream keeping the temperature at 30° C. by external cooling. The mixture was extracted with ethyl acetate and the combined extracts were dried, filtered and evaporated under reduced pressure to give a residue which was added to water (1 L) and extracted with ethyl acetate (2×150 ml). The combined ethyl acetate extracts were dried and evaporated to give a solid which was recrystallised from ethyl acetate. The solid obtained was stirred with methanol (800 ml) and filtered to remove some insoluble material. The filtrate was evaporated to dryness to give a pale yellow solid which was identified as 4-chloro-5-iodo-7H-pyrrolo[2,3-d]-pyrimidine, m.p. 219-221° C.

b) 4-Chloro-5-iodo-7H-pyrrolo[2,3-d]pyrimidine (10.0 g, see Example 17) was added in portions with stirring under nitrogen at 0° C. to a suspension of sodium hydride (1.6 g of a 60% dispersion in mineral oil) in N,N-dimethylformamide (250 ml). When the addition was complete the mixture was allowed to warm up to ambient temperature and when no more gas evolution was observed, a solution of isopropyl bromide (34.0 ml) in N,N-dimethylformamide (20 ml) was added dropwise. The mixture was stirred at ambient temperature overnight then quenched by the dropwise addition of water (300 ml) with external ice-cooling. The mixture was then washed with ethyl acetate (3×300 ml), the combined organic layers were washed with water, dried, filtered and evaporated to give 4-chloro-5-iodo-7-isopropyl-7H-pyrrolo[2,3-d]pyrimidine as a yellow solid, m.p. 116-118° C. The structure was confirmed by 1H nmr.

c) A mixture of 4-chloro-5-iodo-7-isopropyl-7H-pyrrolo[2,3-d]pyrimidine (2.8 g), 4-methoxybenzeneboronic acid (1.32 g), bis(triphenylphosphine)palladium (II) chloride (625 mg), toluene (85 ml), ethanol (11 ml), water (22 ml) and sodium bicarbonate (2.2 g) was heated under nitrogen at 105° C. for 18 hours. The mixture was allowed to cool to ambient temperature and then partitioned between ethyl acetate (100 ml) and brine (100 ml). The organic layer was separated and the aqueous layer was washed with ethyl acetate (2×50 ml). The combined organic layers were washed with water, dried, filtered and evaporated under reduced pressure to give a black oil which solidified on cooling. This material was purified by flash column chromatography on silica using cyclohexane/ethyl acetate (7:3) as the mobile phase. Appropriate fractions were combined and concentrated under reduced pressure to give a yellow oil which solidified on standing to give 4-chloro-7-isopropyl-5-(4-methoxyphenyl)-7H-pyrrolo[2,3-d]pyrimidine. The structure was confirmed by 1H nmr.

d) A mixture of 4-chloro-7-isopropyl-5-(4-methoxyphenyl)-7H-pyrrolo-[2,3-d]-pyrimidine (1.6 g), concentrated ammonia (80 ml, S.G. 0.880) and 1,4-dioxane (80 ml) was heated in a pressure vessel at 120° C. for 18 hours. The mixture was cooled to ambient temperature and the solvent was removed under reduced pressure to give a solid residue which was partitioned between ethyl acetate (100 ml) and water (100 ml). The aqueous layer was extracted with ethyl acetate and the combined organic layers were washed with water, dried, filtered and evaporated to give 4-amino-7-isopropyl-5-(4-methoxyphenyl)-7H-pyrrolo[2,3-d]-pyrimidine. The structure was confirmed by 1H nmr.

e) A solution of boron tribromide (14.4 ml of a 1M solution in dichloromethane) was added dropwise to a stirred solution of 4-amino-7-isopropyl-5-(4-methoxyphenyl) pyrrolo[2,3-d]pyrimidine (1.35 g) in dichloromethane (100 ml) at −10° C. under nitrogen. The reaction mixture was allowed to warm to 0° C. and stirred at this temperature for one hour. Additional boron tribromide (9.6 ml of a 1M solution in dichloromethane) was added at −10° C. and the mixture was allowed to warm to 0° C. and stirred for a further hour. The reaction mixture was quenched by the dropwise addition of saturated sodium bicarbonate solution (50 ml). The mixture was allowed to stand overnight and the dichloromethane layer separated off. Insoluble material at the interface was removed by filtration and dried to yield 4-amino-5-(4-hydroxyphenyl)-7-isopropyl-7H-pyrrolo[2,3-d]pyrimidine. The structure was confirmed by 1H nmr.

f) 4-amino-5-(4-hydroxyphenyl)-7-isopropyl-7H-pyrrolo[2,3-d]pyrimidine (0.05 g), 2-chloropyrimidine (23 mg), potassium carbonate (39 mg) and dimethylformamide (3 ml) were heated at 90° C. with shaking for 26.5 hours. The mixture was then shaken for a further 24 hours at ambient temperature. The reaction mixture was partitioned between ethyl acetate (20 ml) and 2M sodium hydroxide solution (20 ml). The aqueous layer was separated and extracted with ethyl acetate. The combined ethyl acetate extract and washings were combined dried filtered and evaporated to give a solid which was purified by flash column chromatography on silica using dichlormethane/methanol (95:5) as a mobile phase to give a solid which was identified by liquid chromatography LCMS as 7-isopropyl-5-(4-(pyrimidin-2-yloxy)phenyl-7H-pyrrolo[2,3-d]pyrimidin-4-ylamine. The structure was confirmed by 1H nmr spectroscopy.

Example 160

4-(4-amino-7-isopropyl-7H-pyrrolo[2,3-d]pyrimidin-5-yl)benzaldehyde a) A mixture of 4-chloro-5-iodo-7-isopropyl-7H-pyrrolo[2,3-d]pyrimidine (0.50 g), 4-formylbenzene boronic acid (0.48 g), bis (triphenylphosphine) palladium (II) chloride (112 mg), toluene (15 ml), ethanol (2 ml), water (4 ml) and sodium bicarbonate (0.40 g) was 105° C. for 8 hours. The mixture was cooled to ambient temperature, then diluted with brine and extracted with ethyl acetate to give an oil which was purified by flash column chromatography on silica using increasing amounts of ethyl acetate in cyclohexane from 20% to 40% to give 4-(4-chloro-7-isopropyl-7H-pyrrolo[2,3-d]pyrimidin-5-yl)benzaldehyde, m.p. 138-140° C.

b) A mixture of the product from part a) (2.7 g), concentrated aqueous ammonia (75 ml sg 0.880) and 1,4-dioxane (50 ml) was heated at 120° C. for 16 hours in a pressure vessel. The mixture was cooled to ambient temperature and the solvent removed under reduced pressure. Water was added and the mixture was extracted with ethyl acetate to give a solid which was triturated with ethyl acetate and filtered to give a solid which was identified by LCMS as 4-(4-amino-7-isopropyl-7H-pyrrolo[2,3-d]pyrimidin-5-yl)benzaldehyde, m.p. 198-200° C.

Example 161

∝-[4-(4-amino-7-isopropyl-7H-pyrrolo[2,3-d]pyrimidin-5-yl)phenyl]benzyl Alcohol

Phenylmagnesium chloride (1.5 ml of a 2M solution in THF) was added dropwise with stirring under nitrogen to a solution of 4-(4-amino-7-isopropyl-7H-pyrrolo[2,3-d]pyrimidin-5-yl)benzaldehyde (0.25 g) in toluene/THF (1:1, 16 ml) at minus 78° C. under nitrogen. After the addition the mixture was allowed to warm 0° C. and maintained at this temperature for 40 minutes. The reaction was quenched by the dropwise addition of saturated ammonial chloride solution (4 ml) at 0° C. The mixture was allowed to warm to ambient temperature and stood overnight at this temperature. The solvent was removed under reduced pressure and the solid residue obtained was washed with water and filtered. The residue was triturated with hot ethyl acetate, collected by filtration and identified by LCMS as ∝-[4-(4-amino-7-isopropyl-7H-pyrrolo[2,3-d]pyrimidin-5-yl)phenyl]benzyl alcohol, m.p. 279-281° C.

Example 162

7-isopropyl-5-(3-[(phenyl-4-yl)methylene]-2-oxindole)-7H-pyrrolo[2,3-d]pyrimidin-4-ylamine A mixture of 4-(4-amino-7-isopropyl-7H-pyrrolo[2,3-d]pyrimidin-5-yl)benzaldehyde (0.2 g) 2-oxindole (95 mg), piperidine (0.02 ml) and ethanol (5 ml) were boiled under reflux for 3 hours. The mixture was cooled to ambient temperature and the solid which formed was collected by filtration and recrystalised from ethanol to give 7-isopropyl-5-(3-[(phenyl-4-yl)methylene]-2-oxindole)-7H-pyrrolo[2,3-d]pyrimidin-4-ylamine.

Example 163

5-[4-amino-7-isopropyl-7H-pyrrolo[2,3-d]pyrimidin-5-yl]-2-phenoxybenzylalcohol a) A mixture of 5-bromo-2-fluorobenzaldehyde (20.0 g), phenol (9.26 g), potassium carbonate (16.4 g) and dimethylformamide (200 ml) was heated 160° C. for 5 hours. The mixture was cooled and diluted with water then extracted with ethyl acetate to give 5-bromo-2-phenoxybenzaldehyde as an oil.
b) A mixture of the product from part a) (5.71 g), hexamethylditin (10.0 g), tetrakis (triphenylphosphine) palladium (0) (1.5 g) and toluene (200 ml) was boiled under reflux under nitrogen with stirring for 5 hours. The mixture was cooled and filtered and filtrate evaporated to give a residue which was purified by flash column chromatography using petroleum ether b.p. 40-60° C. with increasing amounts of diethyl ether from 2.5-7.5% as a mobile phase to give 5-trimethylstannyl-2-phenoxybenzaldehyde.
c) A mixture of the product from part b) (2.0 g), 4-chloro-5-iodo-7-isopropyl-7H-pyrrolo[2,3-d]pyrimidine (0.99 g), triphenylarsine (0.235 g), and tris (dibenzylideneacetone) dipalladium(0) (0.41 g) and dimethylformamide (20 ml) was heated at 65° C. under nitrogen for 18 hours with stirring. The mixture was cooled and water was added. The mixture was extracted with ethyl acetate to give a residue which was purified by flash column chromatography on silica using increasing amounts of ethyl acetate (5-20%) in cyclohexane as the mobile phase to give 5-[4-chloro-7-isopropyl-7H-pyrrolo[2,3-d]pyrimidine-5-yl]-2-phenoxybenzaldehyde.
d) A mixture of the product from part c) (0.325 g), sodium borohydride (32 mg) and methanol (5 ml) was stirred at 0° C. for 30 minutes and then warmed to ambient temperature and stirred at this temperature for one hour. The mixture was quenched with 50% glacial acetic acid (2 ml). The solvent was removed under reduced pressure and water was added to the residue which was then extracted with ethyl acetate to give 5-[4-chloro-7-isopropyl-7H-pyrrolo[2,3-d]pyrimidine-5-yl]-2-phenoxybenzylalcohol as a solid m.p. 157-159° C.
e) A mixture of the product from part d) (0.18 g), concentrated aqueous ammonia solution (20 ml, sg 0.880) and 1,4-dioxane (20 ml) was heated in a pressure vessel at 120° C. with stirring for 16 hours. The mixture was cooled and partitioned between ethyl acetate and water. Evaporation of the ethyl acetate extract gave an oil which was purified by flash column chromatography to give 5-[4-amino-7-isopropyl-7H-pyrrolo[2,3-d]pyrimidin-5-yl]-2-phenoxybenzylalcohol, m.p. 92-94° C.

Example 164

4-amino-7-cyclopentyl-5-(4-phenoxyphenyl)-7H-pyrrolo-[2,3-d]pyrimidin-6-ylcarbonitrile a) 4-Phenoxyacetophenone (150.0 g) was dissolved in acetic acid (21) and stirred at 50° C. whilst pyridinium tribromide (251.6 g) was added in portions. The brown solution was added to water (31) and the mixture extracted with toluene (1×800 ml and then 2×400 ml). The combined toluene extracts were washed with water and then with aqueous sodium bicarbonate solution until the effervescence ceased. The combined toluene extracts were separated, dried and filtered and used directly in part b) below.
b) The solution of 2-bromo-4'-phenoxyacetophenone in toluene obtained in a) was added to a solution of cyclopentylamine (154 ml) in toluene (11) with stirring under nitrogen over 1.5 hours whilst keeping the temperature below 5° C. The mixture was then stirred for 2.5 hours keeping the temperature below 10° C. and then the mixture was filtered. The filtrate was treated dropwise with concentrated hydrochloric acid (120 ml) whilst keeping the temperature below 10° C. The precipitate was collected by filtration and triturated with propan-2-ol/ether (1:1) to give a solid which was dried under vacuum at 40° C. for 6.5 hours to give 2-cyclopentylamino-4'-phenoxyacetophenone hydrochloride.
c) The product from b) (35.1 g) was added to a solution of malononitrile (9.5 g) in methanol (500 ml) under nitrogen and then an aqueous solution of potassium hydroxide (17.0 g) in water (75 ml) was added dropwise over 30 minutes while keeping the temperature between 0 and 5° C. The mixture was then boiled under reflux for 2.5 hours. Further malononitrile (1.0 g) in methanol (10 ml) was added and the mixture boiled under reflux for a further 3 hours. The mixture was left to stand at ambient temperature for 18 hours and then the methanol was removed under reduced pressure and the residue kept under nitrogen. The residue was dissolved in dichloromethane (600 ml) and washed with water then brine and then dried, filtered and evaporated to give a brown solid which was triturated with diethyl ether to give 2-amino-3-cyano-1-cyclopentyl-4-(4-phenoxyphenyl)pyrrole which was used directly in the next part of this example.

d) The product from c) (25.9 g) was dissolved in a mixture of formamide (155 ml), N,N-dimethylformamide (52 ml) and formic acid (20.2 ml) and the mixture was heated under nitrogen at an internal temperature of 166° C. for four hours. The mixture was cooled and poured into water (3.51) and then extracted with ethyl acetate (3×1500 ml). The combined ethyl acetate extracts were washed with water, dried, filtered and evaporated to give a solid which was triturated with ether and filtered to give a solid which was recrystallised from industrial methylated spirit to give 7-cyclopentyl-5-(4-phenoxyphenyl)-7H-pyrrolo[2,3-d]pyrimidin-4-ylamine, m.p. 178-179° C.

e) The product from d) (3.7 g) was stirred in dry dimethylformamide (120 ml) under nitrogen whilst N-bromosuccinimide (1.8 g) was added in portions under nitrogen in the dark. The mixture was stirred for 18 hours in the dark then worked up to give 6-bromo-7-cyclopentyl-5-(4-phenoxyphenyl)-7H-pyrrolo[2,3-d]pyrimidin-4-ylamine, m.p. 161.5-162.5° C.

f) A mixture of the product from e) (449 mg), zinc cyanide (75 mg) and N-methyl-pyrrolidone (10 ml) was treated with tri(2-furyl)phosphine (63 mg) then thoroughly deoxygenated under nitrogen and tris(dibenzylideneacetone) palladium(0) (45 mg) was added. The mixture was heated to 90° C. and kept at this temperature for 20 hours. Ethyl acetate (20 ml) was added followed by aqueous ammonia solution (20 ml of a 2M solution). The mixture was stirred and then the ethyl acetate layer was separated off and the aqueous layer was further extracted with ethyl acetate. The combined ethyl acetate layer and washings were dried, filtered and evaporated to give a residue which was purified by flash column chromatography on silica using ethyl acetate as the mobile phase to give 4-amino-7-cyclopentyl-5-(4-phenoxyphenyl)-7H-pyrrolo-[2,3-d]pyrimidin-6-ylcarbonitrile, m.p. 117.5-118.5° C.

Example 165

6-aminomethyl-7-cyclopentyl-5-(4-phenoxyphenyl)-7H-pyrrolo[2,3-d]pyrimidin-4-ylamine The product from the previous example (0.881 g) was dissolved in warm ethanol (20 ml) and this solution was added to ethanol saturated with ammonia (200 ml). Raney® nickel (2×1 ml) was added and the mixture was shaken under hydrogen for 6 hours. Positive pressure developed and periodically gas was vented from the apparatus. After 2 hours the vessel was evacuated several times and filled with hydrogen. After a further 2 hours this process was repeated. Finally the mixture was shaken for a further 1.5 hours and then filtered. The filtrate was evaporated to give a solid which was triturated with ether and collected by filtration to give a crude solid which was dissolved in ethyl acetate. Maleic acid (0.2 g) in ethyl acetate was added in portions until no further precipitation occurred. The resulting mixture was warmed and triturated and then allowed to cool over 16 hours. The solid was collected by filtration to give 6-aminomethyl-7-cyclopentyl-5-(4-phenoxyphenyl)-7H-pyrrolo[2,3-d]pyrimidin-4-ylamine, m.p. 196.5-197.5° C.

Example 166

7-tertbutyl-5-(N-formyl-4-phenylaminophenyl)pyrrolo[2,3-d]pyrimidine

A mixture of 7-tertbutyl-5-(4-iodophenyl)pyrrolo[2,3d]pyrimidin-4-ylamine (1.0 g), formanilide (1.0 g), anhydrous potassium carbonate (1.0 g), copper (I), iodide (100 mg), copper powder (80 mg) and N-methylpyrrolidine (5 ml) was heated at 107° C. with stirring under nitrogen for 22 hours. The mixture was cooled and water was added. The mixture was extracted with ethyl acetate to give a residue which was purified by reverse phase preparative HPLC to give 7-tertbutyl-5-(N-formyl-4-phenylaminophenyl) pyrrolo[2,3-d]pyrimidine, m.p. 163-164° C.

Example 167

3-{4-[4-amino-7-tertbutyl-7H-pyrrolo[2,3-d]pyrimidin-7-yl}benzyl Alcohol

In a similar manner to the previous example 7-tert-butyl-5-(4-iodophenyl)-pyrrolo[2,3-]pyrimidin-4-ylamine (392 mg) was reacted with 3-hydroxybenzyl alcohol (372 mg) to give 3-{4-[4-amino-7-tertbutyl-7H-pyrrolo[2,3-d]pyrimidin-7-yl}benzyl alcohol.

Example 168

N-[2-[(4-amino-7-isopropylpyrrolo[2,3-d]pyrimidin-5-yl)phenoxy]phenyl}

A mixture of 5-[4-(2-aminophenoxy)phenyl]-7H-isopropylpyrrolo[2,3-d]-pyrimidin-4-ylamine (43 mg), potassium cyanate (11 mg), glacial acetic acid (7 ml) and ethanol (3 ml) was stirred and heated at 70° C. for 2 hours. Further glacial acetic acid (7 ml) and potassium cyanate (11 mg) were added and heating was continued at 75° C. for 6 hours. The mixture was evaporated under reduced pressure. Water was added to the residue and the mixture was extracted with dichloromethane to give N-[2-[(4-amino-7-isopropylpyrrolo[2,3-d]pyrimidin-5-yl)phenoxy]phenyl}urea as a solid.

Example 169

7-(2-Hydroxyethyl)-5-{4-[4-(2-hydroxyethoxy)phenoxy]phenyl}pyrrolo[2,3-d]-pyrimidin-4-ylamine 7-(2-Hydroxyethyl)-5-{4-[4-(2-hydroxyethoxy)phenoxy]phenyl}pyrrolo[2,3-d]-pyrimidin-4-ylamine, m.p. 166-166.5° C. was prepared by reacting 5-{4-[4-(2-hydroxy)-phenoxy]phenyl}-7H-pyrrolo[2,3-d]pyrimidin-4-ylamine with ethylene carbonate in N,N-dimethylformamide containing a catalytic amount of sodium hydroxide power at boiling point for 1 hour. The product was obtained after work-up and purification by flash column chromatography on silica.

Example 170

5-[4-(4-Amino-7-isopropyl-7H-pyrrolo[2,3-d]pyrimidin-5-yl)phenoxy]indan-1-ol

5-[4-(4-Amino-7-isopropyl-7H-pyrrolo[2,3-d]pyrimidin-5-yl)phenoxy]indan-1-ol was prepared by reducing the product of Example 32 following the procedure of Examples 109 to 137.

Example 171

6-Amino-2-[4-(4-amino-7-isopropyl-7H-pyrrolo[2,3-d]pyrimidin-5-yl)phenoxy]benzonitrile 6-Amino-2-[4-(4-amino-7-isopropyl-7H-pyrrolo[2,3-d]pyrimidin-5-yl)phenoxy]benzonitrile was prepared following the procedure of Examples 35 to 108.

Example 172

2-[4-(4-Amino-7-isopropyl-7H-pyrrolo[2,3-d]pyrimidin-5-yl)phenoxy]-5-methylbenzonitrile 2-[4-(4-Amino-7-isopropyl-7H-pyrrolo[2,3-d]pyrimidin-5-yl)phenoxy]-5-methylbenzonitrile was prepared following the procedure of Examples 35 to 108.

Example 173

7-isopropylsulphonyl-5-(4-phenoxyphenyl)-7H-pyrrolo[2,3-d]pyrimidin-4-ylamine 5-(4-Phenoxyphenyl)-7H-pyrrolo[2,3-d]pyrimidin-4-ylamine (1.57 g) was dissolved in dry dimethylformamide (30 ml) and then sodium hydride (0.22 g of a 60% dispersion in mineral oil) was added with stirring. The mixture was stirred for 30 minutes and then isopropylsulphonyl chloride (0.74 g) was added and the mixture was stirred at ambient temperature for 18 hours. Water was added to the mixture until no further precipitation occurred. The solid was collected by filtration and purified by flash column chromatography on silica using dichloromethane/methanol (9:1) as the mobile phase to give a solid which was further purified by flash column chromatography on silica using ethyl acetate as the mobile phase to give 7-isopropylsulphonyl-5-(4-phenoxyphenyl)-7H-pyrrolo[2,3-d]pyrimidin-4-ylamine, m.p. 162-162.5° C.

Example 174

7-[4-amino-5-(4-phenoxyphenyl)-7H-pyrrolo[2,3-d]pyrimidin-7-yl]bicyclo[3.3.0]octan-3-ol a) Sodium borohydride (547 mg) was added in portions to a solution of cis-bicyclo[3.3.0]octane-3,7-dione, (2.0 g) in methanol (20 ml) at 0° C. The mixture was stirred at 0° C. for 1 hour and then allowed to warm to ambient temperature and then allowed to stand at ambient temperature for 18 hours. The mixture was quenched with 2M sodium hydroxide solution (5 ml) and then concentrated under reduced pressure. The residue was partitioned between ethyl acetate (50 ml) and water (50 ml). The aqueous layer was separated and extracted with ethyl acetate. The combined ethyl acetate extract and washings were dried, filtered and evaporated to leave an oil which crystallised on standing to give cis-bicyclo[3.3.0]octane-3,7-diol.

b) A mixture of the diol from part a) (0.8 g), pyridine (10 ml) and p-toluene-sulphonyl chloride (1.17 g) was stirred at 0° C. for 2 hours and then allowed to stand at ambient temperature for 18 hours. The mixture was poured into 5M hydrochloric acid and extracted with ethyl acetate. The combined ethyl acetate extracts were washed with 2M hydrochloric acid, then dried filtered and evaporated to leave an oil containing mainly cis-7-toluenesulphonyloxy-bicyclo[3.3.0]octan-3-ol which was used directly in the next part of this example.

c) 5-(4-Phenoxyphenyl)-7H-pyrrolo[2,3-d]pyrimidin-4-ylamine (193 mg) was added to a mixture of sodium hydride (52 mg, of a 60% dispersion in mineral oil) in dimethylformamide (10 ml) with stirring at 0° C. under nitrogen. The mixture was stirred at ambient temperature for 1 hour and then the product from c) (190 mg) was added with stirring. The mixture was warmed to 90° C. and then heated at this temperature for 6 hours. The mixture was cooled to ambient temperature and partitioned between water and ethyl acetate. The ethyl acetate layer was separated and the aqueous layer was extracted with ethyl acetate. The combined ethyl acetate extracts and washings were washed with water, dried, filtered and evaporated to leave an oil which was purified by flash column chromatography on silica using ethyl acetate and then with increasing amounts of methanol, up to 10% methanol in ethyl acetate as the mobile phase. Appropriate fractions were collected, combined and evaporated to leave a solid which was washed with cold ether to give 7-[4-amino-5-(4-phenoxyphenyl)-7H-pyrrolo[2,3-d]pyrimidin-7-yl]bicyclo[3.3.0]octan-3-ol, m.p. 193-194° C.

Example 175

4-[4-amino-5-(4-phenoxyphenyl)-7H-pyrrolo[2,3-d]pyrimidin-7-yl]cyclohexanol

Sodium borohydride (500 mg, 13 mmol) was added in one portion to a stirred solution of 4-[4-amino-5-(4-phenoxyphenyl)-7H-pyrrolo[2,3-d]pyrimin-7-yl]cyclohexan-1-one (780 mg, 2.0 mmol) in methanol (500 mL), and the mixture stirred under an atmosphere of nitrogen for 1 hour, then left to stand overnight. The solvent was removed under reduced pressure, and the residue partitioned between 2M aqueous sodium hydroxide solution (100 mL) and dichloromethane (100 mL). The organic layer was separated and the aqueous layer further extracted with dichloromethane (2×100 mL). The combined organic extracts were washed with water (150 mL), dried over potassium carbonate, and purified by chromatography with a Biotage 40S column using ethyl acetate/triethylamine (98:2 to 95:5) and ethyl acetate/ethanol (95:5) as a mobile phase to yield 4-[4-amino-5-(4-phenoxyphenyl)-7H-pyrrolo[2,3-d]pyrimidin-7-yl]cyclohexanol as a white solid (750 mg, 1.9 mmol), melting point: 199-200 deg. C.LC/MS: Hypersil BDS c18 (100×2.1 mm) 0.1M ammoniumacetate/acetonitrile, 10-100% acetonitrile in 8 min.) MH$^+$401, t$_r$=4.12 minutes.

Example 176

Benzyl N-[5-(4-amino-7-cyclopentyl-7H-pyrrolo[2,3-d]pyrimidin-5-yl)-2-methoxyphenyl]carbamate a) 5-bromo-2-methoxyaniline (1)

A mixture of 4-bromo-1-methoxy-2-nitrobenzene (3.0 g, 12.9 mmol) and glacial acetic acid (25 ml) was heated at 100° C. under an atmosphere of nitrogen. Iron powder (2.2 g, 38.8 mmol) was added and the mixture was stirred for one hour at a temperature of 100° C. The mixture was cooled to ambient temperature then water (100 ml) was added and the mixture was extracted with ethyl acetate (3×25 ml). The combined organic extracts were washed with saturated aqueous sodium bicarbonate (3×25 ml) and then brine. The organic solution was dried over magnesium sulfate filtered and the filtrate evaporated under reduced pressure to give a residue. Purification of the material by flash chromatography on silica gel using heptane/ethyl acetate (6:4) as an eluent yielded 5-bromo-2-methoxyaniline (2.0 g): $^1$H NMR (DMSO-d$_6$, 400 MHz) 6.76 (s, 1H), 6.71 (d, 1H), 6.61 (d, 1H), 4.99 (bs, 2H), 3.74 (s, 3H); (TLC (heptane/ethyl acetate 1:1) R$_f$ 0.5; RP-HPLC (Hypersil HyPurity Elite C18, 5 m, 200 A, 250×4.6 mm; 25-100% acetonitrile-0.1 M ammonium acetate over 25 min, 1 ml/min) t$_r$=13.33 min.; MS: MH$^+$443.

b) tert-butyl N-(5-bromo-2-methoxyphenyl)carbamate (2)

A mixture of 5-bromo-2-methoxyaniline (1.50 g, 7.43 mmol), and di-tert-butyl dicarbonate (1.95 g, 8.91 mmol) in THF (20 ml) was heated at reflux for 20 hours. The mixture was cooled to ambient temperature and then the solvent was removed under reduced pressure. The resulting oil was purified by flash chromatography on silica gel using ethyl acetate/heptane (1:9) as an eluent to yield tert-butyl N-(5-bromo-2-methoxyphenyl)carbamate (2.19 g) as a colorless oil: $^1$H NMR (DMSO-d$_6$, 400 MHz) δ 8.05 (s, 1H), 7.93 (d, 1H), 7.16 (d, 1H), 6.95 (d, 1H), 3.8 (s, 1H), 1.47 (s, 9H); TLC (ethyl acetate/heptane 2:8) R$_f$ 0.4; RP-HPLC (Hypersil HyPurity Elite C18, 5 μm, 200 A, 250×4.6 mm; 25-100% acetonitrile-0.1 M ammonium acetate over 25 min, 1 ml/min) t$_r$=21.8 min.

c) tert-butyl N-[2-methoxy-5-(4,4,5,5-tertamethyl-1,3,2-dioxaborolan-2-yl)phenyl]carbamate (3)

A mixture of tert-butyl N-(5-bromo-2-methoxyphenyl)carbamate (1.10 g, 3.64 mmol), diboron pinacol ester (1.11 g, 4.37 mmol), [1.1'-bis(diphenylphosphino)ferrocene]dichloropalladium (II) complex with dichloromethane (1:1) (0.09 g, 0.11 mol) and potassium acetate (1.07 g, 10.9 mol) in N,N-dimethylformamide (20 mL) was heated at 80° C. under an atmosphere of nitrogen for 16 hours. The mixture was allowed to cool to ambient temperature and the solvent removed under reduced pressure. Dichloromethane (20 mL) was added to the residue and the resulting solid was removed by filtration through a pad of celite. The filtrate was concentrated to leave a yellow oil which was purified by flash chromatography on silica using ethyl acetate/heptane (2:8) as mobile phase to yield tert-butyl N-[2-methoxy-5-(4,4,5,5-tetramethyl-1,3,2-dioxaborolan-2-yl)phenyl]carbamate (0.96 g): $^1$H NMR (DMSO-d$_6$, 400 MHz) δ 8.03 (s, 1H), 7.86 (s, 1H), 7.35 (d, 1H), 7.0 (d, 1H), 3.82 (s, 3H), 1.46 (s, 9H), 1.28 (s, 12H); TLC (ethyl acetate/heptane 2:8) R$_f$=0.35; RP-HPLC (Hypersil HyPurity Elite C18, 5 μm, 200 A, 250×4.6 mm; 25-100% acetonitrile-0.1 M ammonium acetate over 25 min, 1 ml/min) t$_r$=22.8 min d) tert-butyl N-(5-(chloro-7-cyclopentyl-7H-pyrrolo[2,3-d]pyrimidin-5-yl)-2-methoxyphenyl)carbamate (4)

A mixture of 4-chloro-7-cyclopentyl-5-iodo-7H-pyrrolo[2,3-d]pyrimidine (0.35 g, 1.0 mmol), tert-butyl N-[2-methoxy-5-(4,4,5,5-tetramethyl-1,3,2-dioxaborolan-2-yl)phenyl]carbamate (0.524 g, 1.5 mmol), tetrakis(triphenylphosphine) palladium (0.07 g, 0.06 mmol) and sodium carbonate (0.265 g, 2.5 mmol) was heated in a mixture of ethylene glycol dimethyl ether (10 mL) and water (5 mL) at 80° C. for 18 hours under an atmosphere of nitrogen. The mixture was allowed to cool to ambient temperature and solvents were removed under reduced pressure. The residue was partitioned between water (15 mL) and ethyl acetate (25 ml), the organic layer separated and the aqueous layer further extracted with ethyl acetate (2×25 ml). The combined organic extracts were washed with water (3×20 ml) then dried over magnesium sulfate, filtered and the filtrate concentrated to an oily residue under reduced pressure. The material was purified by flash column chromatography on silica using heptane/ethyl acetate (5:1) as an eluent to give tert-butyl N-(5-(chloro-7-cyclopentyl-7H-pyrrolo[2,3-d]pyrimidin-5-yl)-2-methoxyphenyl) carbamate (0.325 g): $^1$H NMR (DMSO-d$_6$, 400 MHz) δ 8.64 (s, 1H), 7.93 (s, 1H), 7.87 (m, 2H), 7.17 (d, 1H), 7.06 (d, 1H), 5.21 (m, 1H), 3.86 (s, 3H), 1.65-2.25 (m, 8H), 1.45 (s, 9H); RP-HPLC (Hypersil HyPurity Elite C18, 5 μm, 200 A, 250×4.6 mm; 25-100% acetonitrile-0.1 M ammonium acetate over 25 min, 1 ml/min) t$_r$=24.25 min. MS: MH$^+$443.

e) 5-(3-amino-4-methoxyphenyl)-7-cyclopentyl-7H-pyrrolo[2,3-d]pyrimidin-4-amine A solution of tert-butyl N-(5-(chloro-7-cyclopentyl-7H-pyrrolo[2,3-d]pyrimidin-5-yl)-2-methoxyphenyl)carbamate (0.325 g, 0.735 mmol) in dichloromethane (14 ml) was cooled to 0° C. then treated with trifluoroacetic acid (1.4 ml). The solution was stirred at 0° C. for 5 min then warmed to ambient temperature and stirred for a further 16 hours. The solvents were evaporated under reduced pressure then the residue was partitioned between dichloromethane (30 ml) and saturated aqueous sodium bicarbonate (10 ml). The organic solution was dried over magnesium sulfate, filtered and the filtrate evaporated under reduced pressure to a foam. The material was then dissolved in dioxane (4 ml) and concentrated (28-30%) ammonium hydroxide (4 ml) and the resulting solution was heated at 120° C. in a sealed pressure tube for 20 hours. The solvents were evaporated and the residue was purified by preparative C18 RP-HPLC to give, after lyophilization 5-(3-amino-4-methoxyphenyl)-7-cyclopentyl-7H-pyrrolo[2,3-d]pyrimidin-4-amine (85 mg): $^1$H NMR (DMSO-d$_6$, 400 MHz) δ 8.10 (s, 1H), 7.21 (s, 1H), 6.87 (d, 1H), 6.74 (s, 1H), 6.58 (d, 1H), 5.06 (1H, m), 4.87 (bs, 2H), 3.8 (s, 3H), 1.6-2.2 (m, 8H); RP-HPLC (Hypersil HyPurity Elite C18, 5 μm, 200 A, 250×4.6 mm; 25-100% acetonitrile-0.1 M ammonium acetate over 25 min, 1 ml/min) t$_r$=11.87 min.; MS: MH$^+$324.

f) benzyl N-[5-(4-amino-7-cyclopentyl-7H-pyrrolo[2,3-d]pyrimidin-5-yl)-2-methoxyphenyl]carbamate A solution of 5-(3-amino-4-methoxyphenyl)-7-cyclopentyl-7H-pyrrolo[2,3-d]pyrimidin-4-amine (40 mg, 0.124 mmol) in dichloromethane (1 ml) and pyridine (1 ml) was cooled to 0° C. and then treated with benzyl chloroformate (32 mg, 0.186 mmol) while maintaining a temperature of less than 5° C. The solution was stirred for another 1 hour at 0° C. then the solvents were removed under reduced pressure. Purification by preparative C-18 RP-HPLC then lyophilization provided benzyl N-[5-(4-amino-7-cyclopentyl-7H-pyrrolo[2,3-d]pyrimidin-5-yl)-2-methoxyphenyl]carbamate (25 mg) as a white powder: $^1$H NMR (DMSO-d$_6$, 400 MHz) δ 8.75 (s, 1H), 8.11 (s, 1H), 7.75 (s, 1H), 7.1-7.4 (m, 8H), 6.2 (bs, 2H), 5.15 (s, 2H), 5.07 (m, 1H), 3.8 (s 3H), 1.6-2.2 (m, 8H), RP-HPLC (Hypersil HyPurity Elite C18, 5 μm, 200 A,

Example 177

Benzyl N-[5-(4-amino-7-cyclopentyl-7H-pyrrolo[2,3-d]pyrimidin-5-yl)-2-pyridyl]carbamate a) tert-butyl N-(5-bromo-2-pyridyl)carbamate

The compound was prepared from 5-bromo-2-pyridinamine in the manner described for compound (2): $^1$H NMR (DMSO-$d_6$, 400 MHz) δ 9.96 (s, 1H), 8.49 (d, 1H), 7.93 (dd, 1H), 7.78 (d, 1H), 1.47 (s, 9H); TLC (ethyl acetate/heptane 5:95) $R_f$ 0.28; RP-HPLC (Hypersil HyPurity Elite C18, 5 μm, 200 A, 250×4.6 mm; 25-100% acetonitrile-0.1 M ammonium acetate over 25 min, 1 ml/min) $t_r$=18.50 min.

b) tert-butyl N-[5-(1,1,1-trimethylstannyl)-2-pyridyl]carbamate

A mixture of tert-butyl N-(5-bromo-2-pyridyl)carbamate (1.67 g, 6.12 mmol), hexamethylditin (2.0 g, 6.12 mmol) and tetrakis(triphenylphosphine)palladium (0.424 g, 0.367 mmol) in ethylene glycol dimethyl ether (30 ml) was heated at 80° C. under an atmosphere of nitrogen for 15 hours. The mixture was cooled to ambient temperature and then the solvent was removed under reduced pressure. The resulting material was purified by flash chromatography on silica gel using heptane/ethyl acetate (95:5) as an eluent to yield tert-butyl N-[5-(1,1,1-trimethylstannyl)-2-pyridyl]carbamate (1.11 g): $^1$H NMR (DMSO-$d_6$, 400 MHz) δ 9.98 (s, 1H), 8.2 (t, 1H), 7.74 (m, 2H), 1.47 (s, 9H), 0.30 (t, 9H); TLC (heptane/ethyl acetate 95:5) $R_f$ 0.2; MS: MH$^+$359.

c) tert-butyl N-[5-(4-chloro-7-cyclopentyl-7H-pyrrolo[2,3-d]pyrimidin-5-yl)-2-pyridyl]carbamate A mixture of 4-chloro-7-cyclopentyl-5-iodo-7H-pyrrolo[2,3-d]pyrimidine (0.25 g, 0.72 mmol), tert-butyl N-[5-(1,1,1-trimethylstannyl)-2-pyridyl]carbamate (0.386 g, 1.08 mmol), trwas(dibenzylideneacetone)dipalladium(0) (0.033 g, 0.076 mmol) and triphenylarsine (0.055 g, 0.18 mmol) in N,N-dimethylformamide (8 ml) was heated at 65° C. under an atmosphere of nitrogen for 18 hours. The mixture was cooled to ambient temperature and then the solvent was removed under reduced pressure. The resulting material was purified by flash chromatography on silica gel using heptane/ethyl acetate (75:25) as an eluent to yield tert-butyl N-[5-(4-chloro-7-cyclopentyl-7H-pyrrolo[2,3-d]pyrimidin-5-yl)-2-pyridyl]carbamate (0.13 g): $^1$H NMR (DMSO-$d_6$, 400 MHz) δ 9.83 (s, 1H), 8.68 (s, 1H), 8.40 (d, 1H), 8.02 (s, 1H), 7.85-7.93 (m, 2H), 5.21 (m, 1H), 1.65-2.25 (m, 8H), 1.49 (s, 9H); TLC (heptane/ethyl acetate 8:2) $R_f$ 0.18; RP-HPLC (Hypersil HyPurity Elite C18, 5 μm, 200 A, 250×4.6 mm; 25-100% acetonitrile-0.1 M ammonium acetate over 25 min, 1 ml/min) $t_r$=21.68 min.

d) 5-(4-chloro-7-cyclopentyl-7H-pyrrolo[2,3-d]pyrimidin-5-yl)-2-pyridinamine A solution of tert-butyl N-[5-(4-chloro-7-cyclopentyl-7H-pyrrolo[2,3-d]pyrimidin-5-yl)-2-pyridyl]carbamate (0.13 g, 0.315 mmol) in dichloromethane (5.5 ml) was cooled to 0° C. then treated with trifluoroacetic acid (0.6 ml). The solution was stirred at 0° C. for 5 minutes then warmed to ambient temperature and stirred for a further 18 hours. The solvents were evaporated under reduced pressure then the residue was partitioned between dichloromethane (30 ml) and saturated aqueous sodium bicarbonate (10 ml). The organic solution was dried over magnesium sulfate filtered and the filtrate evaporated under reduced pressure to give 5-(4-chloro-7-cyclopentyl-7H-pyrrolo[2,3-d]pyrimidin-5-yl)-2-pyridinamine (92 mg): RP-HPLC (Hypersil HyPurity Elite C18, 5 μm, 200 A, 250×4.6 mm; 25-100% acetonitrile-0.1 M ammonium acetate over 25 min, 1 ml/min) $t_r$=10.73 min; MS: MH$^+$314.

e) 5-(6-amino-3-pyridyl)-7-cyclopentyl-7H-pyrrolo[2,3-d]pyrimidin-4-amine

The 5-(4-chloro-7-cyclopentyl-7H-pyrrolo[2,3-d]pyrimidin-5-yl)-2-pyridinamine (92 mg, 0.291 mmol) was dissolved in dioxane (2 ml) and concentrated (28-30%) ammonium hydroxide (2 ml) and the resulting solution was heated at 120° C. in a sealed pressure tube for 24 hours. The solvents were evaporated to give 5-(6-amino-3-pyridyl)-7-cyclopentyl-7H-pyrrolo[2,3-d]pyrimidin-4-amine (105 mg): RP-HPLC (Hypersil HyPurity Elite C18, 5 μm, 200 A, 250×4.6 mm; 25-100% acetonitrile-0.1 M ammonium acetate over 25 min, 1 ml/min) $t_r$=6.33 min.; MS: MH$^+$295.

f) N-[5-(4-amino-7-cyclopentyl-7H-pyrrolo[2,3-d]pyrimidin-5-yl)-2-pyridyl]carbamate A solution of 5-(6-amino-3-pyridyl)-7-cyclopentyl-7H-pyrrolo[2,3-d]pyrimidin-4-amine (105 mg, 0.29 mmol) in dichloromethane (1.5 ml) and pyridine (1.5 ml) was cooled to 0° C. and then treated with benzyl chloroformate (75 mg, 0.44 mmol) while maintaining a temperature of less than 5° C. The solution was warmed to ambient temperature then stirred for 3 hours. Benzyl chloroformate (75 mg, 0.44 mmol) was added and the mixture stirred for 18 hours, additional benzyl chloroformate (75 mg, 0.44 mmol) was added and the mixture stirred for another 24 hours. Benzyl chloroformate (150 mg, 0.88 mmol) and pyridine (1 ml) were added and the mixture stirred for another 24 hours. The solvents were evaporated under reduced pressure then the residue was partitioned between ethyl acetate (25 ml) and water (10 ml). The organic solution was dried over magnesium sulfate, filtered and the filtrate evaporated under reduced pressure to give a residue. Purification by preparative C-18 RP-HPLC then trituration with diethyl ether provided N-[5-(4-amino-7-cyclopentyl-7H-pyrrolo[2,3-d]pyrimidin-5-yl)-2-pyridyl]carbamate (21 mg) as a white powder: $^1$H NMR (DMSO-$d_6$, 400 MHz) δ 10.33 (s, 1H), 8.36 (d, 1H), 8.14 (s, 1H), 7.91 (d, 1H), 7.84 (d, 1H), 7.33-7.47 (m, 6H), 6.11 (bs, 2H), 5.2 (s, 2H), 5.06 (m, 1H), 1.6-2.2 (m, 8H); RP-HPLC (Hypersil HyPurity Elite C18, 5 μm, 200 A, 250×4.6 mm; 25-100% acetonitrile-0.1 M ammonium acetate over 25 min, 1 ml/min) $t_r$=16.22 min; MS: MH$^+$429.

Example 178

Benzyl N-[4-(4-amino-7-cyclopentyl-7H-pyrrolo[2,3-d]pyrimidin-5-yl)-3-methoxyphenyl]carbamate a) 4-bromo-3-methoxyaniline

A mixture of 1-bromo-2-methoxy-4-nitrobenzene (3.0 g, 12.9 mmol) and glacial acetic acid (25 ml) was heated at 100° C. under an atmosphere of nitrogen. Iron powder (2.2 g, 38.8 mmol) was added and the mixture was stirred for one hour at a temperature of 100° C. The mixture was cooled to ambient temperature, water (100 ml) was added and the mixture was then extracted with ethyl acetate (3×25 ml). The combined organic extracts were washed with saturated aqueous sodium bicarbonate (3×25 ml) and then brine. The organic solution was dried over magnesium sulfate filtered and the filtrate evaporated under reduced pressure to give a residue. Purification of the material by flash chromatography on silica gel using heptane/ethyl acetate (6:4) as an eluent yielded 4-bromo-3-methoxyaniline (1.22 g): $^1$H NMR (DMSO-$d_6$, 400 MHz) δ 7.1 (d, 1H), 6.31 (s, 1H), 6.1 (d, 1H), 5.27 (bs, 2H), 3.72 (s, 3H); TLC (heptane/ethyl acetate 1:1) $R_f$ 0.33; RP-HPLC (Hypersil HyPurity Elite C18, 5 μm, 200 A, 250× 4.6 mm; 25-100% acetonitrile-0.1 M ammonium acetate over 25 min, 1 ml/min) $t_r$=11.05 min.

b) tert-butyl N-(4-bromo-3-methoxyphenyl)carbamate

The compound was prepared from 4-bromo-3-methoxyaniline in the manner described for compound (2): $^1$H NMR (DMSO-$d_6$, 400 MHz) δ 9.46 (s, 1H), 7.4 (d, 1H), 7.35 (s, 1H), 6.95 (d, 1H), 3.78 (s, 3H), 1.48 (s, 9H); TLC (heptane/ethyl acetate 8:2) $R_f$ 0.37; RP-HPLC (Hypersil HyPurity Elite C18, 5 μm, 200 A, 250×4.6 mm; 25-100% acetonitrile-0.1 M ammonium acetate over 25 min, 1 ml/min) $t_r$=18.60 min.

c) tert-butyl N-[3-methoxy-4-(4,4,5,5-tetramethyl-1,3,2-dioxaborolan-2-yl)phenyl]carbamate The compound was prepared from tert-butyl N-(4-bromo-3-methoxyphenyl)carbamate in the manner described for compound (3): $^1$H NMR (DMSO-$d_6$, 400 MHz) δ 9.44 (s, 1H), 7.41 (d, 1H), 7.17 (s, 1H), 7.01 (d, 1H), 3.68 (s, 3H), 1.48 (s, 9H), 1.24 (s, 12H); TLC (heptane/ethyl acetate 8:2) $R_f$ 0.28; RP-HPLC (Hypersil HyPurity Elite C18, 5 μm, 200 A, 250×4.6 mm; 25-100% acetonitrile-0.1 M ammonium acetate over 25 min, 1 ml/min) $t_r$=180.83 min.

d) tert-butyl N-[4-(4-(chloro-7-cyclopentyl-7H-pyrrolo[2,3-d]pyrimidin-5-yl)-3-methoxyphenyl)carbamate The compound was prepared from tert-butyl N-[3-methoxy-4-(4,4,5,5-tetramethyl-1,3,2-dioxaborolan-2-yl)phenyl]carbamate and 4-chloro-7-cyclopentyl-5-iodo-7H-pyrrolo[2,3-d]pyrimidine in the manner described for compound (4): $^1$H NMR (DMSO-$d_6$, 400 MHz) δ 9.41 (s, 1H)<8.59 (s, 1H), 7.72 (s, 1H), 7.33 (s, 1H), 7.15 (d, 1H), 7.04 (d, 1H), 5.17 (m, 1H), 3.66 (s, 3H), 1.6-2.2 (m, 3H), 1.49 (s, 9H); RP-HPLC (Hypersil HyPurity Elite C18, 5 μm, 200 A, 250×4.6 mm; 25-100% acetonitrile-0.1 M ammonium acetate over 25 min, 1 ml/min) $t_r$=21.22 min; MS: MH$^+$443.

e) benzyl N-[4-(4-amino-7-cyclopentyl-7H-pyrrolo[2,3-d]pyrimidin-5-yl)-3-methoxyphenyl]carbamate The compound was prepared from tert-butyl N-[4-(4-(chloro-7-cyclopentyl-7H-pyrrolo[2,3-d]pyrimidin-5-yl)-3-methoxyphenyl)carbamate in the manner described for conversion of compound (4) into compound (6): $^1$H NMR (DMSO-$d_6$, 400 MHz) δ 9.87 (s, 1H), 8.08 (s, 1H), 7.34-7.45 (m, 6H), 7.09-7.18 (m, 3H), 5.79 (bs, 2H), 5.18 (s, 2H), 5.04 (m, 1H), 3.7 (s, 3H), 1.6-2.2 (m, 8H); RP-HPLC (Hypersil HyPurity Elite C18, 5 μm, 200 A, 250×4.6 mm; 25-100% acetonitrile-0.1 M ammonium acetate over 25 min, 1 ml/min) $t_r$=16.87 min; MS: MH$^+$458.

Example 179

Benzyl N-[4-(4-amino-7-cyclopentyl-7H-pyrrolo[2,3-d]pyrimidin-5-yl)-2-fluorophenyl]carbamate a) 4-[{[7-cyclopentyl-5-(4,4,5,5-tetramethyl-1,3,2-dioxaborolan-2-yl)-7H-pyrrolo[2,3-d]pyrimidin-4-yl]amino}(2,4-dimethoxyphenyl)methyl]phenoxy resin Rink amide resin [4-(2',4'-dimethoxyphenyl-Fmoc-aminomethyl)-phenoxy resin with a loading of 0.66 mmol/g] (6.55 g, 4.32 mmol) was deprotected by washing with N,N-dimethylformamide (2×2 min), 20% piperidine in N,N-dimethylformamide (1×5 min, 1×15 min), N,N-dimethylformamide (5×2 min), dichloromethane (3×2 min), and then methanol (3×2 min). The resin was dried at a temperature of 40° C. under reduced pressure. The deprotected resin, 4-chloro-7-cyclopentyl-5-iodo-7H-pyrrolo[2,3-d]pyrimidine (1.80 g, 5.19 mmol), dimethylsulfoxide (100 ml), and N,N-diisopropylethylamine (4.5 ml) were heated at 100° C. for 3 days, cooled to ambient temperature and then the resin was collected by filtration and washed with N,N-dimethylformamide. The resin was then stirred for 30 min with acetic acid (0.13 g, 2.16 mmol), O-benzothiazol-1-yl-N,N,N',N'-tetramethyluronium tetrafluoroborate (0.69 g, 2.16 mmol), N,N-diisopropylethylamine (0.56 g, 4.32 mmol) and N,N-dimethylformamide (30 ml). The resin was collected by filtration and washed with N,N-dimethylformamide, dichloromethane and methanol. The resin was dried to a constant weight (6.25 g) under reduced pressure. The resin, diboron pinacol ester (1.11 g, 4.37 mmol), potassium acetate (0.822 g, 8.39 mmol) and tetrakis(triphenylphosphine)palladium (0.24 g, 0.21 mmol) in dimethylsulfoxide (125 ml) was heated at 85° C. under an atmosphere of nitrogen for 17 hours. The resin was collected by filtration then washed with N,N-dimethylformamide, dichloromethane, ethyl acetate then ether. The resin was dried under reduced pressure to a weight of 5.49 grams.

b) Benzyl N-[4-(4-amino-7-cyclopentyl-7H-pyrrolo[2,3-d]pyrimidin-5-yl)-2-fluorophenyl]carbamate A mixture of 4-[{[7-cyclopentyl-5-(4,4,5,5-tetramethyl-1,3,2-dioxaborolan-2-yl)-7H-pyrrolo[2,3-d]pyrimidin-4-yl]amino}(2,4-dimethoxyphenyl)methyl]phenoxy resin (0.5 g, 0.254 mmol), 4-bromo-2-fluoroaniline (0.484 g, 2.54 mmol), tetrakis(triphenylphosphine)palladium (0.044 g, 0.038 mmol), 2 M aqueous potassium phosphate (1.27 ml, 2.54 mmol) and dimethylsulfoxide (10 ml) was heated at 85° C. for 18 hours. The mixture was cooled and the resin collected by filtration then washed with N,N-dimethylformamide and dichloromethane. The resin was then subjected to the coupling conditions described above a second time. The resin was suspended in dichloromethane (2 ml) and pyridine (2 ml) then the mixture was cooled to 0° C. and treated with benzyl chloroformate (0.44 g, 2.6 mmol). After stirring at 0° C. for one hour the mixture was allowed to warm to ambient temperature for 18 hours. The resin was collected by filtration then treated with 5% trifluoroacetic acid in dichloromethane (10 ml) for 30 minutes. Removal of the resin by filtration yielded a filtrate which was evaporated under reduced pressure to yield a residue which was purified by preparative C-18 RP-HPLC to give benzyl N-[4-(4-amino-7-cyclopentyl-7H- pyrrolo[2,3-d]pyrimidin-5-yl)-2-fluorophenyl]carbamate (~10 mg): RP-HPLC (Hypersil HS C18, 5 μm, 100 A, 250×4.6 mm; 25-100% acetonitrile-0.1 M ammonium acetate over 10 min, 1 ml/min) t$_r$=11.47 min; MS: MH$^+$446.

Example 180

Benzyl N-[4-(4-amino-7-cyclopentyl-7H-pyrrolo[2,3-d]pyrimidin-5-yl)-2-(trifluoromethyl)phenyl]carbamate This compound was prepared in the same manner as described for PH 454098: RP-HPLC (Hypersil HS C18, 5 μm, 100 A, 250×4.6 mm; 25-100% acetonitrile-0.1 M ammonium acetate over 10 min, 1 ml/min) t$_r$=12.07 min; MS: MH$^+$496.

Example 181

Benzyl N-[4-(4-amino-7-cyclopentyl-7H-pyrrolo[2,3-d]pyrimidin-5-yl)-2-cyanophenyl]carbamate This compound was prepared in the same manner as described for PH 454098: RP-HPLC (Hypersil HS C18, 5 μm, 100 A, 250×4.6 mm; 25-100% acetonitrile-0.1 M ammonium acetate over 10 min, 1 ml/min) t$_r$=10.93 min; MS: MH$^+$453.

Example 182

Methyl 5-(4-amino-7-cyclopentyl-7H-pyrrolo[2,3-d]pyrimidin-5-yl)-2-{[(benzyloxy)carbonyl]amino}benzoate This compound was prepared in the same manner as described for PH 454098: RP-HPLC (Hypersil HS C18, 5 μm, 100 A, 250×4.6 mm; 25-100% acetonitrile-0.1 M ammonium acetate over 10 min, 1 ml/min) t$_r$=13.28 min; MS: MH$^+$486.

Example 183

Benzyl N-[4-(4-amino-7-cyclopentyl-7H-pyrrolo[2,3-d]pyrimidin-5-yl)-2-methylphenyl]carbamate This compound was prepared in the same manner as described for PH 454098: RP-HPLC (Hypersil HS C18, 5 μm, 100 A, 250×4.6 mm; 25-100% acetonitrile-0.1 M ammonium acetate over 10 min, 1 ml/min) t$_r$=11.25 min; MS: MH+442.

Example 184

Benzyl N-[4-(4-amino-7-cyclopentyl-7H-pyrrolo[2,3-d]pyrimidin-5-yl)phenyl]carbamate This compound was prepared in the same manner as described for PH 454098: RP-HPLC (Hypersil HS C18, 5 μm, 100 A, 250×4.6 mm; 25-100% acetonitrile-0.1 M ammonium acetate over 10 min, 1 ml/min) t$_r$=11.27 min; MS: MH$^+$428.

Example 185

N-[4-(4-Amino-7-cyclopentyl-7H-pyrrolo[2,3-d]pyrimidin-5-yl)-2-methoxyphenyl]phenylmethanesulfonamide 5-(4-Amino-3-methoxyphenyl)-7-cyclopentyl-7H-pyrrolo[2,3-d]pyrimidin-4-amine (27 mg, 0.083 mmol) was dissolved in dichloromethane (0.8 mL). Pyridine (0.8 mL) was added followed by phenylmethanesulfonyl chloride (19 mg, 0.105 mmol). After stirring overnight, another 19 mg of phenylmethanesulfonyl chloride was added and the reaction mixture was stirred overnight. The solvent was removed and the residue was purified by preparative thin layer chromatogram eluted with dichlormethane/Methanol (95:5) to give N-[4-(4-amino-7-cyclopentyl-7H-pyrrolo[2,3-d]pyrimidin-5-yl)-2-methoxyphenyl]phenylmethanesulfonamide (9 mg, 0.0188 mmol). 1H NMR (DMSO-d$_6$) δ 1.89 (m, 6H), 2.28 (m, 2H), 3.85 (s, 3H), 4.38 (s, 2H), 5.23 (m, 3H), 6.08 (bs, 1H), 6.99 (m, 2H), 7.27, (m, 2H), 7.33 (m, 3H), 7.58 (d, J=8.17 Hz, 1H), 8.34 (s, 1H). LC/MS MH$^+$=478

Example 186

N1-[4-(4-Amino-7-cyclopentyl-7H-pyrrolo[2,3-d]pyrimidin-5-yl)-2-methoxyphenyl]-2-phenylacetamide 5-(4-Amino-3-methoxyphenyl)-7-cyclopentyl-7H-pyrrolo[2,3-d]pyrimidin-4-amine (28 mg, 0.086 mmol) was dissolved in dichloromethane (1 mL). Pyridine (1 mL) was added followed by 2-phenylethanoyl chloride (14 uL, 0.105 mmol). After stirring overnight, another 14 uL of phenylmethanesulfonyl chloride was added and the reaction mixture was stirred overnight. The solvent was removed and the residue was purified by preparative thin layer chromatogram eluted with dichlormethane/Methanol (95:5) to give N1-[4-(4-amino-7-cyclopentyl-7H-pyrrolo[2,3-d]pyrimidin-5-yl)-2-methoxyphenyl]-2-phenylacetamide (7 mg, 0.0158 mmol). $^1$H NMR (DMSO-d$_6$) 1.89 (m, 6H), 2.25 (m, 2H), 3.77 (s, 3H), 3.79 (s, 2H), 5.21 (m, 1H), 5.56 (bs, 2H), 6.89 (s, 1H), 6.99 (s, 1H), 7.05 (d, J=8.22, 1H), 7.36 (m, 5H), 7.81 (s, 1H), 8.27 (s, 1H), 8.43 (d, J=8.23 Hz, 1H). LC/MS MH$^+$=442.

Example 187

N1-[4-(4-Amino-7-cyclopentyl-7H-pyrrolo[2,3-d]pyrimidin-5-yl)-2-methoxyphenyl]-2-(2-thienyl)acetamide 5-(4-Amino-3-methoxyphenyl)-7-cyclopentyl-7H-pyrrolo[2,3-d]pyrimidin-4-amine (31 mg, 0.096 mmol) was dissolved in dichloromethane (1 mL). Pyridine (1 mL) was added followed by 2-(2-thienyl)ethanoyl chloride (14 uL, 0.113 mmol). After stirring overnight, another 14 uL of 2-(2-thienyl)ethanoyl chloride was added and the reaction mixture was stirred overnight. The solvent was removed and the residue was purified by preparative thin layer chromatogram eluted with dichlormethane/Methanol (95:5) to give N1-[4-(4-amino-7-cyclopentyl-7H-pyrrolo[2,3-d]pyrimidin-5-yl)-2-methoxyphenyl]-2-(2-thienyl)acetamide (14 mg, 0.031 mmol). $^1$H NMR (DMSO-d$_6$) 1.89 (m, 6H), 2.25 (m, 2H), 3.82 (s, 3H), 3.99 (s, 2H), 5.19 (bs, 2H), 5.21 (m, 1H), 6.93 (s, 1H), 6.94 (s, 1H), 7.06 (m, 3H), 7.31 (m, 1H), 8.02 (s, 1H), 8.32 (s, 1H), 8.42 (d, J=8.22 Hz, 1H). LC/MS MH$^+$=448.

The following compounds were prepared by the methods described above:

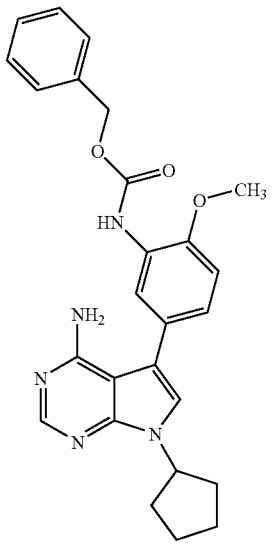
Example 176
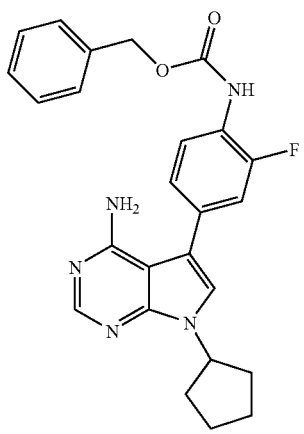
Example 179
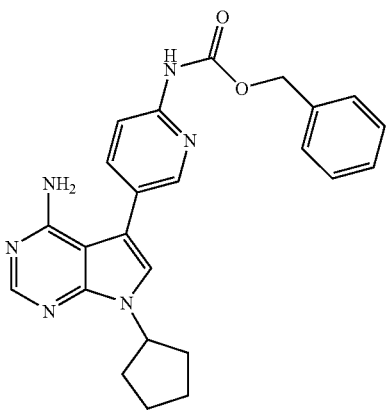
Example 177
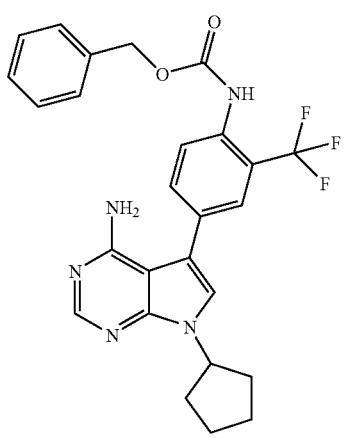
Example 180
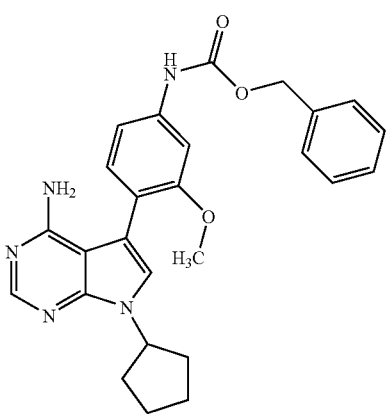
Example 178
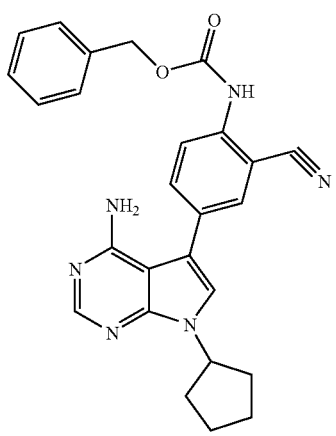
Example 181

Example 182

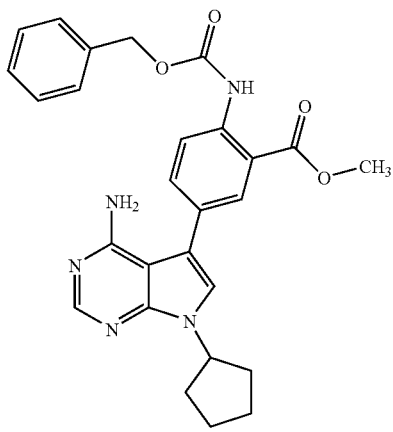

Example 183

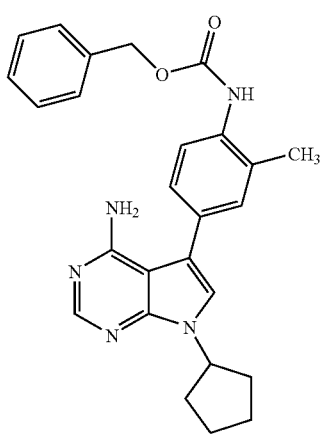

Example 184

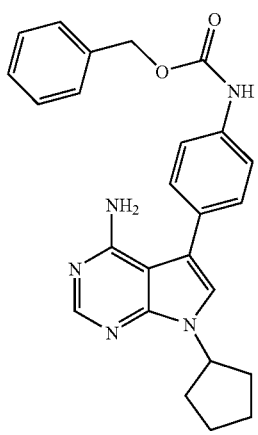

Example 185

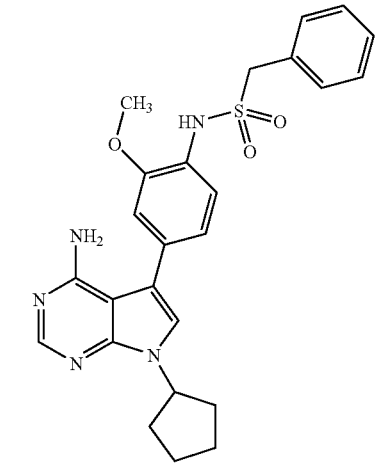

Example 186

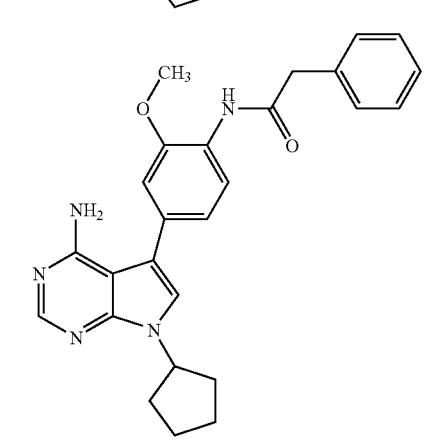

Example 187

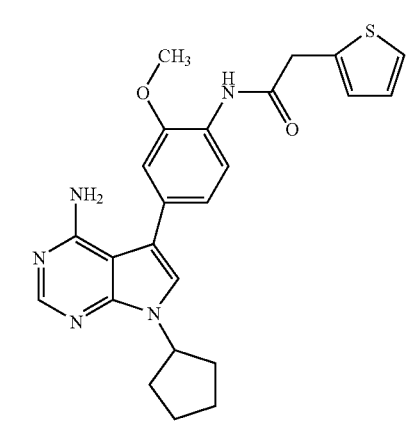

General procedure for preparing pyrrolopyrimidine arylsulfonamides: To a 0.225 M solution of 5-(4-amino-3-fluorophenyl)-7-cyclopentyl-7H-pyrrolo[2,3-d]pyrimidin-4-amino in pyridine was added one equivalent of substituted arylsulfonyl chloride. This mixture was heated with mixing at 45° C. for 24 h. The product was purified from the reaction mixture by preparative RP-HPLC (Hypersil BDS C18, (5 um packing; 100×21.2 mm) using a gradient of 0.05 M, pH 4.5 aqueous ammonium acetate/acetonitrile (0-100% over 12.5 min, at 25 mL/min).

Examples 188-249 were prepared by the general method described above. The molecular weight as determined by mass spectometry (MH+) and the HPLC retention times (RT) in minutes are listed with each example.
Example 188
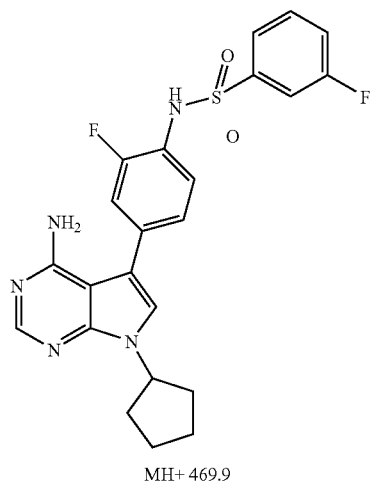
MH+ 469.9
RT 3.03
Example 189
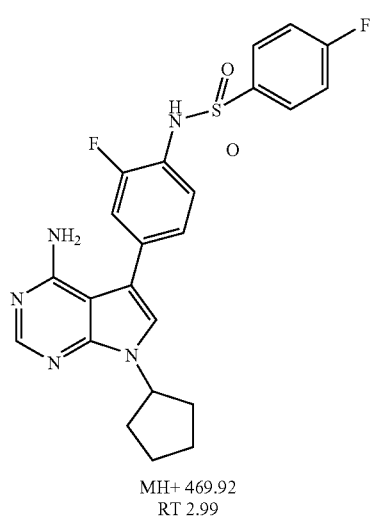
MH+ 469.92
RT 2.99
Example 190
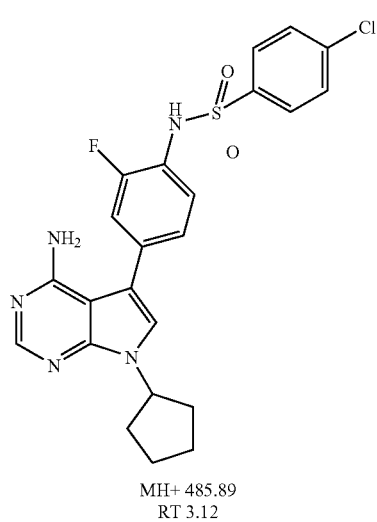
MH+ 485.89
RT 3.12
-continued
Example 191
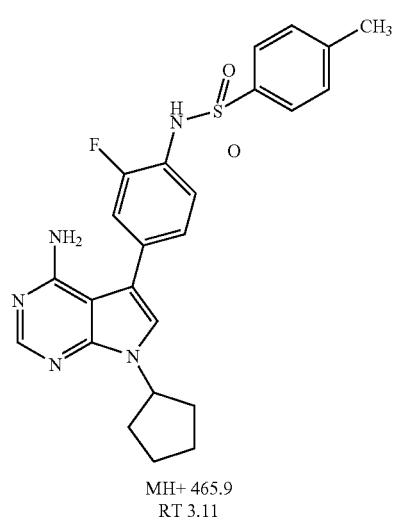
MH+ 465.9
RT 3.11
Example 192
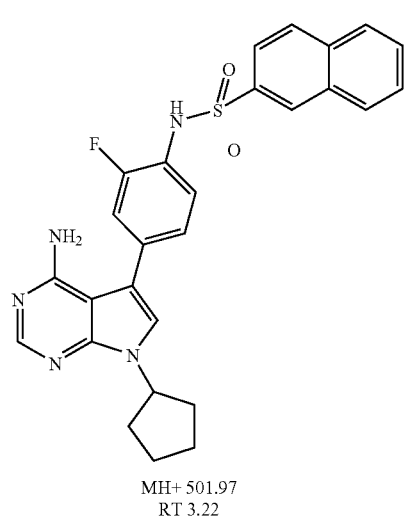
MH+ 501.97
RT 3.22
Example 193
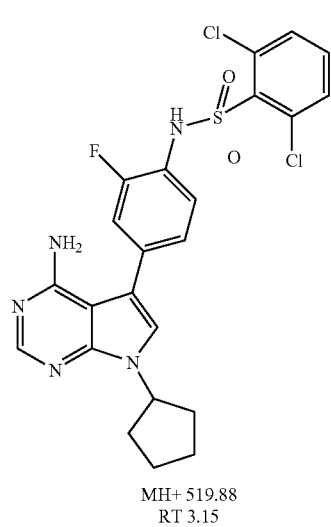
MH+ 519.88
RT 3.15

-continued
Example 194
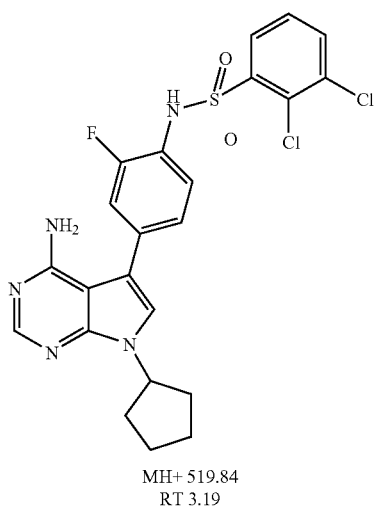
MH+ 519.84
RT 3.19
Example 195
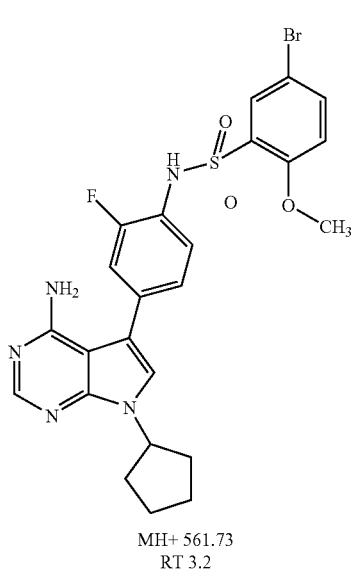
MH+ 561.73
RT 3.2
Example 196
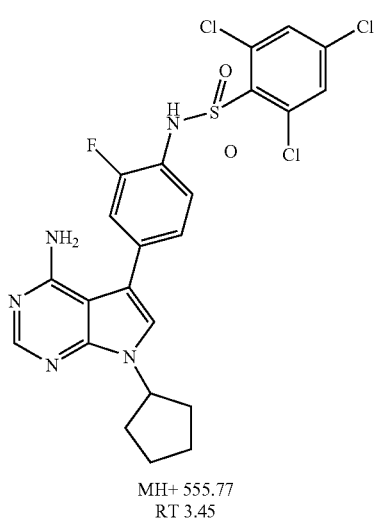
MH+ 555.77
RT 3.45
-continued
Example 197
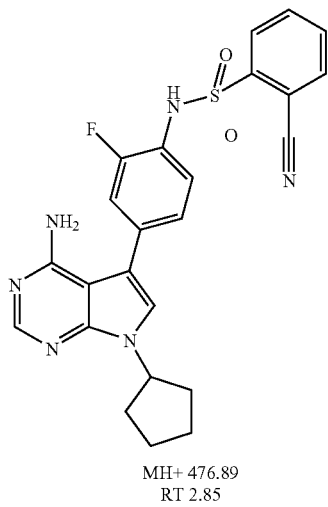
MH+ 476.89
RT 2.85
Example 198
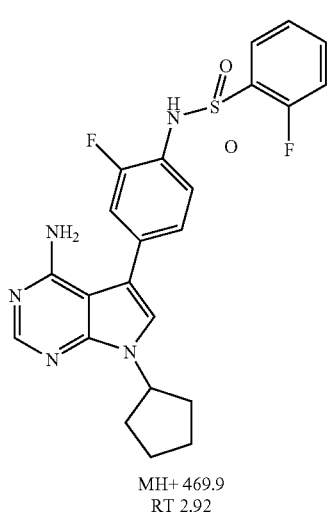
MH+ 469.9
RT 2.92
Example 199
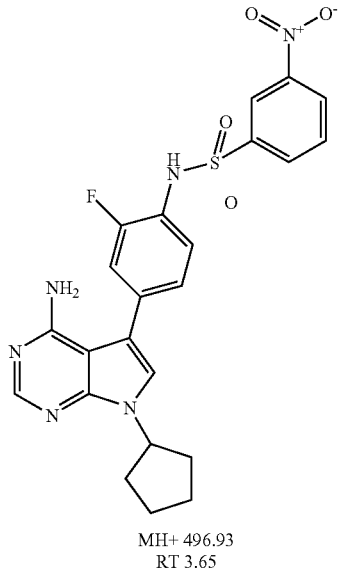
MH+ 496.93
RT 3.65

-continued
Example 200
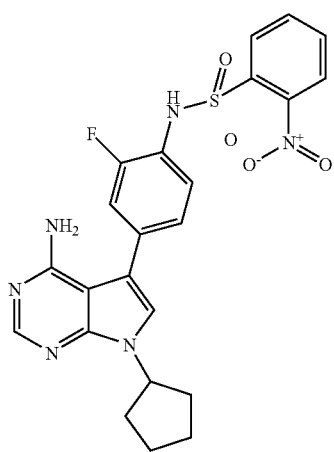
MH+ 496.94
RT 3.66
Example 201
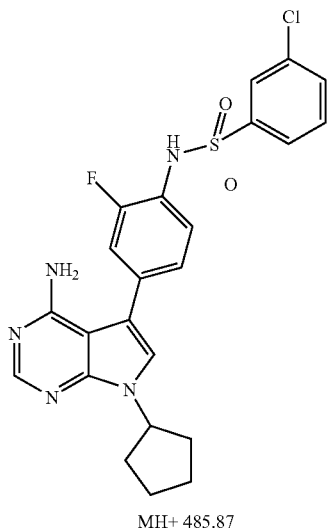
MH+ 485.87
RT 3.79
Example 202
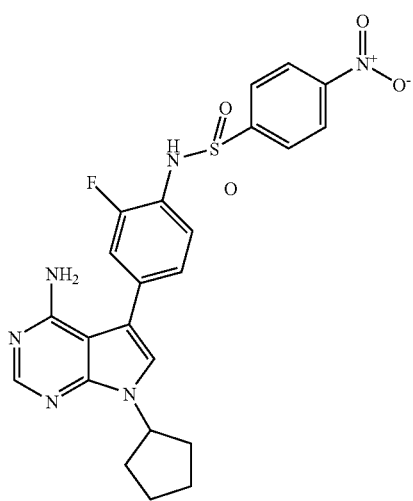
MH+ 496.9
RT 3.65
-continued
Example 203
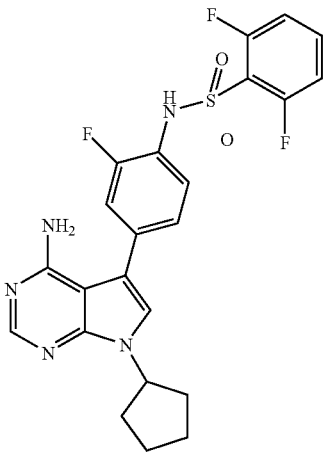
MH+ 487.9
RT 3.55
Example 204
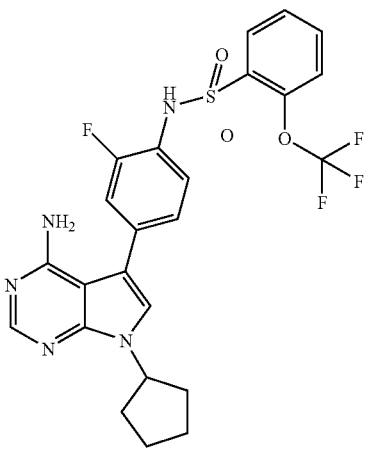
MH+ 535.9
RT 3.82
Example 205
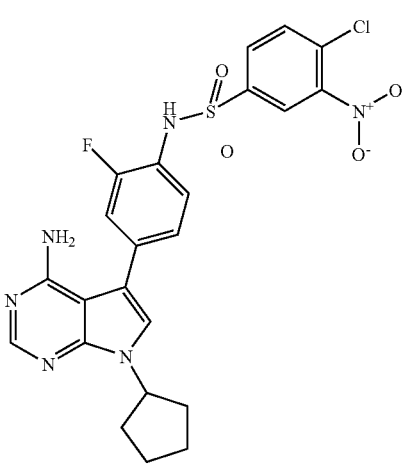
MH+ 530.92
RT 3.43

Example 206
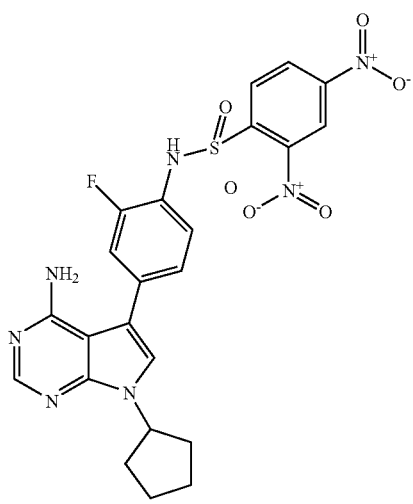
MH+ 541.95
RT 3.55
Example 207
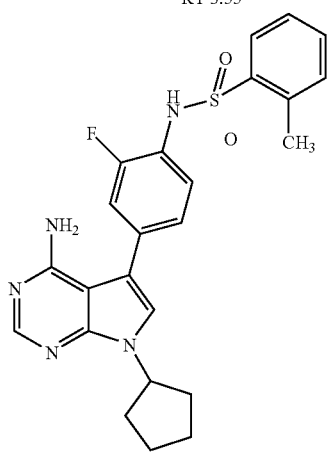
MH+ 465.89
RT 3.45
Example 208
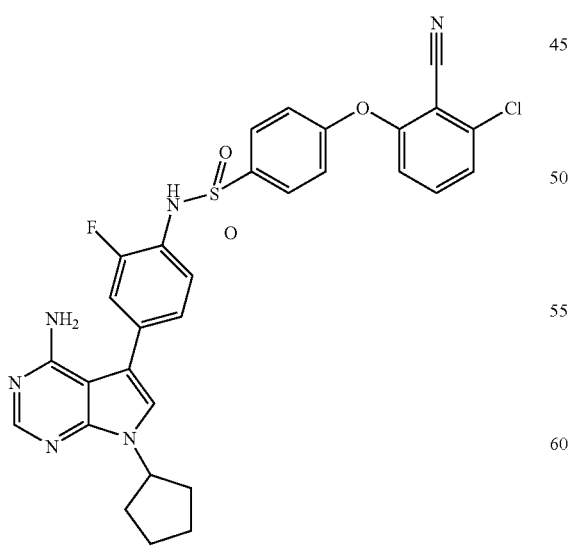
MH+ 602.99
RT 3.56
Example 209
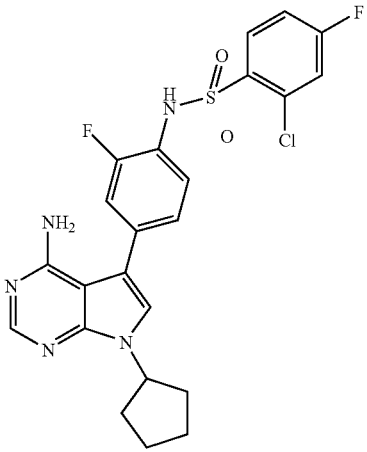
MH+ 503.85
RT 3.48
Example 210
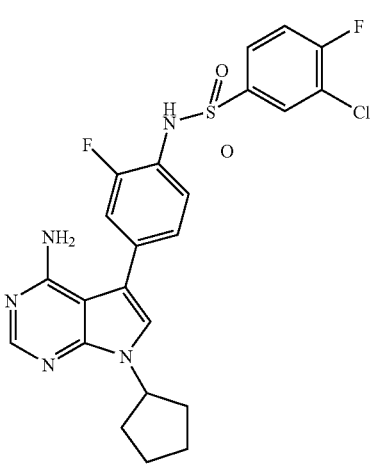
MH+ 503.88
RT 3.53
Example 211
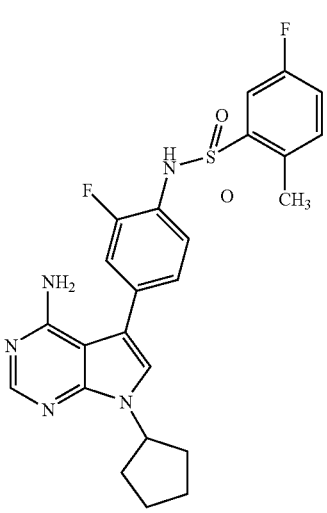
MH+ 483.9
RT 3.47

Example 212
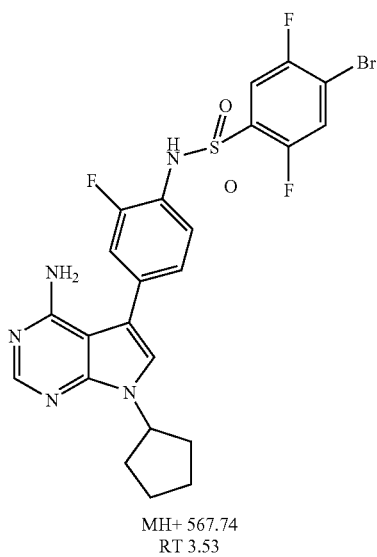
MH+ 567.74
RT 3.53
Example 213
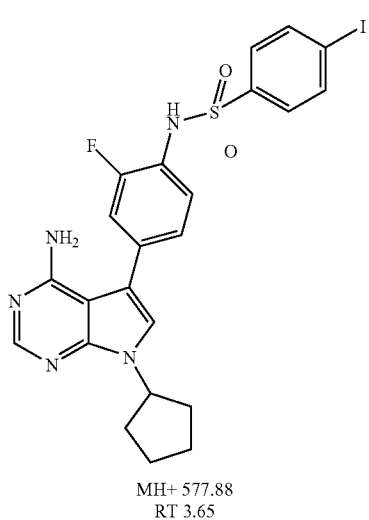
MH+ 577.88
RT 3.65
Example 214
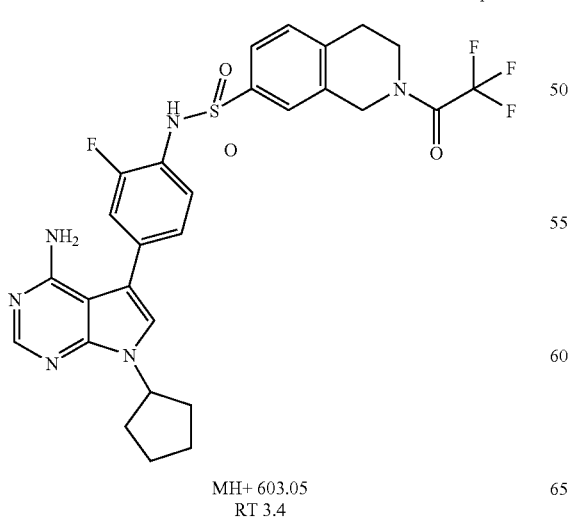
MH+ 603.05
RT 3.4
Example 215
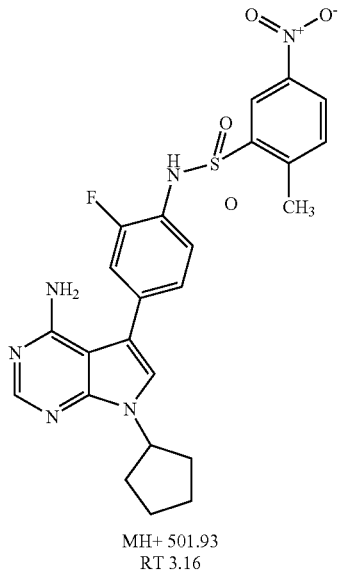
MH+ 501.93
RT 3.16
Example 216
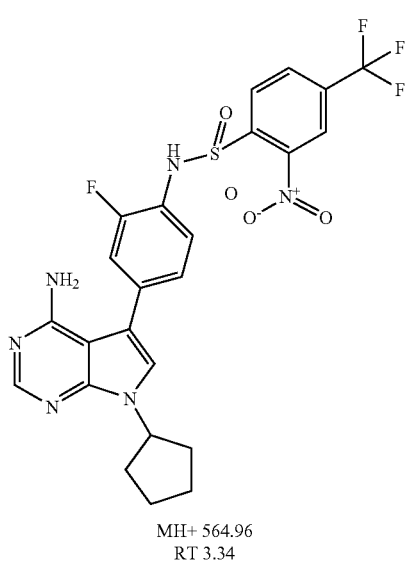
MH+ 564.96
RT 3.34
Example 217
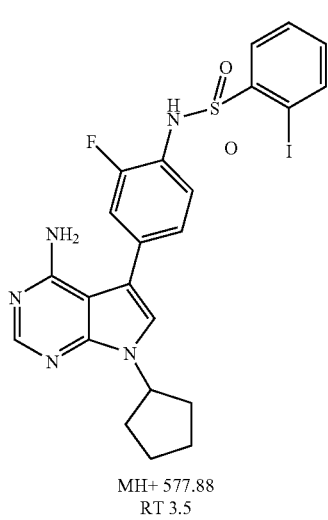
MH+ 577.88
RT 3.5

-continued
Example 218
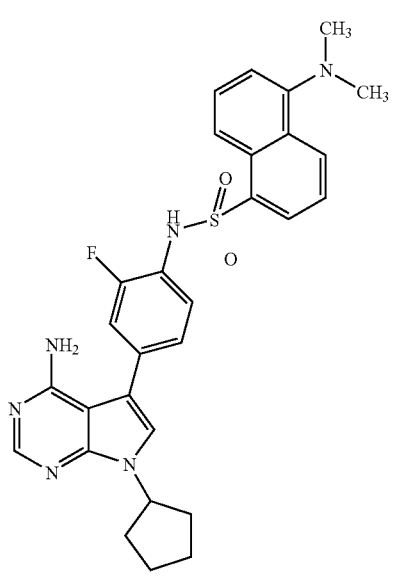
MH+ 545.01
RT 3.5
Example 219
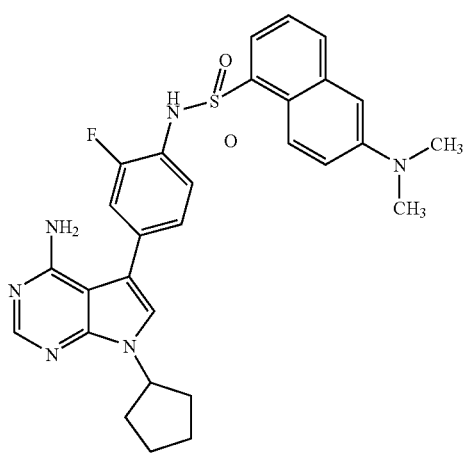
MH+ 545.04
RT 3.58
Example 220
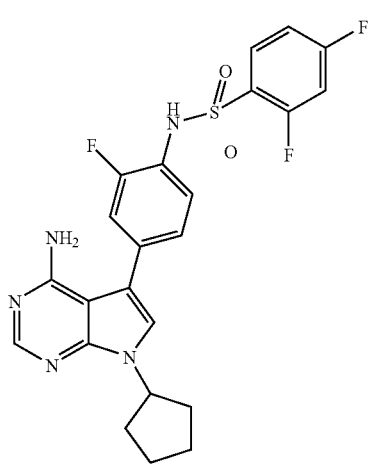
MH+ 487.9
RT 3.43
-continued
Example 221
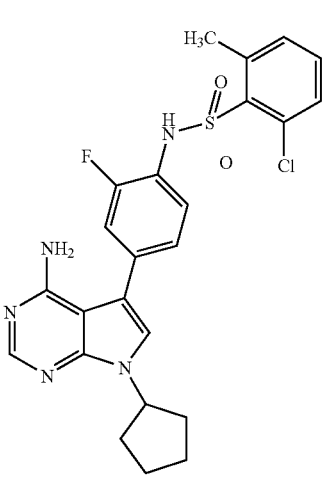
MH+ 499.92
RT 3.46
Example 222
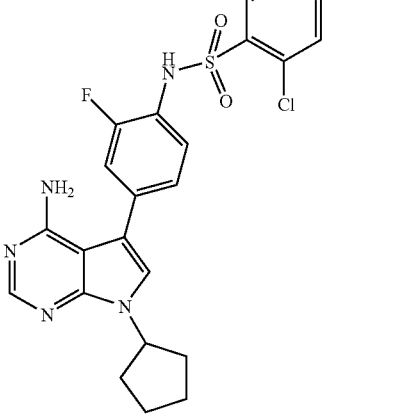
MH+ 510.88
RT 3.41
Example 223
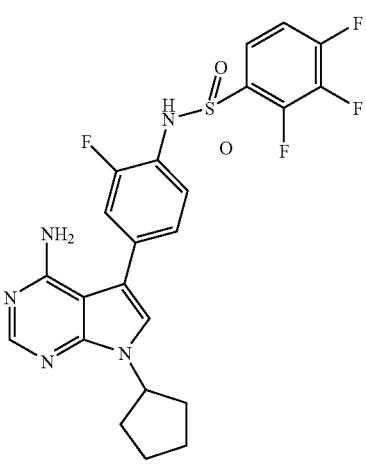
MH+ 577.88
RT 3.5

-continued
Example 224
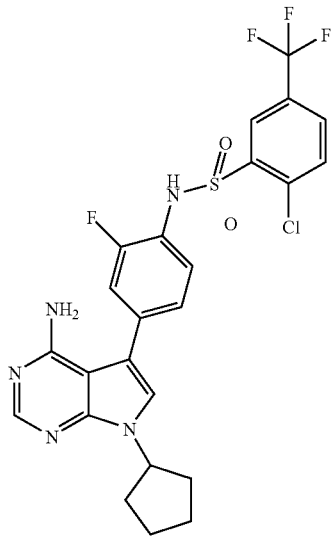
MH+ 553.96
RT 3.55
Example 225
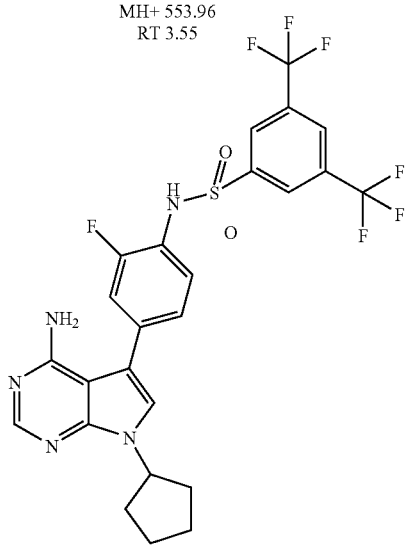
MH+ 587.97
RT 3.6
Example 226
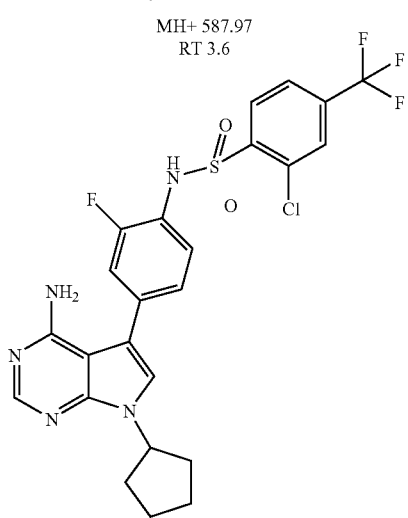
MH+ 553.9
RT 3.88
-continued
Example 227
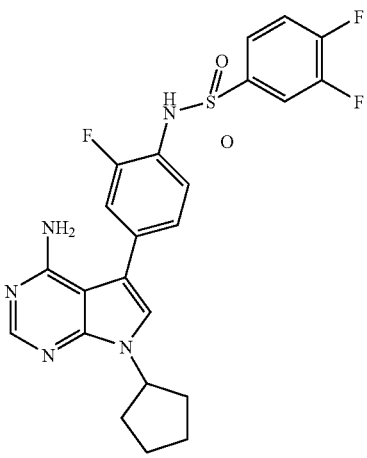
MH+ 487.9
RT 3.6
Example 228
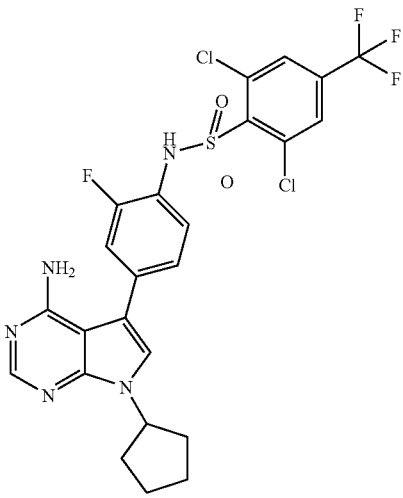
MH+ 587.9
RT 3.9
Example 229
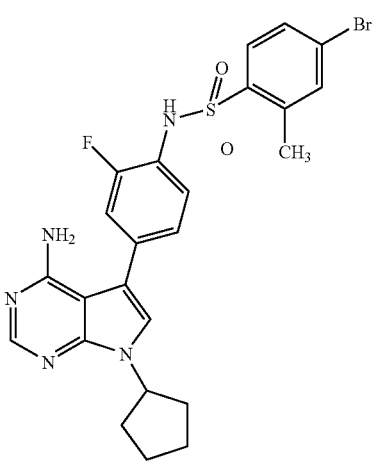
MH+ 545.8
RT 3.93

Example 230
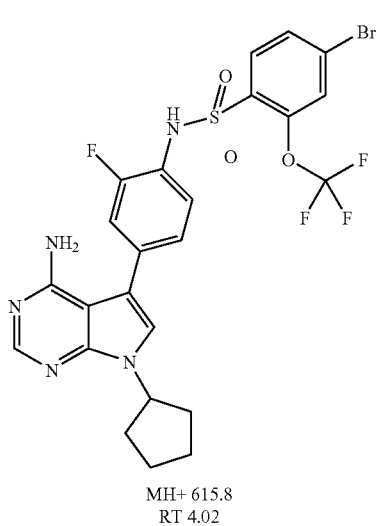
MH+ 615.8
RT 4.02
Example 231
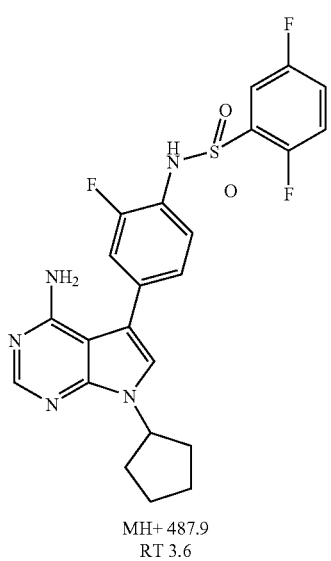
MH+ 487.9
RT 3.6
Example 232
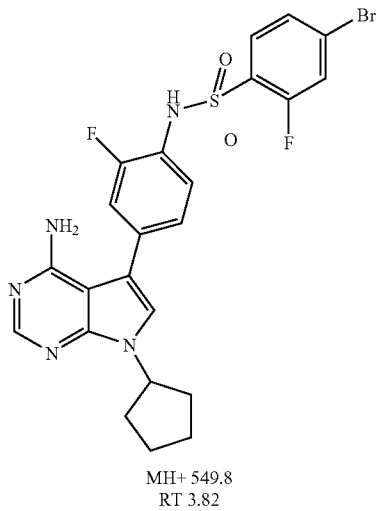
MH+ 549.8
RT 3.82
Example 233
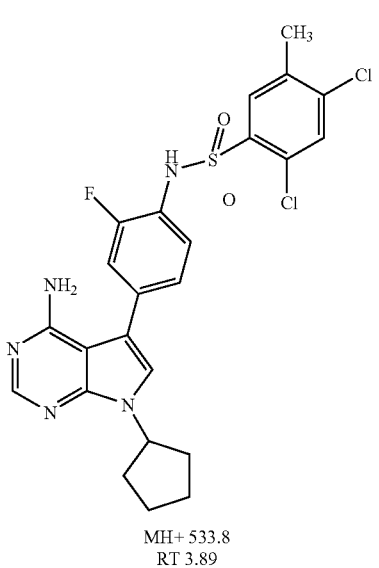
MH+ 533.8
RT 3.89
Example 234
MH+ 519.9
RT 3.74
Example 235
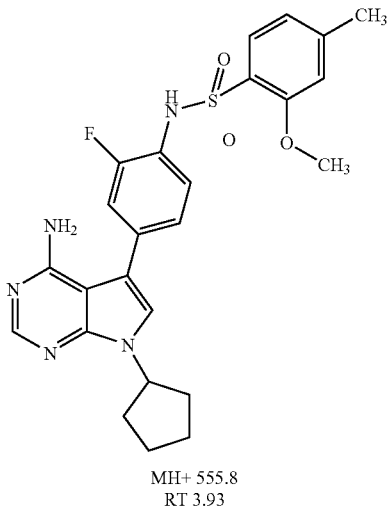
MH+ 555.8
RT 3.93

Example 236
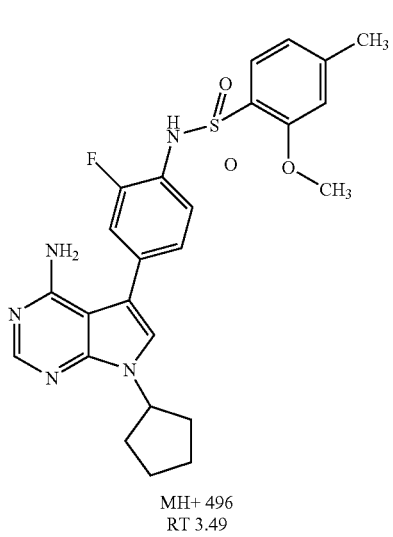
MH+ 496
RT 3.49
Example 237
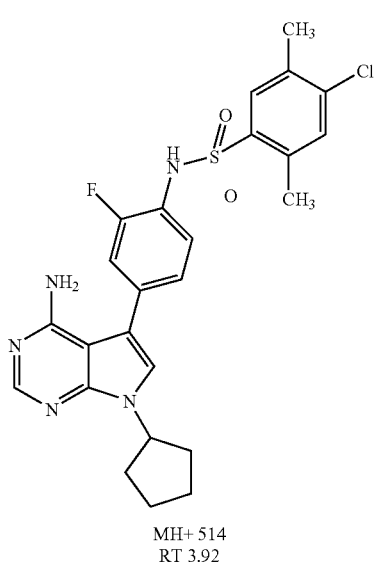
MH+ 514
RT 3.92
Example 238
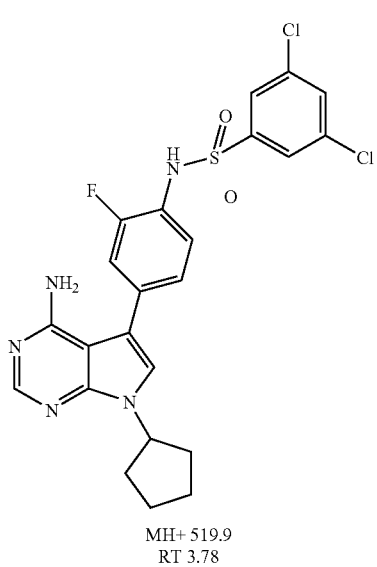
MH+ 519.9
RT 3.78
Example 239
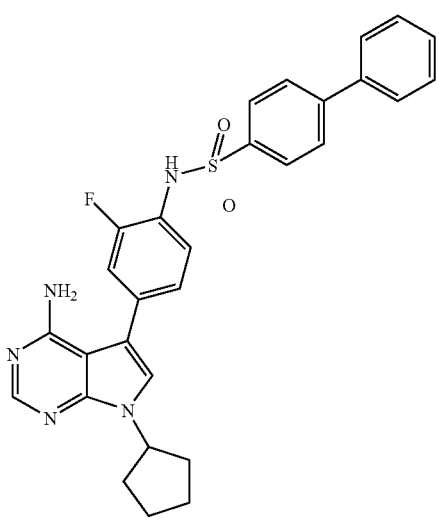
MH+ 528
RT 3.84
Example 240
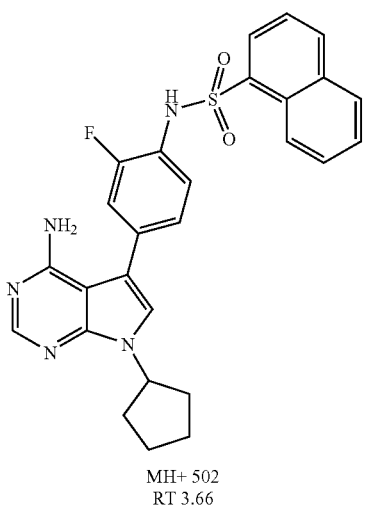
MH+ 502
RT 3.66
Example 241
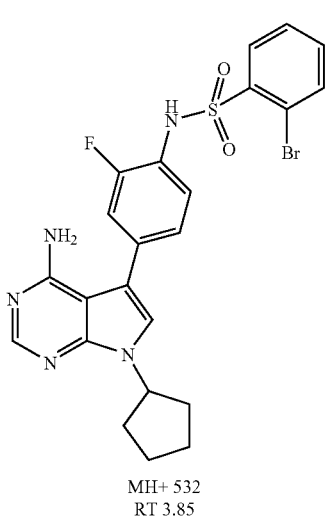
MH+ 532
RT 3.85

-continued
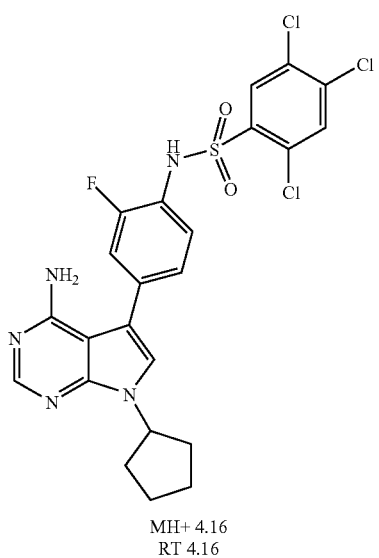
MH+ 4.16
RT 4.16
Example 243
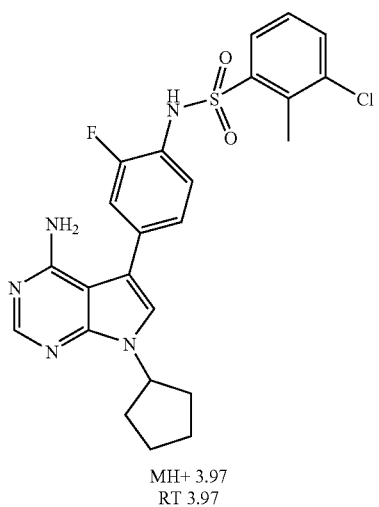
MH+ 3.97
RT 3.97
Example 244
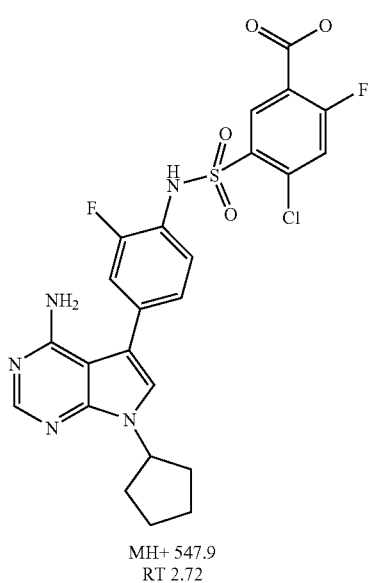
MH+ 547.9
RT 2.72
-continued
Example 245
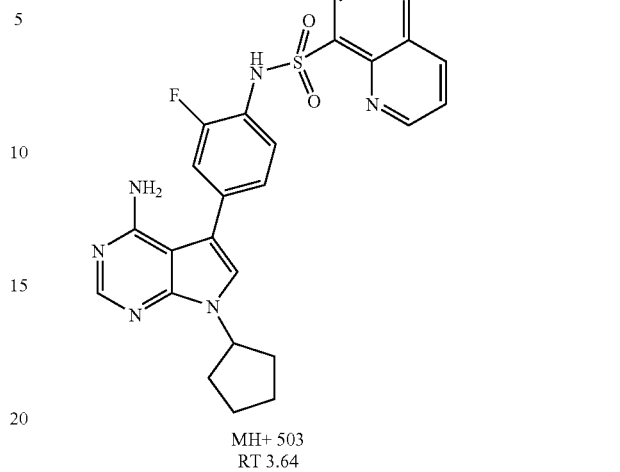
MH+ 503
RT 3.64
Example 246
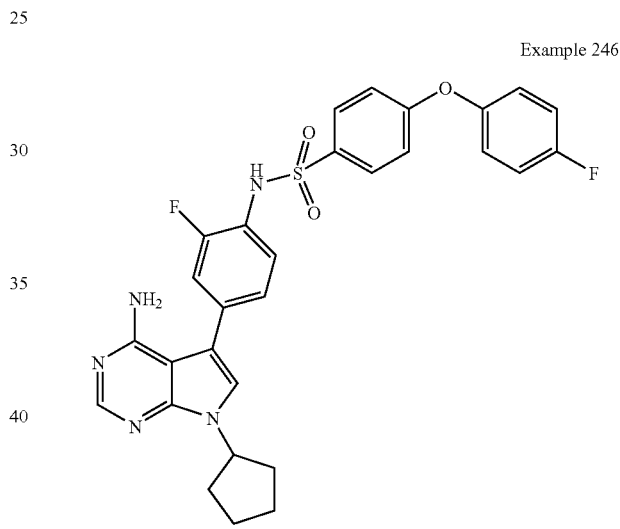
Example 247
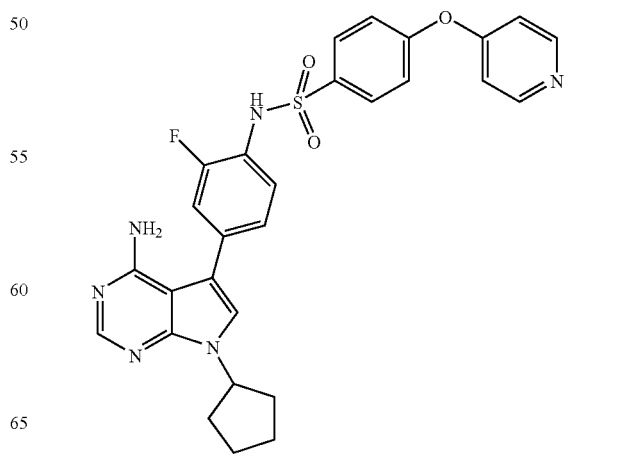

-continued

Example 248

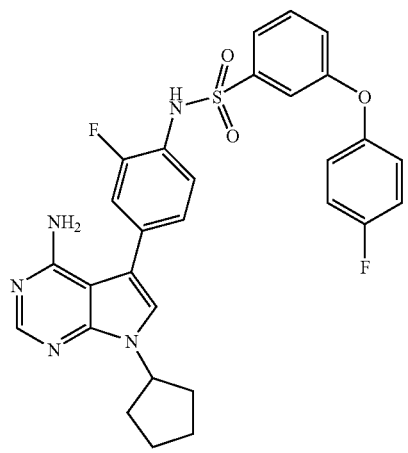

Example 249

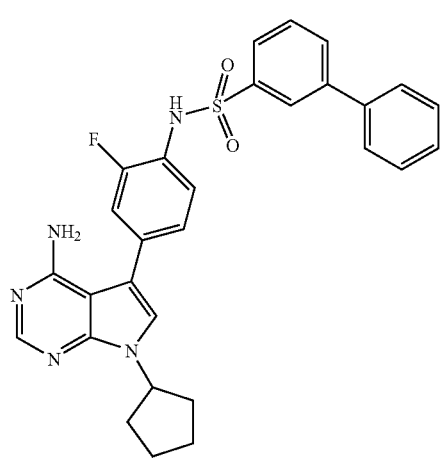

General Synthesis for Examples 250-269

To a 0.225 M solution of 5-(4-amino-3-methoxyphenyl)-7-cyclopentyl-7H-pyrrolo[2,3-d]pyrimidin-4-amine (or 5-(4-amino-3-fluorophenyl)-7-cyclopentyl-7H-pyrrolo[2,3-d]pyrimidin-4-amine or 5-(4-amino-3-chlorophenyl)-7-cyclopentyl-7H-pyrrolo[2,3-d]pyrimidin-4-amine) in pyridine was added one equivalent of substituted arylsulfonyl chloride. This mixture was heated with mixing at 45° C. for 24 h. The product was purified from the reaction mixture by preparative C18 RP-HPLC. Analytical RP-HPLC RT listed in the table were obtained on a Hypersil HyPurity Elite C18 column ((5 μm, 200 A) 250×4.6 mm) using a linear gradient of 25-100% acetonitrile/0.1 M ammonium acetate over 25 min at 1 ml/min.

Note that appropriate protecting group manipulation may be required when introducing reactive substituents.

Compounds 250-269 were prepared by the general method described above. The molecular weight as determined by mass spectometry (MH$^+$) and the HPLC retention times (RT) in minutes are listed with each example Example 250

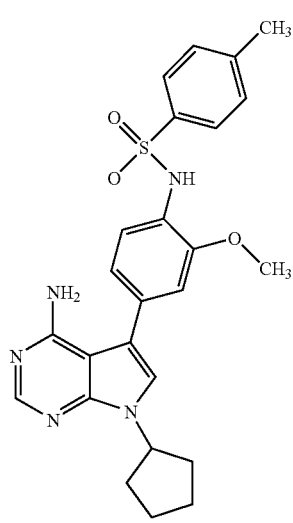

MH+ 478.1
RT 13.9

Example 251

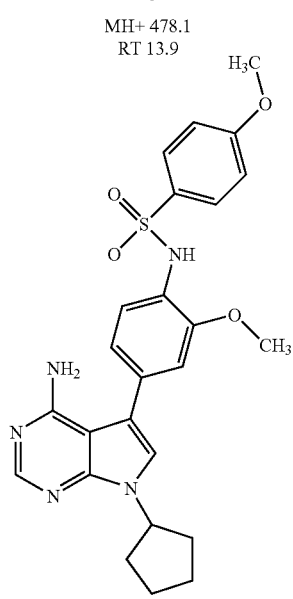

MH+ 494.1
RT 15.68

Example 252

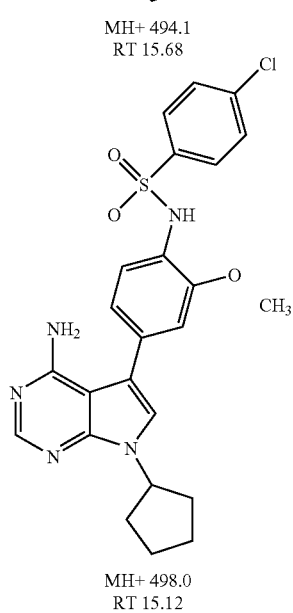

MH+ 498.0
RT 15.12

Example 253
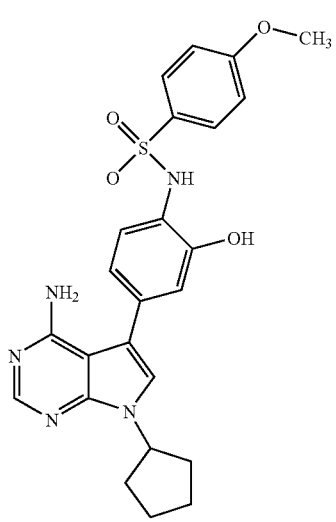
MH+ 514.0
RT 17.7
Example 254
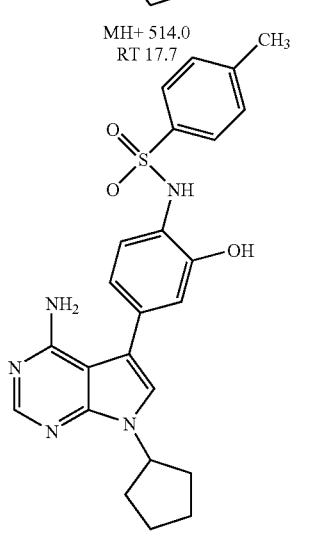
MH+ 464.1
RT 10.4
Example 255
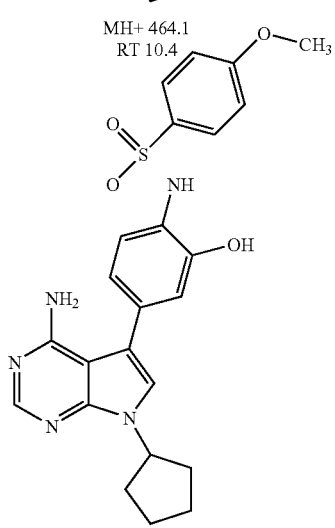
MH+ 480.1
RT 11.2
Made from Example 251
by treatment with BBr3 in
methylene chloride.
Example 256
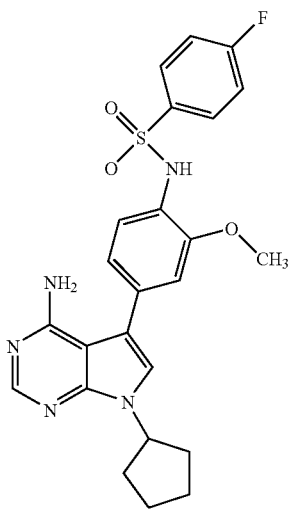
MH+ 482.1
RT 15.65
Example 257
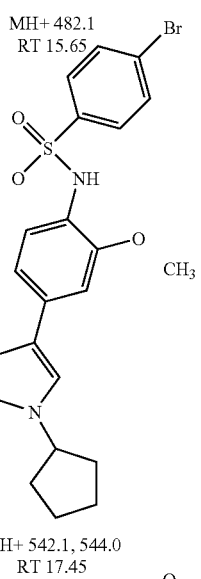
MH+ 542.1, 544.0
RT 17.45
Example 258
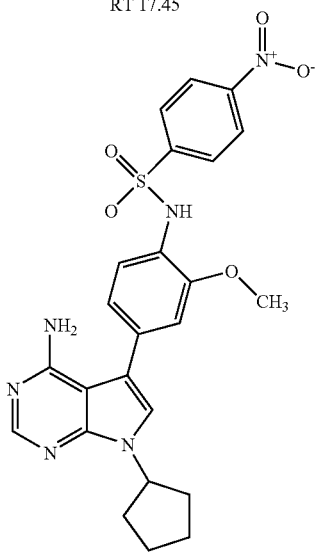
MH+ 509.2
RT 15.8

Example 259
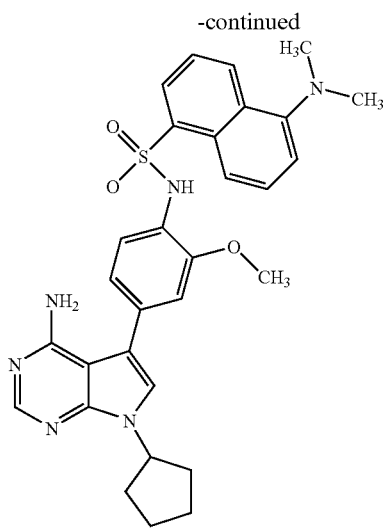
MH + 557.2
RT 19.55
Example 260
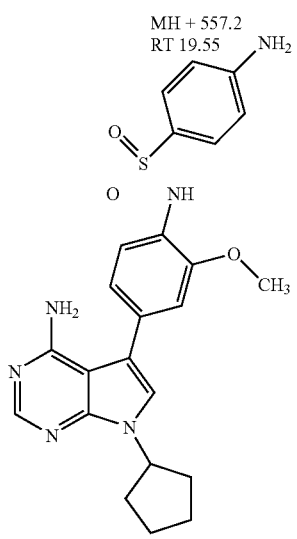
MH + 477.1
RT 11.6
Made by hydrogenation
of Example 258 over Pd-C
Example 261
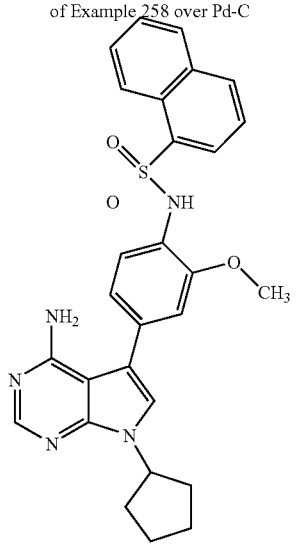
MH + 512.0
RT 17.62
Example 262
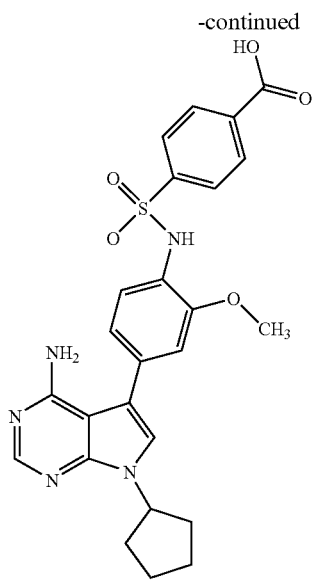
MH+ 506.0
RT 9.93
Example 263
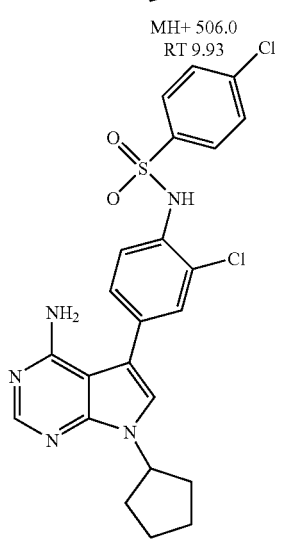
MH+ 502.0
RT 18.23
Example 264
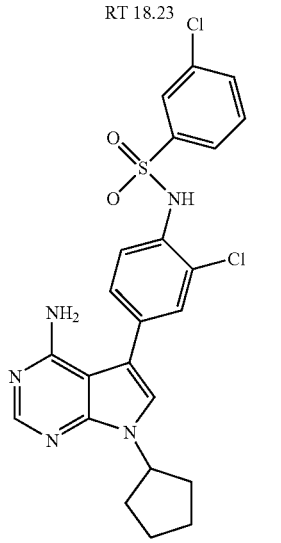
MH+ 502.0
RT 18.02

-continued

Example 265

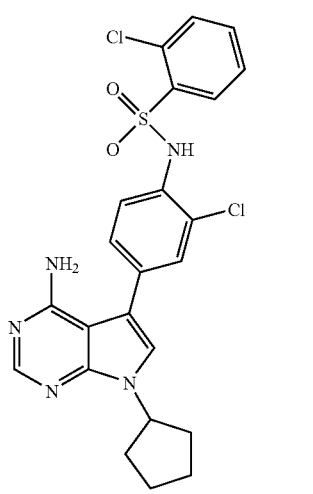

MH+ 502.0
RT 17.6

Example 266

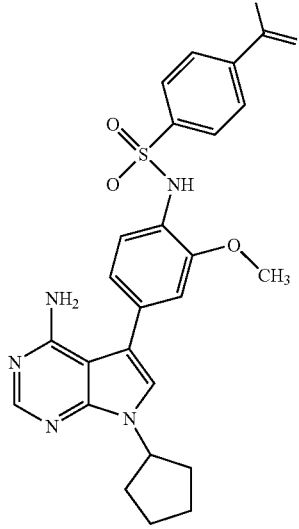

MH+ 507.1
RT 12.2
Made by treating Example
262 with EDC, HOAt,
ME₂NH in DMF

Example 267

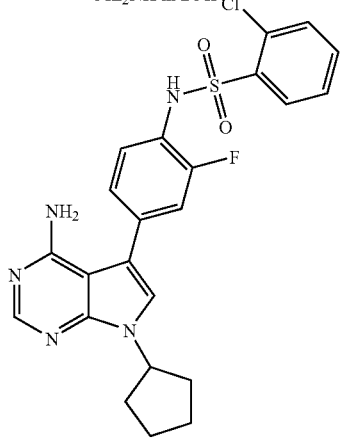

MH+ 486.1
RT 15.68

-continued

Example 268

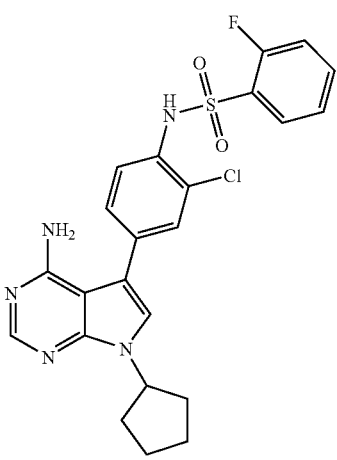

MH+ 486.1
RT 16.35

Example 269

MH+ 486.1
RT 16.7

Compounds 270 to 282 were synthesized using the following methods.

Route 1 a) A mixture of the appropriate bromoarylsulphonamide (0.735 mmol), bispinacolatodiborane (0.225 g, 0.88 mmol), [1.1'-bis(diphenylphosphino)ferrocene]dichloropalladium (II) complex with dichloromethane (1:1) (2 mg, 0.002 mol) and potassium acetate (0.216 g, 2.205 mol) in N,N-dimethylformamide (5 mL) was heated at 100° C. under an atmosphere of nitrogen for 16 hours. The mixture was allowed to cool to ambient temperature and the solvent removed under reduced pressure. Dichloromethane (20 mL) was added to the residue and the resulting solid was removed by filtration through a pad of celite. The filtrate was concentrated to leave a yellow oil which was purified by flash chromatography on silica gel to yield the sulphonamido aryl borate.

b) A mixture of 4-chloro-7-cyclopentyl-5-iodo-7H-pyrrolo[2,3-d]pyrimidine (0.35 g, 1.0 mmol), the sulphonamido aryl borate. (1.5 mmol; from 1(a) above), tetrakis(triphenylphosphine)palladium (0.07 g, 0.06 mmol) and sodium carbonate (0.265 g, 2.5 mmol) was heated in a mixture of ethylene glycol dimethyl ether (10 mL) and water (5 mL) at 80° C. for 18 hours under an atmosphere of nitrogen. The mixture was allowed to cool to ambient temperature and solvents were removed under reduced pressure. The residue was partitioned between water (15 mL) and ethyl acetate (25 ml), the organic layer separated and the aqueous layer further extracted with ethyl acetate (2×25 ml). The combined organic extracts were washed with water (3×20 ml) then dried over magnesium sulfate, filtered and the filtrate concentrated to an oily residue under reduced pressure which was purified by flash column chromatography on silica gel to afford the corresponding sulfonamidoaryl 4-chloro-pyrrolo[2,3-d]pyrimidine.

c) The 4-chloro-pyrrolo[2,3-d]pyrimidine (typically 10-20 mmol; from 1(b) above) was mixed with dioxane (100 ml) and concentrated ammonium hydroxide (100 ml) in a pressure vessel. The mixture was heated to 120° C. overnight. Solvent was removed and the residue was purified by RP-HPLC to give the desired final 4-amino-pyrrolo[2,3-d]pyrimidine product.

Route 2 a) A mixture of the appropriate bromoaniline (2.4 mmol), bispinacolatodiborane (0.735 g, 2,88 mmol), [1.1'-bis(diphenylphosphino)ferrocene]dichloropalladium (II) complex with dichloromethane (1:1) (59 mg, 0.072 mol) and potassium acetate (0.707 g, 7.205 mol) in N,N-dimethylformamide (15 mL) was heated at 100° C. under an atmosphere of nitrogen for 16 hours. The mixture was allowed to cool to ambient temperature and the solvent removed under reduced pressure. Toluene (20 mL) was added and the mixture washed with water (2×15 ml). The organic phases were dried over MgSO$_4$ (s), concentrated in vacuo, and purified by flash chromatography on silica gel to yield the anilino borate.

b) A mixture the anilino borate. (1.01 mmol; from 2(a) above), 4-chloro-7-cyclopentyl-5-iodo-7H-pyrrolo[2,3-d]pyrimidine (0.24 g, 0.67 mmol), tetrakis(triphenylphosphine) palladium (0.04 g, 0.033 mmol) and sodium carbonate (0.215 g, 2.03 mmol) was heated in a mixture of ethylene glycol dimethyl ether (10 mL) and water (5 mL) at 80° C. for 18 hours under an atmosphere of nitrogen. The mixture was allowed to cool to ambient temperature and solvents were removed under reduced pressure. The residue was partitioned between water (15 mL) and ethyl acetate (25 ml), the organic layer separated and the aqueous layer further extracted with ethyl acetate (2×25 ml). The combined organic extracts were washed with water (3×20 ml) then dried over magnesium sulfate, filtered. The filtrate concentrated to an oily residue under reduced pressure which was purified by flash column chromatography on silica gel to give the desired 4-chloro-7-cyclopentyl-5-(4-aminophenyl)-7H-pyrrolo[2,3-d]pyrimidine.

c) A mixture of the 4-chloro-7-cyclopentyl-5-(4-aminophenyl)-7H-pyrrolo[2,3-d]pyrimidine (0.201 mmol; from 2(b) above), the arylsulphonyl chloride (0.402 mmol) and pyridine (1.005 mmol) in methylene chloride was stirred at room temperature for 16 h. The solvents were removed by filtration and the sulfonamido 4-chloro-pyrrolopyrimidine product was purified by RP-HPLC.

d) The sulfonamido 4-chloro-pyrrolo[2,3-d]pyrimidine (typically 10-20 mmol; from 2(c) above) was mixed with dioxane (100 ml) and concentrated ammonium hydroxide (100 ml) in a pressure vessel. The mixture was heated to 120° C. overnight. Solvent was removed and the residue was purified by RP-HPLC to give the desired final sulfonamido 4-amino-pyrrolo[2,3-d]pyrimidine product.

Analytical RP-HPLC RT listed in the table were obtained on a Hypersil HyPurity Elite C18 column ((5 um, 200 A) 250× 4.6 mm) using a linear gradient of 25-100% acetonitrile/0.1 M ammonium acetate over 25 min at 1 ml/min.

Note that appropriate protecting group manipulation may be required when introducing reactive substituents.

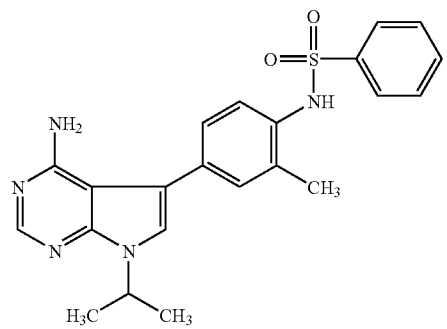

Example 270
MH+ 422.2
RT 14.03

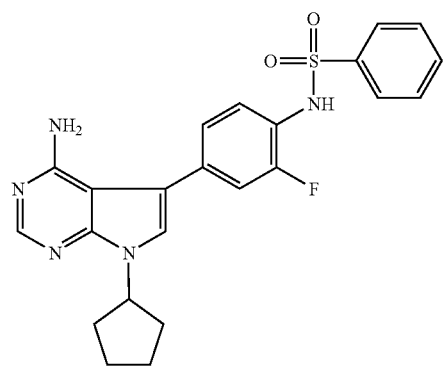

Example 271
MH+ 452
RT 16.28

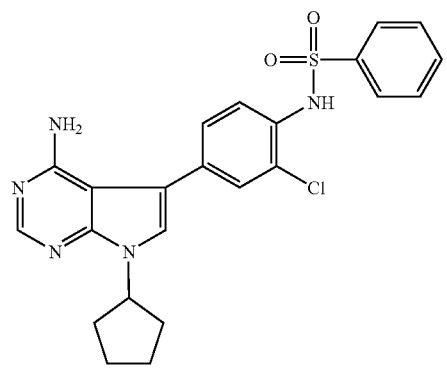

Example 272
MH+ 468.1
RT 17.12

-continued
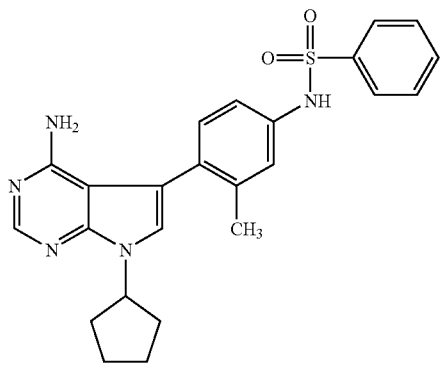
Example 273
MH+ 448.2
RT 18.37
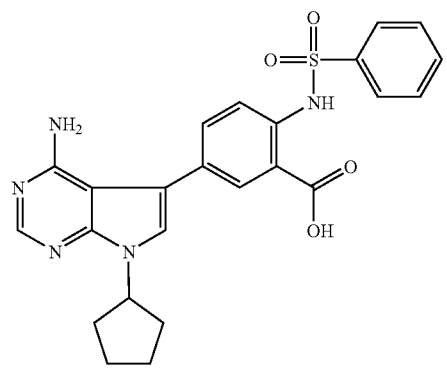
Example 276
MH+ 476
RT 13.26
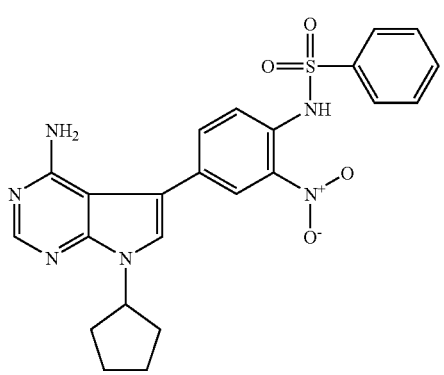
Example 274
MH+ 477.1
RT 20.53
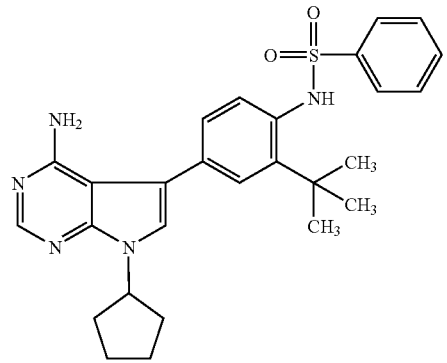
Example 277
MH+ 488.2
RT 17.7
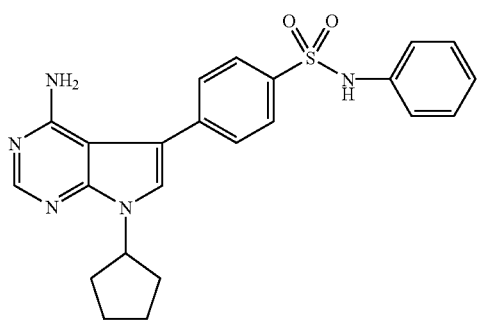
Example 275
MH+ 432.1
RT 18.85
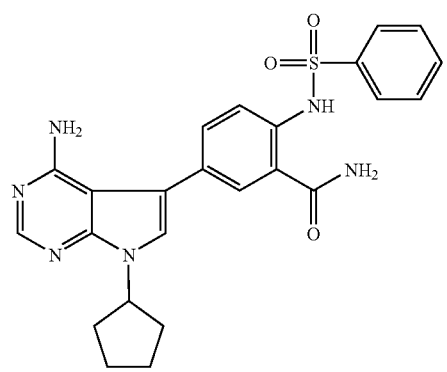
Example 278
MH+ 477.1
RT 13.45

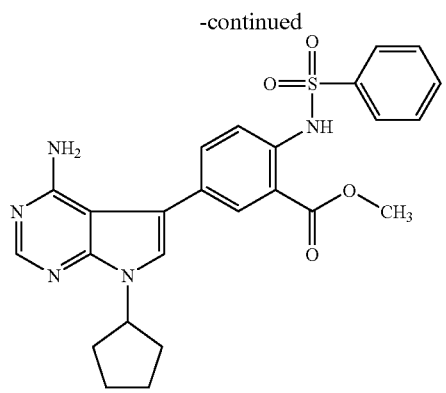
Example 279
MH+ 492.1
RT 17.52
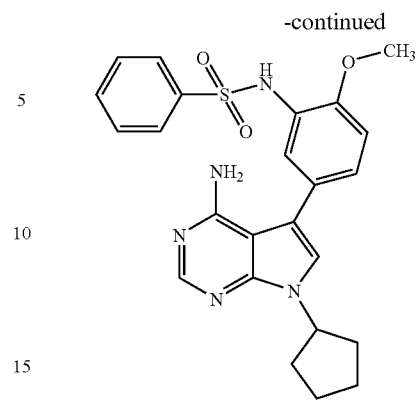
Example 281
MH+ 464.2
RT 14.82
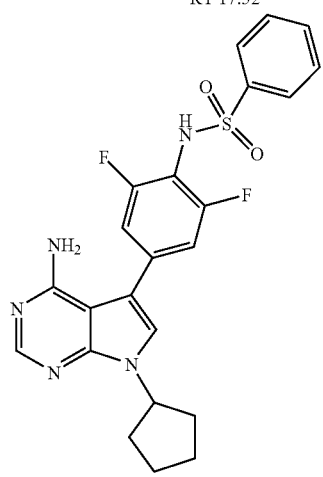
Example 280
MH+ 470.1
RT 15.08
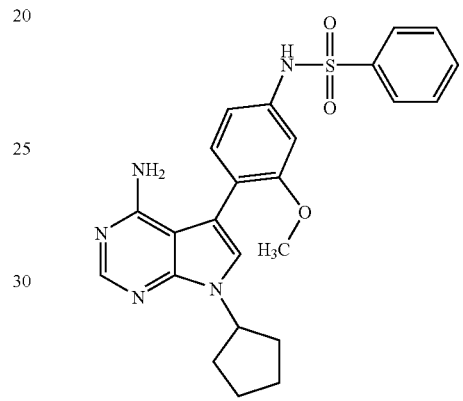
Example 282
MH+ 464.2
RT 14.15
The following compounds were also prepared using the general method as described for Examples 188-249.
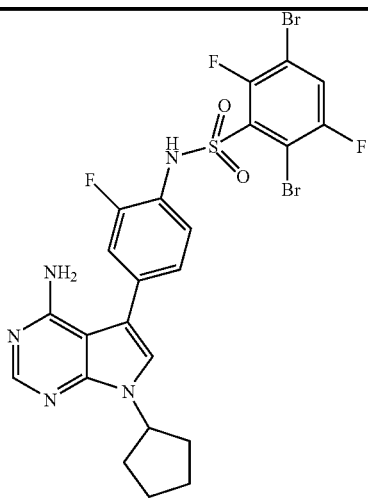
Example 283
MH+ 645.8
RT 3.66

-continued
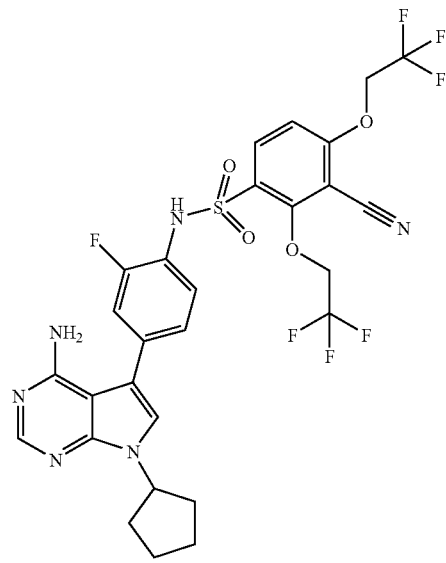
Example 284
MH+ 673.1
RT 3.73
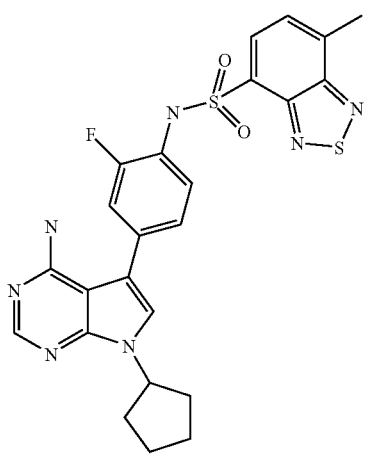
Example 285
MH+ 524
RT 3.52

-continued
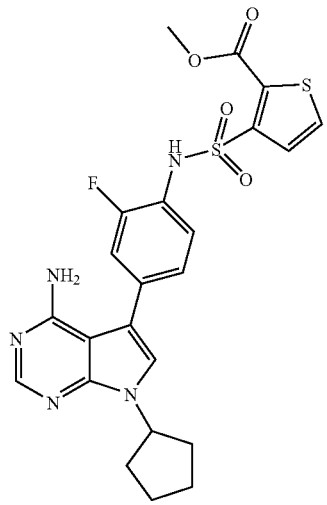
Example 286
MH+ 516.1
RT 3.42
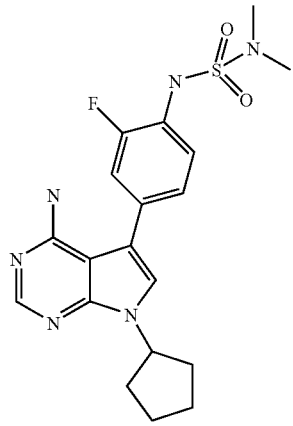
Example 287
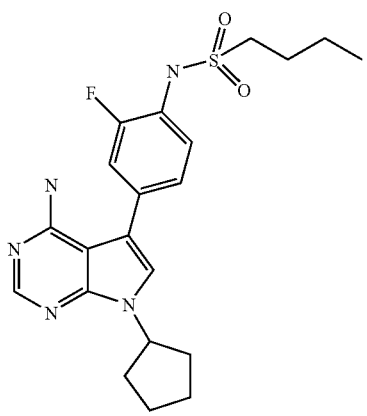
Example 288

-continued
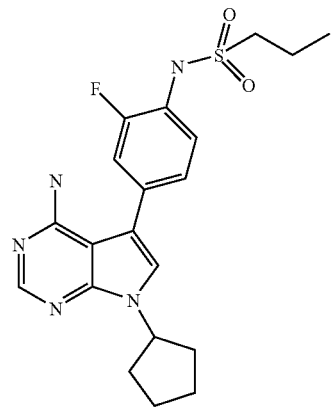
Example 289
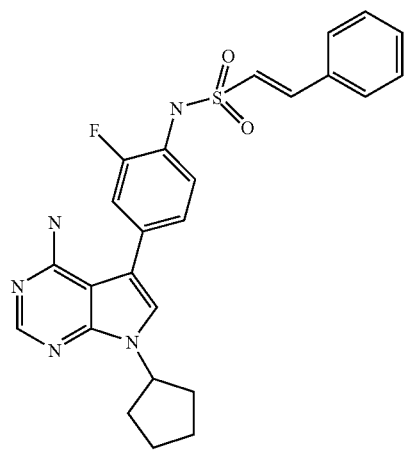
Example 290
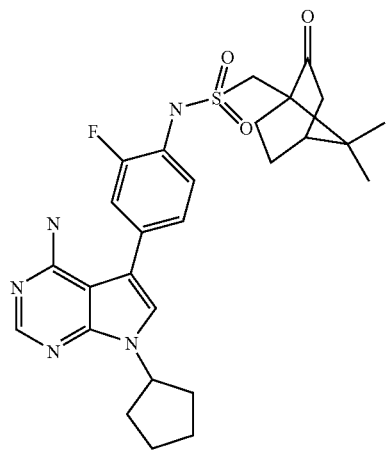
Example 291

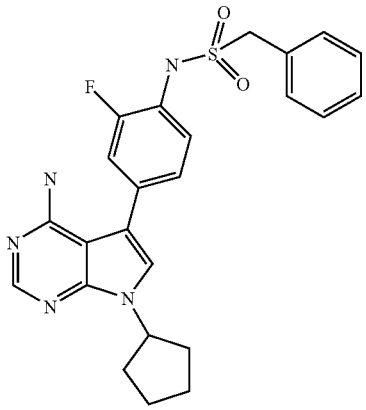
Example 292
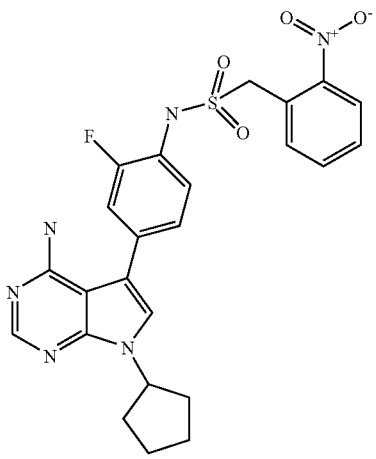
Example 293
| Example | STRUCTURE | HPLC RT | MS MH+ |
|---|---|---|---|
| 294 | 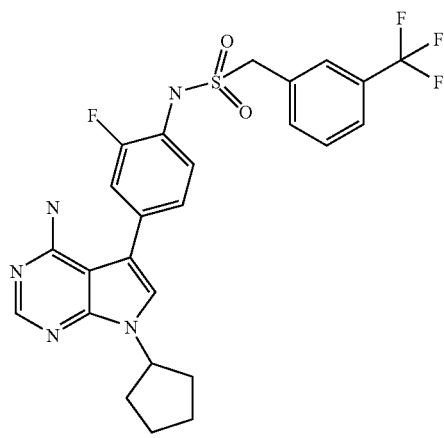 | 3.65 | 534.1 |

-continued
| | | | |
|---|---|---|---|
| 295 | 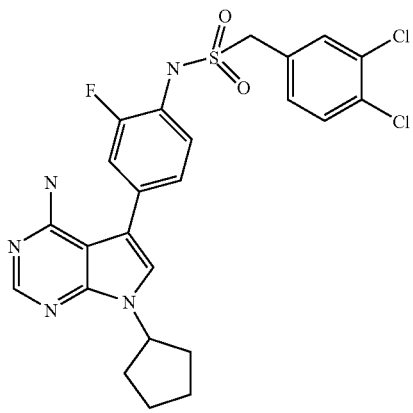 | 3.64 | 534.1 |
| 296 | 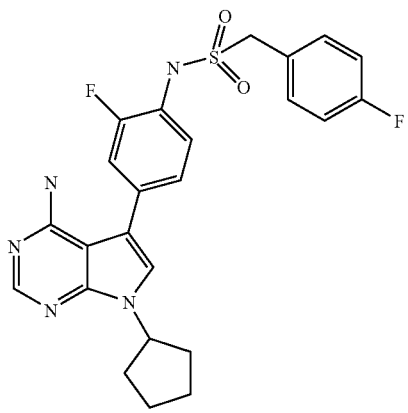 | 3.41 | 484.1 |
| 297 | 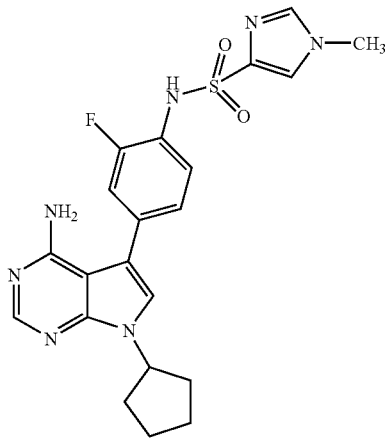 | 2.23 | 455.9 |

-continued
| | | | |
|---|---|---|---|
| 298 | 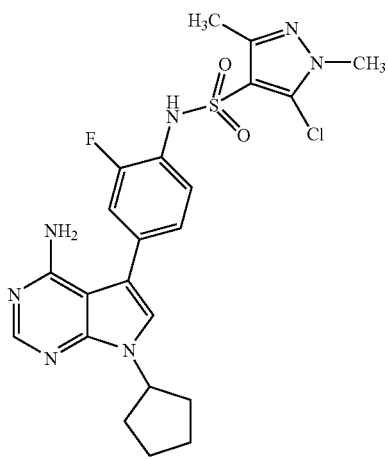 | 3.39 | 503.92 |
| 299 | 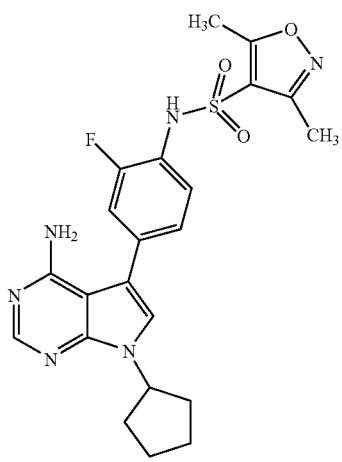 | 3.53 | 470.9 |
| 300 | 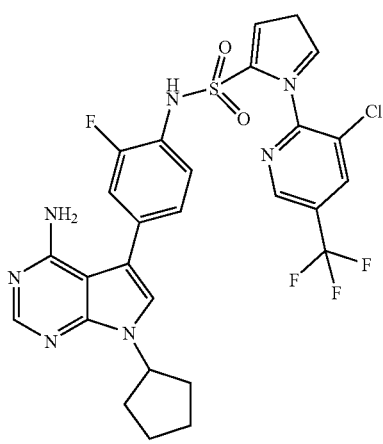 | 3.93 | 620.05 |

| | | | |
|---|---|---|---|
| 301 | 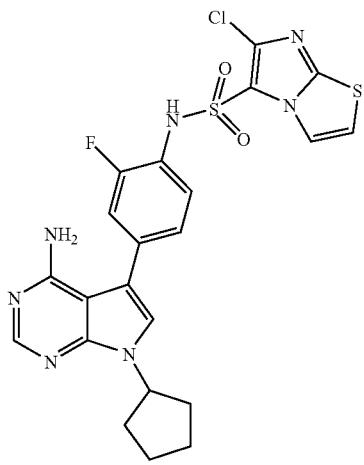 | 3.16 | 531.86 |
| 302 | 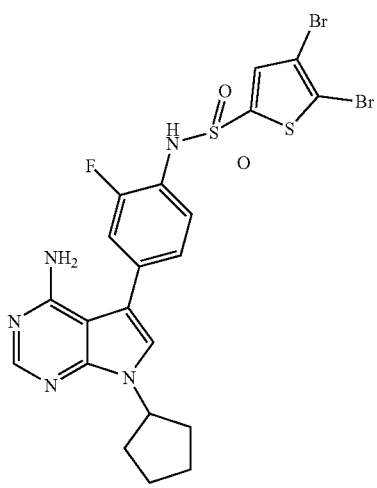 | 3.76 | 615.76 |
| 303 | 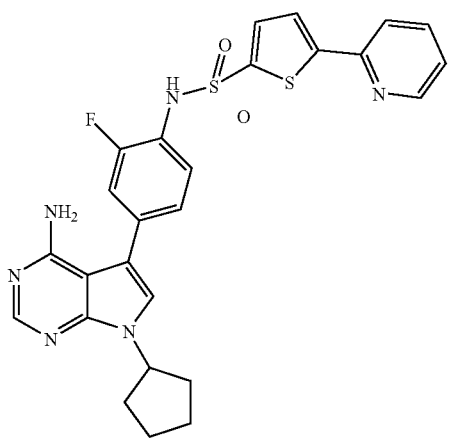 | 3.43 | 534.92 |

-continued
| | | | |
|---|---|---|---|
| 304 | 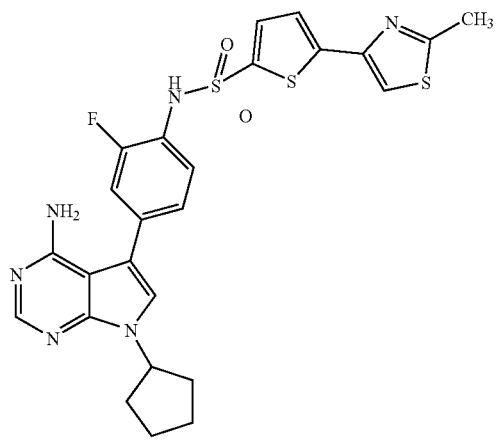 | 3.43 | 554.93 |
| 305 | 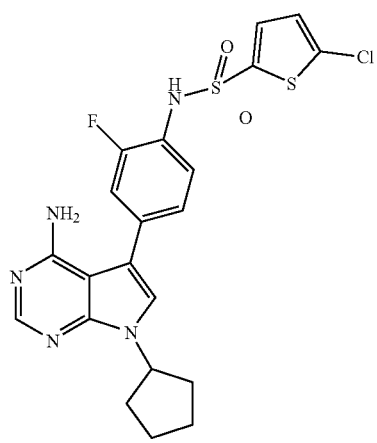 | 3.52 | 491.85 |
| 306 | 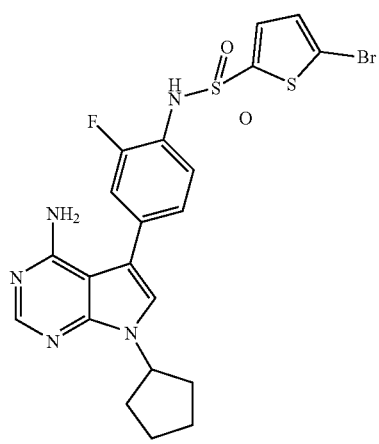 | 3.72 | 535.8 |

-continued
| | | |
|---|---|---|
| 307 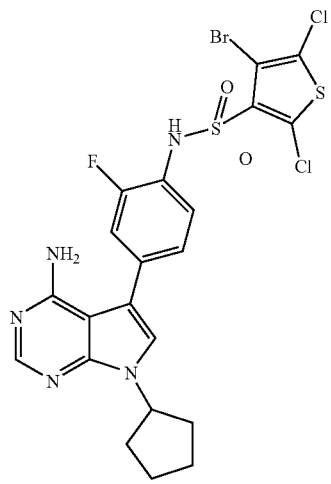 | 4.01 | 605.7 |
| 308 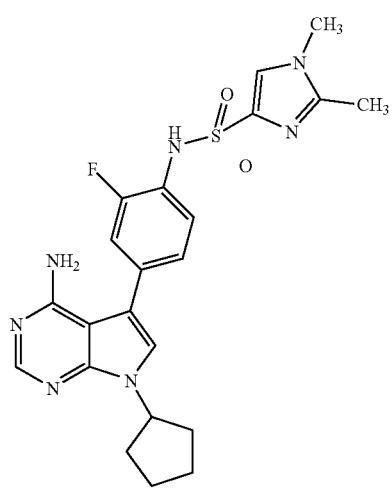 | 2.73 | 470 |
| 309 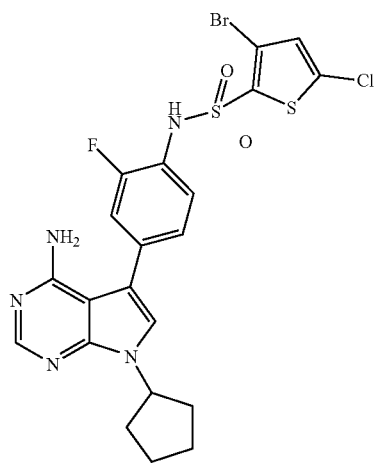 | 3.77 | 571.7 |

-continued
| | | | |
|---|---|---|---|
| 310 | 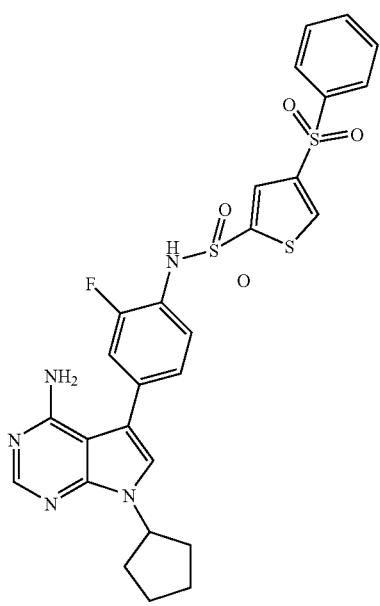 | 3.58 | 598 |
| 311 | 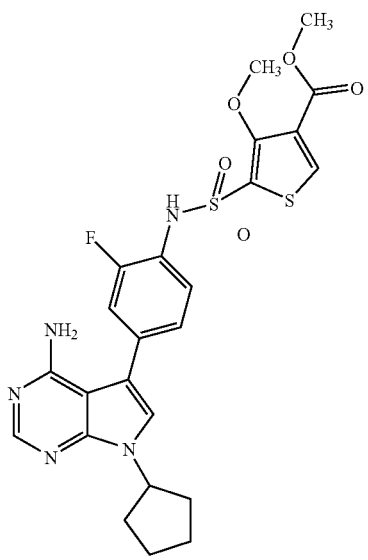 | 3.46 | 545.9 |
| 312 | 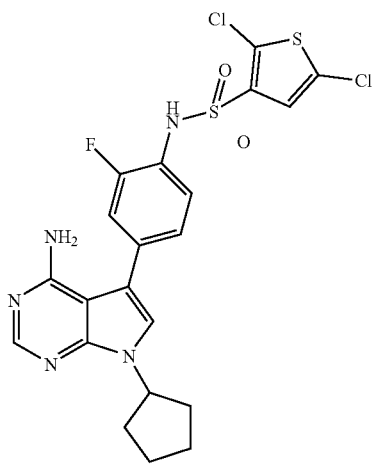 | 3.88 | 525.8 |

-continued
| 313 | 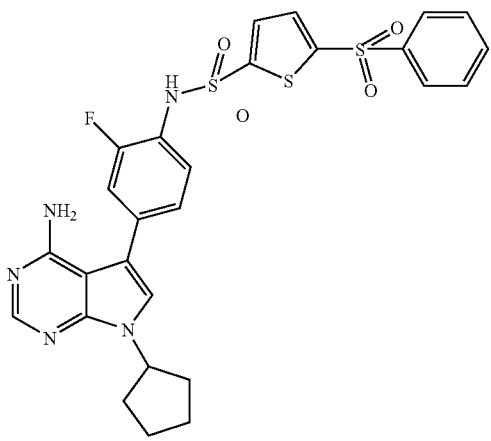 | 3.57 | 598 |
| 314 | 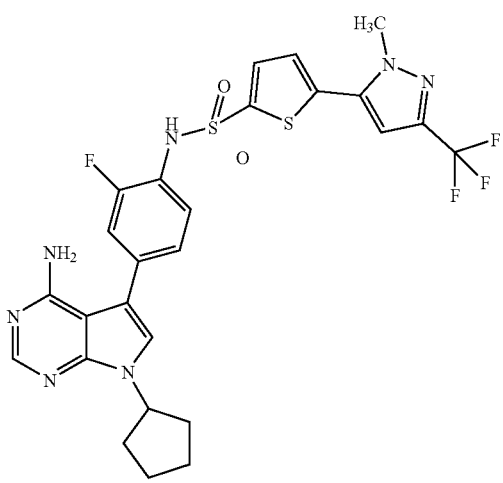 | 3.96 | 606 |
| 315 | 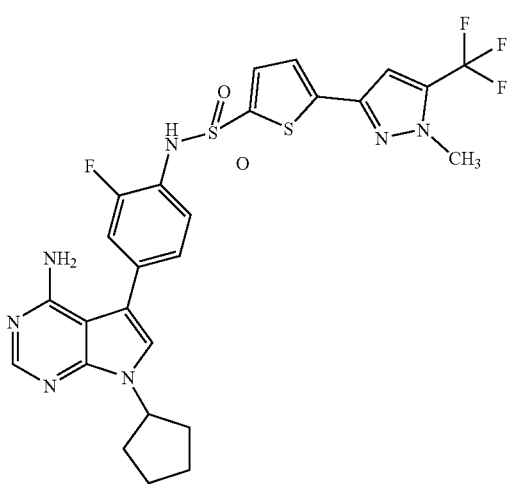 | 3.77 | 606 |

| | | | |
|---|---|---|---|
| 316 | 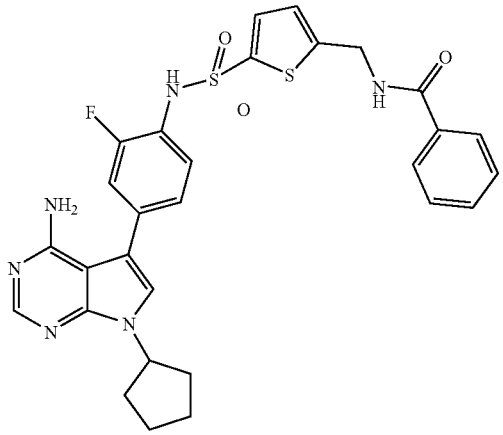 | 3.34 | 591 |
| 317 | 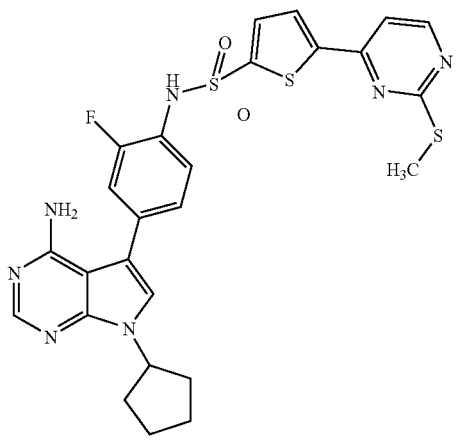 | 3.69 | 582 |
| 318 | 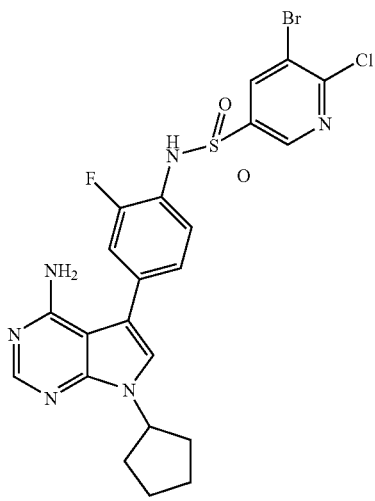 | 3.72 | 566.7 |

-continued
| | | | |
|---|---|---|---|
| 319 | 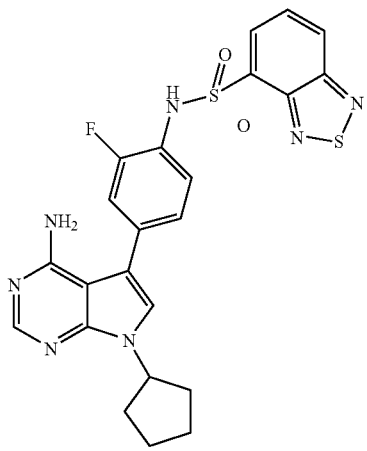 | 3.37 | 509.9 |
| 320 | 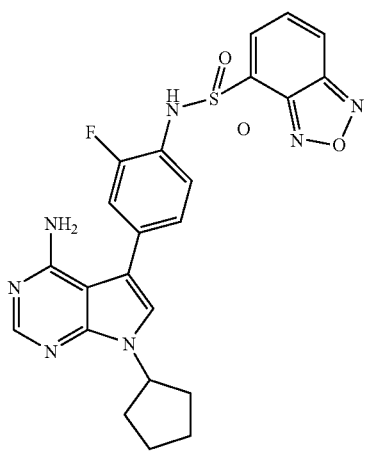 | 3.4 | 494 |
| 321 | 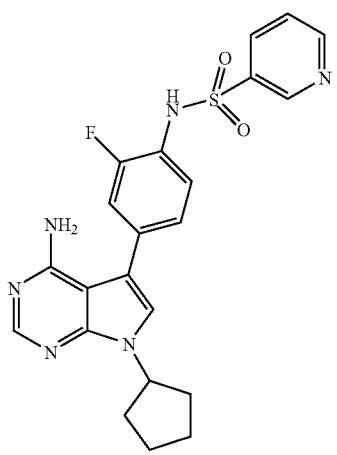 | 3.24 | 453.1 |

-continued
| | | | |
|---|---|---|---|
| 322 | 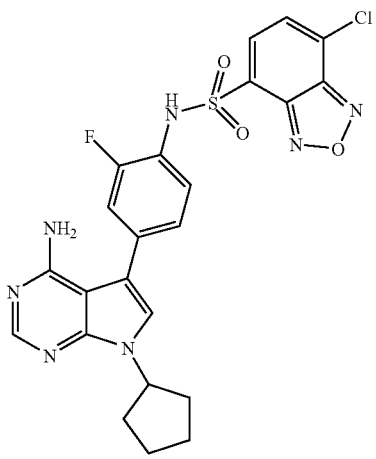 | 3.73 | 528.1 |
| 323 | 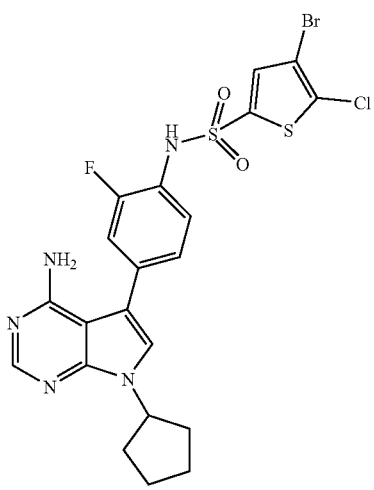 | 4.02 | 571.7 |
| 324 | 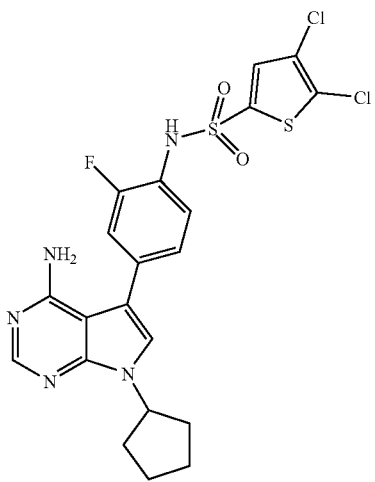 | 4.06 | 525.9 |

We claim:
1. A compound represented by the following structural formula:

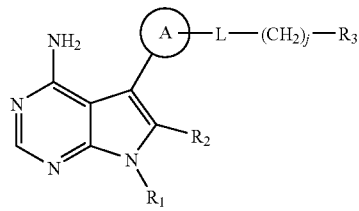

or pharmaceutically acceptable salts thereof, wherein:

Ring A is a five or six membered heteroaromatic ring which is substituted with one or more substituents selected from the group consisting of a substituted or unsubstituted aromatic group, substituted or unsubstituted heteroaromatic group, substituted or unsubstituted cycloalkyl, substituted or unsubstituted heterocycloalkyl, substituted or unsubstituted heteroaralkyl, cyano, —NR$_4$R$_5$, —C(O)$_2$-haloalkyl, a substituted or unsubstituted alkylthio, a substituted or unsubstituted alkylsulfinyl, a substituted or unsubstituted alkylsulfonyl, a substituted or unsubstituted arylthio, a substituted or unsubstituted arylsulfinyl, a substituted or unsubstituted arylsulfonyl, a substituted or unsubstituted alkyl carbonyl, —C(O)-haloalkyl, a substituted or unsubstituted aryloxy, a substituted or unsubstituted carboxamido, substituted or unsubstituted tetrazolyl, trifluoromethylsulphonamido, trifluoromethylcarbonylamino, a substituted or unsubstituted alkynyl, a substituted or unsubstituted alkyl amido or alkylcarboxamido, a substituted or unsubstituted aryl amido or arylcarboxamido, a substituted or unsubstituted styryl, —S(substituted or unsubstituted heteroaryl) and a substituted or unsubstituted aralkyl amido, aralkylcarboxamido or —C(O)NR$_f$R$_g$, R$_c$ and CH$_2$OR$_c$;

wherein R$_f$, R$_g$ and the nitrogen atom together form a 3-, 4-, 5-, 6- or 7-membered, substituted or unsubstituted heterocycloalkyl, substituted or unsubstituted heterobicycloalkyl or a substituted or unsubstituted heteroaromatic;

R$_c$ is substituted or unsubstituted aryl, —W—(CH$_2$)$_t$—O-alkyl, —W—(CH$_2$)$_t$—S-alkyl, —W—(CH$_2$)$_t$—OH, or —W—(CH$_2$)$_t$—NR$_d$R$_e$;

t is an integer from 0 to about 6;

W is —O—, —S—, —S(O)—, —S(O)$_2$— or —NR$_k$—;

R$_k$ is —H or alkyl;

R$_d$, R$_e$ and the nitrogen atom to which they are attached together form a 3, 4, 5, 6 or 7-membered substituted or unsubstituted heterocycloalkyl or substituted or unsubstituted heterobicyclic group; or R$_d$ and R$_e$ are each, independently alkanoyl or —K-D;

wherein K is —S(O)$_2$—, —C(O)NH, or a direct bond; and

D is a substituted or unsubstituted heteroaryl, a substituted or unsubstituted aralkyl, a substituted or unsubstituted heteroaromatic group, a substituted or unsubstituted heteroaralkyl, a substituted or unsubstituted cycloalkyl, a substituted or unsubstituted heterocycloalkyl, a substituted or unsubstituted aminoalkyl;

L is —N(C(O)OR)—; —N(C(O)R)—; —N(SO$_2$R)—; —CH$_2$O—; —CH$_2$S—; —CH$_2$N(C(O)R))—; —CH$_2$N(C(O)OR)—; —CH$_2$N(SO$_2$R)—; —CH(NHR)—; —CH(NHC(O)R)—; —CH(NHSO$_2$R)—; —CH(NHC (O)OR)—; —CH(OC(O)R)—; —CH(OC(O)NHR)—; —CH=CH—; —C(=NOR)—; —C(O)—; —CH (OR)—; —N(R)S(O)—; —OC(O)N(R)—; —NRC(O) O—; —S(O)N(R)—; —N(C(O)R)S(O)—; —N(C(O) R)S(O)$_2$—; —N(R)S(O)N(R)—; —N(R)S(O)$_2$N(R)—; —C(O)N(R)C(O)—; —S(O)N(R)C(O)—; —S(O)$_2$N (R)C(O)—; —OS(O)N(R)—; —OS(O)$_2$ N(R)—; —N(R)S(O)$_2$O—; —N(R)S(O)C(O)—; —N(R)S(O)$_2$C(O)—; —SON(C(O)R)—; —SO$_2$N(C (O)R)—; —N(R)P(OR')O—; —N(R)P(OR')—; —N(R)P(O)(OR')O—; —N(R)P(O)(OR')—; —N(C (O)R)P(OR')O—; —N(C(O)R)P(OR')—; —N(C(O)R) P(O)(OR')O— or —N(C(O)R)P(OR')—, wherein R and R' are each, independently, —H, a substituted or unsubstituted aliphatic group, a substituted or unsubstituted aromatic group, a substituted or unsubstituted heteroaromatic group, or a substituted or unsubstituted cycloalkyl group; or L is represented by one of the following structural formulas:

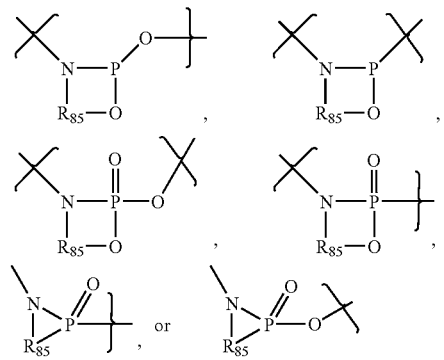

wherein R$_{85}$ taken together with the phosphinamide, or phosphonamide is a 5-, 6-, or 7-membered, aromatic, heteroaromatic or heterocycloalkyl ring system;

R$_1$ is —H, 2-phenyl-1,3-dioxan-5-yl, a C$_1$-C$_6$ alkyl group, a C$_3$-C$_8$ cycloalkyl group, a C$_5$-C$_7$ cycloalkenyl group or an optionally substituted phenyl(C$_1$-C$_6$ alkyl) group, wherein the alkyl, cycloalkyl and cycloalkenyl groups are optionally substituted by one or more groups of formula —OR$^a$; provided that —OR$^a$ is not located on the carbon attached to nitrogen;

R$^a$ is —H or a C$_1$-C$_6$ alkyl group or a C$_3$-C$_6$ cycloalkyl;

R$_2$ is —H, a substituted or unsubstituted aliphatic group, a substituted or unsubstituted cycloalkyl, a halogen, —OH, cyano, a substituted or unsubstituted aromatic group, a substituted or unsubstituted heteroaromatic group, a substituted or unsubstituted heterocycloalkyl, a substituted or unsubstituted aralkyl, a substituted or unsubstituted heteroaralkyl, —NR$_4$R$_5$, or —C(O) NR$_4$R$_5$;

R$_3$ is a substituted or unsubstituted cycloalkyl, a substituted or unsubstituted aromatic group, a substituted or unsubstituted heteroaromatic group, or a substituted or unsubstituted heterocycloalkyl; or L is —NRC(O)—, —NRC (O)O—, —S(O)$_2$NR—, —C(O)NR— or —OC(O) NR—, and R$_3$ is substituted or unsubstituted alkyl, substituted or unsubstituted alkenyl or substituted or unsubstituted aralkyl;

R$_4$, R$_5$ and the nitrogen atom together form a 3, 4, 5, 6 or 7-membered, substituted or unsubstituted heterocycloalkyl, substituted or unsubstituted heterobicycloalkyl or a substituted or unsubstituted heteroaromatic; or R$_4$ and R$_5$ are each, independently, azabicycloalkyl, or Y—Z;

Y is selected from the group consisting of —(CH$_2$)$_p$—, —S(O)$_2$—, —C(O)O—, —SO$_2$NH—, —CONH—, (CH$_2$)$_p$O—, —(CH$_2$)$_p$NH—, —(CH$_2$)$_p$S—, —(CH$_2$)$_p$S(O)—, and —(CH$_2$)S(O)$_2$—;

p is an integer from 0 to 6;

Z is a substituted or unsubstituted amino, substituted or unsubstituted aryl, substituted or unsubstituted heteroaryl or substituted or unsubstituted heterocycloalkyl group; and j is an integer from 0 to 6.

2. The compound of claim 1, wherein R$_3$ is selected from the group consisting of a substituted or unsubstituted phenyl, a substituted or unsubstituted naphthyl, a substituted or unsubstituted pyridyl, a substituted or unsubstituted thienyl, a substituted or unsubstituted benzotriazole, a substituted or unsubstituted tetrahydropyranyl, a substituted or unsubstituted tetrahydrofuranyl, a substituted or unsubstituted dioxane, a substituted or unsubstituted dioxolane, a substituted or unsubstituted quinoline, a substituted or unsubstituted thiazole, substituted or unsubstituted isoxazole, substituted or unsubstituted cyclopentanyl, a substituted or unsubstituted benzofuran, substituted or unsubstituted benzothiophene, substituted or unsubstituted benzisoxazole, substituted or unsubstituted benzisothiazole, substituted or unsubstituted benzothiazole, substituted or unsubstituted benzoxazole, substituted or unsubstituted benzoxazole, substituted or unsubstituted benzimidazole, substituted or unsubstituted benzoxadiazole, substituted or unsubstituted benzothiadiazole, substituted or unsubstituted isoquinoline, substituted or unsubstituted quinoxaline, substituted or unsubstituted indole and substituted or unsubstituted pyrazole.

3. The compound of claim 2 wherein R$_3$ is substituted with one or more substituents selected from the group consisting of —OCF$_3$, CN, CO$_2$CH$_3$, CF$_3$, pyridyl, substituted or unsubstituted oxazolyl, substituted or unsubstituted benzyl, substituted or unsubstituted benzenesulfonyl, substituted or unsubstituted phenyl, carboxyl, substituted or unsubstituted tetrazolyl, styryl, —S-(substituted or unsubstituted aryl), —S-(substituted or unsubstituted heteroaryl), substituted or unsubstituted heteroaryl, substituted or unsubstituted heterocycloalkyl, alkynyl, —C(O)NR$_f$R$_g$, R$_c$, and CH$_2$OR$_c$;

wherein R$_f$, R$_g$ and the nitrogen atom together form a 3, 4, 5, 6 or 7-membered, substituted or unsubstituted heterocycloalkyl, substituted or unsubstituted heterobicycloalkyl or a substituted or unsubstituted heteroaromatic;

R$_c$ is substituted or unsubstituted aryl, —W—(CH$_2$)$_t$—NR$_d$R$_e$, —W—(CH$_2$)$_t$—O-alkyl, —W—(CH$_2$)$_t$—S-alkyl, or —W—(CH$_2$)$_t$—OH;

t is an integer from 0 to 6;

W is —O—, —S—, —S(O)—, —S(O)$_2$—, or —NR$_k$—;

R$_k$ is —H or alkyl; and

R$_d$, R$_e$ and the nitrogen atom to which they are attached together form a 3, 4, 5, 6 or 7-membered substituted or unsubstituted heterocycloalkyl or substituted or unsubstituted heterobicyclic group; or R$_d$ and R$_e$ are each, independently, alkanoyl or —K-D;

K is —S(O)$_2$—, —C(O)NH— or a direct bond;

D is a substituted or unsubstituted heteroaryl, a substituted or unsubstituted aralklyl, a substituted or unsubstituted heteroaromatic group, a substituted or unsubstituted heteroaralkyl, a substituted or unsubstituted cycloalkyl, a substituted or unsubstituted heterocycloalkyl, a substituted or unsubstituted aminoalkyl, a substituted or unsubstituted aminocycloalkyl.

4. The compound of claim 3, wherein R$_3$ is a substituted or unsubstituted phenyl, thienyl, benzoxadiazolyl, or benzothiadiazolyl.

5. The compound of claim 1, wherein ring A is a substituted pyridyl.

6. The compound of claim 5 wherein ring A is substituted with one or more substitutents selected from the group consisting of cyano, pyridyl, substituted or unsubstituted oxazolyl, substituted or unsubstituted benzyl, substituted or unsubstituted benzenesulfonyl, substituted or unsubstituted phenoxy, substituted or unsubstituted phenyl, NR$^4$R$^5$, substituted or unsubstituted tetrazolyl, styryl, —S-(substituted or unsubstituted aryl), substituted or unsubstituted arylthio, substituted or unsubstituted heteroaryl, substituted or unsubstituted heterocycloalkyl, alkynyl, —C(O)NR$_f$R$_g$, R$_c$ and CH$_2$OR$_c$;

R$_f$, R$_g$ and the nitrogen atom together form a 3, 4, 5, 6 or 7-membered, substituted or unsubstituted heterocycloalkyl, substituted or unsubstituted heterobicycloalkyl or a substituted or unsubstituted heteroaromatic;

R$_c$ is substituted or unsubstituted aryl, —W—(CH$_2$)$_t$—NR$_d$R$_e$, —W—(CH$_2$)$_t$—O-alkyl, —W—(CH$_2$)$_t$—S-alkyl, or —W—(CH$_2$)$_t$—OH;

t is an integer from 0 to 6;

W is —O—, —S—, —S(O)—, —S(O)$_2$—, or —NR$_k$—;

R$_k$ is —H or alkyl; and

R$_d$, R$_e$ and the nitrogen atom to which they are attached together form a 3, 4, 5, 6 or 7-membered substituted or unsubstituted heterocycloalkyl, substituted or unsubstituted heterobicycloalkyl or a substituted or unsubstituted heteroaromatic; or R$_d$ and R$_e$ are each, independently, alkanoyl, or —K-D;

K is —S(O)$_2$—, —C(O)NH—, or a direct bond;

D is substituted or unsubstituted heteroaryl, substituted or unsubstituted aralkyl, substituted or unsubstituted heteroaromatic group, substituted or unsubstituted heteroaralkyl, substituted or unsubstituted cycloalkyl, substituted or unsubstituted heterocycloalkyl, -substituted or unsubstituted aminoalkyl, substituted or unsubstituted aminocycloalkyl.

7. The compound of claim 1, wherein R$^1$ is a cyclopentyl group, a hydroxycyclopentyl or an isopropyl.

8. The compound of claim 1, wherein R$_2$ is —H.

9. A compound represented by the following structural formula

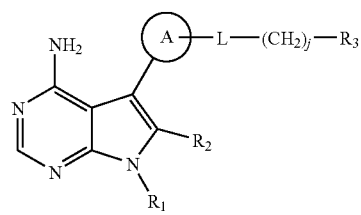

or pharmaceutically acceptable salts thereof, wherein:

Ring A is a five or six membered heteroaromatic ring which is substituted with one or more substituents selected from the group consisting of a substituted or unsubstituted aliphatic group, a halogen, a substituted or unsubstituted aromatic group, substituted or unsubstituted heteroaromatic group, substituted or unsubstituted cycloalkyl, substituted or unsubstituted heterocycloalkyl, substituted or unsubstituted aralkyl, substituted or unsubstituted heteroaralkyl, cyano, nitro, —NR$_4$R$_5$, —C(O)$_2$H, a substituted or unsubstituted alkoxycarbonyl, —C(O)$_2$-haloalkyl, a substituted or unsubstituted alkylthio, a substituted or unsubstituted alkylsulfinyl, a substituted or unsubstituted alkylsulfonyl, a substituted or unsubstituted arylthio, a substituted or unsubstituted arylsulfinyl, a substituted or unsubstituted arylsulfonyl, a substituted or unsubstituted alkyl carbonyl, —C(O)-haloalkyl, a substituted or unsubstituted aryloxy, a substituted or unsubstituted carboxamido, tetrazolyl, trifluoromethylsulphonamido, trifluoromethylcarbonylamino, a substituted or unsubstituted alkynyl, a substituted or unsubstituted alkyl amido or alkylcarboxamido; a substituted or unsubstituted aryl amido or arylcarboxamido, a substituted or unsubstituted styryl and a substituted or unsubstituted aralkyl amido or aralkylcarboxamido;

wherein L is —NHSO$_2$R—, —NHC(O)O— or —NHC(O)R—;

wherein R is a substituted or unsubstituted aliphatic group, a substituted or unsubstituted aromatic group, a substituted or unsubstituted heteroaromatic group, or a substituted or unsubstituted cycloalkyl group;

R$_1$ is —H, 2-phenyl-1,3-dioxan-5-yl, a C$_1$-C$_6$ alkyl group, a C$_3$-C$_8$ cycloalkyl group, a C$_5$-C$_7$ cycloalkenyl group or an optionally substituted phenyl C$_1$-C$_6$ alkyl group, wherein the alkyl, cycloalkyl and cycloalkenyl groups are optionally substituted by one or more groups of formula —OR$^a$; provided that —OR$^a$ is not located on the carbon attached to nitrogen;

R$^a$ is —H or a C$_1$-C$_6$ alkyl group or a C$_3$-C$_6$ cycloalkyl;

R$_2$ is —H, a substituted or unsubstituted aliphatic group, a substituted or unsubstituted cycloalkyl, a halogen, —OH, cyano, a substituted or unsubstituted aromatic group, a substituted or unsubstituted heteroaromatic group, a substituted or unsubstituted heterocycloalkyl, a substituted or unsubstituted aralkyl, a substituted or unsubstituted heteroaralkyl, —NR$_4$R$_5$, or —C(O)NR$_4$R$_5$;

R$_3$ is a substituted or unsubstituted cycloalkyl, a substituted or unsubstituted aromatic group, a substituted or unsubstituted heteroaromatic group, or a substituted or unsubstituted heterocycloalkyl; and R$_4$, R$_5$ and the nitrogen atom together form a 3, 4, 5, 6 or 7-membered, substituted or unsubstituted heterocloalkyl, substituted or unsubstituted heterobicycloalkyl or a substituted or unsubstituted heteroaromatic; or R$_4$ and R$_5$ are each, independently, —H, azabicycloalkyl, a substituted or unsubstituted alkyl group or Y—Z;

Y is selected from the group consisting of —C(O)—, —(CH$_2$)$_p$—, —S(O)$_2$—, —C(O)O—, —SO$_2$NH—, —CONH—, (CH$_2$)$_p$O—, —(CH$_2$)$_p$NH—, —(CH$_2$)$_p$S—, —(CH$_2$)$_p$S(O)—, and —(CH$_2$)S(O)$_2$—;

p is an integer from 0 to 6;

Z is a substituted or unsubstituted alkyl, substituted or unsubstituted amino, substituted or unsubstituted aryl, substituted or unsubstituted heteroaryl or substituted or unsubstituted heterocycloalkyl group; and j an integer from 0 to 6.

10. A compound according to claim 1 wherein L is —N(C(O)OR)—; —N(C(O)R)—; —N(SO$_2$R)—; —CH$_2$O—; —CH$_2$S—; —CH$_2$N(C(O)R))—; —CH$_2$N(C(O)OR)—; —CH$_2$N(SO$_2$R)—; —CH(NHR)—; —CH(NHC(O)R)—; —CH(NHSO$_2$R)—; —CH(NHC(O)OR)—; —CH(OC(O)R)—; —CH(OC(O)NHR)—; —CH═CH—; —C(═NOR)—; —C(O)—; —CH(OR)—; —N(R)S(O)—; —OC(O)N(R)—; —S(O)N(R)—; —N(C(O)R)S(O)—; —N(C(O)R)S(O)$_2$—; —N(R)S(O)N(R)—; —N(R)S(O)$_2$N(R)—; —C(O)N(R)C(O)—; —S(O)N(R)C(O)—; —S(O)$_2$N(R)C(O)—; —OS(O)N(R)—; —OS(O)$_2$N(R)—; —N(R)S(O)O—; —N(R)S(O)$_2$O—; —N(R)S(O)C(O)—; —N(R)S(O)$_2$C(O)—; —SON(C(O)R)—; —SO$_2$N(C(O)R)—; —N(R)SON(R)—; —N(R)SO$_2$N(R)—; —N(R)P(OR')O—; —N(R)P(OR')—; —N(R)P(O)(OR')O—; —N(R)P(O)(OR')—; —N(C(O)R)P(OR')O—; —N(C(O)R)P(OR')—; —N(C(O)R)P(O)(OR')O— or —N(C(O)R)P(OR')—, wherein R and R' are each, independently, —H, an acyl group, a substituted or unsubstituted aliphatic group, a substituted or unsubstituted aromatic group, a substituted or unsubstituted heteroaromatic group, or a substituted or unsubstituted cycloalkyl group.

11. A compound according to claim 1 wherein R$_3$ is a substituted or unsubstituted cycloalkyl, or a substituted or unsubstituted heterocycloalkyl; or L is —NRC(O)—, —NRC(O)O—, —S(O)$_2$NR—, —C(O)NR— or —OC(O)NR—, and R$_3$ is substituted or unsubstituted alkyl, substituted or unsubstituted alkenyl or substituted or unsubstituted aralkyl.

* * * * *